US010519458B2

(12) United States Patent
Fu et al.

(10) Patent No.: US 10,519,458 B2
(45) **Date of Patent: *Dec. 31, 2019**

(54) WHOLE SEED SPECIFIC PROMOTER

(75) Inventors: Huihua Fu, Cary, NC (US); Jeffrey A. Brown, Apex, NC (US); Kirk Francis, Cary, NC (US); Hee-Sook Song, Raleigh, NC (US)

(73) Assignee: BASF Plant Science Company GmbH, Ludwigshafen (DE)

( * ) Notice: Subject to any disclaimer, the term of this patent is extended or adjusted under 35 U.S.C. 154(b) by 1010 days.

This patent is subject to a terminal disclaimer.

(21) Appl. No.: 13/265,205

(22) PCT Filed: Apr. 22, 2010

(86) PCT No.: PCT/EP2010/055362

§ 371 (c)(1), (2), (4) Date: Oct. 19, 2011

(87) PCT Pub. No.: WO2010/122110

PCT Pub. Date: Oct. 28, 2010

(65) Prior Publication Data

US 2012/0036595 A1 Feb. 9, 2012

(30) Foreign Application Priority Data

Apr. 22, 2009 (EP) .................................... 09158449

(51) Int. Cl.
*C12N 15/82* (2006.01)
*C12N 15/113* (2010.01)

(52) U.S. Cl.
CPC ........ *C12N 15/8234* (2013.01); *C12N 15/113* (2013.01)

(58) Field of Classification Search
None
See application file for complete search history.

(56) References Cited

U.S. PATENT DOCUMENTS

| | | | | |
|---|---|---|---|---|
| 5,504,200 | A | 4/1996 | Hall et al. | |
| 5,792,922 | A | 8/1998 | Moloney | |
| 5,824,863 | A | 10/1998 | Miki et al. | |
| 7,098,324 | B2 * | 8/2006 | Haigler et al. | 536/24.1 |
| 9,150,871 | B2 * | 10/2015 | Kuhn | C12N 15/8234 |
| 9,970,019 | B2 * | 5/2018 | Kuhn | C12N 15/8234 |
| 10,041,081 | B2 * | 8/2018 | Kuhn | C12N 15/8234 |
| 10,041,082 | B2 * | 8/2018 | Kuhn | C12N 15/8234 |
| 10,041,083 | B2 * | 8/2018 | Kuhn | C12N 15/8234 |
| 2007/0039067 | A1 * | 2/2007 | Feldmann et al. | 800/278 |
| 2007/0130645 | A1 * | 6/2007 | Wu et al. | 800/278 |
| 2012/0090049 | A1 | 4/2012 | Wang et al. | |

FOREIGN PATENT DOCUMENTS

| | | | |
|---|---|---|---|
| RU | 94046161 | A | 5/1997 |
| RU | 2148647 | C1 | 5/2000 |
| WO | WO-99/53067 | A2 | 10/1999 |
| WO | WO-00/26388 | A2 | 5/2000 |

OTHER PUBLICATIONS

Ezcurra et al. Interaction between composite elements in the napA promoter: both the B-box ABA-responsive complex and the RY/G complex are necessary for seed-specific expression. Plant Molecular Biology. 1999. 40: 699-709.*

Kim et al. A 20 nucleotide upstream element is essential for the nopaline synthase (nos) promoter activity. Plant Molecular Biology. 1994. 24: 105-117.*

Doerks. Protein Annotation: detective work for function prediction. TIG. 1998. 14(6): 248-250.*

Brenner. Errors in genome annotation. TIG. 1999. 15(4): 132-133.*

Bork. Go hunting in sequence databases but watch out for traps. TIG. 1996. 12(10): 425-427.*

Kennell. Principles and practices of nucleic acid hybridization. Progress in Nucleic Acid Research and Molecular Biology. 1971. 11: 259-301.*

Maniatis et al. Molecular cloning: a laboratory manual. Cold Spring Harbor Laboratory. 1982. pp. 324-343 and 387-389.*

Hsieh et al. Promoter structure and activity of type 1 rice metallothionein-like gene. Mitochondrial DNA. 1998. 9(1): 9-18.*

International Preliminary Report on Patentability for PCT/EP2010/055362, dated Oct. 25, 2011.

Baumlein, H., et al., "A Novel Seed Protein Gene from *Vicia faba* is Developmentally Regulated in Transgenic Tobacco and *Arabidopsis* Plants", Mol. Gen. Genet, 1991, vol. 225, pp. 459-467.

Bustos, M.M, et al., "Regulation of β-Glucuronidase Expression in Transgenic Tobacco Plants by an A/T-Rich, cis-Acting Sequence Found Upstream of a French Bean β-Phaseolin Gene", The Plant Cell, 1989, vol. 1, pp. 839-853.

Fobert, P.R., et al., "T-DNA Tagging of a Seed Coat-Specific Cryptic Promoter in Tobacco", The Plant Journal, 1994, vol. 6, No. 4, pp. 567-577.

Higo, K., et al., "Plant cis-acting Regulatory DNA Elements (PLACE) Database: 1999", Nucleic Acids Research, 1999, vol. 27, No. 1, pp. 297-300.

Josefsson, L.-G., et al., "Structure of a Gene Encoding the 1.7 S Storage Protein, Napin, from *Brassica napus*", The Journal of Biological Chemistry, 1987, vol. 262, No. 25, pp. 12196-12201.

Kasuga, M., et al., "Improving Plant Drought, Salt and Freezing Tolerance by Gene Transfer of a Single Stress-Inducible Transcription Factor", Nature Biotechnology, 1999, vol. 17, pp. 287-291.

(Continued)

*Primary Examiner* — Ashley K Buran

(74) *Attorney, Agent, or Firm* — Drinker Biddle & Reath LLP

(57) ABSTRACT

The present invention is concerned with the provision of means and methods for gene expression. Specifically, it relates to a polynucleotide comprising an expression control sequence which allows for seed specific of a nucleic acid of interest being operatively linked thereto in plants. Furthermore, vectors, host cells, transgenic plants and methods for expressing nucleic acids of interest are provided which are based on the said polynucleotide.

20 Claims, 44 Drawing Sheets

Figure 3:
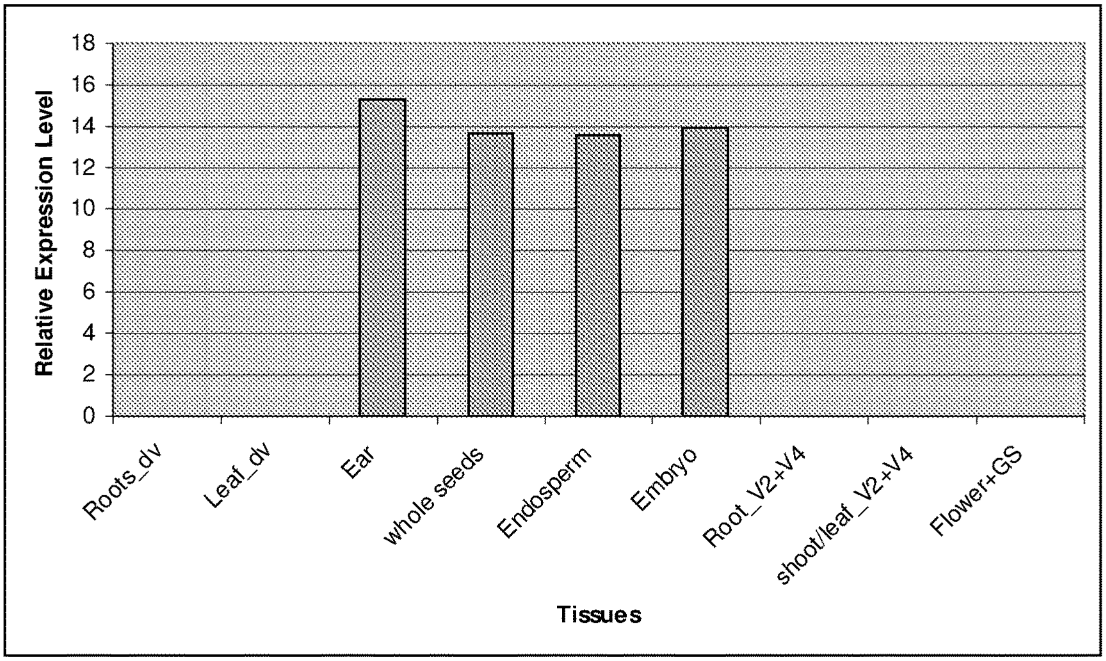

Specification includes a Sequence Listing.

(56) References Cited

OTHER PUBLICATIONS

Lam, E., et al., "Tetramer of a 21-Base Pair Synthetic Element Confers Seed Expression and Transcriptional Enhancement in Response to Water Stress and Abscisic Acid", The Journal of Biological Chemistry, 1991, vol. 266, No. 26, pp. 17131-17135.
Lohmer, S., et al., "Translation of the mRNA of the Maize Transcriptional Activator Opaque-2 Is Inhibited by Upstream Open Reading Frames Present in the Leader Sequence", The Plant Cell, vol. 5, pp. 65-73.
McElroy, D., et al., "Construction of Expression Vectors Based on the Rice Actin 1 (Act1) 5' Region for Use in Monocot Transformation", Mol. Gen. Genet, 1991, vol. 231, pp. 150-160.
Mutisya, J. et al., "Starch Branching Enzymes in Sorghum (*Sorghum bicolor*) and Barley (*Hordeum vulgare*): Comparative Analyses of Enzyme Structure and Gene Expression", J. Plant Physiol. 2003, vol. 160, pp. 921-930.
Odell, J.T., et al., "Identification of DNA Sequences Required for Activity of the Cauliflower Mosaic Virus 35S Promoter", Letters to Nature, 1985, vol. 313. pp. 810-812.
Rouster, J., et al., "The Untranslated Leader Sequence of the Barely lipoxygenase 1 (Lox1) Gene Confers Embryo-Specific Expression", The Plant Journal, 1998, vol. 15, No. 3, pp. 435-440.
Schoffl, F., et al., "The Function of Plant Heat Shock Promoter Elements in the Regulated Expression of Chimaeric Genes in Transgenic Tobacco", Mol. Gen. Genet, 1989, vol. 217, pp. 246-253.
Shirsat, A., et al., "Sequence Responsible for the Tissue Specific Promoter Activity of a Pea Legumin Gene in Tobacco", Mol. Gen. Genet, 1989, vol. 215, pp. 326-331.
Stalberg, K., et al., "Disruption of an Overlapping E-box/ABRE Motif Abolished High Transcription of the napA Storage-Protein Promoter in Transgenic *Brassica napus* Seeds", Planta, 1996, vol. 199, pp. 515-519.
"Aquaporin [Vernicia fordii]", GenBank Accession No. AAC39480, Jun. 24, 1998.
"F17L21.26 [*Arabidopsis thaliana*]", GenBank Accession No. AAF99742.1, Aug. 15, 2000.
"Putative alliin lyase [Aegilops tauschii]", GenBank Accession AAM69848.1, Nov. 28, 2008.
"Unknown [Picea sitchensis]", GenBank Accession No. ABK22242, Mar. 24, 2009.
"Unknown [Picea sitchensis]", GenBank Accession No. ABK22410.1, Mar. 24, 2009.
"Unknown, partial [*Arabidopsis thaliana*]", GenBank Accession No. ABK28018.1, Nov. 4, 2006.
"Unknown [*Arabidopsis thaliana*]", GenBank Accession No. ABK28287.1, Nov. 4, 2006.
"Unknown [*Zea mays*]", GenBank Accession No. ACF80703.1, Jul. 30, 2008.
"Unknown [*Zea mays*]", GenBank Accession No. ACF84237.1, Jul. 30, 2008.
"Tryptophan aminotransferase [*Zea mays*]", GenBank Accession No. ACG56678.1, Aug. 11, 2008.
"Hypothetical protein [*Oryza sativa* Japonica Group]", GenBank Accession No. BAC22280.1, Feb. 16, 2008.
"Maize promoter sequence SEQ ID 10408", Accession No. AQE62678, Jun. 12, 2008.
"MP23 precursor [Cucurbita cv. Kurokawa Amakuri]", GenBank Accession No. BAA08107.1, Aug. 18, 2007.
"MP28 [Cucurbita cv. Kurokawa Amakuri]" GenBank Accession No. BAA08108.1, Aug. 18, 2007.
"Tonoplast intrinsic protein [Prunus persica]", GenBank Accession No. BAD04010.1, Dec. 13, 2003.
"Putative alliinase precursor [*Oryza sativa* Japonica Group]", GenBank Accession No. BAD68317, Feb. 15, 2008.
"Tonoplast intrinsic protein [Phaseolus vulgaris]" GenBank Accession No. CAA44669.1, Apr. 18, 2005.
"Tonoplast intrinsic protein [Tulipa gesneriana]", GenBank Accession No. CAA64952.1, Apr. 18, 2005.
"Major intrinsic protein [Picea abies]", GenBank Accession No. CAB39758.1, Apr. 15, 2005.
"Hypothetical protein VITISV_013936 [Vitis vinifera]", GenBank Accession No. CAN72846.1, Feb. 5, 2008.
"Hypothetical protein VITISV_013176 [Vitis vinifera]", GenBank Accession No. CAN80923.1, Feb. 5, 2008.
"Unnamed protein product [Vitis vinifera]", GenBank Accession No. CAO14607.1, Oct. 8, 2007.
"Unnamed protein product [Vitis vinifera]", GenBank Accession No. CAO16122.1, Oct. 8, 2007.
"Unnamed protein product [Vitis vinifera]", GenBank Accession No. CAO61483.1, Oct. 8, 2007.
"Unnamed protein product [Vitis vinifera]", GenBank Accession No. CAO62035.1, Oct. 8, 2007.
"Unnamed protein product [Vitis vinifera]", GenBank Accession No. CAO64270.1, Oct. 8, 2007.
"OG3AC21TV ZM_0.7_1.5_KB *Zea mays* genomic clone ZMMBMa0749D16, genomic survey sequence", Accession No. CG335014, Aug. 30, 2003.
"Hypothetical protein OsJ-023945 [*Oryza sativa* (japonica cultivar-group)]", GenBank Accession No. EAZ40462.1, Feb. 12, 2007.
"Hypothetical protein OsI_00569 [*Oryza sativa* Indica Group}", GenBank Accession No. EAY72702.1, Dec. 17, 2008.
"Hypothetical protein OsI_16723 [*Oryza sativa* Indica Group]", GenBank Accession No. EAY94920.1, Dec. 17, 2008.
"Hypothetical protein OsI_017928 [*Oryza sativa* (indica cultivar-group)]", GenBank Accession No. EAY96695.1, Feb. 9, 2007.
"Hypothetical protein OsI_18618 [*Oryza sativa* Indica Group]", GenBank Accession No. EAY96696.1, Dec. 17, 2008.
"Hypothetical protein OsI_26656 [*Oryza sativa* Indica Group]", GenBank Accession No. EAZ04505.1, Dec. 17, 2008.
"Hypothetical protein OsJ_00535 [*Oryza sativa* Japonica Group]", GenBank Accession No. EAZ10701.1, Feb. 5, 2009.
"Hypothetical protein OsJ_016506 {*Oryza sativa* (japonica cultivar-group)]", GenBank Accession No. EAZ33023.1, Feb. 12, 2007.
"Sequence 10555 from U.S. Pat. No. 7,491,813", Accession No. GP220724, Apr. 30, 2009.
"Uncharacterized protein [*Arabidopsis thaliana*]", NCBI Accession No. NP_198895, May 28, 2011.
"Os01g0169800 [*Oryza sativa* Japonica Group]", NCBI Accession No. NP_001042135.1, Jun. 8, 2010.
"Os04g0527900 [*Oryza sativa* Japonica Group]", NCBI Accession No. NP_001053371.1, Jun. 8, 2010.
"Os05g0169300 [*Oryza sativa* Japonica Group]", NCBI Accession No. NP_001054761.1, Jun. 8, 2010.
"Os10g0492600 [*Oryza sativa* Japonica Group]", NCBI Accession No. NP_001064933.1, Jun. 8, 2010.
"Os11g0241200 [*Oryza sativa* (japonica cultivar-group)]" NCBI Accession No. NP_001067585.1, Feb. 14, 2008.
"Aquaporin TIP3-1 [*Zea mays*]", NCBI Accession No. NP_001105032.1, Dec. 18, 2011.
"Aquaporin TIP3-2 [*Zea mays*]", NCBI Accession No. NP_001105045.1, Nov. 26, 2011.
"Uncharacterized protein [*Arabidopsis thaliana*]", NCBI Accession No. NP_001117365.1, May 28, 2011.
"Predicted protein [*Physcomitrella patens* subsp. *patens*]", NCBI Accession No. XP_001751813.1, May 22, 2009.
"Predicted protein [*Physcomitrella patens* subsp. *patens*]" NCBI Accession No. XP_001763429.1, May 23, 2009.
"Predicted protein [*Physcomitrella patens* subsp. *patens*]", NCBI Accession No. XP_001778474.1, May 22, 2009.
International Search Report for PCT/EP2010/055362, dated Aug. 25, 2010.
Alexandrov, N. N., et. al., "Insights into Corn Genes Derived from Large-Scale cDNA Sequencing", Plant Molecular Biology, 2009, vol. 69, pp. 179-194.
"*Zea mays* Hypothetical Protein LOC100279098 (LOC100279098), mRNA," GenBank Accession No. NM_001152143, Apr. 10, 2009.
"*Zea mays* Tonoplast Membrane Integral Protein ZmTIP3-1 (LOC541896), mRNA," GenBank Accession No. NM_001111562, Dec. 14, 2007.

(56) References Cited

OTHER PUBLICATIONS

"*Zea mays* Clone 387386 mRNA Sequence," GenBank Accession No. EU972758, Dec. 5, 2008.

* cited by examiner

Fig. 1

GCGTACGAGTGGGAGGACGACGGGAAGGTCACCTCCATCGCTGCACCCTGCGAC-
GTCAGCCGGCTGCAGTGCGAGTCAGAGATACCTCTTCGCCTGGAGGTTCCGCAC-
CGCCGCCGCCGACGCCGACGCATCCGTTGGGCACAGCTCAGAGGAGATTAGTGAGAG-
TTAGGGAAGGTTGAGCTGCATCCAATGAAACCAAGTGCATAGACTAAGCCGCTAGCTGCATGT-
TAA

Fig. 2

CCGGGGTGGTCTCCGACTCAGGCAACCGCGTCCGGCTCGTGAACGACGCGTACAAGGA-
GATGGTGGGGCAGCCCGAGTGCCCGTGGCTCGACGCCGTGGCTGCCACGTCGAGGAG-
GATCAGCGGGGAGGTGGCGCTGGTGGTAGCGGACCGGTCCTCTCTGCCGGACTCGTAC-
GGGGCGTTCACATGCACGGCAAAGATCGAGTGGGAGGACGACGGGAAGGTCAC-
CTCCATCGCTGCACCCTGCGACGTCAGCCGGCTGCAGTGCGAGTCCAGGGATTAC-
CTCTTCGCCTGGAGGCTCCGCACCGCCGCCGCCGACGCCGACGCATCCGTT-
GGACACAGCTCCGAGGAGATTAGTGAGAGTTAGGGAAGCTTGAGCTGCATCCAATGAAAC-
CAAGTGCATAGACTAAGCCGCTAGCTGCATGTTAAAACTGAGCAGCTTCCTCTTTCGCG

Fig. 4

ATGGCCATGGTGCAGCCGGCGGACACGGCCGTCAAGGCCAACGA-
GATCCTGGCGCGGTTCCGGCCCATCGCGCCCAAGCCCACACTGGCAG-
CAGCCGCCGCCGCCGCCGCGGCGCCCGTGGCG-
CAGGCCGCGGCCGAGGGCGTCGTGGCCGCGAACCGCGTGCTGTGCCATCTGCAGAG-
CAGGCCGTGCCGCGCGCGCAAGCGCGGCCGCCCCAC-
CGTCGTGCCGGTGTCGCCCAAGTCGGGCGCGCAGCCGCCCGCGAAGCGGAGGAGAGCCTC-
TACGCCGTACCCGCCTCTCCGGTGCGCGGCGGCGACCACGGGGGCG-
CATGTGTCCGCGGTCGTCCCAGGCAGTGCGCGTCTCCCACCGGCGAGTGCGGGTGTCGAAGA-
CATCGCGAAGGCGGCGGCGGCGGCGGCGACAGAGGAGGGGAGGGACGTCCCCGTG-
GAGCGCGACCTGCTGCGGAAGCTGCTGGAGCCCAGGGTCATA-
TCGCCGCGGGCGGTGCGCCCGGTGTGGTCTGCCATCCACGTCGGGTGCATCCACCGCACCGAC-
GACGCGGCCTGCACCGACGCCGCCGTCTCGAAGACGGCGGTTCAGGTGGAGGCGGAGCTG-
GAGGTCGACGCGCTCCCGGCGGTGGTCTCCGACTCAGGCAACCGCGTCCGGCTCGTGAAC-
GACGCGTACAAGGAGATGGTGGGGCAGCCCGAGTGCCCGTGGCTCGACGCCGTGGCTGCCAC-
GTCGAGGAGGATCAGCGGGGAGGTGGCGCTGGTGGTAGCGGACCGGTCCTCTCTGCCG-
GACTCGTACGGGGCGTTCACATGCACGGCAAAGATCGAGTGGGAGGACGACGGGAAGGTCAC-
CTCCATCGCTGCACCCTGCGACGTCAGCCGGCTGCAGTGCGAGTCCAGGGATTAC-
CTCTTCGCCTGGAGGTTCCGCACCGCCGCCGCCGACGCCGACGCATCCGTT-
GGACACAGCTCCGAGGAGATTAGTGAGAGTTAG

Fig. 5

MAMVQPADTAVKANEILARFRPIAPKPT-
LAAAAAAAAAPVAQAAAEGVVAANRVLCHLQSRPCRARKRGRPTVVPVSPKSGAQP-
PAKRRRASTPYPPLRCAAATTGAHVSAVVPGSARLPPASAGVEDIAKAAAAAATEE-
GRDVPVERDLLRKLLEPRVISPRAVRPVWSAIHVGCIHRTDDAACTDAAVSKTAVQVE-
AELEVDALPAVVSDSGNRVRLVNDAYKEMVGQPECPWLDAVAATSRRISGEVALVVADRS-
SLPDSYGAFTCTAKIEWEDDGKVTSIAAPCDVSRLQCESRDYLFAWRFRTAAADA-
DASVGHSSEEISES

Fig. 6A

TGTCATTATGTTTAAAATATTGTGTTAGACTATTGTATAACCGTAACTTGTTATGTT-
GTTATGTCTATCGATGTTCTACACAATAGTGAAGATAAGTAATTCATGCATTATCCGA-
TATCCGACCATACAATATTCGTATCCGTATCCCACGTTTATCTGTATCTGTCTCGTTTCTAAC-
TATCTGTATCCGATCTTGAATACGATCGAAATATAATAGGGTAGGATATAGAATGATCTAC-
CATTCGTTCATATCCGTCCGATTTTTATCTCTATCCAAACCTCTATCGACAACTGCGAATAC-
GTTGTTGTGGTTGCAGAACACGGATGACTTTCTCGTCCGGCGATAACCAGTGAAAAC-
CAATGATTTTTCTCGTTATCGGTGTAGACCGAGATACGAAAACCGATCCGGTTTTTAGTG-
TATTTCGGTTTCAAAATTAGAAATATAAAAGTTAAATTTTGATCAACAAAACGGGTTTT-
GAAAAAAATCGAAACGAGAATGAAATCCCTGTTGCGGAACCATCGTC-
TACAAGTCGCCGGTGCCCATGAAGCATGAACGAACTGCAACAGGCAACAGCCAA-
GCAAGGCTCGCATTAACTGTAGCATGGCTCCCTCGCCAACAGCTGTAGGCTGTAGCG-
CAGCGCGCACAGGCGGCAGAAGCACCGGATCATGCTATTGCTAGCTCCAGCG-
CAGGCGTGTGGCCTCTGGCGTCGTCGCAGGCAGCCCTCGCGACGCGCGCCGAGTCCTCTGA-
GAAACCCCGCTCGGGCCAGCCGGCCGACCCCACTCGCCAGGACAGGGAGCGCGCGCGCGG-
CATGCGTCGACCACGCGCTGCCGCGCGCACCTGCGCCCGCCAATGGCAGCGCGGCCAC-
TCGTCGCGCGCCCTTCCTGTCCGGTCGCCACGGCGCGCAGCACATGCCGCGCATGCAG-
CAGAAAACGATTAAAGAGATCGCGCCAGTGGCGTCCAAAAGGCAGGCTAGACGCTA-
GAGCTAAGCTAGGCTACCAAGGCCCCGGCCCGGTTGGTCTCGTGCGGCTGGCTAC-
CAAGGCTAGCTAGGCCCGTGGTTGGGTTCCAGTCGGACATGGCGCTTGGGCTTTTGCGTT-
GCATGCATGCATGTCCCACGTGTGTTGGCTCGTGTACGAGGAGTGTGTAC-
GTATCCGGCCTTACGTGTCCCGTGTCCGTCAATGTGATACTACTAGCATAGTACTAGTAC-
CATGCATACACACAGCAGGTCGGCCGCCTGGATGGATCGATGATGATACTA-
CATCATCCTGTCATCCATCCAGGCGATCTAGAAGGGGCGTGGCTAGCTAGCAAACTGTGAC-
CGGTTTTTCTACGCCGATAATAATACTTTGTCATGGTACAGACGTACAG-
TACTGGTTATATATATCTGTAGATTTCAACTGAAAAGCTAGGATAGCTAGATTAATTCCTGA-
GAAACACAGATAAAATTCGAGCTTGGCTATAGATGACAAAACGGAAGACGCATGCATTGGAC-
GACGTATGCAATGCGAGCGCGTCTCGTGTCGTCCCGTCCAAGTCTGGCGATCTCACGCCAC-
GTGCTCAACAGCTCAAGGACTGTTCGTCACCAGCGTTAAATTCATTGAAGGGATGAC-
GCATTTCGGCATTTGTCATTGCTTCTTGTAGCTATATATATATCCAACAGATTTCTCTCAA-
GCTTTTGTATGCGTGAATGTAAAGTCTAGCTTATACGACAGCACGTGCAGATACATTAAC-
GTCATTAGGTGGAGAGCAAAGATCTGGTGGAAATTGTCGAAAACACAAGAGAGAGTGAAGTG-
CACACTTCTGGGTATAGGAGCTAAGGAGTGTATACGCCGCTGGTTGGTGGGCAATGCGCGCCG-
CAATATTGGCCAATGAAACCTAGCAACGCCCACTCGCCACGCCCCATGAATGGCCCCCGCAC-
GGCAGCGAGCCAGCCAGTGCCCGCGCGCGGCCCAGCCGGAGTCGGCGGAACGCGCCACGGGG-
GACGAGGCGCCCGAGGGCCGAGGCATGGCAAGCAAGCCGAAGCGGGCAAGCGACCCG-
CATGCAGCCCCTGCCCCTCGCCCTCGTCCCAGCCTCCCACTG-
GAATCCACCCAACCCGCCCTTCCTCTCCAAAGCACGCGCCCCGCGACTCGCCTCCGCCTAC-
GTGTCGGCAGCGTCCCCGCCGGTCGCCCACGTACCCCGCCCCGTTCTCCCAC-
GTGCCCCTCCCTCTGCGCGCGTCCGATTGGCTGACCCGCCCTTCT*TAA-*
*GCCGCGCCAGCCTCCTGTCCGGGCCCCAACGCCGTGCTCCGTCGTCGTCTCCGCCCCCAGAG-*
*TGATCGAGCCCACTGAC*

Fig. 6B

*CTGGCCCCCGAGCCTCAGCTCGTGAGTCCGGCACCGCGCCTCGCC*ATGGCCATGGTG-
CAGCCGGCGGACACGGCCGTCAAGGCCAACGA-
GATCCTGGCGCGGTTCCGGCCCATCGCGCCCAAGCCCACACTGGCAG-
CAGCCGCCGCCGCCGCCGCGGCGCCCGTGGCG-
CAGGCCGCGGCCGAGGGCGTCGTGGCCGCGAACCGCGTGCTGTGCCATCTGCAGAG-
CAGGCCGTGCCGCGCGCGCAAGCGCGGCCGCCCCAC-
CGTCGTGCCGGTGTCGCCCAAGTCGGGCGCGCAGCCGCCCGCGAAGCGGAGGAGAGCCTC-
TACGCCGTACCCGCCTCTCCGGTGCGCGGCGGCGACCACGGGGGCG-
CATGTGTCCGCGGTCGTCCCAGGCAGTGCGCGTCTCCCACCGGCGAGTGCGGGTGTCGAAGA-
CATCGCGAAGGCGGCGGCGGCGGCGGCGACAGAGGAGGGGAGGGACGTCCCCGTG-
GAGCGCGACCTGCTGCGGAAGCTGCTGGAGCCCAGGGTCATA-
TCGCCGCGGGCGGTGCGCCCGGTGTGGTCTGCCATCCACGTCGGGTGCATCCACCGCACCGAC-
GACGCGGCCTGCACCGACGCCGCCGTCTCGAAGACGGCGGTTCAGGTGGAGGCGGAGCTG-
GAGGTCGACGCGCTCCCGGCGGTGGTCTCCGACTCAGGCAACCGCGTCCGGCTCGTGAAC-
GACGCGTACAAGGAGATGGTGGGGCAGCCCGAGTGCCCGTGGCTCGACGCCGTGGCTGCCAC-
GTCGAGGAGGATCAGCGGGGAGGTGGCGCTGGTGGTAGCGGACCGGTCCTCTCTGCCG-
GACTCGTACGGGGCGTTCACATGCACGGCAAAGATCGAGTGGGAGGACGACGGGAAGGTCAC-
CTCCATCGCTGCACCCTGCGACGTCAGCCGGCTGCAGTGCGAGTCCAGGGATTAC-
CTCTTCGCCTGGAGGTTCCGCACCGCCGCCGCCGACGCCGACGCATCCGTT-
GGACACAGCTCCGAGGAGATTAGTGAGAGTTAGGGAAGCTTGAGCTGCATCCAATGAAAC-
CAAGTGCATAGACTAAGCCGCTAGCTGCATGTTAAAACTGAG-
CAGCTTCCTCTTTCGCGAAGTCCAATAGGATGTAGACCCAGTTCTGAAATCCTGAGTAAA-
TATAAGATGTTGACTGGAGAATGCAAAGGAAGTATAACCTGCCCTTTCAGGAAACTGAC-
CTACCCGACTCTCATTTCATAACTGCGTGGGTTGCCCATGAACACACGGACATGCAAGAG-
TGGTCGTGCGTAGCGACTGGCAGCTCATTTGTGAATGTGTGATAGGGCCAAAA-
GCAAGTAGGCGTCATCATTCAACTCAGAAATGGCATGATGTATCTTTTCAGATACCAGCCAA-
GAAAGCACACAAGGTTGCAAAAGCAATGTCATCCACGAATTAACGTTTT-
GGAAGTACAAGTACACCATTTTGTTTGATTGCACATCATGCTTATTACAAGTTTGATA-
GATGCATTCTCTAGTTCGTACTTTAACAATGGGCACGGTTGAAAGCAAAA-
TAAAATCGAGCCAGGAGGAAAACGACATCGTGCCAATGTCAG-
CATCACAGATGTCTCGAGCTCATGCTTGCTCCGCTTTTGGAGGGCCTCTCCACTT-
GAAGTTCTCAGCGTAGGCCTTAGGCTGCATGGTTGAAAAACAGTCCGGTTATCACACCCAA-
GCCGATGTATTTTCAGCAACACCGATTAGCAATCAGAAGGAAAAAATATTAATTCAAAC-
GCAAACACAACTATTCTATTAGCACAAAACATGGCAYGTTTGAGCCATATCTCACAT-
ATGACAGACACCAAATGATGCAATTGGCTGGACAGTAATGCAGGTTATCACCTTATAATGAA-
GCATAGCAATGGAAAGGTGAAACCATTCCTCCAGTTCATGATAGATACACTACTTT-
GAAATGTCCCAAAGCAAGCTTATTCCGGCAGCTGTATTGCTTTAAGCTAGCAATTGCTTC-
TATAATATTACGGTAAAGTACAGCTCGGTCCTGGCAGCCGTACCAAAAGCAAAAGTCCAG-
TCAAGCAAAGACTACTGGTAATGAGCCAGTTCCATCGCCTGATTGGACCTGTGCCCGGAC-
GGCCAGTACAAACCAATAACACGCACGTTGCATCAAATAATTGGATATCAGACTTGTACAG-
TGTCAGGCAAGTAAAGAAATAGCGCAGGAGAATGATTTTTGGCCTCACTGTTTTAGCTTTCAG-
GACATTCCACAAGCATGCAAATATTTAACTTCGATAACCATATCACCTGTATGCCCG

Fig. 6C

TATCTGTTCCTTACTGCTTATCAAATAATTGTGTTTTGATGTAGTAATGCATTTTCTGCTT-
GTAATTCTACATGCTGGCATAACATAGTGAACGACACAT
ACCTCAAATGCTAAAGCAAAGTCGCTGGTCTATGGGATAACAAGTCTGATTCTTAG-
CAGGTAGGGGGAGTATATGTCTTACGTGTAAGAATGCATGCACCGCGA-
GAAAACTGCCAAAACAGCAGTCACATTGCATCAACACACATGGTTTCAACCTACTGAG-
TACATGGCAGCTAGCCCTAGCAGCTTGTCCTTATCCACATCCTGCTAACGAAAGA-
TAGGGTTCAAGGGTCAACCAGGATGGTAAAACTTCGCCAACTGTTCCTAG-
TCCACACATTCATATTCATCGTATCTACAACATTAATGCCGATTTT-
GGCTTTCTCTTTCCAACCTCTGACGTATCAGATTCTCAGTTACAAAAAAAAA

Fig. 7

TCCCGTGTCCGTCAATGTGATACTACTAGCATAGTACTAGTACCATGCATACACACAG-
CAGGTCGGCCGCCTGGATGGATCGATGATGATACTA-
CATCATCCTGTCATCCATCCAGGCGATCTAGAAGGGGCGTGGCTAGCTAGCAAACTGTGAC-
CGGTTTTTCTACGCCGATAATAATACTTTGTCATGGTACAGACGTACAG-
TACTGGTTATATATATCTGTAGATTTCAACTGAAAAGCTAGGATAGCTAGATTAATTCCTGA-
GAAACACAGATAAAATTCGAGCTTGGCTATAGATGACAAAACGGAAGACGCATGCATTGGAC-
GACGTATGCAATGCGAGCGCGTCTCGTGTCGTCCCGTCCAAGTCTGGCGATCTCACGCCAC-
GTGCTCAACAGCTCAAGGACTGTTCGTCACCAGCGTTAAATTCATTGAAGGGATGAC-
GCATTTCGGCATTTGTCATTGCTTGTAGCTATATATATATATCCAACAGATTTCTCTCAA-
GCTTTTGTATGCGTGAATGTAAAGTCTAGCTTATACGACAGCACGTGCAGATATATTAAC-
GTCATTATTAGGTGGAGAGCAAGATGCATGATCTGGTAGAAATTGTCGAAAACACAAGAGA-
GAGTGAAGTGCACACTTCTGGTATAGGAGTGTATACGCCGCTGGTTGGTGGG-
CAATGCGCGCCGCAATATTGGCCAATGAAACCTAGCAACGCCCACTCGCCAC-
GCCCCATGAATGGCCCCCGCACGGCAGCGAGCCAGCCAGTGCCCGCGCGCGGCCCAGCCG-
GAGTCGGCGGAACGCGCCACGGGGGACGAGGCGCCCGAGGGCCGAGGCAGCGCGGCATGG-
CAAGCAAGCCGAAGCGGGCAAGCGACCTGCATGCAGCCCCTGCCCCTCGCCCTCGTCAG-
TCGTCCCAGCCTCCCACTGGAATCCACCCAACCCGCCCTTCCTCTCCAAAGCAC-
GCGCCCCGCGACTCGCCTCCGCCTACGTGTCGGCAGCGTCCCCGCCGGTCGCCCAC-
GTACCCCGCCCCGTTCTCCCAC-
GTGCCCCTCCCTCTGCGCGCGTCCGATTGGCTGACCCGCCCTTCTTAA-
GCCGCGCCAGCCTCCTGTCCGGGCCCCAACGCCGTGCTCCGTCGTCGTCTCCGCCCCCAGAG-
TGATCGAGCCCACTGACCTGGCCCCCGAGCCTCAGCTCGTGAGTCC

Fig. 9A

GTGATTTTGTGCCGAGCTGCCGGTCGGGGAGCTGTTGGCTGGCTGGTGGCAGGATA-
TATTGTGGTGTAAACAAATTGACGCTTAGACAACTTAATAACACATTGCGGAC-
GTCTTTAATGTACTGAATTAGTACTCTAGTTTACAGCACTCGTCTCCGTCTTGG-
TAGGTTCTTTGAGCTTAAGAAGGTTGACGTTGTGGTGATAGGTCTAAGGCG-
GAGGCTAGGCTAGTTGATATCGGTACCAAGCTTCCGCGGCTGCAGTG-
CAGCGTGACCCGGTCGTGCCCCTCTCTAGAGATAATGAGCATT-
GCATGTCTAAGTTATAAAAAATTACCACATATTTTTTTTGTCACACTTGTTTGAAGTGCAGTT-
TATCTATCTTTATACATATATTTAAACTTTACTCTACGAATAATATAATCTATAGTACTACAA-
TAATATCAGTGTTTTAGAGAATCATATAAATGAACAGTTAGACATGGTCTAAAGGACAATT-
GAGTATTTTGACAACAGGACTCTACAGTTTTATCTTTTTAGTGTG-
CATGTGTTCTCCTTTTTTTTTGCAAATAGCTTCACCTATATAATACTTCATCCATTTTATTAG-
TACATCCATTTAGGGTTTAGGGTTAATGGTTTTTATAGACTAATTTTTTTAGTACATCTATTT-
TATTCTATTTTAGCCTCTAAATTAAGAAAACTAAAACTCTATTTTAGTTTTTTTATTTAA-
TAGTTTAGATATAAAATAGAATAAAATAAAGTGACTAAAAATTAAACAAATACCCTTTAA-
GAAATTAAAAAAACTAAGGAAACATTTTTCTTGTTTCGAGTAGA-
TAATGCCAGCCTGTTAAACGCCGTCGACGAGTCTAACGGACACCAACCAGCGAACCAG-
CAGCGTCGCGTCGGGCCAAGCGAAGCAGACGGCACGGCATCTCTGTCGCTGCCTCTG-
GACCCCTCTCGAGAGTTCCGCTCCACCGTTGGACTTGCTCCGCTGTCGGCATCCAGAAATT-
GCGTGGCGGAGCGGCAGACGTGAGCCGGCACGGCAGGCGGCCTCCTCCTCCTCTCACGGCAC-
CGGCAGCTACGGGGGATTCCTTTCCCACCGCTCCTTCGCTTTCCCTTCCTCGCCCGCCGTAA-
TAAATAGACACCCCCTCCACACCCTCTTTCCCCAACCTCGTGTTGTTCGGAGCG-
CACACACACACAACCAGATCTCCCCCAAATCCACCCGTCGGCACCTCCGCTTCAAGGTAC-
GCCGCTCGTCCTCCCCCCCCCCCCCCTCTCTACCTTCTCTA-
GATCGGCGTTCCGGTCCATGGTTAGGGCCCGGTAGTTCTACTTCTGTTCATGTTTGTGTTA-
GATCCGTGTTTGTGTTAGATCCGTGCTGCTAGCGTTCGTACACGGATGCGACCTGTAC-
GTCAGACACGTTCTGATTGCTAACTTGCCAGTGTTTCTCTTTGGGGAATCCTGG-
GATGGCTCTAGCCGTTCCGCAGACGGGATCGATTTCATGATTTTTTTTGTTTCGTT-
GCATAGGGTTTGGTTTGCCCTTTTCCTTTATTTCAATATATGCCGTGCACTTGTTT-
GTCGGGTCATCTTTTCATGCTTTTTTTTGTCTTGGTTGTGATGATGTGGTCTGGTT-
GGGCGGTCGTTCTAGATCGGAGTAGAATTCTGTTTCAAACTACCTGGTGGAT-
TTATTAATTTTGGATCTGTATGTGTGTGCCATACATATTCATAGTTACGAATTGAA-
GATGATGGATGGAAATATCGATCTAGGATAGGTATACATGTT-
GATGCGGGTTTTACTGATGCATATACAGAGATGCTTTTTGTTCGCTTGGTT-
GTGATGATGTGGTGTGGTTGGGCGGTCGTTCATTCGTTCTAGATCGGAGTAGAA-
TACTGTTTCAAACTACCTGGTGTATTTATTAATTTTGGAACTGTATGTGTGTGTCATA-
CATCTTCATAGTTACGAGTTTAAGATGGATGGAAATATCGATCTAGGATAGGTATACATGTT-
GATGTGGGTTTTACTGATGCATATACATGATGGCATATGCAGCATCTATTCAT-
ATGCTCTAACCTTGAGTACCTATCTATTATAA-
TAAACAAGTATGTTTTATAATTATTTCGATCTTGATATACTTGGATGATGGCATATGCAG-
CAGCTATATGTGGATTTTTTTAGCCCTGCCTTCATACGCTATTTATTTGCTTGG

Fig. 9B

TACTGTTTCTTTTGTCGATGCTCACCCTGTTGTTTGGTGTTACTTCTGCAGGGTAC-
GGATCCTCATCTAAGCGCAAAGAGACGTACTATGGAAAAC-
GCTAAAATGAACTCGCTCATCGCCCAGTATCCGTTGGTAAAGGATCTGGTTGCTCTTAAA
GAAACCACCTGGTTTAATCCTGGCACGACCTCATTGGCTGAAGGTTTACCTTATGTT-
GGCCTGACCGAACAGGATGTTCAGGACGCCCATGCGCGCTTATCCCGTTTT-
GCACCCTATCTGGCAAAAGCATTTCCTGAAACTGCTGCCACTGGGGGGAT-
TATTGAATCAGAACTGGTTGCCATTCCAGCTATGCAAAAACGGCTGGAAAAAGAATATCAG-
CAACCGATCAGCGGGCAACTGTTACTGAAAAAAGATAGCCATTTGCCCATTTCCGGCTCCA-
TAAAAGCACGCGGCGGGATTTATGAAGTCCTGGCACACGCAGAAAAACTGGCTCTGGAA-
GCGGGGTTGCTGACGCTTGATGATGACTACAGCAAACTGCTTTCTCCGGAGTTTAAACAG-
TTCTTTAGCCAATACAGCATTGCTGTGGGCTCAACCGGAAATCTGGGGTTATCAATCGG-
CATTATGAGCGCCCGCATTGGCTTTAAGGTGACAGTTCATATGTCTGCTGATGCCCGGG-
CATGGAAAAAAGCGAAACTGCGCAGCCATGGCGTTACGGTCGTGGAATATGAGCAAGAT-
TATGGTGTTGCCGTCGAGGAAGGACGTAAAGCAGCGCAG-
TCTGACCCGAACTGTTTCTTTATTGATGACGAAAATTCCCGCACGTTGTTCCTTGGG-
TATTCCGTCGCTGGCCAGCGTCTTAAAGCGCAATTTGCCCAGCAAGGCCG-
TATCGTCGATGCTGATAACCCTCTGTTTGTCTATCTGCCGTGTGGTGTT-
GGCGGTGGTCCTGGTGGCGTCGCATTCGGGCTTAAACTGGCGTTTGGCGATCATGTTCAC-
TGCTTTTTTGCCGAACCAACGCACTCCCCTTGTATGTTGTTAGGCGTCCATACAGGATTACAC-
GATCAGATTTCTGTTCAGGATATTGGTATCGACAACCTTACCGCAGCGGATGGCCTTGCAG-
TTGGTCGCGCATCAGGCTTTGTCGGGCGGGCAATGGAGCGTCTGCTGGATGGCTTC-
TATACCCTTAGCGATCAAACCATGTATGACATGCTTGGCTGGCTGGCGCAGGAA-
GAAGGTATTCGTCTTGAACCTTCGGCACTGGCGGGTATGGCCGGACCTCAGCGCGTGTGTG-
CATCAGTAAGTTACCAACAGATGCACGGTTTCAGCGCAGAACAACTGCGTAATACCAC-
TCATCTGGTGTGGGCGACGGGAGGTGGAATGGTGCCGGAAGAAGAGATGAATCAATATCTGG-
CAAAAGGCCGTTAATAACGTTTCAACGCAGCATGGATCGTACCGAGCTCAATCGATCCTGCTT-
TAATGAGATATGCGAGACGCCTATGATCGCATGATATTTGCTTTCAATTCTGTTGTGCAC-
GTTGTAAAAAACCTGAGCATGTGTAGCTCAGATCCTTAC-
CGCCGGTTTCGGTTCATTCTAATGAATATATCACCCGTTACTATCGTATTTTTATGAATAA-
TATTCTCCGTTCAATTTACTGATTGTACCCTACTACTTATATGTACAA-
TATTAAAATGAAAACAATATATTGTGCTGAATAGGTTTATAGCGACATCTATGATA-
GAGCGCCACAATAACAAACAATTGCGTTTTATTATTACAAATCCAATTTTAAAAAAAGCGG-
CAGAACCGGTCAAACCTAAAAGACTGAT-
TACATAAATCTTATTCAAATTTCAAAAGTGCCCCAGGGGCTAGTATCTACGACACAC-
CGAGCGGCGAACTAATAACGCTCACTGAAGGGAACTCCGGTTCCCCGCCGGCGCG-
CATGGGTGAGATTCCTTGAAGTTGAGTATTGGCCGTCCGCTCTACCGAAAGTTACGGGCAC-
CATTCAACCCGGTCCAGCACGGCGGCCGGGTAACCGACTTGCTGCCCCGAGAATTATGCAG-
CATTTTTTTGGTGTATGTGGGCCCCAAATGAAGTGCAGGTCAAACCTTGACAGTGAC-
GACAAATCGTTGGGCGGGTCCAGGGCGAATTTTGCGACAACATGTCGAGGCTCAGCAG-
GATGGGCCCAGGTACAGAATTCGCGGCCGTACAACGCGTAC-
CGGTTAATTAATCCCGTGTCCGTCAATGTGATACTACTAGCATAGTACTAGTACCATGCATA

Fig. 9C

CACACAGCAGGTCGGCCGCCTGGATGGATCGATGATGATACTA-
CATCATCCTGTCATCCATCCAGGCGATCTAGAAGGGGCGTGGCTAGCTAGCAAACTGTGAC
CGGTTTTTCTACGCCGATAATAATACTTTGTCATGGTACAGACGTACAG-
TACTGGTTATATATATCTGTAGATTTCAACTGAAAAGCTAGGATAGCTAGATTAATTCCTGA-
GAAACACAGATAAAATTCGAGCTTGGCTATAGATGACAAAACGGAAGAC
GCATGCATTGGACGAC-
GTATGCAATGCGAGCGCGTCTCGTGTCGTCCCGTCCAAGTCTGGCGATCTCACGCCAC-
GTGCTCAACAGCTCAAGGACTGTTCGTCACCAGCGTTAAATTCATTGAAGGGATGAC-
GCATTTCGGCATTTGTCATTGCTTGTAGCTATATATATATATCCAACAGATTTCTCTCAA-
GCTTTTGTATGCGTGAATGTAAAGTCTAGCTTATACGACAGCACGTGCAGATATATTAAC-
GTCATTATTAGGTGGAGAGCAAGATGCATGATCTGGTAGAAATTGTCGAAAACACAAGAGA-
GAGTGAAGTGCACACTTCTGGTATAGGAGTGTATACGCCGCTGGTTGGTGGG-
CAATGCGCGCCGCAATATTGGCCAATGAAACCTAGCAACGCCCACTCGCCAC-
GCCCCATGAATGGCCCCCGCACGGCAGCGAGCCAGCCAGTGCCCGCGCGCGGCCCAGCCG-
GAGTCGGCGGAACGCGCCACGGGGGACGAGGCGCCCGAGGGCCGAGGCAGCGCGGCATGG-
CAAGCAAGCCGAAGCGGGCAAGCGACCTGCATGCAGCCCCTGCCCCTCGCCCTCGTCAG-
TCGTCCCAGCCTCCCACTGGAATCCACCCAACCCGCCCTTCCTCTCCAAAGCAC-
GCGCCCCGCGACTCGCCTCCGCCTACGTGTCGGCAGCGTCCCCGCCGGTCGCCCAC-
GTACCCCGCCCCGTTCTCCCAC-
GTGCCCCTCCCTCTGCGCGCGTCCGATTGGCTGACCCGCCCTTCTTAA-
GCCGCGCCAGCCTCCTGTCCGGGCCCCAACGCCGTGCTCCGTCGTCGTCTCCGCCCCCAGAG-
TGATCGAGCCCACTGACCTGGCCCCCGAGCCTCAGCTCGTGAGTCCCGTAC-
GGCCTAGGCCTTCACCTGCGGAGGGTAAGATCCGATCACCATCTTCTGAATTTCTGTTCTT-
GATCTGTCATGTATAATAACTGTCTAGTCTTGGTGTTGGTGAGATGGAAATTCGGTG-
GATCTCGGAAGGGATATTGTTCGTTTGCTGGGGTTTTTTTGTGTGTTGTGATCCGTAGA-
GAATTTGTGTTTATCCATGTTGTTGATCTTGG-
TATGTATTCATGACATATTGACATGCATGTGTTGTATGTGTCATATGTGTGCCTCTCCTTGG-
GATTTGTTTTGGATAATAGAACATGTTATGGACTCAATAGTCTGTGAACAAATCTTTTTTTA-
GATGGTGGCCAAATCTGATGATGATCTTTCTTGAGAGGAAAAAGTTCATGATA-
GAAAAATCTTTTTTGAGATGGTGGCTTAATGTGATGATGATCTTTCTTGAGAGGAAAAAAAA-
GATTCATTATAGGAGATTTTGATTTAGCTCCTTTCCACCGATATTAAATGAGGAG-
CATGCATGCTGATTGCTGATAAGGATCTGATTTTTTTATCCCCTCTTCTTTGAACAGACAA-
GAAATAGGCTCTGAATTTCTGATTGATTATTTGTACATGCAGAAGGGCGAATTCGAC-
CTAGGCCAAGTTTGTACAAAAAAGCAGGCTTGATAACCAACCATGGTCCGTCCTG-
TAGAAACCCCAACCCGTGAAATCAAAAAACTCGACGGCCTGTGGGCATTCAGTCTG-
GATCGCGAAAACTGTGGAATTGATCAGCGTTGGTGGGAAAGCGCGTTACAAGAAAGCCGGG-
CAATTGCTGTGCCAGGCAGTTTTAACGATCAGTTCGCCGATGCAGATATTCG-
TAATTATGCGGGCAACGTCTGGTATCAGCGCGAAGTCTTTATACCGAAAGGTTGGG-
CAGGCCAGCGTATCGTGCTGCGTTTCGATGCGGTCACTCATTACGGCAAAGTGTGGGTCAA-
TAATCAGGAAGTGATGGAGCATCAGGGCGGCTATACGCCATTTGAAGCCGATGTCACGCCG-
TATGTTATTGCCGGGAAAAGTGTACGTAAGTTTCTGCTTCTACCTTTGATATATATATAA

Fig. 9D

TAATTATCATTAATTAGTAGTAATATAATATTTCAAATATTTTTTTCAAAATAAAA-
GAATGTAGTATATAGCAATTGCTTTTCTGTAGTTTATAAGTGTG
TATATTTTAATTTATAACTTTTCTAATATATGACCAAAATTTGTTGATGTGCAGGTATCAC-
CGTTTGTGTGAACAACGAACTGAACTGGCAGACTATCCCGCCGGGAATGGTGATTACCGAC
GAAAACGGCAAGAAAAAGCAGTCTTACTTCCATGATTTCTTTAACTATGCCGGAATCCATCG-
CAGCGTAATGCTCTACACCACGCCGAACACCTGGGTGGACGATATCACCGTGGTGAC-
GCATGTCGCGCAAGACTGTAACCAC
GCGTCTGTTGACTGGCAGGTGGTGGCCAATGGTGATGTCAGCGTTGAACTGCGTGATGCG-
GATCAACAGGTGGTTGCAACTGGACAAGGCACTAGCGGGACTTTGCAAGTGGTGAATCCG-
CACCTCTGGCAACCGGGTGAAGGTTATCTCTATGAACTGTGCGTCACAGCCAAAAGCCAGA-
CAGAGTGTGATATCTACCCGCTTCGCGTCGGCATCCGGTCAGTGGCAGTGAAGGGCGAACAG-
TTCCTGATTAACCACAAACCGTTCTACTTTACTGGCTTTGGTCGTCATGAAGATGCGGACTT-
GCGTGGCAAAGGATTCGATAACGTGCTGATGGTGCACGACCACGCATTAATGGACTG-
GATTGGGGCCAACTCCTACCGTACCTCGCATTACCCTTACGCTGAAGAGATGCTCGACTGGG-
CAGATGAACATGGCATCGTGGTGATTGATGAAACTGCTGCTGTCGGCTTTAAC-
CTCTCTTTAGGCATTGGTTTCGAAGCGGGCAACAAGCCGAAAGAACTGTACAGCGAA-
GAGGCAGTCAACGGGGAAACTCAGCAAGCGCACTTACAGGCGATTAAAGAGCTGA-
TAGCGCGTGACAAAAACCACCCAAGCGTGGTGATGTGGAGTATTGCCAACGAACCGGA-
TACCCGTCCGCAAGGTGCACGGGAATATTTCGCGCCACTGGCGGAAGCAACGCG-
TAAACTCGACCCGACGCGTCCGATCACCTGCGTCAATGTAATGTTCTGCGACGCTCACACCGA-
TACCATCAGCGATCTCTTTGATGTGCTGTGCCTGAACCGTTATTACGGATGGTATGTCCAAA-
GCGGCGATTTGGAAACGGCAGAGAAGGTACTGGAAAAAGAACTTCTGGCCTGGCAGGA-
GAAACTGCATCAGCCGATTATCATCACCGAATACGGCGTGGATACGTTAGCCGGGCTGCAC-
TCAATGTACACCGACATGTGGAGTGAAGAGTATCAGTGTGCATGGCTGGATATGTATCAC-
CGCGTCTTTGATCGCGTCAGCGCCGTCGTCGGTGAACAGGTATGGAATTTCGCCGATTTT-
GCGACCTCGCAAGGCATATTGCGCGTTGGCGGTAACAAGAAAGGGATCTTCACTCGCGACCG-
CAAACCGAAGTCGGCGGCTTTTCTGCTGCAAAAACGCTGGACTGG-
CATGAACTTCGGTGAAAAACCGCAGCAGGGAGGCAAACAATGAATCAACCCAGCTTTCTT-
GTACAAAGTGGGAGCTCGATCGTTCAAACATTTGGCAATAAAGTTTCTTAA-
GATTGAATCCTGTTGCCGGTCTTGCGATGATTATCATATAATTTCTGTTGAATTACGTTAA-
GCATGTAATAATTAACATGTAATGCATGACGTTATTTATGAGATGGGTTTTTATGATTAGAG-
TCCCGCAATTATACATTTAATACGCGATAGAAAACAAAATATAGCGCGCAAACTAGGATAAAT-
TATCGCGCGCGGTGTCATCTATGTTACTAGATCGAATTCAACTTTATTATACATAGTTGA-
TAATTCACTGGGCCGGCCCTGTCTATCTTGTTGGGAAAAGCCGACCTACCCGGACGCGAT-
TACTTAAGCAAAAGATACTATCGAACGAAGAAAGCTAGTAGGTAGACTA-
TATCAGGCCTGATTGTCGTTTCCCGCCTTCAGTTTAAACTATCAGTGTTTGACAGGATA-
TATTGGCGGGTAAACCTAAGAGAAAAGAGCGTTTATTAGAATAATCGGA-
TATTTAAAAGGGCGTGAAAAGGTTTATCCGTTCGTCCATTTGTATGTCAA-
TATTGGGGGGGGGGGAAAGCCACGTTGTGTCTCAAAATCTCTGATGTTACATTGCACAAGA-
TAAAAATATATCATCATGAACAATAAAACTGTCTGCTTACATAAACAG-
TAATACAAGGGGTGTTCGCCACCATGAGCCATATCCAGCGTGAAAC

Fig. 9E

CTCGTGCTCCCGCCCGCGCCTCAATTCCAATATGGATGCCGACCTTTATGGC-
TACAAGTGGGCGCGCGACAACGTCGGCCAGTCGGGCGCGACCATTTATCGGCTTTATGG
CAAACCCGATGCCCCGGAACTGTTCCTGAAGCACGGCAAAGGCAGCGTCGCAAAC-
GATGTCACCGATGAGATGGTCCGCCTGAACTGGCTTACCGAGTTCATGCCGCTGCCGACGAT-
TAAGCATTTCATCCGTACCCCGGACGATGCCTGGCTCTTGACCACGGCCATTCCGGG
CAAAACGGCCTTTCAGGTCCTTGAAGAGTACCCGGACTCCGGTGAGAATATCGTGGAC-
GCCCTCGCGGTCTTCCTCCGCCGTTTGCATAGCATCCCCGTGTGCAACTGCCCCTTCAACTCG-
GACCGGGTTTTCCGCCTGGCACAGGCCCAGTCGCGCATGAATAACGGCCTCGTTGAC-
GCGAGCGATTTCGACGATGAACGGAATGGCTGGCCGGTG
GAACAGGTTTGGAAGGAAATGCACAAACTGCTTCCGTTCTCGCCGGATTCGGTGGTCAC-
GCATGGTGATTTTTCCCTGGATAATCTGATCTTTGACGAGGGCAAGCTGATCGGCTG-
CATCGACGTGGGTCGCGTCGGTATCGCCGACCGCTATCAGGACCTGGCGATCTTGTGGAATT-
GCCTCGGCGAGTTCTCGCCCTCGCTCCAGAAGCGCCTGTTCCAGAAGTACGG-
CATCGACAACCCGGATATGAACAAGCTCCAGTTCCACCTCATGCTGGACGAATTTTTTT-
GAACAGAATTGGTTAATTGGTTGTAACACTGGCAGAGCATTACGCTGACTTGACGGGAC-
GGCGGCTTTGTTGAATAAATCGAACTTTTGCTGAGTTGAAGGATCGATGAGTT-
GAAGGACCCCGTAGAAAAGATCAAAGGATCTTCTTGAGATCCTTTTTTTCTGCGCG-
TAATCTGCTGCTTGCAAACAAAAAAACCACCGCTACCAGCGGTGGTTTGTTTGCCGGATCAA-
GAGCTACCAACTCTTTTTCCGAAGGTAACTGGCTTCAGCAGAGCGCAGATACCAAA-
TACTGTCCTTCTAGTGTAGCCGTAGTTAGGCCACCACTTCAAGAACTCTGTAGCACCGCC-
TACATACCTCGCTCTGCTAATCCTGTTACCAGTGGCTGCTGCCAGTGGCGATAAGTCGTGTCT-
TACCGGGTTGGACTCAAGACGATAGTTACCGGATAAGGCGCAGCGGTCGGGCTGAAC-
GGGGGGTTCGTGCACACAGCCCAGCTTGGAGCGAACGACCTACACCGAACTGAGATAC-
CTACAGCGTGAGCTATGAGAAAGCGCCACGCTTCCCGAAGGGAGAAAGGCG-
GACAGGTATCCGGTAAGCGGCAGGGTCGGAACAGGAGAGCGCACGAGGGAGCTTCCAGGGG-
GAAACGCCTGGTATCTTTATAGTCCTGTCGGGTTTCGCCACCTCTGACTTGAGCGTCGAT-
TTTTGTGATGCTCGTCAGGGGGGCGGAGCCTATGGAAAAACGCCAGCAAC-
GCGGCCTTTTTACGGTTCCTGGCCTTTTGCTGGCCTTTT-
GCTCACATGTTCTTTCCTGCGTTATCCCCTGATTCTGTGGATAACCGTATTACCGCCTTT-
GAGTGAGCTGATACCGCTCGCCGCAGCCGAACGACCGAGCGCAGCGAGTCAGTGAGCGAG-
GAAGCGGAAGAGCGCCTGATGCGGTATTTTCTCCTTACGCATCTGTGCGGTATTTCACACCG-
CATAGGCCGCGATAGGCCGACGCGAAGCGGCGGGGCGTAGGGAGCGCAGCGACCGAAGGG-
TAGGCGCTTTTTGCAGCTCTTCGGCTGTGCGCTGGCCAGACAG-
TTATGCACAGGCCAGGCGGGTTTTAAGAGTTTTAATAAGTTTTAAAGAGTTTTAGGCG-
GAAAAATCGCCTTTTTTCTCTTTTATATCAGTCACTTACATGTGTGAC-
CGGTTCCCAATGTACGGCTTTGGGTTCCCAATGTACGGGTTCCGGTTCCCAATGTAC-
GGCTTTGGGTTCCCAATGTACGTGCTATCCACAGGAAAGAGACCTTTTCGAC-
CTTTTTCCCCTGCTAGGGCAATTTGCCCTAGCATCTGCTCCGTACATTAGGAACCGGCG-
GATGCTTCGCCCTCGATCAGGTTGCGGTAGCGCATGACTAG-
GATCGGGCCAGCCTGCCCCGCCTCCTCCTTCAAATCGTACTCCGGCAGGTCATTT-
GACCCGATCAGCTTGCGCACGGTGAAACAGAACTTCTTGAACTCTCCGGCGCTGCCAC-
TGCGTTCGTAGATCGTCTTGAACAACCATCTGGCTTCTGCCTT

Fig. 9F

GCCTGCGGCGCGGCGTGCCAGGCGGTAGAGAAAAC-
GGCCGATGCCGGGGTCGATCAAAAAGTAATCGGGGTGAACCGTCAGCACGTCCGGGTTCTT
GCCTTCTGTGATCTCGCGGTACATCCAATCAGCAA-
GCTCGATCTCGATGTACTCCGGCCGCCCGGTTTCGCTCTTTACGATCTT-
GTAGCGGCTAATCAAGGCTTCACCCTCGGATACCGTCACCAGGCGGCCGTTCTT-
GGCCTTCTTGGTACGCTGCATGGCAACGTGCGTGGTGTTTAACCGAATGCAGGTTTCTAC
CAGGTCGTCTTTCTGCTTTCCGCCATCGGCTCGCCGGCAGAACTTGAGTACGTCCGCAAC-
GTGTGGACGGAACACGCGGCCGGGCTTGTCTCCCTTCCCTTCCCGGTATCGGTTCATGGAT-
TCGGTTAGATGGGAAACCGCCATCAGTACCAGGTCGTAATCCCACACAC-
TGGCCATGCCGGCGGGGCCTGCGGAAACCTCTACGTGCCCGTCTGGAAGCTCGTAGCG-
GATCACCTCGCCAGCTCGTCGGTCACGCTTCGACAGACGGAAAACGGCCAC-
GTCCATGATGCTGCGACTATCGCGGGTGCCCACGTCATAGAGCATCGGAAC
GAAAAAATCTGGTTGCTCGTCGCCCTTGGGCGGCTTCCTAATCGACGGCGCAC-
CGGCTGCCGGCGGTTGCCGGGATTCTTTGCGGATTCGATCAGCGGCCCCTTGCCACGAT-
TCACCGGGGCGTGCTTCTGCCTCGATGCGTT-
GCCGCTGGGCGGCCTGCGCGGCCTTCAACTTCTCCAC-
CAGGTCATCACCCAGCGCCGCGCCGATTTGTACCGGGCCGGATGGTTTGCGACCGCTCAC-
GCCGATTCCTCGGGCTTGGGGGTTCCAGTGCCATTGCAGGGCCGGCAGA-
CAACCCAGCCGCTTACGCCTGGCCAACCGCCCGTTCCTCCACACATGGGGCATTCCAC-
GGCGTCGGTGCCTGGTTGTTCTTGAT-
TTTCCATGCCGCCTCCTTTAGCCGCTAAAATTCATCTACTCATTTATTCATTT-
GCTCATTTACTCTGGTAGCTGCGCGATGTATTCAGATAGCAGCTCGGTAATGGTCTTGCCTT-
GGCGTACCGCGTACATCTTCAGCTTGGTGTGATCCTCCGCCGGCAACTGAAAGTT-
GACCCGCTTCATGGCTGGCGTGTCTGCCAGGCTGGCCAACGTTGCAGCCTT-
GCTGCTGCGTGCGCTCGGACGGCCGGCACTTAGCGTGTTTGTGCTTTT-
GCTCATTTTCTCTTTACCTCATTAACTCAAATGAGTTTTGAT-
TTAATTTCAGCGGCCAGCGCCTGGACCTCGCGGGCAGCGTCGCCCTCGGGTTCTGATTCAA-
GAACGGTTGTGCCGGCGGCGGCAGTGCCTGGGTAGCTCACGCGCTGCGTGATACGGGACTCAA-
GAATGGGCAGCTCGTACCCGGCCAGCGCCTCGGCAACCTCACCGCCGATGCGCGTGCCTTT-
GATCGCCCGCGACACGACAAAGGCCGCTTGTAGCCTTCCATCCGTGAC-
CTCAATGCGCTGCTTAACCAGCTCCACCAGGTCGGCGGTGGCCCAAATGTCGTAAGGGCTT-
GGCTGCACCGGAATCAGCACGAAGTCGGCTGCCTTGATCGCG-
GACACAGCCAAGTCCGCCGCCTGGGGCGCTCCGTCGATCACTAC-
GAAGTCGCGCCGGCCGATGGCCTTCAC-
GTCGCGGTCAATCGTCGGGCGGTCGATGCCGACAACGGTTAGCGGTTGATCTTCCCGCAC-
GGCCGCCCAATCGCGGGCACTGCCCTGGGGATCG-
GAATCGACTAACAGAACATCGGCCCCGGCGAGTTGCAGGGCGCGGGCTAGATGGGTT-
GCGATGGTCGTCTTGCCTGACCCGCCTTTCTGGTTAAGTACAGCGATAAC-
CTTCATGCGTTCCCCTTGCGTATTTGTTTATTTACTCATCGCATCATATACGCAGCGACCG-
CATGACGCAAGCTGTTTTACTCAAATACACATCACCTTTTTAGATGATCA

Fig. 11A

GGGTTCGCGCTCGCGTCCGGGGTCGGGGACTGGCACGCCGTGCTGCTGGAGGCCGTCATGAC-
GTTCGGCCTCATGTACGCCTACTACGCCACGGTGATCGACCCGAAGCGGGGGCACGTGGGCAC-
CATCGCGCCGCTGGCCGTGGGCTTCCTGCTCGGCGCCAACGTGCTGGCGG-
GAGGGCCCTTTCGACGGCG-
CAGGGATGAACCCGGCGCGGGTCTTCGGCCCGGCGCTCGTCGGGTGGCGGTGGAGGCACCAC-
TGGGTGTACTGGCTGGGCCCTTTCCTCGGCGCCGGGCTTGCAGGGCTGGTGTACGAGTAC-
CTGGTTATCCCGTCCGCCGACGCCGCCGTGCCCCACGCGCACCAGCCGCTCGCGCCAGAGGAC-
TACTAGCTTGAAAATTGTATTGTGGGGTCGTGTAAGTGGTTAATAAGGGGGGCATAGGTAC-
GTACTTGTCTGTCGCCCCAGCGTGTGTTGGAGACGGTGAATCAGGTGATGTG-
TACATGCTGCTTCACTGTAGTGTATGTGTATGTGTATGTAGTAAATAATTCCAAGTATA-
TAAGGCACGACTTGTGTAGTATCATATCTGGTTCTGACTTCTGATTATCTAAAGGGAAGGAT-
TCGAATGTCTAGAAAAAAAAAAAAAAAAA

Fig. 11B

CTCAACTTCGTGCCGCTAAGATTATNCGGGGCAATATGTAATGGCTATGAGCCGGTAC-
CATCCTCTGGTAAAACAA-
GCCAACTCTTCCATTTCGCCAAGGAAAAAATGGCGGCTCGCTGGGCTAGACTTCGTG-
CAGCTGTGGCAGCCTCAGACATCTTTACTCTCCCTTATGAGCTATCTGGC-
TATTGTAGCTTTTCCAATGAGACTGTCACCGCCAATCCTCCATTTGCATGGCTTCGC-
TACAACAAGGATGATATTGAAGATCTGGAGGCCTTCCTACTCGAGAAAAAGATTATCAC-
TCGAGGTGGCACAAGGTTTGGAGTGGATGCAAGGGCTGTCAGAGTTAGTATGGTT-
GACACAGACCAAGCCTTCAATGTGTTCATCAATCGTCTGGCCACAATGAAGTGAAATTTCAG-
TGCAAATTAATAAAGCACTTTGTGGCTACTACAAGGATGACCGCGTTCTA-
GATGGAACAATCGATGCTTTGGAAAGCTTAATAATGTTTTATGTTGTTGAA-
TAATTCCGTGTGTTTTCGGGTATGTTGTGTAATACTCAATGTCAAATCC-
TATGCTTAATCGATGTTGTGGTCCATCCTGTTATCAG-
CATGGCCAATTATNAAAAAAAAAAAAAAAAA

Fig. 11C

GGGGGGGGTTTTCCCCCCGGTTGGGGGGGAAGCCCTTTGAAGGGGGAACCCAGGGTTTT-
GGGGGGCCCGGCTCCTCTTCATCTTTTCCGGGCCGGGTT-
GTCGCGTGTCTTTCCCTGCCAATGGCGGCCCCCCCCTGACGTT-
GTTTTCCCGGCCCCGGTTTATTTTTTTTCCCCATTTGTGCCCACTATTTAAACTTTGCGCTC-
TACCGTTGGGCTGGTGATGCCAATACATT-
AGATGCCGACACATGTATTGAGCTCGTCTGCTCCCCAAACACCCNTGATGGTGGCCTCCG-
GAAGCCTGTCATCAAATCCAAGTCTAGCAAGCCTGTTTATGACTTCGCCTACTACTGGCCG-
CAGTACACACCCATCACCGAGGCAGCTGCCCATGATATCATGCTGTTCAC-
TGTCTCCAAATGCACCGGCCATGCCGGCACCAGGCTGGGGTGGGCATTGGTGAAGGATACT-
AAGGTGGCTCAGAAGATGATCAAGTTTATAGAGCTCAACACAATCGGTG-
TATCCAAGGACTCTCAACTTCGTGCCGCTAAGATTATCGGGGCAATATGTAATGGC-
TATGAGCCGGTACCATCCTCTGGTAAAACAA-
GCCAACTCTTCCATTTCGCCAAGGAAAAAATGGCGGCTCGCTGGGCTAGACTTCGTG-
CAGCTGTGGCAGCCTCAGACATCTTTACTCTCCCTTATGAGCTATCTGGC-
TATTGTAGCTTTTCCAATGAGACTGTCACCGCCAATCCTCCATTTGCATGGCTTCGC-
TACAACAAGGATGATATTGAAGATCTGGAGGCCTTCCTACTCGAGAAAAAGATTATCAC-
TCGAGGTGGCACAAGGTTTGGAGTGGATGCAAGGGCTGTCAGAGTTAGTATGGTT-
GACACAGACCAAGCCTTCAATGTGTTCATCAATCGTCTGGCCACAATGAAGTGAAATTTCAG-
TGCAAATTAATAAAGCACTTTGTGGCTACTACAAGGATGACCGCGTTCTA-
GATGGAACAATCGATGCTTTGGAAAGCTTAATAATGTTTTATGTTGTTGAA-
TAATTCCGTGTGTTTTCGGGTATGTTGTGTAATACTCAATGTCAAATCC-
TATGCTTAATCGATGTTGTGGTCCATCCTGTTATCAGCATGGCCAATTATATATGGATGAC-
CGTCACTGCTGAAAAAAAAAAAAAAAA

Fig. 14

ATGAGCACGGGCGTGCGACCGGGGCGGCGGTTCACGGTGGGGCGGAGCGAGGACGCCAC-
GCACCCGGACACCATCCGCGCCGCCATCTCCGAGTTCATCGCCAC-
CGCCATCTTCGTCTTCGCCGCCGAGGGATCCGTCCTCTCGCTCGGGAAGATGTACCAC-
GACATGAGCACGGCGGGCGGCCTGGTGGCTGTGGCGCTGGCGCAC-
GCGCTGGCCCTGGCCGTGGCCGTGGCAGTGGCCGTCAACATCTCGGGCGGGCAC-
GTGAACCCGGCGGTCAC-
CTTCGGCGCGCTCGTCGGCGGCCGCGTCTCCCTCGTCCGCGCGGTCTTGTACTGGGTCGCG-
CAGCTGCTGGGCGCCGTCGCCGCCACGCTGCTCCTGCGGCTCGCCACGGGGGG-
CATGCGGCCGCCGGGGTTCGCGCTCGCGTCCGGGGTCGGGGACTGGCACGCCGTGCTGCTG-
GAGGCCGTCATGACGTTCGGCCTCATGTACGCCTACTACGCCACGGTGATCGACCCGAA-
GCGGGGGCACGTGGGCACCATCGCGCCGCTGGCCGTGGGCTTCCTGCTCGGCGCCAAC-
GTGCTGGCGGGAGGGCCCTTCGACGGCG-
CAGGGATGAACCCGGCGCGGGTCTTCGGCCCGGCGCTCGTCGGGTGGCGGTGGAGGCACCAC-
TGGGTGTACTGGCTGGGCCCTTTCCTCGGCGCCGGGCTTGCAGGGCTGGTGTACGAGTAC-
CTGGTTATCCCGTCCGCCGACGCCGCCGTGCCCCACGCGCACCAGCCGCTCGCGCCAGAGGAC-
TACTAG

Fig. 15

MSTGVRPGRRFTVGRSEDATHPDTIRAAISEFIATAIFVFAAEGSVLSLGKMYHDMSTAG-
GLVAVALAHALALAVAVAVAVNISGGHVNPAVTFGALVGGRVSLVRAVLYWVAQLLGA-
VAATLLLRLATGGMRPPGFALASGVGDWHAVLLEAVMTFGLMYAYYAT-
VIDPKRGHVGTIAPLAVGFLLGANVLAGGPFDGAGMNPARVFGPALVGWRWRHHWVYWLGPFL-
GAGLAGLVYEYLVIPSADAAVPHAHQPLAPEDY

Fig. 16

ATGGCGGCGGCGCTGCGCTGCGCTGGAAGGATCGGGATCCTGGCCACCGTCGCAGTGAAC-
CTCGCGTGGATCGCGACGTACATCCGCCGGCGCTACTTCGGCGGCGGGAAC-
CGATCCGACAACAACGGTGGCGGCGGGGAGGTGGAGCCGTCAAGAGGGAAGCCGCCGGTCAC-
TTCGGACTCCATCGTCAACCTCGATGGCGACCCGACTATGTACGAGGAGTTCTGGCGCGG-
CACAGGAGATAGCGCCTCGATCTTCATCCCTGGTTGGCAAACAATGAGCTACTTCTCCGAC-
CTCGGCGGCATCTGTTGGTTCCTGGAGCCTGGAT-
TCGAGCGCGAGGTGCGGCGTCTCCACAGGCTCGTGGGGAATGCCGTTGTAGACGGGTAC-
CATGTGCTCGTCGGGACAGGCTCCACTCAGCTCTTTCAGGCCGTGCTGTACGCGCTCTCAC-
CTGCAAGTGACGGCACACCCATGAACGTCGTCTCACCGGCACCGTACTACTCGGTAAGAA-
TACGTTCAGCCATCAACCAATCAATCAATAAAATTGTGGTTCGATTGAT-
TAATCATCTGCTAGCTGATGATCGATTTTGA

Fig. 17

MAAALRCAGRIGILATVAVNLAWIATYIRRRYFGGGNRSDNNGGGGEVEPSRGKPPV-
TSDSIVNLDGDPTMYEEFWRGTGDSASIFIPGWQTMSYFSDLGGICWFLEPGFEREVRRLHR-
LVGNAVVDGYHVLVGTGSTQLFQAVLYALSPASDGTPMNVVSPAPYYSVRIR-
SAINQSINKIVVRLINHLLADDRF

Fig. 18A

TAACTCATATCCGGTTAGATACCAACTACACATATTGAATAGCATAAATCTAA-
TAAATATATGGCGCAATGAAAATAGTAAATAATTAAATATGAGTAAATAATATGATGACAA-
TAATGAATAATATTGGAACATGTACATTGACCCTATTTTGCTAATATATACTTATTATATTT-
GCTTAATTTGGTAGGATGTATATGTGATTGAGGCGGGTATAAATTATCCATAGGTATGTGGG-
TATAAATAGTCTATACTTATACCCATACTCATATACCCGACGGGTATATGATTGTGTCCATT-
GCCATATCTGCGGGTAAAAAACTCATTATATACTTGTCCTTATAAGTAAAACCTGTTGGACAC-
TAGAGTTTAGGTACCATATAATTATTAATTTTGAACGAAGGAAGTAATTTGCAGCG-
TATTAAGGTGCTTCTGGTCTAGAAGAAATGTCACAATGTTTGGTGTTAGTTTTTGGTGAAATT-
TAAGGTTAATTACTTTTTGAAAGATGTTTCCACTAGGTGGAACCGAAAGAAAC-
GGTGCCAAACACACCTTACAACAAGAAAATATTTGTAAAAAAATTATTTTGAATAA-
GATGTCTAAAAATAGAAAGCGTGTATACTTTAGGACGGAGGAATACATATGTATGATTGG-
GAAAACCGAAAACGTACACCTCCTCGCTGCAATACGCTGGTGACTTGGCAGTTCGATCG-
CACCCAGCGGATAAAGATGAGCACGGAGAACTCACAAGGCACAGCCGCACAGGCAGGCAC-
CAGCGCGAACGCATGGACGGGCGGCCCCTGAGAC-
GTGCCGCCCAGCTGGCCCGCTGCGCCCACACGTGGCGCGGAGCTGCGCGCGGCTCGGCCACGT-
TATAAGCCACGCGCGCTGGCCGTCGCCGCACCTCCTGACTACT*GCACACTCGTCTCCGCAG-*
*TTTGAAACGAAGCCCGCGGCTACTGCAAGCTACTCCGTCTCCGTAGCTAAAGGA-*
*GAGGTAGGTTTTTATTTGGCGACGAC*ATGAGCACGGGCGTGCGACCGGGGCGGCGGTTCAC-
GGTGGGGCGGAGCGAGGACGCCACGCACCCGGACACCATCCGCGCCGCCATCTCCGAG-
TTCATCGCCACCGCCATCTTCGTCTTCGCCGCCGAGGGATCCGTCCTCTCGCTCGGTAC-
GCACGCACGCACGCTTCGTCTTCCGATCCGCTCGAAAGTGTTCGACGACGACGACGAC-
GATGCGTGTGGGGTTTGCCGTTTATTTAATTTATTGTTGTGTTGTGTGCGCAGGGAA-
GATGTACCACGACATGAGCACGGCGGGCGGCCTGGTGGCTGTGGCGCTGGCGCAC-
GCGCTGGCCCTGGCCGTGGCCGTGGCAGTGGCCGTCAACATCTCGGGCGGGCAC-
GTGAACCCGGCGGTCAC-
CTTCGGCGCGCTCGTCGGCGGCCGCGTCTCCCTCGTCCGCGCGGTCTTGTACTGGGTCGCG-
CAGCTGCTGGGCGCCGTCGCCGCCACGCTGCTCCTGCGGCTCGCCACGGGGGG-
CATGCGGCCGCCGGGGTTCGCGCTCGCGTCCGGGGTCGGGGACTGGCACGCCGTGCTGCTG-
GAGGCCGTCATGACGTTCGGCCTCATGTACGCCTACTACGCCACGGTGATCGACCCGAA-
GCGGGGGCACGTGGGCACCATCGCGCCGCTGGCCGTGGGCTTCCTGCTCGGCGCCAAC-
GTGCTGGCGGGAGGGCCCTTCGACGGCG-
CAGGGATGAACCCGGCGCGGGTCTTCGGCCCGGCGCTCGTCGGGTGGCGGTGGAGGCACCAC-
TGGGTGTACTGGCTGGGCCCTTTCCTCGGCGCCGGGCTTGCAGGGCTGGTGTACGAGTAC-
CTGGTTATCCCGTCCGCCGACGCCGCCGTGCCCCACGCGCACCAGCCGCTCGCGCCAGAGGAC-
TACTAGCTTGAAAATTGTATTGTGGGGTCGTGTAAGTGGTTAATAAGGGGGGCATAGGTAC-
GTACTTGTCTGTCGCCCCAGCGTGTGTTGGAGACGGTGAATCAGGTGATGTG-
TACATGCTGCTTCACTGTAGTGTATGTGTATGTGTATGTAGTAAATAATTCCAGGTATA-
TAAGGCACGACTTGTGTAGTATCATATCTGGTTCTGACTTCTGATTATCTAAAGGGAAGGAT-
TCGAATGTCTGGATTTGGATGTCTGAAGAT

FIG. 18B

TCGAATTAACATCAGAATGTTTCCTAATGAAGTGCTAATATAGA-
TACTATGGATGTTAAATGGACGTATCCGACGAATTTGGTGGTTTAAGATTTCGACAAAATTCA-
TAAAACCATTTAAAACTTATTGTTAATACTAATTACAAATAATTTTAAATTTTAATAA-
TATACTAGAAAACTGATGTACACCATTTAAAATATTGAAAAATATTTATATTATAAATAAA-
TAATTATGTTAATCTTACATTAGTAGGAGTATCATAGGAATTTTTAGAATCTAAAATACAAA-
TATATTTAATATACAAAAGAATATATTTAGAGTCTAAAATATAAATATACCTGGTATAAA-
TAATTTATGGAAAAATATATTCATAATTTGTTTGTAATATGATTTTTACCAAC-
TATAAATACATCGATAAAACAAATTAATACTTATTATGATGTTATGTTTCAAATCAAA-
TAAGTGTCCAAATATGACTCGAATTCAAAGTATTCGTTCATATGGATTCGTTTTCAT-
ATGTATTCGATCCGAATTCATCCCTATCTATTTCGTACTCGCATTATCGCATTACCAG-
TTAAGGGATGTTCCGATTTTTTGGTGGATTATGAAGTCAAATTAGAAGAGTGACCGCAG-
GATGAGCTCCCTCCCCTGAATCGCCTAGCCCCTGACCCCTGCAACCCACCTCAC-
CGGCGTGTCCCCAACCCCTACAACCATGTCGAACGTTGCCCGGCCGATGCAGCCCCTCACTG-
CAAGTATCTAGAGGATGTCGCAACCCTCAGCTGGCCACCACCTCAGTGGTCAGCGCCAC-
GGGCTTTAGGTAAGGATCATATCTTCCCGAGACCACTTCTTCAAGATCTCTTCCTG-
CACAACTTCTCCACCATTTGGTCGTCTCCGATCGTTCATAAACATGTTGCGTTCATCTT-
GTTCGTCCCAACCTTCTCCTCATCCCACTTCACCAATGACTTCGTTAGCAACATGTT-
GAGCTTCGCTTCGACGGTGCCACCGTTTCGCCTACACGTAGCTTGCAAACATCGGCCTCCAC-
TGATGATCTACCCTAAACCCAAAACACATCTAGTGTACGCCAGTCGGCCCCCAC-
TGCTCCTAGCTTTGAGCGAGACAGCGGCGTTGCCTCCACCTTCGGCTCCTCGTCGCTTGAC-
GCCATCCAGTCCTAGGGTGGTGAGTCCTCTGGCTCCAATGAAAGCATTGGACAGGGTGAC-
GTGGGAGGCAACCACAACAGTACCTTGAGACATGGATGCCCCCTGCGAC-
CATGCCCTCAAAAATCGCATCCTTCATGCCTATACCATCGAGGGGCAGTGGTTGAGCTG-
GAATCCATGATCTGTCTATGCGCCTGCCTCCAGTGCATCGCCCCCGAAGTGCTAGTG-
GATCTGCTACCCTCCTCTAGGTGTGTGGCAATCCTCTTGTTCAACTCCCAAGCCCATCGCAA-
GCTCATCCGCGCCCTCAACCCCCTGGCCTTTGAAGGTATGTCCCACTCCTTCGAGCACCTG-
GAGGAAACATCCAACCGCTTCATTCATGTCCCTGTGTGGCTT-
GCTCTTCCCGTGTCGATCGACTTCCCACCGAAGCGTCGAATCGCTATGTCGTCCACCAC-
GCCTTTGCGGCTGGCTGTGAAGTCAGGGAAATCCATGCCAATGACCTGAACCCCAAC-
TACTTTAGGCCTATCTGGGTCGTCATCGAGGTCAACCACCACCTTGACATCCCGCACGAGCTC-
TAGATCTCCGAAAGGCGTGGAATTACTAGA-
GAAGGGTGTGTGGCCTAGGTGCTGCTGGTCCGAATTGGCCAAGACGTGAGTAGCTGGAT

FIG. 18C

AACGCCCCGTTAAGGTATTACTCGTAATTTTTCTATAGCATTTAAATGTGTTGGA-
TAATCTTTTGCATGGATATGTGTTGTGAATTCGCACCATGTGCCCACGAAAGCAGCATGGG-
GATCGCCCCACCAATTTTTTTTTACCAGCTCTAACTCTCAAC-
CAGAAAACATGCAAATTTATTTGTCATTGCACACCAGCAACCTAGGGATGG

FIG. 18D

TAATCCCAAAATGCAATGATTTTTAGAGCATAGATGTGGGCGAATTTACCTAACTATGGA-
TATGTTAATTGACAATAAAACACCATAACCACTGGGTTCATGGGTACGAGTATGGTTTT-
GTACATGAAAGAATAAACTTATGAGAGTGTGTATATACTCAACATA-
CAAGTATAATTCCCAAAGCCATCTCCAACCTATTGTAGTCCAAAATATGCATGGTCCAACAA-
GCACACCTATTGACATGCATATAAGCCATCACATATATATATACACTAATTTTTACTATTACA-
TATGTTATATATTTATAGATATATGTTATTTGTTTATATTGTCAG-
TGTTTACTGCGTGTGTTATATTTTTTTTCTTAGGTACGGTGTAGGTAACCACCGTGTC-
TATCTCGACACGCGTACGGGCACAAAATTACATCAACACATGGTATGAGAT-
TTTTCATGTGTCAAATAAATTTTGATGGCTAGTTTAAAAACTTAAATCACTCATGAGATTAC-
CGGAGACGATTGAGGGGAAAATTTCCTAGTATTACGGACGGAATTTAAGTTTTTCAAAC-
TATCCCTAATAAAATAAATATGGGTATGTAGGTATGAGCGCGATACCATAGGGTATATAC-
CTGTTGCGGCGGGACTGCAGGTTTGGTGACAGCTAAAAACATGCATTTAGGTGTTGAATCTT-
GATTATTTGCAGTTAATCGTGCTTGCTGTGTTGCCGCAAACACGAGAT-
TCACACCCTGATGAGCGGAGCCAGGCTGCCCTTGCTTCGATTCAC-
GGTGGCCGTCGTCCCGGCCAGGCCAGCACACCAGTCCAATCCACATAGCAACAAC-
CGCGCCTCGGTCAGTTATAGATGCGTGGCCTTCTGAAACAAACCCTCATATGGGGTCACGCCG-
CACTCACACATGCATCCATAAACCCTCAGCAGAGCCTTGTGTCGCGTCCTCTCCTCGA-
TAACCCAGGCCACATCGTCCTTCCGCGCCGCGCCGCCGGCGAC-
CTAACAACCCAGAGGCCTCAGCACCGCACGCTTGCACGTAC-
GTCCAGGCGCGCTCGCCGTTACGCCCACGGGGATCCAGGCTTTCCTTCGCTGCCGTT-
GCTGGTCGAGTGCGCCACGCCGAAAGGTGATCGAGCTGACGAGCGCTAGACGCCAC-
CGGCCGGCGCGGCGTGGCAAGGCAAGACGCCGTGCGGGTCTCGCCCTCGTCAGCTATAAGAC-
CGCATCCCCCCCTGCGGAGGGAGGCACACACACAGACACAGC*GCTCTCACTAGCCTCG-*
*CATTCCGTCCCTGCAGTGCAGGGGCAGGCCGGTGAGGTCTGGGAGAGGAGGAGGAGGAGGAG-*
*GAGGAGGAGGAGGAG*ATGGCCGGTAGGGAGAGCGGCGG-
GATGGCGGCGGCGCTGCGCTGCGCTGGAAGGATCGGGATCCTGGCCACCGTCGCAGTGAAC-
CTCGCGTGGATCGCGACGTACATCCGCCGGCGCTACTTCGGCGGCGGGAAC-
CGATCCGACAACAACGGTGGCGGCGGGGAGGTGGAGCCGTCAAGAGGGAAGCCGCCGGTCAC-
TTCGGACTCCATCGTCAACCTCGATCAGTGAGTGATATGCTTTGCTGCCTGGG-
GATCCGATCCATCATCGATAAATCACTCGTTATTATTTTTACCGTCTGTACTG-
TATGTATTGGTCTCTCCCACTGCTCGTCCATCGATCTATTCTGTCCTGCTGGAGTCACTAG-
TGAAGGTCCGTTCCATTTGGGGAACCAGATCGAGCCCTAGCTATGCATATATGTGAG-
TGAGGCATCTGGAACGAAGACGTACACTAG-
TGAAGTCCCGCTCAGGGTCCTGCCCTCTCCATCTAGCAAGGACATGTGCATCGATCCTTGTT-
GCCTGATTAGTTGTTGATTATTAGCAGCTAGTGTTTGTATACTTTTCCTGATTAATTGCAGA
TATATAGTAGTATTTGTTTATTTCGTTTGATTATTATATATATCGTGCTTTTGTTCTGTTT-
GTTTGTTTGGTTGGTTAATTATTTAGGAAATAGTGCGAAGTTAAAATAGAGATGGGTT-
GGAAAAGATCGAAATGGCATATATAGTGGCCCTAAACCAAAATATACATACTGTTAG-
TTTCAGACAAAACAGTACAGCCTTGCAATTACCAACCCCTTATACACATATAGATGCATGGAC-
GAGTACTCTTATTTGAATCTTAACTTTGTTGACTGTTCTCTGTATGC

FIG. 18E

TATGAACTTAATCGTCGTCGTCCATGCAAAGCATGCATGCTACTGTATGTTTTTGACTTTT-
GGTTGGTTGGTTGCAGTGGCGACCCGACTATGTACGAGGAGTTCTGGCGCGGCACAGGAGA-
TAGCGCCTCGATCTTCATCCCTGGTTGGCAAACAATGAGCTACTTCTCCGACCTCGGCGG-
CATCTGTTGGTTCCTGGAGCCTGGATTCGAGCGCGAGGTGCGGCGTCTCCACAGGCTCGTGGG-
GAATGCCGTTGTAGACGGGTACCATGTGCTCGTCGGGACAGGCTCCAC-
TCAGCTCTTTCAGGCCGTGCTGTACGCGCTCTCACCTGCAAGTGACGGCACACCCATGAAC-
GTCGTCTCACCGGCACCGTACTACTCGGTAAGAATACGTTCAGCCATCAACCAATCAATCAA-
TAAAATTGTGGTTCGATTGATTAATCATCTGCTAGCTGATGATCGATTTTGAACACATGTG-
CAGTCTTACCCATCTGTGACCAACTATCTAAACTCTGCGCTCTACCGTT-
GGGCTGGTGATGCCAATACATTT-
GATGGCGACACATGTATTGAGCTCGTCTGCTCCCCAAACAACCCTGATGGTGGCCTCCGGAA-
GCCTGTCATCAAATCCAAGTCTAGCAAGCCTGTTTATGACTTCGCCTACTACTGGCCGCAG-
TACACACCCATCACCGAGGCAGCTGCCCATGACATCATGCTGTTCACCGTCTCCAAATGCAC-
CGGCCATGCCGGCACCAGGCTGGGGTAACCATTTCTTGGTCATCAGTTGTTAATTTCAT-
ATATATACACGTAGTAATTACGAGATATGATATGAAGTACGGTGGTTTGTTTACGTGGA-
GATGCTTGTAGGTGGGCATTGGTGAAGGATACTAAGGTGGCTCAGAAGATGATCAAGTTTATA-
GAGCTCAACACAATCGGTGTATCCAAGGACTCTCAACTTCGTGCCGCTAAGATTATCGGGG-
CAATATGTAATGGCTATGAGCCGGTACCATCCTCTGGTAAAACAA-
GCCAACTCTTCCATTTCGCCAAGGAAAAAATGGCGGCTCGCTGGGCTAGACTTCGTG-
CAGCTGTGGCAGCCTCAGACATCTTTACTCTCCCTTATGAGCTATCTGGC-
TATTGTAGCTTTTCCAATGAGACTGTCACCGCCAATCCTCGTAAGGAAC-
CACACATTTTAAATTTCCATTCTTACATCTACGACTAGTGCAATTATATTGTT-
GTTTTTATGCTTTTATTTGTAAATAACATCGTCGAG-
GACAAAAAAAAACTCATTATTTTCCTTGGTTAGCATTTGCATGGCTTCGC-
TACAACAAGGATGATATTGAAGATCTGGAGGCCTTCCTACTCGAGAAAAAGATTATCAC-
TCGAGGTGGCACAAGGTTTGGAGTGGATGCAAGGGCTGTCAGAGTTAGTATGGTT-
GACACAGACCAAGCCTTCAATGTGTTCATCAATCGTCTGGCCACAATGAAGTGAAATTTCAG-
TGCAAATTAATAAAGCACTTTGTGGCTACTACAAGGATGACCGCGTTCTA-
GATGGAACAATCGATGCTTTGGAAAGCTTAATAATGTTTTATGTTGTTGAA-
TAATTCCGTGTGTTTTCGGGTATGTTGTGTAATACTCAATGTCAAATCC-
TATGCTTAATCGATGTTGTGGTCCATCCTGTTATCAGCATGGCCAATTATATATGGATGAC-
CGTCACTGCTCAGTCTTTACTCCTAATTACATGGCAAGTGTTTAATGGTGCTTCAATATCAG-
TTGATGACTATAACTTGGTACTAAAGCAGGATGGTACACTAACGTGTCAC-
TAATTTTTTACAGTGACATTTTTTTAAAACAAATCACTAACGACTGTGCACATGTGA-
TATCTATTGTAAAAACGTGTCAATAATATCGAAATATGGTAATAACCCAG-
TGACATCTTTTATTTTACGTGTCTCTATTGTGATCTGTTTAGTGACATGTACATATAAA-
TATGTCACTGGCTTTAGACGTCAAATTTATTTAGTGAAGTGTATATAGAAACATGTCAC-
TGACTTCAGATGTCAGATCTGTTTAGTGACATGTATTTAAATGCACGTCACAAA-
TACTTATACCTTAGTGATGTGTATTAAGAAACATGTCACTGGTTTTAAATG

Fig. 19A

TAACTCATATCCGGTTAGATACCAACTACACATATTGAATAGCATAAATCTAA-
TAAATATATGGCGCAATGAAAATAGTAAATAATTAAATATGAGTAAATAATATGATGACAA-
TAATGAATAATATTGGAACATGTACATTGACCCTATTTTGCTAATATATACTTATTATATTT-
GCTTAATTTGGTAGGATGTATATGTGATTGAGGCGGGTATAAATTATCCATAGGTATGTGGG-
TATAAATAGTCTATACTTATACCCATACTCATATACCCGACGGGTATATGATTGTGTCCATT-
GCCATATCTGCGGGTAAAAAACTCATTATATACTTGTCCTTATAAGTAAAACCTGTTGGACAC-
TAGAGTTTAGGTACCATATAATTATTAATTTTGAACGAAGGAAGTAATTTGCAGCG-
TATTAAGGTGCTTCTGGTCTAGAAGAAATGTCACAATGTTTGGTGTTAGTTTTTGGTGAAATT-
TAAGGTTAATTACTTTTTGAAAGATGTTTCCACTAGGTGGAACCGAAAGAAAC-
GGTGCCAAACACACCTTACAACAAGAAAATATTTGTAAAAAAATTATTTTGAATAA-
GATGTCTAAAAATAGAAAGCGTGTATACTTTAGGACGGAGGAATACATATGTATGATTGG-
GAAAACCGAAAACGTACACCTCCTCGCTGCAATACGCTGGTGACTTGGCAGTTCGATCG-
CACCCAGCGGATAAAGATGAGCACGGAGAACTCACAAGGCACAGCCGCACAGGCAGGCAC-
CAGCGCGAACGCATGGACGGGCGGCCCCTGAGAC-
GTGCCGCCCAGCTGGCCCGCTGCGCCCACACGTGGCGCGGAGCTGCGCGCGGCTCGGCCACGT-
TATAAGCCACGCGCGCTGGCCGTCGCCGCACCTCCTGACTACTGCACACTCGTCTCCGCAG-
TTTGAAACGAAGCCCGCGGCTACTGCAAGCTACTCCGTCTCCGTAGCTAAAGGA-
GAGGTAGGTTTTTATTTGGCGACGAC

Fig. 19B

GTGTTGGATAATCTTTTGCATGGATATGTGTTGTGAATTCGCACCATGTGCCCACGAAAGCAG-
CATGGGGATCGCCCCACCAATTTTTTTTTACCAGCTCTAACTCTCAAC-
CAGAAAACATGCAAATTTATTTGTCATTGCACACCAGCAACCTAGGGATGG-
TAATCCCAAAATGCAATGATTTTTAGAGCATAGATGTGGGCGAATTTACCTAACTATGGA-
TATGTTAATTGACAATAAAACACCATAACCACTGGGTTCATGGGTACGAGTATGGTTTT-
GTACATGAAAGAATAAACTTATGAGAGTGTGTATATACTCAACATA-
CAAGTATAATTCCCAAAGCCATCTCCAACCTATTGTAGTCCAAAATATGCATGGTCCAACAA-
GCACACCTATTGACATGCATATAAGCCATCACATATATATATACACTAATTTTTACTATTACA-
TATGTTATATATTTATAGATATATGTTATTTGTTTATATTGTCAG-
TGTTTACTGCGTGTGTTATATTTTTTTTCTTAGGTACGGTGTAGGTAACCACCGTGTC-
TATCTCGACACGCGTACGGGCACAAAATTACATCAACACATGGTATGAGAT-
TTTTCATGTGTCAAATAAATTTTGATGGCTAGTTTAAAAACTTAAATCACTCATGAGATTAC-
CGGAGACGATTGAGGGGAAAATTTCCTAGTATTACGGAC-
GGAATTTAAGTTTTTCAAACTAGCCCTAATAAAATAAATATGGGTATGTAGGTATGAGCGCGA-
TACCACCTGTTGCGGCGGGACTGCAGGTTTGGTGACAGCTAGAAACATGCATTTAGGTGTT-
GAATCTTGATTATTTGCAGTTAATCGTGCTTGCTGTGTTGCCGCAAACACGAGAT-
TCACACCCTGATGAGCGGAGCCAGGCTGCCCTTGCTTCGATTCAC-
GGTGGCCGTCGTCCCGGCCAGGCCAGCACACCAGTCCAATCCACATAGCAACAAC-
CGCGCCTCGGTCAGTTATAGATGCGTGGCCTTCTGAAACAAACCCTCATATGGGGTCACGCCG-
CACTCACACATGCATCCATAAACCCTCAGCAGAGCCTTGTGTCGCGTCCTCTCCTCGA-
TAACCCAGGCCACATCGTCCTTCCGCGCCGCGCCGCCGGCGAC-
CTAACAACCCAGAGGCCTCAGCACCGCACGCTTGCACGTAC-
GTCCAGGCGCGCTCGCCGTTACGCCCACGGGGATCCAGGCTTTCCTTCGCTGCCGTT-
GCTGGTCGAGTGCGCCACGCCGAAAGGTGATCGAGCTGACGAGCGCTAGACGCCAC-
CGGCCGGCGCGGCGTGGCAAGGCAAGACGCCGTGCGGGTCTCGCCCTCGTCAGCTATAAGAC-
CGCATCCCCCCCTGCGGAGGGAGGCACACACACAGACACAGCGCTCTCACTAGCCTCG-
CATTCCGTCCCTGCAGTGCAGGGGCAGGCCGGTGAGGTCTGGGAGAGGAGGAGGAGGAGGAG-
GAGGAG

Fig. 21A

GCAAGCTGTTTTACTCAAATACACATCACCTTTTTAGATGATCAGTGATTTT-
GTGCCGAGCTGCCGGTCGGGGAGCTGTTGGCTGGCTGGTGGCAGGATATATTGTGGTG-
TAAACAAATTGACGCTTAGACAACTTAATAACACATTGCGGAC-
GTCTTTAATGTACTGAATTTAGTTACTGATCACTGATTAAGTACTGATATCGGTACCAA-
GCTTCCGCGGCTGCAGTGCAGCGTGACCCGGTCGTGCCCCTCTCTAGAGATAATGAGCATT-
GCATGTCTAAGTTATAAAAAATTACCACATATTTTTTTTGTCACACTTGTTTGAAGTGCAGTT-
TATCTATCTTTATACATATATTTAAACTTTACTCTACGAATAATATAATCTATAGTACTACAA-
TAATATCAGTGTTTTAGAGAATCATATAAATGAACAGTTAGACATGGTCTAAAGGACAATT-
GAGTATTTTGACAACAGGACTCTACAGTTTTATCTTTTTAGTGTG-
CATGTGTTCTCCTTTTTTTTTGCAAATAGCTTCACCTATATAATACTTCATCCATTTTATTAG-
TACATCCATTTAGGGTTTAGGGTTAATGGTTTTTATAGACTAATTTTTTTAGTACATCTATTT-
TATTCTATTTTAGCCTCTAAATTAAGAAAACTAAAACTCTATTTTAGTTTTTTTATTTAA-
TAGTTTAGATATAAAATAGAATAAAATAAAGTGACTAAAAATTAAACAAATACCCTTTAA-
GAAATTAAAAAAACTAAGGAAACATTTTTCTTGTTTCGAGTAGA-
TAATGCCAGCCTGTTAAACGCCGTCGACGAGTCTAACGGACACCAACCAGCGAACCAG-
CAGCGTCGCGTCGGGCCAAGCGAAGCAGACGGCACGGCATCTCTGTCGCTGCCTCTG-
GACCCCTCTCGAGAGTTCCGCTCCACCGTTGGACTTGCTCCGCTGTCGGCATCCAGAAATT-
GCGTGGCGGAGCGGCAGACGTGAGCCGGCACGGCAGGCGGCCTCCTCCTCCTCTCACGGCAC-
CGGCAGCTACGGGGGATTCCTTTCCCACCGCTCCTTCGCTTTCCCTTCCTCGCCCGCCGTAA-
TAAATAGACACCCCCTCCACACCCTCTTTCCCCAACCTCGTGTTGTTCGGAGCG-
CACACACACACAACCAGATCTCCCCCAAATCCACCCGTCGGCACCTCCGCTTCAAGGTAC-
GCCGCTCGTCCTCCCCCCCCCCCCCCTCTCTACCTTCTCTA-
GATCGGCGTTCCGGTCCATGGTTAGGGCCCGGTAGTTCTACTTCTGTTCATGTTTGTGTTA-
GATCCGTGTTTGTGTTAGATCCGTGCTGCTAGCGTTCGTACACGGATGCGACCTGTAC-
GTCAGACACGTTCTGATTGCTAACTTGCCAGTGTTTCTCTTTGGGGAATCCTGG-
GATGGCTCTAGCCGTTCCGCAGACGGGATCGATTTCATGATTTTTTTTGTTTCGTT-
GCATAGGGTTTGGTTTGCCCTTTTCCTTTATTTCAATATATGCCGTGCACTTGTTT-
GTCGGGTCATCTTTTCATGCTTTTTTTTGTCTTGGTTGTGATGATGTGGTCTGGTT-
GGGCGGTCGTTCTAGATCGGAGTAGAATTCTGTTTCAAACTACCTGGTGGAT-
TTATTAATTTTGGATCTGTATGTGTGTGCCATACATATTCATAGTTACGAATTGAA-
GATGATGGATGGAAATATCGATCTAGGATAGGTATACATGTT-
GATGCGGGTTTTACTGATGCATATACAGAGATGCTTTTTGTTCGCTTGGTT-
GTGATGATGTGGTGTGGTTGGGCGGTCGTTCATTCGTTCTAGATCGGAGTAGAA-
TACTGTTTCAAACTACCTGGTGTATTTATTAATTTTGGAACTGTATGTGTGTGTCATA-
CATCTTCATAGTTACGAGTTTAAGATGGATGGAAATATCGATCTAGGATAGGTATACATGTT-
GATGTGGGTTTTACTGATGCATATACATGATGGCATATGCAGCATCTATTCAT-
ATGCTCTAACCTTGAGTACCTATCTATTATAA-
TAAACAAGTATGTTTTATAATTATTTCGATCTTGATATACTTGGATGATGGCATATGCAG-
CAGCTATATGTGGATTTTTTTAGCCCTGCCTTCATACGCTATTTATTTGCTTGG-
TACTGTTTCTTTTGTCGATGCTCACCCTGTTGTTTGGTGTTACTTCTGCAGCCCGGGG

Fig. 21B

GATCCACTAGTTCTAGAAACCATGGCCACCGCCGCCGCCGCGTCTACCGCGCTCAC-
TGGCGCCACTACCGCTGCGCCCAAGGCGAGGCGCCGGGCGCAC-
CTCCTGGCCACCCGCCGCGCCCTCGCCGCGCCCATCAGGTGCTCAGCGGCGTCACCCGCCATGC
CGATGGCTCCCCCGGCCACCCCGCTCCGGCCGTGGGGCCCCACCGATCCCCG-
CAAGGGCGCCGACATCCTCGTCGAGTCCCTCGAGCGCTGCGGCGTCCGCGACGTCTTCGCC-
TACCCCGGCGGCACGTCCATGGAGATCCACCAGGCACTCACCCGCTCCCCCGTCATCGCCAAC-
CACCTCTTCCGCCACGAGCAAGGGGAGGCCTTTGCGGCCTCCGGCTAC-
GCGCGCTCCTCGGGCCGCGTCGGCGTCTGCATCGCCACCTCCGGCCCCGGCGCCACCAAC-
CTTGTCTCCGCGCTCGCCGACGCGCTGCTCGATTCCGTCCCCATGGTCGCCATCACGG-
GACAGGTGCCGCGACGCATGATTGGCACCGACGCCTTCCAGGAGAC-
GCCCATCGTCGAGGTCACCCGCTCCATCACCAAGCACAACTACCTGGTCCTCGACGTCGAC-
GACATCCCCCGCGTCGTGCAGGAGGCTTTCTTCCTCGCCTCCTCTGGTCGAC-
CGGGGCCGGTGCTTGTCGACATCCCCAAGGACATCCAGCAGCAGATGGCGGTGCCTGTCTGG-
GACAAGCCCATGAGTCTGCCTGGGTACATTGCGCGCCTTCCCAAGCCCCCTGCGACTGAGTT-
GCTTGAGCAGGTGCTGCGTCTTGTTGGTGAATCCCGGCGCCCTGTTCTTTATGTT-
GGCGGTGGCTGCGCAGCATCTGGTGAGGAGTTGCGACGCTTTGTGGAGCTGACTG-
GAATCCCGGTCACAACTACTCTTATGGGCCTCGGCAACTTCCCCAGCGACGACCCAC-
TGTCTCTGCGCATGCTAGGTATGCATGGCACGGTGTATGCAAATTATGCAGTGGA-
TAAGGCCGATCTGTTGCTTGCACTTGGTGTGCGGTTTGATGATCGTGTGACAGGGAA-
GATTGAGGCTTTTGCAAGCAGGGCTAAGATTGTGCACGTTGATATTGATCCGGCTGAGATTGG-
CAAGAACAAGCAGCCACATGTGTCCATCTGTGCAGATGTTAAGCTTGCTTTGCAGGG-
CATGAATGCTCTTCTTGAAGGAAGCACATCAAAGAAGAGCTTTGACTTTGGCTCATGGAAC-
GATGAGTTGGATCAGCAGAAGAGGGAATTCCCCCTTGGGTATAAAACATCTAATGAGGA-
GATCCAGCCACAATATGCTATTCAGGTTCTTGATGAGCTGACGAAAGGCGAGGCCATCATCGG-
CACAGGTGTTGGGCAGCACCAGATGTGGGCGGCACAGTACTACACTTACAA-
GCGGCCAAGGCAGTGGTTGTCTTCAGCTGGTCTTGGGGCTATGGGATTTGGTTT-
GCCGGCTGCTGCTGGTGCTTCTGTGGCCAACCCAGGTGTTACTGTTGTTGACATCGATGGA-
GATGGTAGCTTTCTCATGAACGTTCAGGAGCTAGCTATGATCCGAATTGAGAAC-
CTCCCGGTGAAGGTCTTTGTGCTAAACAACCAGCACCTGGGGATGGTGGTGCAGTGGGAG-
GACAGGTTCTATAAGGCCAACAGAGCGCACACATACTTGGGAAACCCAGAGAATGAAAGTGA-
GATATATCCAGATTTCGTGACGATCGCCAAAGGGTTCAACATTCCAGCGGTCCGTGTGACAAA-
GAAGAACGAAGTCCGCGCAGCGATAAAGAAGATGCTCGAGACTCCAGGGCCGTACCTCTTGGA-
TATAATCGTCCCACACCAGGAGCATGTGTTGCCTATGATCCCTAATGGTGGGGCTTTCAAGGA-
TATGATCCTGGATGGTGATGGCAGGACTGTGTACTGATCTAAAATCCAGCAA-
GCAACTGATCTAAAATCCAGCAAGCACCGCCTCCCTGCTAGTACAAGGGTGA-
TATGTTTTTATCTGTGTGATGTTCTCCTGTATTCTATCTTTTTTTGTAGGCCGTCAGC-
TATCTGTTATGGTAATCCTATGTAGCTTCCGACCTTGTAATTGTGTAGTCTGTT-
GTTTTCCTTCTGGCATGTGTCATAAGAGATCATTTAAGTGCCTTTTGCTACATATAAATAAGA-
TAATAAGCACTGCTATGCAGTGGTTCTGAATTGGCTTCTGTT-
GCCAAATTTAAGTGTCCAACTGGTCCTTGCTTTTGTTTTCGCTATTTTTTTCCTTTTTTAG

Fig. 21C

TTATTATTATATTGGTAATTTCAACTCAACATATGATGTATGGAATAATGCTAGGGCTG-
CAATTTCAAACTATTTTACAAACCAGAATGGCATTTTCGTGGTTTGAGGGGAG-
TGAAAAAAAATGAGGCATTTGACTGAATTAGTTACCTGATCCATTTTCGTGGTTT-
GGATCATTGGAATTAAATTCCATTCTAATAATAGTAATTTTGGCATA-
TATCAATTAAGTTAATTCGGTTTTATGCAAAATATATTTGTATACTATTATTATCAA-
GATGTCGGAGATATTTATATGCTACATTTTTACTATACAGGAGTGAGATGAAGAG-
TGTCATGTAAGTTACACAGTAGAAACAAATTC-
TATTAATGCATAAAATCATTTCCATCATCCACCCTATGAATTTGAGATAGACCTA-
TATCTAAACTTTGAAAAGTGGTTGAATATCAAATTCCAAATTAAATAAGTTATTTTATTGAG-
TGAATTCTAATTTCTCTAAAACGAAGGGATCTAAACGCCCTCTAAAGCTAATTT-
GGAAACTCAAACTTTCTTAGCATTGGAGGGGATTGAGAAAAAA-
TATTAATTCATTTTCATCTCAATCATTCAATCTCCAAAGAGATTTGAGTTCCTTATTAG-
TCTGTTCCATGCATCAAATCGGCTCAATGTGTCATTATTTGCCATGACGATTGACGAGTT-
GTTCTGGGGCCTAGCGCTTTCCACGCCGATGTGCTGGGGCCTGGTCCTGGAGAAGACAGCTT-
GATATTTAAAGCTATCAATTGTTTCAATTGATTCCCACTTCATTTTTCTAAATGTAGAAAAC-
GGTGACGTATAAGAAAAAGAATGAATTAGGACTTTTATTCCGTACACTAATCTAGAGCGGCCG-
CAAGCTTGTACAACGCGTACCGGTTAATTAAATTACGCCAAGCTATCAACTTTGTATA-
GAAAAGTTGGCGCCCTAGGCGGCCGCACTAAGCGCTATTTAAATTAACTCATATCCGGTTAGA-
TACCAACTACACATATTGAATAGCATAAATCTAATAAATATATGGCGCAATGAAAATAGTAAA-
TAATTAAATATGAGTAAATAATATGATGACAATAATGAATAATATTGGAACATGTACATT-
GACCCTATTTTGCTAATATATACTTATTATATTTGCTTAATTTGGTAG-
GATGTATATGTGATTGAGGCGGGTATAAATTATCCATAGGTATGTGGGTATAAATAGTC-
TATACTTATACCCATACTCATATACCCGACGGGTATATGATTGTGTCCATT-
GCCATATCTGCGGGTAAAAAACTCATTATATACTTGTCCTTATAAGTAAAACCTGTTGGACAC-
TAGAGTTTAGGTACCATATAATTATTAATTTTGAACGAAGGAAGTAATTTGCAGCG-
TATTAAGGTGCTTCTGGTCTAGAAGAAATGTCACAATGTTTGGTGTTAGTTTTTGGTGAAATT-
TAAGGTTAATTACTTTTTGAAAGATGTTTCCACTAGGTGGAACCGAAAGAAAC-
GGTGCCAAACACACCTTACAACAAGAAAATATTTGTAAAAAAATTATTTTGAATAA-
GATGTCTAAAAATAGAAAGCGTGTATACTTTAGGACGGAGGAATACATATGTATGATTGG-
GAAAACCGAAAACGTACACCTCCTCGCTGCAATACGCTGGTGACTTGGCAGTTCGATCG-
CACCCAGCGGATAAAGATGAGCACGGAGAACTCACAAGGCACAGCCGCACAGGCAGGCAC-
CAGCGCGAACGCATGGACGGGCGGCCCCTGAGAC-
GTGCCGCCCAGCTGGCCCGCTGCGCCCACACGTGGCGCGGAGCTGCGCGCGGCTCGGCCACGT-
TATAAGCCACGCGCGCTGGCCGTCGCCGCACCTCCTGACTACTGCACACTCGTCTCCGCAG-
TTTGAAACGAAGCCCGCGGCTACTGCAAGCTACTCCGTCTCCGTAGCTAAAGGA-
GAGGTAGGTTTTTATTTGGCGACGACACGTACGGCCTAGGCCTTCACCTGCGGAGGGTAA-
GATCCGATCACCATCTTCTGAATTTCTGTTCTTGATCTGTCATGTATAATAACTGTCTAG-
TCTTGGTGTTGGTGAGATGGAAATTCGGTGGATCTCGGAAGGGATATTGTTCGTTT-
GCTGGGGTTTTTTTTGTGTGTTGTGATCCGTAGAGAATTTGTGTTTATCCATGTTGTT-
GATCTTGGTATGTATTCATGACATATTGACATGCATGTGTTGTATGTGTCAT

Fig. 21D

ATGTGTGCCTCTCCTTGGGATTTGTTTTGGATAATAGAACATGTTATGGACTCAA-
TAGTCTGTGAACAAATCTTTTTTTAGATGGTGGCCAAATCTGATGATGATCTTTCTTGAGAG-
GAAAAAGTTCATGATAGAAAAATCTTTTTTGA-
GATGGTGGCTTAATGTGATGATGATCTTTCTTGAGAGGAAAAAAAAGATTCATTATAGGA-
GATTTTGATTTAGCTCCTTTCCACCGATATTAAATGAGGAGCATGCATGCTGATTGCTGA-
TAAGGATCTGATTTTTTTATCCCCTCTTCTTTGAACAGACAAGAAA-
TAGGCTCTGAATTTCTGATTGATTATTTGTACATGCAGAAGGGCGAATTCGAC-
CTAGGCCAAGTTTGTACAAAAAAGCAGGCTTGATAACCAACCATGGTCCGTCCTG-
TAGAAACCCCAACCCGTGAAATCAAAAAACTCGACGGCCTGTGGGCATTCAGTCTG-
GATCGCGAAAACTGTGGAATTGATCAGCGTTGGTGGGAAAGCGCGTTACAAGAAAGCCGGG-
CAATTGCTGTGCCAGGCAGTTTTAACGATCAGTTCGCCGATGCAGATATTCG-
TAATTATGCGGGCAACGTCTGGTATCAGCGCGAAGTCTTTATACCGAAAGGTTGGG-
CAGGCCAGCGTATCGTGCTGCGTTTCGATGCGGTCACTCATTACGGCAAAGTGTGGGTCAA-
TAATCAGGAAGTGATGGAGCATCAGGGCGGCTATACGCCATTTGAAGCCGATGTCACGCCG-
TATGTTATTGCCGGGAAAAGTGTACGTAAGTTTCTGCTTCTACCTTTGATATATATATAA-
TAATTATCATTAATTAGTAGTAATATAATATTTCAAATATTTTTTTCAAAATAAAA-
GAATGTAGTATATAGCAATTGCTTTTCTGTAGTTTATAAGTGTG-
TATATTTTAATTTATAACTTTTCTAATATATGACCAAAATTTGTTGATGTGCAGGTATCAC-
CGTTTGTGTGAACAACGAACTGAACTGGCAGACTATCCCGCCGGGAATGGTGATTACCGAC-
GAAAACGGCAAGAAAAAGCAGTCTTACTTCCATGATTTCTTTAACTATGCCGGAATCCATCG-
CAGCGTAATGCTCTACACCACGCCGAACACCTGGGTGGACGATATCACCGTGGTGAC-
GCATGTCGCGCAAGACTGTAACCACGCGTCTGTTGACTGG-
CAGGTGGTGGCCAATGGTGATGTCAGCGTTGAACTGCGTGATGCGGATCAACAGGTGGTT-
GCAACTGGACAAGGCACTAGCGGGACTTTGCAAGTGGTGAATCCGCACCTCTGGCAAC-
CGGGTGAAGGTTATCTCTATGAACTGTGCGTCACAGCCAAAAGCCAGACAGAGTGTGA-
TATCTACCCGCTTCGCGTCGGCATCCGGTCAGTGGCAGTGAAGGGCGAACAGTTCCTGAT-
TAACCACAAACCGTTCTACTTTACTGGCTTTGGTCGTCATGAAGATGCGGACTTGCGTGG-
CAAAGGATTCGATAACGTGCTGATGGTGCACGACCACGCATTAATGGACTG-
GATTGGGGCCAACTCCTACCGTACCTCGCATTACCCTTACGCTGAAGAGATGCTCGACTGGG-
CAGATGAACATGGCATCGTGGTGATTGATGAAACTGCTGCTGTCGGCTTTAAC-
CTCTCTTTAGGCATTGGTTTCGAAGCGGGCAACAAGCCGAAAGAACTGTACAGCGAA-
GAGGCAGTCAACGGGGAAACTCAGCAAGCGCACTTACAGGCGATTAAAGAGCTGA-
TAGCGCGTGACAAAAACCACCCAAGCGTGGTGATGTGGAGTATTGCCAACGAACCGGA-
TACCCGTCCGCAAGGTGCACGGGAATATTTCGCGCCACTGGCGGAAGCAACGCG-
TAAACTCGACCCGACGCGTCCGATCACCTGCGTCAATGTAATGTTCTGCGACGCTCACACCGA-
TACCATCAGCGATCTCTTTGATGTGCTGTGCCTGAACCGTTATTACGGATGGTATGTCCAAA-
GCGGCGATTTGGAAACGGCAGAGAAGGTACTGGAAAAAGAACTTCTGGCCTGGCAGGA-
GAAACTGCATCAGCCGATTATCATCACCGAATACGGCGTGGATACGTTAGCCGGGCTGCAC-
TCAATGTACACCGACATGTGGAGTGAAGAGTATCAGTGTGCATGGCTGGATATGTATCAC-
CGCGTCTTTGATCGCGTCAGCGCCGTCGTCGGTGAACAGGTATGGAATTTCGCCGATTTT

Fig. 21E

GCGACCTCGCAAGGCATATTGCGCGTTGGCGGTAACAAGAAAGGGATCTTCACTCGCGACCG-
CAAACCGAAGTCGGCGGCTTTTCTGCTGCAAAAACGCTGGACTGG-
CATGAACTTCGGTGAAAAACCGCAGCAGGGAGGCAAACAATGAATCAAACCCAGCTTTCTT-
GTACAAAGTGGGACCTAGGATCGTTCAAACATTTGGCAATAAAGTTTCTTAA-
GATTGAATCCTGTTGCCGGTCTTGCGATGATTATCATATAATTTCTGTTGAATTACGTTAA-
GCATGTAATAATTAACATGTAATGCATGACGTTATTTATGAGATGGGTTTTTATGATTAGAG-
TCCCGCAATTATACATTTAATACGCGATAGAAAACAAAATATAGCGCGCAAACTAGGATAAAT-
TATCGCGCGCGGTGTCATCTATGTTACTAGATCGAATTCAACTTTATTATACATAGTTGA-
TAATTCACTGGGCCGGCCAGGCCTTAGTTACTAATCAG-
TGATCAGATTGTCGTTTCCCGCCTTCAGTTTAAACTATCAGTGTTTGACAGGATA-
TATTGGCGGGTAAACCTAAGAGAAAAGAGCGTTTATTAGAATAATCGGA-
TATTTAAAAGGGCGTGAAAAGGTTTATCCGTTCGTCCATTTGTATGTCAA-
TATTGGGGGGGGGGGAAAGCCACGTTGTGTCTCAAAATCTCTGATGTTACATTGCACAAGA-
TAAAAATATATCATCATGAACAATAAAACTGTCTGCTTACATAAACAG-
TAATACAAGGGGTGTTCGCCACCATGAGCCATATCCAGCGTGAAAC-
CTCGTGCTCCCGCCCGCGCCTCAATTCCAATATGGATGCCGACCTTTATGGC-
TACAAGTGGGCGCGCGACAACGTCGGCCAGTCGGGCGCGACCATTTATCGGCTTTATGG-
CAAACCCGATGCCCCGGAACTGTTCCTGAAGCACGGCAAAGGCAGCGTCGCAAAC-
GATGTCACCGATGAGATGGTCCGCCTGAACTGGCTTACCGAGTTCATGCCGCTGCCGACGAT-
TAAGCATTTCATCCGTACCCCGGACGATGCCTGGCTCTTGACCACGGCCATTCCGGG-
CAAAACGGCCTTTCAGGTCCTTGAAGAGTACCCGGACTCCGGTGAGAATATCGTGGAC-
GCCCTCGCGGTCTTCCTCCGCCGTTTGCATAGCATCCCCGTGTGCAACTGCCCCTTCAACTCG-
GACCGGGTTTTCCGCCTGGCACAGGCCCAGTCGCGCATGAATAACGGCCTCGTTGAC-
GCGAGCGATTTCGACGATGAACGGAATGGCTGGCCGGTGGAACAGGTTT-
GGAAGGAAATGCACAAACTGCTTCCGTTCTCGCCGGATTCGGTGGTCACGCATGGTGAT-
TTTTCCCTGGATAATCTGATCTTTGACGAGGGCAAGCTGATCGGCTGCATCGAC-
GTGGGTCGCGTCGGTATCGCCGACCGCTATCAGGACCTGGCGATCTTGTGGAATT-
GCCTCGGCGAGTTCTCGCCCTCGCTCCAGAAGCGCCTGTTCCAGAAGTACGG-
CATCGACAACCCGGATATGAACAAGCTCCAGTTCCACCTCATGCTGGACGAATTTTTTT-
GAACAGAATTGGTTAATTGGTTGTAACACTGGCAGAGCATTACGCTGACTTGACGGGAC-
GGCGGCTTTGTTGAATAAATCGAACTTTTGCTGAGTTGAAGGATCGATGAGTT-
GAAGGACCCCGTAGAAAAGATCAAAGGATCTTCTTGAGATCCTTTTTTTCTGCGCG-
TAATCTGCTGCTTGCAAACAAAAAAACCACCGCTACCAGCGGTGGTTTGTTTGCCGGATCAA-
GAGCTACCAACTCTTTTTCCGAAGGTAACTGGCTTCAGCAGAGCGCAGATACCAAA-
TACTGTCCTTCTAGTGTAGCCGTAGTTAGGCCACCACTTCAAGAACTCTGTAGCACCGCC-
TACATACCTCGCTCTGCTAATCCTGTTACCAGTGGCTGCTGCCAGTGGCGATAAGTCGTGTCT-
TACCGGGTTGGACTCAAGACGATAGTTACCGGATAAGGCGCAGCGGTCGGGCTGAAC-
GGGGGGTTCGTGCACACAGCCCAGCTTGGAGCGAACGACCTACACCGAACTGAGATAC-
CTACAGCGTGAGCTATGAGAAAGCGCCACGCTTCCCGAAGGGAGAAAGGCG-
GACAGGTATCCGGTAAGCGGCAGGGTCGGAACAGGAGAGCGCACGAGGGAGCTTCCAGGGG

Fig. 21F

GAAACGCCTGGTATCTTTATAGTCCTGTCGGGTTTCGCCACCTCTGACTTGAGCGTCGAT-
TTTTGTGATGCTCGTCAGGGGGGCGGAGCCTATGGAAAAACGCCAGCAAC-
GCGGCCTTTTTACGGTTCCTGGCCTTTTGCTGGCCTTTT-
GCTCACATGTTCTTTCCTGCGTTATCCCCTGATTCTGTGGATAACCGTATTACCGCCTTT-
GAGTGAGCTGATACCGCTCGCCGCAGCCGAACGACCGAGCGCAGCGAGTCAGTGAGCGAG-
GAAGCGGAAGAGCGCCTGATGCGGTATTTTCTCCTTACGCATCTGTGCGGTATTTCACACCG-
CATAGGCCGCGATAGGCCGACGCGAAGCGGCGGGGCGTAGGGAGCGCAGCGACCGAAGGG-
TAGGCGCTTTTTGCAGCTCTTCGGCTGTGCGCTGGCCAGACAG-
TTATGCACAGGCCAGGCGGGTTTTAAGAGTTTTAATAAGTTTTAAAGAGTTTTAGGCG-
GAAAAATCGCCTTTTTTCTCTTTTATATCAGTCACTTACATGTGTGAC-
CGGTTCCCAATGTACGGCTTTGGGTTCCCAATGTACGGGTTCCGGTTCCCAATGTAC-
GGCTTTGGGTTCCCAATGTACGTGCTATCCACAGGAAAGAGACCTTTTCGAC-
CTTTTTCCCCTGCTAGGGCAATTTGCCCTAGCATCTGCTCCGTACATTAGGAACCGGCG-
GATGCTTCGCCCTCGATCAGGTTGCGGTAGCGCATGACTAG-
GATCGGGCCAGCCTGCCCCGCCTCCTCCTTCAAATCGTACTCCGGCAGGTCATTT-
GACCCGATCAGCTTGCGCACGGTGAAACAGAACTTCTTGAACTCTCCGGCGCTGCCAC-
TGCGTTCGTAGATCGTCTTGAACAACCATCTGGCTTCTGCCTT-
GCCTGCGGCGCGGCGTGCCAGGCGGTAGAGAAAAC-
GGCCGATGCCGGGGTCGATCAAAAAGTAATCGGGGTGAACCGTCAGCACGTCCGGGTTCTT-
GCCTTCTGTGATCTCGCGGTACATCCAATCAGCAA-
GCTCGATCTCGATGTACTCCGGCCGCCCGGTTTCGCTCTTTACGATCTT-
GTAGCGGCTAATCAAGGCTTCACCCTCGGATACCGTCACCAGGCGGCCGTTCTT-
GGCCTTCTTGGTACGCTGCATGGCAACGTGCGTGGTGTTTAACCGAATGCAGGTTTCTAC-
CAGGTCGTCTTTCTGCTTTCCGCCATCGGCTCGCCGGCAGAACTTGAGTACGTCCGCAAC-
GTGTGGACGGAACACGCGGCCGGGCTTGTCTCCCTTCCCTTCCCGGTATCGGTTCATGGAT-
TCGGTTAGATGGGAAACCGCCATCAGTACCAGGTCGTAATCCCACACAC-
TGGCCATGCCGGCGGGGCCTGCGGAAACCTCTACGTGCCCGTCTGGAAGCTCGTAGCG-
GATCACCTCGCCAGCTCGTCGGTCACGCTTCGACAGACGGAAAACGGCCAC-
GTCCATGATGCTGCGACTATCGCGGGTGCCCACGTCATAGAGCATCGGAAC-
GAAAAAATCTGGTTGCTCGTCGCCCTTGGGCGGCTTCCTAATCGACGGCGCAC-
CGGCTGCCGGCGGTTGCCGGGATTCTTTGCGGATTCGATCAGCGGCCCCTTGCCACGAT-
TCACCGGGGCGTGCTTCTGCCTCGATGCGTT-
GCCGCTGGGCGGCCTGCGCGGCCTTCAACTTCTCCAC-
CAGGTCATCACCCAGCGCCGCGCCGATTTGTACCGGGCCGGATGGTTTGCGACCGCTCAC-
GCCGATTCCTCGGGCTTGGGGGTTCCAGTGCCATTGCAGGGCCGGCAGA-
CAACCCAGCCGCTTACGCCTGGCCAACCGCCCGTTCCTCCACACATGGGGCATTCCAC-
GGCGTCGGTGCCTGGTTGTTCTTGAT-
TTTCCATGCCGCCTCCTTTAGCCGCTAAAATTCATCTACTCATTTATTCATTT-
GCTCATTTACTCTGGTAGCTGCGCGATGTATTCAGATAGCAGCTCGGTAATGGTCTTGCCTT-
GGCGTACCGCGTACATCTTCAGCTTGGTGTGATCCTCCGCCGGCAACTGAAAGTT

Fig. 21G

GACCCGCTTCATGGCTGGCGTGTCTGCCAGGCTGGCCAACGTTGCAGCCTT-
GCTGCTGCGTGCGCTCGGACGGCCGGCACTTAGCGTGTTTGTGCTTTT-
GCTCATTTTCTCTTTACCTCATTAACTCAAATGAGTTTTGAT-
TTAATTTCAGCGGCCAGCGCCTGGACCTCGCGGGCAGCGTCGCCCTCGGGTTCTGATTCAA-
GAACGGTTGTGCCGGCGGCGGCAGTGCCTGGGTAGCTCACGCGCTGCGTGATACGGGACTCAA-
GAATGGGCAGCTCGTACCCGGCCAGCGCCTCGGCAACCTCACCGCCGATGCGCGTGCCTTT-
GATCGCCCGCGACACGACAAAGGCCGCTTGTAGCCTTCCATCCGTGAC-
CTCAATGCGCTGCTTAACCAGCTCCACCAGGTCGGCGGTGGCCCAAATGTCGTAAGGGCTT-
GGCTGCACCGGAATCAGCACGAAGTCGGCTGCCTTGATCGCG-
GACACAGCCAAGTCCGCCGCCTGGGGCGCTCCGTCGATCACTAC-
GAAGTCGCGCCGGCCGATGGCCTTCAC-
GTCGCGGTCAATCGTCGGGCGGTCGATGCCGACAACGGTTAGCGGTTGATCTTCCCGCAC-
GGCCGCCCAATCGCGGGCACTGCCCTGGGGATCG-
GAATCGACTAACAGAACATCGGCCCCGGCGAGTTGCAGGGCGCGGGCTAGATGGGTT-
GCGATGGTCGTCTTGCCTGACCCGCCTTTCTGGTTAAGTACAGCGATAAC-
CTTCATGCGTTCCCCTTGCGTATTTGTTTATTTACTCATCGCATCATATACGCAGCGACCG-
CATGAC

Fig. 23A

GTGATTTTGTGCCGAGCTGCCGGTCGGGGAGCTGTTGGCTGGCTGGTGGCAGGATA-
TATTGTGGTGTAAACAAATTGACGCTTAGACAACTTAATAACACATTGCGGAC-
GTCTTTAATGTACTGAATTTAGTTACTGATCACTGATTAAGTACTGATATCGGTACCAA-
GCTTCCGCGGCTGCAGTGCAGCGTGACCCGGTCGTGCCCCTCTCTAGAGATAATGAGCATT-
GCATGTCTAAGTTATAAAAAATTACCACATATTTTTTTTGTCACACTTGTTTGAAGTGCAGTT-
TATCTATCTTTATACATATATTTAAACTTTACTCTACGAATAATATAATCTATAGTACTACAA-
TAATATCAGTGTTTTAGAGAATCATATAAATGAACAGTTAGACATGGTCTAAAGGACAATT-
GAGTATTTTGACAACAGGACTCTACAGTTTTATCTTTTTAGTGTG-
CATGTGTTCTCCTTTTTTTTTGCAAATAGCTTCACCTATATAATACTTCATCCATTTTATTAG-
TACATCCATTTAGGGTTTAGGGTTAATGGTTTTTATAGACTAATTTTTTTAGTACATCTATTT-
TATTCTATTTTAGCCTCTAAATTAAGAAAACTAAAACTCTATTTTAGTTTTTTTATTTAA-
TAGTTTAGATATAAAATAGAATAAAATAAAGTGACTAAAAATTAAACAAATACCCTTTAA-
GAAATTAAAAAAACTAAGGAAACATTTTTCTTGTTTCGAGTAGA-
TAATGCCAGCCTGTTAAACGCCGTCGACGAGTCTAACGGACACCAACCAGCGAACCAG-
CAGCGTCGCGTCGGGCCAAGCGAAGCAGACGGCACGGCATCTCTGTCGCTGCCTCTG-
GACCCCTCTCGAGAGTTCCGCTCCACCGTTGGACTTGCTCCGCTGTCGGCATCCAGAAATT-
GCGTGGCGGAGCGGCAGACGTGAGCCGGCACGGCAGGCGGCCTCCTCCTCCTCTCACGGCAC-
CGGCAGCTACGGGGGATTCCTTTCCCACCGCTCCTTCGCTTTCCCTTCCTCGCCCGCCGTAA-
TAAATAGACACCCCCTCCACACCCTCTTTCCCCAACCTCGTGTTGTTCGGAGCG-
CACACACACACAACCAGATCTCCCCCAAATCCACCCGTCGGCACCTCCGCTTCAAGGTAC-
GCCGCTCGTCCTCCCCCCCCCCCCCCCTCTCTACCTTCTCTA-
GATCGGCGTTCCGGTCCATGGTTAGGGCCCGGTAGTTCTACTTCTGTTCATGTTTGTGTTA-
GATCCGTGTTTGTGTTAGATCCGTGCTGCTAGCGTTCGTACACGGATGCGACCTGTAC-
GTCAGACACGTTCTGATTGCTAACTTGCCAGTGTTTCTCTTTGGGGAATCCTGG-
GATGGCTCTAGCCGTTCCGCAGACGGGATCGATTTCATGATTTTTTTTGTTTCGTT-
GCATAGGGTTTGGTTTGCCCTTTTCCTTTATTTCAATATATGCCGTGCACTTGTTT-
GTCGGGTCATCTTTTCATGCTTTTTTTTGTCTTGGTTGTGATGATGTGGTCTGGTT-
GGGCGGTCGTTCTAGATCGGAGTAGAATTCTGTTTCAAACTACCTGGTGGAT-
TTATTAATTTTGGATCTGTATGTGTGTGCCATACATATTCATAGTTACGAATTGAA-
GATGATGGATGGAAATATCGATCTAGGATAGGTATACATGTT-
GATGCGGGTTTTACTGATGCATATACAGAGATGCTTTTTGTTCGCTTGGTT-
GTGATGATGTGGTGTGGTTGGGCGGTCGTTCATTCGTTCTAGATCGGAGTAGAA-
TACTGTTTCAAACTACCTGGTGTATTTATTAATTTTGGAACTGTATGTGTGTGTCATA-
CATCTTCATAGTTACGAGTTTAAGATGGATGGAAATATCGATCTAGGATAGGTATACATGTT-
GATGTGGGTTTTACTGATGCATATACATGATGGCATATGCAGCATCTATTCAT-
ATGCTCTAACCTTGAGTACCTATCTATTATAA-
TAAACAAGTATGTTTTATAATTATTTCGATCTTGATATACTTGGATGATGGCATATGCAG-
CAGCTATATGTGGATTTTTTTAGCCCTGCCTTCATACGCTATTTATTTGCTTGG

Fig. 23B

TACTGTTTCTTTTGTCGATGCTCACCCTGTTGTTTGGTGTTACTTCTGCAGCCCGGGG-
GATCCACTAGTTCTAGAAACCATGGCCACCGCCGCCGCCGCGTCTACCGCGCTCAC-
TGGCGCCACTACCGCTGCGCCCAAGGCGAGGCGCCGGGCGCAC-
CTCCTGGCCACCCGCCGCGCCCTCGCCGCGCCCATCAGGTGCTCAGCGGCGTCACCCGCCATGC
CGATGGCTCCCCCGGCCACCCCGCTCCGGCCGTGGGGCCCCACCGATCCCCG-
CAAGGGCGCCGACATCCTCGTCGAGTCCCTCGAGCGCTGCGGCGTCCGCGACGTCTTCGCC-
TACCCCGGCGGCACGTCCATGGAGATCCACCAGGCACTCACCCGCTCCCCCGTCATCGCCAAC-
CACCTCTTCCGCCACGAGCAAGGGGAGGCCTTTGCGGCCTCCGGCTAC-
GCGCGCTCCTCGGGCCGCGTCGGCGTCTGCATCGCCACCTCCGGCCCCGGCGCCACCAAC-
CTTGTCTCCGCGCTCGCCGACGCGCTGCTCGATTCCGTCCCCATGGTCGCCATCACGG-
GACAGGTGCCGCGACGCATGATTGGCACCGACGCCTTCCAGGAGAC-
GCCCATCGTCGAGGTCACCCGCTCCATCACCAAGCACAACTACCTGGTCCTCGACGTCGAC-
GACATCCCCCGCGTCGTGCAGGAGGCTTTCTTCCTCGCCTCCTCTGGTCGAC-
CGGGGCCGGTGCTTGTCGACATCCCCAAGGACATCCAGCAGCAGATGGCGGTGCCTGTCTGG-
GACAAGCCCATGAGTCTGCCTGGGTACATTGCGCGCCTTCCCAAGCCCCCTGCGACTGAGTT-
GCTTGAGCAGGTGCTGCGTCTTGTTGGTGAATCCCGGCGCCCTGTTCTTTATGTT-
GGCGGTGGCTGCGCAGCATCTGGTGAGGAGTTGCGACGCTTTGTGGAGCTGACTG-
GAATCCCGGTCACAACTACTCTTATGGGCCTCGGCAACTTCCCCAGCGACGACCCAC-
TGTCTCTGCGCATGCTAGGTATGCATGGCACGGTGTATGCAAATTATGCAGTGGA-
TAAGGCCGATCTGTTGCTTGCACTTGGTGTGCGGTTTGATGATCGTGTGACAGGGAA-
GATTGAGGCTTTTGCAAGCAGGGCTAAGATTGTGCACGTTGATATTGATCCGGCTGAGATTGG-
CAAGAACAAGCAGCCACATGTGTCCATCTGTGCAGATGTTAAGCTTGCTTTGCAGGG-
CATGAATGCTCTTCTTGAAGGAAGCACATCAAAGAAGAGCTTTGACTTTGGCTCATGGAAC-
GATGAGTTGGATCAGCAGAAGAGGGAATTCCCCCTTGGGTATAAAACATCTAATGAGGA-
GATCCAGCCACAATATGCTATTCAGGTTCTTGATGAGCTGACGAAAGGCGAGGCCATCATCGG-
CACAGGTGTTGGGCAGCACCAGATGTGGGCGGCACAGTACTACACTTACAA-
GCGGCCAAGGCAGTGGTTGTCTTCAGCTGGTCTTGGGGCTATGGGATTTGGTTT-
GCCGGCTGCTGCTGGTGCTTCTGTGGCCAACCCAGGTGTTACTGTTGTTGACATCGATGGA-
GATGGTAGCTTTCTCATGAACGTTCAGGAGCTAGCTATGATCCGAATTGAGAAC-
CTCCCGGTGAAGGTCTTTGTGCTAAACAACCAGCACCTGGGGATGGTGGTGCAGTGGGAG-
GACAGGTTCTATAAGGCCAACAGAGCGCACACATACTTGGGAAACCCAGAGAATGAAAGTGA-
GATATATCCAGATTTCGTGACGATCGCCAAAGGGTTCAACATTCCAGCGGTCCGTGTGACAAA-
GAAGAACGAAGTCCGCGCAGCGATAAAGAAGATGCTCGAGACTCCAGGGCCGTACCTCTTGGA-
TATAATCGTCCCACACCAGGAGCATGTGTTGCCTATGATCCCTAATGGTGGGGCTTTCAAGGA-
TATGATCCTGGATGGTGATGGCAGGACTGTGTACTGATCTAAAATCCAGCAA-
GCAACTGATCTAAAATCCAGCAAGCACCGCCTCCCTGCTAGTACAAGGGTGA-
TATGTTTTTATCTGTGTGATGTTCTCCTGTATTCTATCTTTTTTTGTAGGCCGTCAGC-
TATCTGTTATGGTAATCCTATGTAGCTTCCGACCTTGTAATTGTGTAGTCTGTT-
GTTTTCCTTCTGGCATGTGTCATAAGAGATCATTTAAGTGCCTTTTGCTACATATAAATAAGA-
TAATAAGCACTGCTATGCAGTGGTTCTGAATTGGCTTCTGTT

Fig. 23C

GCCAAATTTAAGTGTCCAACTGGTCCTTGCTTTTGTTTTCGCTATTTTTTTCCTTTTTTAG-
TTATTATTATATTGGTAATTTCAACTCAACATATGATGTATGGAATAATGCTAGGGCTG-
CAATTTCAAACTATTTTACAAACCAGAATGGCATTTTCGTGGTTTGAGGGGAG-
TGAAAAAAAATGAGGCATTTGACTGAATTAGTTACCTGATCCATTTTCGTGGTTT-
GGATCATTGGAATTAAATTCCATTCTAATAATAGTAATTTTGGCATA-
TATCAATTAAGTTAATTCGGTTTTATGCAAAATATATTTGTATACTATTATTATCAA-
GATGTCGGAGATATTTATATGCTACATTTTTACTATACAGGAGTGAGATGAAGAG-
TGTCATGTAAGTTACACAGTAGAAACAAATTC-
TATTAATGCATAAAATCATTTCCATCATCCACCCTATGAATTTGAGATAGACCTA-
TATCTAAACTTTGAAAAGTGGTTGAATATCAAATTCCAAATTAAATAAGTTATTTTATTGAG-
TGAATTCTAATTTCTCTAAAACGAAGGGATCTAAACGCCCTCTAAAGCTAATTT-
GGAAACTCAAACTTTCTTAGCATTGGAGGGGATTGAGAAAAAA-
TATTAATTCATTTTCATCTCAATCATTCAATCTCCAAAGAGATTTGAGTTCCTTATTAG-
TCTGTTCCATGCATCAAATCGGCTCAATGTGTCATTATTTGCCATGACGATTGACGAGTT-
GTTCTGGGGCCTAGCGCTTTCCACGCCGATGTGCTGGGGCCTGGTCCTGGAGAAGACAGCTT-
GATATTTAAAGCTATCAATTGTTTCAATTGATTCCCACTTCATTTTTCTAAATGTAGAAAAC-
GGTGACGTATAAGAAAAAGAATGAATTAGGACTTTTATTCCGTACACTAATCTAGAGCGGCCG-
CAAGCTTGTACAACGCGTACCGGTTAATTAAATTACGCCAAGCTATCAACTTTGTATA-
GAAAAGTTGGCGCCCTAGGCGGCCGCACTAAGCGCTATTTAAATGTGTTGGATAATCTTTT-
GCATGGATATGTGTTGTGAATTCGCACCATGTGCCCACGAAAGCAGCATGGGGATCGCCCCAC-
CAATTTTTTTTTACCAGCTCTAACTCTCAACCAGAAAACATGCAAATTTATTTGTCATT-
GCACACCAGCAACCTAGGGATGGTAATCCCAAAATGCAATGATTTTTAGAGCATA-
GATGTGGGCGAATTTACCTAACTATGGATATGTTAATTGACAATAAAACACCATAACCAC-
TGGGTTCATGGGTACGAGTATGGTTTTGTACATGAAAGAATAAACTTATGAGAGTGTGTATA-
TACTCAACATACAAGTATAATTCCCAAAGCCATCTCCAACCTATTGTAGTCCAAAA-
TATGCATGGTCCAACAAGCACACCTATTGACATGCATATAAGCCATCACATATATATATACAC-
TAATTTTTACTATTACATATGTTATATATTTATAGATATATGTTATTTGTTTATATTGTCAG-
TGTTTACTGCGTGTGTTATATTTTTTTTCTTAGGTACGGTGTAGGTAACCACCGTGTC-
TATCTCGACACGCGTACGGGCACAAAATTACATCAACACATGGTATGAGAT-
TTTTCATGTGTCAAATAAATTTTGATGGCTAGTTTAAAAACTTAAATCACTCATGAGATTAC-
CGGAGACGATTGAGGGGAAAATTTCCTAGTATTACGGAC-
GGAATTTAAGTTTTTCAAACTAGCCCTAATAAAATAAATATGGGTATGTAGGTATGAGCGCGA-
TACCACCTGTTGCGGCGGGACTGCAGGTTTGGTGACAGCTAGAAACATGCATTTAGGTGTT-
GAATCTTGATTATTTGCAGTTAATCGTGCTTGCTGTGTTGCCGCAAACACGAGAT-
TCACACCCTGATGAGCGGAGCCAGGCTGCCCTTGCTTCGATTCAC-
GGTGGCCGTCGTCCCGGCCAGGCCAGCACACCAGTCCAATCCACATAGCAACAAC-
CGCGCCTCGGTCAGTTATAGATGCGTGGCCTTCTGAAACAAACCCTCATATGGGGTCACGCCG-
CACTCACACATGCATCCATAAACCCTCAGCAGAGCCTTGTGTCGCGTCCTCTCCTCGA-
TAACCCAGGCCACATCGTCCTTCCGCGCCGCGCCGCCGGCGAC-
CTAACAACCCAGAGGCCTCAGCACCGCACGCTTGCACGTAC

Fig. 23D

GTCCAGGCGCGCTCGCCGTTACGCCCACGGGGATCCAGGCTTTCCTTCGCTGCCGTT-
GCTGGTCGAGTGCGCCACGCCGAAAGGTGATCGAGCTGACGAGCGCTAGACGCCAC-
CGGCCGGCGCGGCGTGGCAAGGCAAGACGCCGTGCGGGTCTCGCCCTCGTCAGCTATAAGAC-
CGCATCCCCCCCTGCGGAGGGAGGCACACACACAGACACAGCGCTCTCACTAGCCTCG-
CATTCCGTCCCTGCAGTGCAGGGGCAGGCCGGTGAGGTCTGGGAGAGGAGGAGGAGGAG-
GAGGAGCGTACGGCCTAGGCCTTCACCTGCGGAGGGTAAGATCCGATCAC-
CATCTTCTGAATTTCTGTTCTTGATCTGTCATGTATAATAACTGTCTAGTCTTGGTGTT-
GGTGAGATGGAAATTCGGTGGATCTCGGAAGGGATATTGTTCGTTTGCTGGGGTTTTTTT-
GTGTGTTGTGATCCGTAGAGAATTTGTGTTTATCCATGTTGTTGATCTTGG-
TATGTATTCATGACATATTGACATGCATGTGTTGTATGTGTCATATGTGTGCCTCTCCTTGG-
GATTTGTTTTGGATAATAGAACATGTTATGGACTCAATAGTCTGTGAACAAATCTTTTTTTA-
GATGGTGGCCAAATCTGATGATGATCTTTCTTGAGAGGAAAAAGTTCATGATA-
GAAAAATCTTTTTTGAGATGGTGGCTTAATGTGATGATGATCTTTCTTGAGAGGAAAAAAAA-
GATTCATTATAGGAGATTTTGATTTAGCTCCTTTCCACCGATATTAAATGAGGAG-
CATGCATGCTGATTGCTGATAAGGATCTGATTTTTTTATCCCCTCTTCTTTGAACAGACAA-
GAAATAGGCTCTGAATTTCTGATTGATTATTTGTACATGCAGAAGGGCGAATTCGAC-
CTAGGCCAAGTTTGTACAAAAAAGCAGGCTTGATAACCAACCATGGTCCGTCCTG-
TAGAAACCCCAACCCGTGAAATCAAAAAACTCGACGGCCTGTGGGCATTCAGTCTG-
GATCGCGAAAACTGTGGAATTGATCAGCGTTGGTGGGAAAGCGCGTTACAAGAAAGCCGGG-
CAATTGCTGTGCCAGGCAGTTTTAACGATCAGTTCGCCGATGCAGATATTCG-
TAATTATGCGGGCAACGTCTGGTATCAGCGCGAAGTCTTTATACCGAAAGGTTGGG-
CAGGCCAGCGTATCGTGCTGCGTTTCGATGCGGTCACTCATTACGGCAAAGTGTGGGTCAA-
TAATCAGGAAGTGATGGAGCATCAGGGCGGCTATACGCCATTTGAAGCCGATGTCACGCCG-
TATGTTATTGCCGGGAAAAGTGTACGTAAGTTTCTGCTTCTACCTTTGATATATATATAA-
TAATTATCATTAATTAGTAGTAATATAATATTTCAAATATTTTTTTCAAAATAAAA-
GAATGTAGTATATAGCAATTGCTTTTCTGTAGTTTATAAGTGTG-
TATATTTTAATTTATAACTTTTCTAATATATGACCAAAATTTGTTGATGTGCAGGTATCAC-
CGTTTGTGTGAACAACGAACTGAACTGGCAGACTATCCCGCCGGGAATGGTGATTACCGAC-
GAAAACGGCAAGAAAAAGCAGTCTTACTTCCATGATTTCTTTAACTATGCCGGAATCCATCG-
CAGCGTAATGCTCTACACCACGCCGAACACCTGGGTGGACGATATCACCGTGGTGAC-
GCATGTCGCGCAAGACTGTAACCACGCGTCTGTTGACTGG-
CAGGTGGTGGCCAATGGTGATGTCAGCGTTGAACTGCGTGATGCGGATCAACAGGTGGTT-
GCAACTGGACAAGGCACTAGCGGGACTTTGCAAGTGGTGAATCCGCACCTCTGGCAAC-
CGGGTGAAGGTTATCTCTATGAACTGTGCGTCACAGCCAAAAGCCAGACAGAGTGTGA-
TATCTACCCGCTTCGCGTCGGCATCCGGTCAGTGGCAGTGAAGGGCGAACAGTTCCTGAT-
TAACCACAAACCGTTCTACTTTACTGGCTTTGGTCGTCATGAAGATGCGGACTTGCGTGG-
CAAAGGATTCGATAACGTGCTGATGGTGCACGACCACGCATTAATGGACTG-
GATTGGGGCCAACTCCTACCGTACCTCGCATTACCCTTACGCTGAAGAGATGCTCGACTGGG-
CAGATGAACATGGCATCGTGGTGATTGATGAAACTGCTGCTGTCGGCTTTAAC-
CTCTCTTTAGGCATTGGTTTCGAAGCGGGCAACAAGCCGAAAGAACTGTACAGCGAA

Fig. 23E

GAGGCAGTCAACGGGGAAACTCAGCAAGCGCACTTACAGGCGATTAAAGAGCTGA-
TAGCGCGTGACAAAAACCACCCAAGCGTGGTGATGTGGAGTATTGCCAACGAACCGGA-
TACCCGTCCGCAAGGTGCACGGGAATATTTCGCGCCACTGGCGGAAGCAACGCG-
TAAACTCGACCCGACGCGTCCGATCACCTGCGTCAATGTAATGTTCTGCGACGCTCACACCGA-
TACCATCAGCGATCTCTTTGATGTGCTGTGCCTGAACCGTTATTACGGATGGTATGTCCAAA-
GCGGCGATTTGGAAACGGCAGAGAAGGTACTGGAAAAAGAACTTCTGGCCTGGCAGGA-
GAAACTGCATCAGCCGATTATCATCACCGAATACGGCGTGGATACGTTAGCCGGGCTGCAC-
TCAATGTACACCGACATGTGGAGTGAAGAGTATCAGTGTGCATGGCTGGATATGTATCAC-
CGCGTCTTTGATCGCGTCAGCGCCGTCGTCGGTGAACAGGTATGGAATTTCGCCGATTTT-
GCGACCTCGCAAGGCATATTGCGCGTTGGCGGTAACAAGAAAGGGATCTTCACTCGCGACCG-
CAAACCGAAGTCGGCGGCTTTTCTGCTGCAAAAACGCTGGACTGG-
CATGAACTTCGGTGAAAAACCGCAGCAGGGAGGCAAACAATGAATCAAACCCAGCTTTCTT-
GTACAAAGTGGGACCTAGGATCGTTCAAACATTTGGCAATAAAGTTTCTTAA-
GATTGAATCCTGTTGCCGGTCTTGCGATGATTATCATATAATTTCTGTTGAATTACGTTAA-
GCATGTAATAATTAACATGTAATGCATGACGTTATTTATGAGATGGGTTTTTATGATTAGAG-
TCCCGCAATTATACATTTAATACGCGATAGAAAACAAAATATAGCGCGCAAACTAGGATAAAT-
TATCGCGCGCGGTGTCATCTATGTTACTAGATCGAATTCAACTTTATTATACATAGTTGA-
TAATTCACTGGGCCGGCCAGGCCTTAGTTACTAATCAG-
TGATCAGATTGTCGTTTCCCGCCTTCAGTTTAAACTATCAGTGTTTGACAGGATA-
TATTGGCGGGTAAACCTAAGAGAAAAGAGCGTTTATTAGAATAATCGGA-
TATTTAAAAGGGCGTGAAAAGGTTTATCCGTTCGTCCATTTGTATGTCAA-
TATTGGGGGGGGGGGAAAGCCACGTTGTGTCTCAAAATCTCTGATGTTACATTGCACAAGA-
TAAAAATATATCATCATGAACAATAAAACTGTCTGCTTACATAAACAG-
TAATACAAGGGGTGTTCGCCACCATGAGCCATATCCAGCGTGAAAC-
CTCGTGCTCCCGCCCGCGCCTCAATTCCAATATGGATGCCGACCTTTATGGC-
TACAAGTGGGCGCGCGACAACGTCGGCCAGTCGGGCGCGACCATTTATCGGCTTTATGG-
CAAACCCGATGCCCCGGAACTGTTCCTGAAGCACGGCAAAGGCAGCGTCGCAAAC-
GATGTCACCGATGAGATGGTCCGCCTGAACTGGCTTACCGAGTTCATGCCGCTGCCGACGAT-
TAAGCATTTCATCCGTACCCCGGACGATGCCTGGCTCTTGACCACGGCCATTCCGGG-
CAAAACGGCCTTTCAGGTCCTTGAAGAGTACCCGGACTCCGGTGAGAATATCGTGGAC-
GCCCTCGCGGTCTTCCTCCGCCGTTTGCATAGCATCCCCGTGTGCAACTGCCCCTTCAACTCG-
GACCGGGTTTTCCGCCTGGCACAGGCCCAGTCGCGCATGAATAACGGCCTCGTTGAC-
GCGAGCGATTTCGACGATGAACGGAATGGCTGGCCGGTGGAACAGGTTT-
GGAAGGAAATGCACAAACTGCTTCCGTTCTCGCCGGATTCGGTGGTCACGCATGGTGAT-
TTTTCCCTGGATAATCTGATCTTTGACGAGGGCAAGCTGATCGGCTGCATCGAC-
GTGGGTCGCGTCGGTATCGCCGACCGCTATCAGGACCTGGCGATCTTGTGGAATT-
GCCTCGGCGAGTTCTCGCCCTCGCTCCAGAAGCGCCTGTTCCAGAAGTACGG-
CATCGACAACCCGGATATGAACAAGCTCCAGTTCCACCTCATGCTGGACGAATTTTTTT-
GAACAGAATTGGTTAATTGGTTGTAACACTGGCAGAGCATTACGCTGACTTGACGGGAC-
GGCGGCTTTGTTGAATAAATCGAACTTTTGCTGAGTTGAAGGATCGATGAGTT

Fig. 23F

GAAGGACCCCGTAGAAAAGATCAAAGGATCTTCTTGAGATCCTTTTTTTCTGCGCG-
TAATCTGCTGCTTGCAAACAAAAAAACCACCGCTACCAGCGGTGGTTTGTTTGCCGGATCAA-
GAGCTACCAACTCTTTTTCCGAAGGTAACTGGCTTCAGCAGAGCGCAGATACCAAA-
TACTGTCCTTCTAGTGTAGCCGTAGTTAGGCCACCACTTCAAGAACTCTGTAGCACCGCC-
TACATACCTCGCTCTGCTAATCCTGTTACCAGTGGCTGCTGCCAGTGGCGATAAGTCGTGTCT-
TACCGGGTTGGACTCAAGACGATAGTTACCGGATAAGGCGCAGCGGTCGGGCTGAAC-
GGGGGGTTCGTGCACACAGCCCAGCTTGGAGCGAACGACCTACACCGAACTGAGATAC-
CTACAGCGTGAGCTATGAGAAAGCGCCACGCTTCCCGAAGGGAGAAAGGCG-
GACAGGTATCCGGTAAGCGGCAGGGTCGGAACAGGAGAGCGCACGAGGGAGCTTCCAGGGG-
GAAACGCCTGGTATCTTTATAGTCCTGTCGGGTTTCGCCACCTCTGACTTGAGCGTCGAT-
TTTTGTGATGCTCGTCAGGGGGGCGGAGCCTATGGAAAAACGCCAGCAAC-
GCGGCCTTTTTACGGTTCCTGGCCTTTTGCTGGCCTTTT-
GCTCACATGTTCTTTCCTGCGTTATCCCCTGATTCTGTGGATAACCGTATTACCGCCTTT-
GAGTGAGCTGATACCGCTCGCCGCAGCCGAACGACCGAGCGCAGCGAGTCAGTGAGCGAG-
GAAGCGGAAGAGCGCCTGATGCGGTATTTTCTCCTTACGCATCTGTGCGGTATTTCACACCG-
CATAGGCCGCGATAGGCCGACGCGAAGCGGCGGGGCGTAGGGAGCGCAGCGACCGAAGGG-
TAGGCGCTTTTTGCAGCTCTTCGGCTGTGCGCTGGCCAGACAG-
TTATGCACAGGCCAGGCGGGTTTTAAGAGTTTTAATAAGTTTTAAAGAGTTTTAGGCG-
GAAAAATCGCCTTTTTTCTCTTTTATATCAGTCACTTACATGTGTGAC-
CGGTTCCCAATGTACGGCTTTGGGTTCCCAATGTACGGGTTCCGGTTCCCAATGTAC-
GGCTTTGGGTTCCCAATGTACGTGCTATCCACAGGAAAGAGACCTTTTCGAC-
CTTTTTCCCCTGCTAGGGCAATTTGCCCTAGCATCTGCTCCGTACATTAGGAACCGGCG-
GATGCTTCGCCCTCGATCAGGTTGCGGTAGCGCATGACTAG-
GATCGGGCCAGCCTGCCCCGCCTCCTCCTTCAAATCGTACTCCGGCAGGTCATTT-
GACCCGATCAGCTTGCGCACGGTGAAACAGAACTTCTTGAACTCTCCGGCGCTGCCAC-
TGCGTTCGTAGATCGTCTTGAACAACCATCTGGCTTCTGCCTT-
GCCTGCGGCGCGGCGTGCCAGGCGGTAGAGAAAAC-
GGCCGATGCCGGGGTCGATCAAAAAGTAATCGGGGTGAACCGTCAGCACGTCCGGGTTCTT-
GCCTTCTGTGATCTCGCGGTACATCCAATCAGCAA-
GCTCGATCTCGATGTACTCCGGCCGCCCGGTTTCGCTCTTTACGATCTT-
GTAGCGGCTAATCAAGGCTTCACCCTCGGATACCGTCACCAGGCGGCCGTTCTT-
GGCCTTCTTGGTACGCTGCATGGCAACGTGCGTGGTGTTTAACCGAATGCAGGTTTCTAC-
CAGGTCGTCTTTCTGCTTTCCGCCATCGGCTCGCCGGCAGAACTTGAGTACGTCCGCAAC-
GTGTGGACGGAACACGCGGCCGGGCTTGTCTCCCTTCCCTTCCCGGTATCGGTTCATGGAT-
TCGGTTAGATGGGAAACCGCCATCAGTACCAGGTCGTAATCCCACACAC-
TGGCCATGCCGGCGGGGCCTGCGGAAACCTCTACGTGCCCGTCTGGAAGCTCGTAGCG-
GATCACCTCGCCAGCTCGTCGGTCACGCTTCGACAGACGGAAAACGGCCAC-
GTCCATGATGCTGCGACTATCGCGGGTGCCCACGTCATAGAGCATCGGAAC-
GAAAAAATCTGGTTGCTCGTCGCCCTTGGGCGGCTTCCTAATCGACGGCGCAC-
CGGCTGCCGGCGGTTGCCGGGATTCTTTGCGGATTCGATCAGCGGCCCCTTGCCACGAT

Fig. 23G

TCACCGGGGCGTGCTTCTGCCTCGATGCGTT-
GCCGCTGGGCGGCCTGCGCGGCCTTCAACTTCTCCAC-
CAGGTCATCACCCAGCGCCGCGCCGATTTGTACCGGGCCGGATGGTTTGCGACCGCTCAC-
GCCGATTCCTCGGGCTTGGGGGTTCCAGTGCCATTGCAGGGCCGGCAGA-
CAACCCAGCCGCTTACGCCTGGCCAACCGCCCGTTCCTCCACACATGGGGCATTCCAC-
GGCGTCGGTGCCTGGTTGTTCTTGAT-
TTTCCATGCCGCCTCCTTTAGCCGCTAAAATTCATCTACTCATTTATTCATTT-
GCTCATTTACTCTGGTAGCTGCGCGATGTATTCAGATAGCAGCTCGGTAATGGTCTTGCCTT-
GGCGTACCGCGTACATCTTCAGCTTGGTGTGATCCTCCGCCGGCAACTGAAAGTT-
GACCCGCTTCATGGCTGGCGTGTCTGCCAGGCTGGCCAACGTTGCAGCCTT-
GCTGCTGCGTGCGCTCGGACGGCCGGCACTTAGCGTGTTTGTGCTTTT-
GCTCATTTTCTCTTTACCTCATTAACTCAAATGAGTTTTGAT-
TTAATTTCAGCGGCCAGCGCCTGGACCTCGCGGGCAGCGTCGCCCTCGGGTTCTGATTCAA-
GAACGGTTGTGCCGGCGGCGGCAGTGCCTGGGTAGCTCACGCGCTGCGTGATACGGGACTCAA-
GAATGGGCAGCTCGTACCCGGCCAGCGCCTCGGCAACCTCACCGCCGATGCGCGTGCCTTT-
GATCGCCCGCGACACGACAAAGGCCGCTTGTAGCCTTCCATCCGTGAC-
CTCAATGCGCTGCTTAACCAGCTCCACCAGGTCGGCGGTGGCCCAAATGTCGTAAGGGCTT-
GGCTGCACCGGAATCAGCACGAAGTCGGCTGCCTTGATCGCG-
GACACAGCCAAGTCCGCCGCCTGGGGCGCTCCGTCGATCACTAC-
GAAGTCGCGCCGGCCGATGGCCTTCACTCGCGGTCAATCGTCGGGCGGTCGATGCCGACAAC-
GGTTAGCGGTTGATCTTCCCGCACGGCCGCCCAATCGCGGGCACTGCCCTGGGGATCG-
GAATCGACTAACAGAACATCGGCCCCGGCGAGTTGCAGGGCGCGGGCTAGATGGGTT-
GCGATGGTCGTCTTGCCTGACCCGCCTTTCTGGTTAAGTACAGCGATAAC-
CTTCATGCGTTCCCCTTGCGTATTTGTTTATTTACTCATCGCATCATATACGCAGCGACCG-
CATGACGCAAGCTGTTTTACTCAAATACACATCACCTTTTTAGATGATCA

SEQUENCE LISTING

```
<160> NUMBER OF SEQ ID NOS: 131

<210> SEQ ID NO 1
<211> LENGTH: 1198
<212> TYPE: DNA
<213> ORGANISM: Zea mays

<400> SEQUENCE: 1

tcccgtgtcc gtcaatgtga tactactagc atagtactag taccatgcat acacacagca      60

ggtcggccgc ctggatggat cgatgatgat actacatcat cctgtcatcc atccaggcga     120

tctagaaggg gcgtggctag ctagcaaact gtgaccggtt tttctacgcc gataataata     180

ctttgtcatg gtacagacgt acagtactgg ttatatatat ctgtagattt caactgaaaa     240

gctaggatag ctagattaat tcctgagaaa cacagataaa attcgagctt ggctatagat     300
```

-continued

```
gacaaaacgg aagacgcatg cattggacga cgtatgcaat gcgagcgcgt ctcgtgtcgt    360
cccgtccaag tctggcgatc tcacgccacg tgctcaacag ctcaaggact gttcgtcacc    420
agcgttaaat tcattgaagg gatgacgcat ttcggcattt gtcattgctt gtagctatat    480
atatatatcc aacagatttc tctcaagctt ttgtatgcgt gaatgtaaag tctagcttat    540
acgacagcac gtgcagatat attaacgtca ttattaggtg gagagcaaga tgcatgatct    600
ggtagaaatt gtcgaaaaca caagagagag tgaagtgcac acttctggta taggagtgta    660
tacgccgctg gttggtgggc aatgcgcgcc gcaatattgg ccaatgaaac ctagcaacgc    720
ccactcgcca cgccccatga atggcccccg cacggcagcg agccagccag tgcccgcgcg    780
cggcccagcc ggagtcggcg gaacgcgcca cgggggacga ggcgcccgag ggccgaggca    840
gcgcggcatg gcaagcaagc cgaagcgggc aagcgacctg catgcagccc ctgcccctcg    900
ccctcgtcag tcgtcccagc ctcccactgg aatccaccca acccgccctt cctctccaaa    960
gcacgcgccc cgcgactcgc ctccgcctac gtgtcggcag cgtccccgcc ggtcgcccac   1020
gtaccccgcc ccgttctccc acgtgcccct ccctctgcgc gcgtccgatt ggctgacccg   1080
cccttcttaa gccgcgccag cctcctgtcc gggccccaac gccgtgctcc gtcgtcgtct   1140
ccgcccccag agtgatcgag cccactgacc tggcccccga gcctcagctc gtgagtcc     1198
```

<210> SEQ ID NO 2
<211> LENGTH: 1008
<212> TYPE: DNA
<213> ORGANISM: Zea mays

<400> SEQUENCE: 2

```
taactcatat ccggttagat accaactaca catattgaat agcataaatc taataaatat     60
atggcgcaat gaaaatagta aataattaaa tatgagtaaa taatatgatg acaataatga    120
ataatattgg aacatgtaca ttgaccctat tttgctaata tatacttatt atatttgctt    180
aatttggtag gatgtatatg tgattgaggc gggtataaat tatccatagg tatgtgggta    240
taaatagtct atacttatac ccatactcat atacccgacg ggtatatgat tgtgtccatt    300
gccatatctg cgggtaaaaa actcattata tacttgtcct tataagtaaa acctgttgga    360
cactagagtt taggtaccat ataattatta attttgaacg aaggaagtaa tttgcagcgt    420
attaaggtgc ttctggtcta gaagaaatgt cacaatgttt ggtgttagtt tttggtgaaa    480
tttaaggtta attacttttt gaaagatgtt tccactaggt ggaaccgaaa gaaacggtgc    540
caaacacacc ttacaacaag aaaatatttg taaaaaaatt attttgaata agatgtctaa    600
aaatagaaag cgtgtatact ttaggacgga ggaatacata tgtatgattg ggaaaaccga    660
aaacgtacac ctcctcgctg caatacgctg gtgacttggc agttcgatcg cacccagcgg    720
ataaagatga gcacggagaa ctcacaaggc acagccgcac aggcaggcac cagcgcgaac    780
gcatggacgg gcggcccctg agacgtgccg cccagctggc ccgctgcgcc cacacgtggc    840
gcggagctgc gcgcggctcg gccacgttat aagccacgcg cgctggccgt cgccgcacct    900
cctgactact gcacactcgt ctccgcagtt tgaaacgaag cccgcggcta ctgcaagcta    960
ctccgtctcc gtagctaaag gagaggtagg tttttatttg gcgacgac                1008
```

<210> SEQ ID NO 3
<211> LENGTH: 1492
<212> TYPE: DNA
<213> ORGANISM: Zea mays

<400> SEQUENCE: 3

```
gtgttggata atcttttgca tggatatgtg ttgtgaattc gcaccatgtg cccacgaaag     60
cagcatgggg atcgccccac caattttttt ttaccagctc taactctcaa ccagaaaaca    120
tgcaaattta tttgtcattg cacaccagca acctagggat ggtaatccca aaatgcaatg    180
atttttagag catagatgtg ggcgaattta cctaactatg gatatgttaa ttgacaataa    240
aacaccataa ccactgggtt catgggtacg agtatggttt tgtacatgaa agaataaact    300
tatgagagtg tgtatatact caacatacaa gtataattcc caaagccatc tccaacctat    360
tgtagtccaa aatatgcatg gtccaacaag cacacctatt gacatgcata taagccatca    420
catatatata tacactaatt tttactatta catatgttat atatttatag atatatgtta    480
tttgtttata ttgtcagtgt ttactgcgtg tgttatattt tttttcttag gtacggtgta    540
ggtaaccacc gtgtctatct cgacacgcgt acgggcacaa aattacatca acacatggta    600
tgagattttt catgtgtcaa ataaattttg atggctagtt taaaaactta aatcactcat    660
gagattaccg gagacgattg aggggaaaat ttcctagtat tacggacgga atttaagttt    720
ttcaaactag ccctaataaa ataaatatgg gtatgtaggt atgagcgcga taccacctgt    780
tgcggcggga ctgcaggttt ggtgacagct agaaacatgc atttaggtgt tgaatcttga    840
ttatttgcag ttaatcgtgc ttgctgtgtt gccgcaaaca cgagattcac accctgatga    900
gcggagccag gctgcccttg cttcgattca cggtggccgt cgtcccggcc aggccagcac    960
accagtccaa tccacatagc aacaaccgcg cctcggtcag ttatagatgc gtggccttct   1020
gaaacaaacc ctcatatggg gtcacgccgc actcacacat gcatccataa accctcagca   1080
gagccttgtg tcgcgtcctc tcctcgataa cccaggccac atcgtccttc cgcgccgcgc   1140
cgccggcgac ctaacaaccc agaggcctca gcaccgcacg cttgcacgta cgtccaggcg   1200
cgctcgccgt tacgcccacg gggatccagg ctttccttcg ctgccgttgc tggtcgagtg   1260
cgccacgccg aaaggtgatc gagctgacga gcgctagacg ccaccggccg gcgcggcgtg   1320
gcaaggcaag acgccgtgcg ggtctcgccc tcgtcagcta taagaccgca tcccccccctg   1380
cggagggagg cacacacaca gacacagcgc tctcactagc ctcgcattcc gtccctgcag   1440
tgcaggggca ggccggtgag gtctgggaga ggaggaggag gaggaggagg ag            1492
```

<210> SEQ ID NO 4
<211> LENGTH: 984
<212> TYPE: DNA
<213> ORGANISM: Zea mays

<400> SEQUENCE: 4

```
atggccatgg tgcagccggc ggacacggcc gtcaaggcca acgagatcct ggcgcggttc     60
cggcccatcg cgcccaagcc cacactggca gcagccgccg ccgccgccgc ggcgcccgtg    120
gcgcaggccg cggccgaggg cgtcgtggcc gcgaaccgcg tgctgtgcca tctgcagagc    180
aggccgtgcc gcgcgcgcaa gcgcggccgc cccaccgtcg tgccggtgtc gcccaagtcg    240
ggcgcgcagc cgcccgcgaa gcggaggaga gcctctacgc cgtacccgcc tctccggtgc    300
gcggcggcga ccacgggggc gcatgtgtcc gcggtcgtcc caggcagtgc gcgtctccca    360
ccggcgagtg cgggtgtcga agacatcgcg aaggcggcgg cggcggcggc gacagaggag    420
gggagggacg tccccgtgga gcgcgacctg ctgcggaagc tgctggagcc cagggtcata    480
tcgccgcggg cggtgcgccc ggtgtggtct gccatccacg tcgggtgcat ccaccgcacc    540
gacgacgcgg cctgcaccga cgccgccgtc tcgaagacgg cggttcaggt ggaggcggag    600
```

-continued

```
ctggaggtcg acgcgctccc ggcggtggtc tccgactcag gcaaccgcgt ccggctcgtg    660

aacgacgcgt acaaggagat ggtggggcag cccgagtgcc cgtggctcga cgccgtggct    720

gccacgtcga ggaggatcag cggggaggtg gcgctggtgg tagcggaccg gtcctctctg    780

ccggactcgt acggggcgtt cacatgcacg gcaaagatcg agtgggagga cgacgggaag    840

gtcacctcca tcgctgcacc ctgcgacgtc agccggctgc agtgcgagtc cagggattac    900

ctcttcgcct ggaggttccg caccgccgcc gccgacgccg acgcatccgt tggacacagc    960

tccgaggaga ttagtgagag ttag                                           984


<210> SEQ ID NO 5
<211> LENGTH: 327
<212> TYPE: PRT
<213> ORGANISM: Zea mays

<400> SEQUENCE: 5

Met Ala Met Val Gln Pro Ala Asp Thr Ala Val Lys Ala Asn Glu Ile
1               5                   10                  15

Leu Ala Arg Phe Arg Pro Ile Ala Pro Lys Pro Thr Leu Ala Ala Ala
            20                  25                  30

Ala Ala Ala Ala Ala Ala Pro Val Ala Gln Ala Ala Ala Glu Gly Val
        35                  40                  45

Val Ala Ala Asn Arg Val Leu Cys His Leu Gln Ser Arg Pro Cys Arg
    50                  55                  60

Ala Arg Lys Arg Gly Arg Pro Thr Val Val Pro Val Ser Pro Lys Ser
65                  70                  75                  80

Gly Ala Gln Pro Pro Ala Lys Arg Arg Arg Ala Ser Thr Pro Tyr Pro
                85                  90                  95

Pro Leu Arg Cys Ala Ala Ala Thr Thr Gly Ala His Val Ser Ala Val
            100                 105                 110

Val Pro Gly Ser Ala Arg Leu Pro Pro Ala Ser Ala Gly Val Glu Asp
        115                 120                 125

Ile Ala Lys Ala Ala Ala Ala Ala Ala Thr Glu Glu Gly Arg Asp Val
    130                 135                 140

Pro Val Glu Arg Asp Leu Leu Arg Lys Leu Leu Glu Pro Arg Val Ile
145                 150                 155                 160

Ser Pro Arg Ala Val Arg Pro Val Trp Ser Ala Ile His Val Gly Cys
                165                 170                 175

Ile His Arg Thr Asp Asp Ala Ala Cys Thr Asp Ala Ala Val Ser Lys
            180                 185                 190

Thr Ala Val Gln Val Glu Ala Glu Leu Glu Val Asp Ala Leu Pro Ala
        195                 200                 205

Val Val Ser Asp Ser Gly Asn Arg Val Arg Leu Val Asn Asp Ala Tyr
    210                 215                 220

Lys Glu Met Val Gly Gln Pro Glu Cys Pro Trp Leu Asp Ala Val Ala
225                 230                 235                 240

Ala Thr Ser Arg Arg Ile Ser Gly Glu Val Ala Leu Val Val Ala Asp
                245                 250                 255

Arg Ser Ser Leu Pro Asp Ser Tyr Gly Ala Phe Thr Cys Thr Ala Lys
            260                 265                 270

Ile Glu Trp Glu Asp Asp Gly Lys Val Thr Ser Ile Ala Ala Pro Cys
        275                 280                 285

Asp Val Ser Arg Leu Gln Cys Glu Ser Arg Asp Tyr Leu Phe Ala Trp
    290                 295                 300
```

Arg Phe Arg Thr Ala Ala Ala Asp Ala Asp Ala Ser Val Gly His Ser
305 310 315 320

Ser Glu Glu Ile Ser Glu Ser
325

<210> SEQ ID NO 6
<211> LENGTH: 789
<212> TYPE: DNA
<213> ORGANISM: Zea mays

<400> SEQUENCE: 6
atgagcacgg gcgtgcgacc ggggcggcgg ttcacggtgg ggcggagcga ggacgccacg 60
cacccggaca ccatccgcgc cgccatctcc gagttcatcg ccaccgccat cttcgtcttc 120
gccgccgagg gatccgtcct ctcgctcggg aagatgtacc acgacatgag cacggcgggc 180
ggcctggtgg ctgtggcgct ggcgcacgcg ctggccctgg ccgtggccgt ggcagtggcc 240
gtcaacatct cgggcgggca cgtgaacccg gcggtcacct tcggcgcgct cgtcggcggc 300
cgcgtctccc tcgtccgcgc ggtcttgtac tgggtcgcgc agctgctggg cgccgtcgcc 360
gccacgctgc tcctgcggct cgccacgggg ggcatgcggc cgccggggtt cgcgctcgcg 420
tccggggtcg gggactggca cgccgtgctg ctggaggccg tcatgacgtt cggcctcatg 480
tacgcctact acgccacggt gatcgacccg aagcgggggc acgtgggcac catcgcgccg 540
ctggccgtgg gcttcctgct cggcgccaac gtgctggcgg gagggccctt cgacggcgca 600
gggatgaacc cggcgcgggt cttcggcccg gcgctcgtcg ggtggcggtg gaggcaccac 660
tgggtgtact ggctgggccc tttcctcggc gccgggcttg cagggctggt gtacgagtac 720
ctggttatcc cgtccgccga cgccgccgtg ccccacgcgc accagccgct cgcgccagag 780
gactactag 789

<210> SEQ ID NO 7
<211> LENGTH: 262
<212> TYPE: PRT
<213> ORGANISM: Zea mays

<400> SEQUENCE: 7

Met Ser Thr Gly Val Arg Pro Gly Arg Arg Phe Thr Val Gly Arg Ser
1 5 10 15

Glu Asp Ala Thr His Pro Asp Thr Ile Arg Ala Ala Ile Ser Glu Phe
20 25 30

Ile Ala Thr Ala Ile Phe Val Phe Ala Ala Glu Gly Ser Val Leu Ser
35 40 45

Leu Gly Lys Met Tyr His Asp Met Ser Thr Ala Gly Gly Leu Val Ala
50 55 60

Val Ala Leu Ala His Ala Leu Ala Leu Ala Val Ala Val Ala Val Ala
65 70 75 80

Val Asn Ile Ser Gly Gly His Val Asn Pro Ala Val Thr Phe Gly Ala
85 90 95

Leu Val Gly Gly Arg Val Ser Leu Val Arg Ala Val Leu Tyr Trp Val
100 105 110

Ala Gln Leu Leu Gly Ala Val Ala Ala Thr Leu Leu Leu Arg Leu Ala
115 120 125

Thr Gly Gly Met Arg Pro Pro Gly Phe Ala Leu Ala Ser Gly Val Gly
130 135 140

Asp Trp His Ala Val Leu Leu Glu Ala Val Met Thr Phe Gly Leu Met
145 150 155 160

Tyr Ala Tyr Tyr Ala Thr Val Ile Asp Pro Lys Arg Gly His Val Gly
165 170 175

Thr Ile Ala Pro Leu Ala Val Gly Phe Leu Leu Gly Ala Asn Val Leu
180 185 190

Ala Gly Gly Pro Phe Asp Gly Ala Gly Met Asn Pro Ala Arg Val Phe
195 200 205

Gly Pro Ala Leu Val Gly Trp Arg Trp Arg His His Trp Val Tyr Trp
210 215 220

Leu Gly Pro Phe Leu Gly Ala Gly Leu Ala Gly Leu Val Tyr Glu Tyr
225 230 235 240

Leu Val Ile Pro Ser Ala Asp Ala Ala Val Pro His Ala His Gln Pro
245 250 255

Leu Ala Pro Glu Asp Tyr
260

<210> SEQ ID NO 8
<211> LENGTH: 588
<212> TYPE: DNA
<213> ORGANISM: Zea mays

<400> SEQUENCE: 8
atggcggcgg cgctgcgctg cgctggaagg atcgggatcc tggccaccgt cgcagtgaac 60
ctcgcgtgga tcgcgacgta catccgccgg cgctacttcg gcggcgggaa ccgatccgac 120
aacaacggtg gcggcgggga ggtggagccg tcaagaggga agccgccggt cacttcggac 180
tccatcgtca acctcgatgg cgacccgact atgtacgagg agttctggcg cggcacagga 240
gatagcgcct cgatcttcat ccctggttgg caaacaatga gctacttctc cgacctcggc 300
ggcatctgtt ggttcctgga gcctggattc gagcgcgagg tgcggcgtct ccacaggctc 360
gtggggaatg ccgttgtaga cggtaccat gtgctcgtcg ggacaggctc cactcagctc 420
tttcaggccg tgctgtacgc gctctcacct gcaagtgacg gcacacccat gaacgtcgtc 480
tcaccggcac cgtactactc ggtaagaata cgttcagcca tcaaccaatc aatcaataaa 540
attgtggttc gattgattaa tcatctgcta gctgatgatc gattttga 588

<210> SEQ ID NO 9
<211> LENGTH: 195
<212> TYPE: PRT
<213> ORGANISM: Zea mays

<400> SEQUENCE: 9

Met Ala Ala Ala Leu Arg Cys Ala Gly Arg Ile Gly Ile Leu Ala Thr
1 5 10 15

Val Ala Val Asn Leu Ala Trp Ile Ala Thr Tyr Ile Arg Arg Arg Tyr
20 25 30

Phe Gly Gly Gly Asn Arg Ser Asp Asn Asn Gly Gly Gly Gly Glu Val
35 40 45

Glu Pro Ser Arg Gly Lys Pro Pro Val Thr Ser Asp Ser Ile Val Asn
50 55 60

Leu Asp Gly Asp Pro Thr Met Tyr Glu Glu Phe Trp Arg Gly Thr Gly
65 70 75 80

Asp Ser Ala Ser Ile Phe Ile Pro Gly Trp Gln Thr Met Ser Tyr Phe
85 90 95

Ser Asp Leu Gly Gly Ile Cys Trp Phe Leu Glu Pro Gly Phe Glu Arg
100 105 110

-continued

```
Glu Val Arg Arg Leu His Arg Leu Val Gly Asn Ala Val Val Asp Gly
        115                 120                 125

Tyr His Val Leu Val Gly Thr Gly Ser Thr Gln Leu Phe Gln Ala Val
    130                 135                 140

Leu Tyr Ala Leu Ser Pro Ala Ser Asp Gly Thr Pro Met Asn Val Val
145                 150                 155                 160

Ser Pro Ala Pro Tyr Tyr Ser Val Arg Ile Arg Ser Ala Ile Asn Gln
                165                 170                 175

Ser Ile Asn Lys Ile Val Val Arg Leu Ile Asn His Leu Leu Ala Asp
            180                 185                 190

Asp Arg Phe
        195


<210> SEQ ID NO 10
<211> LENGTH: 231
<212> TYPE: DNA
<213> ORGANISM: Zea mays

<400> SEQUENCE: 10

gcgtacgagt gggaggacga cgggaaggtc acctccatcg ctgcaccctg cgacgtcagc     60

cggctgcagt gcgagtcaga gatacctctt cgcctggagg ttccgcaccg ccgccgccga    120

cgccgacgca tccgttgggc acagctcaga ggagattagt gagagttagg gaaggttgag    180

ctgcatccaa tgaaaccaag tgcatagact aagccgctag ctgcatgtta a             231


<210> SEQ ID NO 11
<211> LENGTH: 451
<212> TYPE: DNA
<213> ORGANISM: Zea mays

<400> SEQUENCE: 11

ccggggtggt ctccgactca ggcaaccgcg tccggctcgt gaacgacgcg tacaaggaga     60

tggtggggca gcccgagtgc ccgtggctcg acgccgtggc tgccacgtcg aggaggatca    120

gcggggaggt ggcgctggtg gtagcggacc ggtcctctct gccggactcg tacggggcgt    180

tcacatgcac ggcaaagatc gagtgggagg acgacgggaa ggtcacctcc atcgctgcac    240

cctgcgacgt cagccggctg cagtgcgagt ccagggatta cctcttcgcc tggaggctcc    300

gcaccgccgc cgccgacgcc gacgcatccg ttggacacag ctccgaggag attagtgaga    360

gttagggaag cttgagctgc atccaatgaa accaagtgca tagactaagc cgctagctgc    420

atgttaaaac tgagcagctt cctctttcgc g                                    451


<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12

cagctagcgg cttagtct                                                    18


<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
```

ctcttcgcct ggaggttc 18

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
tggtttcatt ggatgcagc 19

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
tgcagtgcga gtcagaga 18

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
gtaaagttct tcctgatctg aat 23

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
tcggaagcag ccttaata 18

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
tcccgtgtcc gtcaatgtga ta 22

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
ggactcacga gctgaggctc gg 22

<210> SEQ ID NO 20
<211> LENGTH: 18
<212> TYPE: DNA

<213> ORGANISM: Artificial Sequence
<220> FEATURE:
<223> OTHER INFORMATION: consensus motif

<400> SEQUENCE: 20
attgacggac acgggart 18

<210> SEQ ID NO 21
<211> LENGTH: 13
<212> TYPE: DNA
<213> ORGANISM: Artificial Sequence
<220> FEATURE:
<223> OTHER INFORMATION: consensus motif

<400> SEQUENCE: 21
cacattgacg gac 13

<210> SEQ ID NO 22
<211> LENGTH: 11
<212> TYPE: DNA
<213> ORGANISM: Artificial Sequence
<220> FEATURE:
<223> OTHER INFORMATION: consensus motif

<400> SEQUENCE: 22
accatgcata c 11

<210> SEQ ID NO 23
<211> LENGTH: 13
<212> TYPE: DNA
<213> ORGANISM: Artificial Sequence
<220> FEATURE:
<223> OTHER INFORMATION: consensus motif

<400> SEQUENCE: 23
tagctagcca cgc 13

<210> SEQ ID NO 24
<211> LENGTH: 11
<212> TYPE: DNA
<213> ORGANISM: Artificial Sequence
<220> FEATURE:
<223> OTHER INFORMATION: consensus motif

<400> SEQUENCE: 24
cgcatgcatt g 11

<210> SEQ ID NO 25
<211> LENGTH: 13
<212> TYPE: DNA
<213> ORGANISM: Artificial Sequence
<220> FEATURE:
<223> OTHER INFORMATION: consensus motif

<400> SEQUENCE: 25
tctcacgcca cgt 13

<210> SEQ ID NO 26
<211> LENGTH: 13
<212> TYPE: DNA
<213> ORGANISM: Artificial Sequence
<220> FEATURE:
<223> OTHER INFORMATION: consensus motif

<400> SEQUENCE: 26
gagcacgtgg cgt 13

<210> SEQ ID NO 27
<211> LENGTH: 13
<212> TYPE: DNA
<213> ORGANISM: Artificial Sequence
<220> FEATURE:
<223> OTHER INFORMATION: consensus motif

<400> SEQUENCE: 27
cgccacgtgc tca 13

<210> SEQ ID NO 28
<211> LENGTH: 13
<212> TYPE: DNA
<213> ORGANISM: Artificial Sequence
<220> FEATURE:
<223> OTHER INFORMATION: consensus motif

<400> SEQUENCE: 28
gctggtgacg aac 13

<210> SEQ ID NO 29
<211> LENGTH: 13
<212> TYPE: DNA
<213> ORGANISM: Artificial Sequence
<220> FEATURE:
<223> OTHER INFORMATION: consensus motif

<400> SEQUENCE: 29
agggatgacg cat 13

<210> SEQ ID NO 30
<211> LENGTH: 13
<212> TYPE: DNA
<213> ORGANISM: Artificial Sequence
<220> FEATURE:
<223> OTHER INFORMATION: consensus motif

<400> SEQUENCE: 30
ctgcacgtgc tgt 13

<210> SEQ ID NO 31
<211> LENGTH: 13
<212> TYPE: DNA
<213> ORGANISM: Artificial Sequence
<220> FEATURE:
<223> OTHER INFORMATION: consensus motif

<400> SEQUENCE: 31
cagcacgtgc aga 13

<210> SEQ ID NO 32
<211> LENGTH: 13
<212> TYPE: DNA
<213> ORGANISM: Artificial Sequence
<220> FEATURE:
<223> OTHER INFORMATION: consensus motif

<400> SEQUENCE: 32
attaacgtca tta 13

<210> SEQ ID NO 33
<211> LENGTH: 13
<212> TYPE: DNA
<213> ORGANISM: Artificial Sequence
<220> FEATURE:

-continued

<223> OTHER INFORMATION: consensus motif

<400> SEQUENCE: 33
aataatgacg tta 13

<210> SEQ ID NO 34
<211> LENGTH: 11
<212> TYPE: DNA
<213> ORGANISM: Artificial Sequence
<220> FEATURE:
<223> OTHER INFORMATION: consensus motif

<400> SEQUENCE: 34
atcatgcatc t 11

<210> SEQ ID NO 35
<211> LENGTH: 11
<212> TYPE: DNA
<213> ORGANISM: Artificial Sequence
<220> FEATURE:
<223> OTHER INFORMATION: consensus motif

<400> SEQUENCE: 35
caccaaccag c 11

<210> SEQ ID NO 36
<211> LENGTH: 13
<212> TYPE: DNA
<213> ORGANISM: Artificial Sequence
<220> FEATURE:
<223> OTHER INFORMATION: consensus motif

<400> SEQUENCE: 36
ccactcgcca cgc 13

<210> SEQ ID NO 37
<211> LENGTH: 11
<212> TYPE: DNA
<213> ORGANISM: Artificial Sequence
<220> FEATURE:
<223> OTHER INFORMATION: consensus motif

<400> SEQUENCE: 37
ggggccattc a 11

<210> SEQ ID NO 38
<211> LENGTH: 11
<212> TYPE: DNA
<213> ORGANISM: Artificial Sequence
<220> FEATURE:
<223> OTHER INFORMATION: consensus motif

<400> SEQUENCE: 38
tgggccgcgc g 11

<210> SEQ ID NO 39
<211> LENGTH: 13
<212> TYPE: DNA
<213> ORGANISM: Artificial Sequence
<220> FEATURE:
<223> OTHER INFORMATION: consensus motif

<400> SEQUENCE: 39
gaacgcgcca cgg 13

<210> SEQ ID NO 40
<211> LENGTH: 11
<212> TYPE: DNA
<213> ORGANISM: Artificial Sequence
<220> FEATURE:
<223> OTHER INFORMATION: consensus motif

<400> SEQUENCE: 40
agggccgagg c 11

<210> SEQ ID NO 41
<211> LENGTH: 11
<212> TYPE: DNA
<213> ORGANISM: Artificial Sequence
<220> FEATURE:
<223> OTHER INFORMATION: consensus motif

<400> SEQUENCE: 41
tgcatgcagg t 11

<210> SEQ ID NO 42
<211> LENGTH: 11
<212> TYPE: DNA
<213> ORGANISM: Artificial Sequence
<220> FEATURE:
<223> OTHER INFORMATION: consensus motif

<400> SEQUENCE: 42
tgcatgcagc c 11

<210> SEQ ID NO 43
<211> LENGTH: 13
<212> TYPE: DNA
<213> ORGANISM: Artificial Sequence
<220> FEATURE:
<223> OTHER INFORMATION: consensus motif

<400> SEQUENCE: 43
acgactgacg agg 13

<210> SEQ ID NO 44
<211> LENGTH: 13
<212> TYPE: DNA
<213> ORGANISM: Artificial Sequence
<220> FEATURE:
<223> OTHER INFORMATION: consensus motif

<400> SEQUENCE: 44
gcctacgtgt cgg 13

<210> SEQ ID NO 45
<211> LENGTH: 13
<212> TYPE: DNA
<213> ORGANISM: Artificial Sequence
<220> FEATURE:
<223> OTHER INFORMATION: consensus motif

<400> SEQUENCE: 45
gggtacgtgg gcg 13

<210> SEQ ID NO 46
<211> LENGTH: 19
<212> TYPE: DNA
<213> ORGANISM: Artificial Sequence
<220> FEATURE:
<223> OTHER INFORMATION: consensus motif

<400> SEQUENCE: 46
cccgccccgt tctcccacg 19

<210> SEQ ID NO 47
<211> LENGTH: 13
<212> TYPE: DNA
<213> ORGANISM: Artificial Sequence
<220> FEATURE:
<223> OTHER INFORMATION: consensus motif

<400> SEQUENCE: 47
gggcacgtgg gag 13

<210> SEQ ID NO 48
<211> LENGTH: 13
<212> TYPE: DNA
<213> ORGANISM: Artificial Sequence
<220> FEATURE:
<223> OTHER INFORMATION: consensus motif

<400> SEQUENCE: 48
tcccacgtgc ccc 13

<210> SEQ ID NO 49
<211> LENGTH: 15
<212> TYPE: DNA
<213> ORGANISM: Artificial Sequence
<220> FEATURE:
<223> OTHER INFORMATION: consensus motif

<400> SEQUENCE: 49
gctgacccgc ccttc 15

<210> SEQ ID NO 50
<211> LENGTH: 11
<212> TYPE: DNA
<213> ORGANISM: Artificial Sequence
<220> FEATURE:
<223> OTHER INFORMATION: consensus motif

<400> SEQUENCE: 50
ggggcccgga c 11

<210> SEQ ID NO 51
<211> LENGTH: 11
<212> TYPE: DNA
<213> ORGANISM: Artificial Sequence
<220> FEATURE:
<223> OTHER INFORMATION: consensus motif

<400> SEQUENCE: 51
cgggccccaa c 11

<210> SEQ ID NO 52
<211> LENGTH: 11
<212> TYPE: DNA
<213> ORGANISM: Artificial Sequence
<220> FEATURE:
<223> OTHER INFORMATION: consensus motif

<400> SEQUENCE: 52
tgggctcgat c 11

<210> SEQ ID NO 53
<211> LENGTH: 15

-continued

<212> TYPE: DNA
<213> ORGANISM: Artificial Sequence
<220> FEATURE:
<223> OTHER INFORMATION: consensus motif

<400> SEQUENCE: 53
ccaggtcagt gggct 15

<210> SEQ ID NO 54
<211> LENGTH: 15
<212> TYPE: DNA
<213> ORGANISM: Artificial Sequence
<220> FEATURE:
<223> OTHER INFORMATION: consensus motif

<400> SEQUENCE: 54
actgacctgg ccccc 15

<210> SEQ ID NO 55
<211> LENGTH: 11
<212> TYPE: DNA
<213> ORGANISM: Artificial Sequence
<220> FEATURE:
<223> OTHER INFORMATION: consensus motif

<400> SEQUENCE: 55
ggggccaggt c 11

<210> SEQ ID NO 56
<211> LENGTH: 13380
<212> TYPE: DNA
<213> ORGANISM: Artificial Sequence
<220> FEATURE:
<223> OTHER INFORMATION: vector

<400> SEQUENCE: 56
gtgattttgt gccgagctgc cggtcgggga gctgttggct ggctggtggc aggatatatt 60
gtggtgtaaa caaattgacg cttagacaac ttaataacac attgcggacg tctttaatgt 120
actgaattag tactctagtt tacagcactc gtctccgtct tggtaggttc tttgagctta 180
agaaggttga cgttgtggtg ataggtctaa ggcggaggct aggctagttg atatcggtac 240
caagcttccg cggctgcagt gcagcgtgac ccggtcgtgc ccctctctag agataatgag 300
cattgcatgt ctaagttata aaaaattacc acatattttt tttgtcacac ttgtttgaag 360
tgcagtttat ctatctttat acatatattt aaactttact ctacgaataa tataatctat 420
agtactacaa taatatcagt gttttagaga atcatataaa tgaacagtta gacatggtct 480
aaaggacaat tgagtatttt gacaacagga ctctacagtt ttatcttttt agtgtgcatg 540
tgttctcctt tttttttgca aatagcttca cctatataat acttcatcca ttttattagt 600
acatccattt agggtttagg gttaatggtt tttatagact aatttttta gtacatctat 660 tttattctat tttagcctct aaattaagaa aactaaaact ctattttagt tttttattt 720 aatagtttag atataaaata gaataaaata aagtgactaa aaattaaaca aataccettt 780 aagaaattaa aaaaactaag gaaacatttt tcttgtttcg agtagataat gccagcctgt 840
taaacgccgt cgacgagtct aacggacacc aaccagcgaa ccagcagcgt cgcgtcgggc 900
caagcgaagc agacggcacg gcatctctgt cgctgcctct ggacccctct cgagagttcc 960
gctccaccgt tggacttgct ccgctgtcgg catccagaaa ttgcgtggcg gagcggcaga 1020
cgtgagccgg cacggcaggc ggcctcctcc tcctctcacg gcaccggcag ctacggggga 1080

-continued

```
ttcctttccc accgctcctt cgctttccct tcctcgcccg ccgtaataaa tagacacccc   1140
ctccacaccc tctttcccca acctcgtgtt gttcggagcg cacacacaca caaccagatc   1200
tcccccaaat ccacccgtcg gcacctccgc ttcaaggtac gccgctcgtc ctcccccccc   1260
cccccctct ctaccttctc tagatcggcg ttccggtcca tggttagggc ccggtagttc    1320
tacttctgtt catgtttgtg ttagatccgt gtttgtgtta gatccgtgct gctagcgttc   1380
gtacacggat gcgacctgta cgtcagacac gttctgattg ctaacttgcc agtgtttctc   1440
tttggggaat cctgggatgg ctctagccgt tccgcagacg ggatcgattt catgattttt   1500
tttgtttcgt tgcatagggt ttggtttgcc cttttccttt atttcaatat atgccgtgca   1560
cttgtttgtc gggtcatctt ttcatgcttt tttttgtctt ggttgtgatg atgtggtctg   1620
gttgggcggt cgttctagat cggagtagaa ttctgtttca aactacctgg tggatttatt   1680
aattttggat ctgtatgtgt gtgccataca tattcatagt tacgaattga agatgatgga   1740
tggaaatatc gatctaggat aggtatacat gttgatgcgg gttttactga tgcatataca   1800
gagatgcttt ttgttcgctt ggttgtgatg atgtggtgtg gttgggcggt cgttcattcg   1860
ttctagatcg gagtagaata ctgtttcaaa ctacctggtg tatttattaa ttttggaact   1920
gtatgtgtgt gtcatacatc ttcatagtta cgagtttaag atggatggaa atatcgatct   1980
aggataggta tacatgttga tgtgggtttt actgatgcat atacatgatg gcatatgcag   2040
catctattca tatgctctaa ccttgagtac ctatctatta taataaacaa gtatgtttta   2100
taattatttc gatcttgata tacttggatg atggcatatg cagcagctat atgtggattt   2160
ttttagccct gccttcatac gctatttatt tgcttggtac tgtttctttt gtcgatgctc   2220
accctgttgt ttggtgttac ttctgcaggg tacggatcct catctaagcg caaagagacg   2280
tactatggaa aacgctaaaa tgaactcgct catcgcccag tatccgttgg taaaggatct   2340
ggttgctctt aaagaaacca cctggtttaa tcctggcacg acctcattgg ctgaaggttt   2400
accttatgtt ggcctgaccg aacaggatgt tcaggacgcc catgcgcgct tatcccgttt   2460
tgcaccctat ctggcaaaag catttcctga aactgctgcc actgggggga ttattgaatc   2520
agaactggtt gccattccag ctatgcaaaa acggctggaa aaagaatatc agcaaccgat   2580
cagcgggcaa ctgttactga aaaaagatag ccatttgccc atttccggct ccataaaagc   2640
acgcggcggg atttatgaag tcctggcaca cgcagaaaaa ctggctctgg aagcggggtt   2700
gctgacgctt gatgatgact acagcaaact gctttctccg gagtttaaac agttctttag   2760
ccaatacagc attgctgtgg gctcaaccgg aaatctgggg ttatcaatcg gcattatgag   2820
cgcccgcatt ggctttaagg tgacagttca tatgtctgct gatgcccggg catggaaaaa   2880
agcgaaactg cgcagccatg gcgttacggt cgtggaatat gagcaagatt atggtgttgc   2940
cgtcgaggaa ggacgtaaag cagcgcagtc tgacccgaac tgtttcttta ttgatgacga   3000
aaattcccgc acgttgttcc ttgggtattc cgtcgctggc cagcgtctta aagcgcaatt   3060
tgcccagcaa ggccgtatcg tcgatgctga taaccctctg tttgtctatc tgccgtgtgg   3120
tgttggcggt ggtcctggtg gcgtcgcatt cgggcttaaa ctggcgtttg gcgatcatgt   3180
tcactgcttt tttgccgaac caacgcactc cccttgtatg ttgttaggcg tccatacagg   3240
attacacgat cagatttctg ttcaggatat tggtatcgac aaccttaccg cagcggatgg   3300
ccttgcagtt ggtcgcgcat caggctttgt cgggcgggca atggagcgtc tgctggatgg   3360
cttctatacc cttagcgatc aaaccatgta tgacatgctt ggctggctgg cgcaggaaga   3420
aggtattcgt cttgaacctt cggcactggc gggtatggcc ggacctcagc gcgtgtgtgc   3480
```

-continued

```
atcagtaagt taccaacaga tgcacggttt cagcgcagaa caactgcgta ataccactca   3540
tctggtgtgg gcgacgggag gtggaatggt gccggaagaa gagatgaatc aatatctggc   3600
aaaaggccgt taataacgtt tcaacgcagc atggatcgta ccgagctcaa tcgatcctgc   3660
tttaatgaga tatgcgagac gcctatgatc gcatgatatt tgctttcaat tctgttgtgc   3720
acgttgtaaa aaacctgagc atgtgtagct cagatcctta ccgccggttt cggttcattc   3780
taatgaatat atcacccgtt actatcgtat ttttatgaat aatattctcc gttcaattta   3840
ctgattgtac cctactactt atatgtacaa tattaaaatg aaaacaatat attgtgctga   3900
ataggtttat agcgacatct atgatagagc gccacaataa caaacaattg cgttttatta   3960
ttacaaatcc aattttaaaa aaagcggcag aaccggtcaa acctaaaaga ctgattacat   4020
aaatcttatt caaatttcaa aagtgcccca ggggctagta tctacgacac accgagcggc   4080
gaactaataa cgctcactga agggaactcc ggttccccgc cggcgcgcat gggtgagatt   4140
ccttgaagtt gagtattggc cgtccgctct accgaaagtt acgggcacca ttcaacccgg   4200
tccagcacgg cggccgggta accgacttgc tgccccgaga attatgcagc atttttttgg   4260
tgtatgtggg ccccaaatga agtgcaggtc aaaccttgac agtgacgaca aatcgttggg   4320
cgggtccagg gcgaattttg cgacaacatg tcgaggctca gcaggatggg cccaggtaca   4380
gaattcgcgg ccgtacaacg cgtaccggtt aattaatccc gtgtccgtca atgtgatact   4440
actagcatag tactagtacc atgcatacac acagcaggtc ggccgcctgg atggatcgat   4500
gatgatacta catcatcctg tcatccatcc aggcgatcta gaaggggcgt ggctagctag   4560
caaactgtga ccggtttttc tacgccgata ataatacttt gtcatggtac agacgtacag   4620
tactggttat atatatctgt agatttcaac tgaaaagcta ggatagctag attaattcct   4680
gagaaacaca gataaaattc gagcttggct atagatgaca aaacggaaga cgcatgcatt   4740
ggacgacgta tgcaatgcga gcgcgtctcg tgtcgtcccg tccaagtctg gcgatctcac   4800
gccacgtgct caacagctca aggactgttc gtcaccagcg ttaaattcat tgaagggatg   4860
acgcatttcg gcatttgtca ttgcttgtag ctatatatat atatccaaca gatttctctc   4920
aagcttttgt atgcgtgaat gtaaagtcta gcttatacga cagcacgtgc agatatatta   4980
acgtcattat taggtggaga gcaagatgca tgatctggta gaaattgtcg aaaacacaag   5040
agagagtgaa gtgcacactt ctggtatagg agtgtatacg ccgctggttg gtgggcaatg   5100
cgcgccgcaa tattggccaa tgaaacctag caacgcccac tcgccacgcc ccatgaatgg   5160
cccccgcacg gcagcgagcc agccagtgcc cgcgcgcggc ccagccggag tcggcggaac   5220
gcgccacggg ggacgaggcg cccgagggcc gaggcagcgc ggcatggcaa gcaagccgaa   5280
gcgggcaagc gacctgcatg cagcccctgc ccctcgccct cgtcagtcgt cccagcctcc   5340
cactggaatc cacccaaccc gcccttcctc tccaaagcac gcgccccgcg actcgcctcc   5400
gcctacgtgt cggcagcgtc cccgccggtc gcccacgtac cccgccccgt tctcccacgt   5460
gcccctccct ctgcgcgcgt ccgattggct gacccgccct tcttaagccg cgccagcctc   5520
ctgtccgggc cccaacgccg tgctccgtcg tcgtctccgc ccccagagtg atcgagccca   5580
ctgacctggc ccccgagcct cagctcgtga gtcccgtacg gcctaggcct tcacctgcgg   5640
agggtaagat ccgatcacca tcttctgaat ttctgttctt gatctgtcat gtataataac   5700
tgtctagtct tggtgttggt gagatggaaa ttcggtggat ctcggaaggg atattgttcg   5760
tttgctgggg tttttttgt gtgttgtgat ccgtagagaa tttgtgttta tccatgttgt   5820
```

-continued

```
tgatcttggt atgtattcat gacatattga catgcatgtg ttgtatgtgt catatgtgtg   5880
cctctccttg ggatttgttt tggataatag aacatgttat ggactcaata gtctgtgaac   5940
aaatcttttt ttagatggtg gccaaatctg atgatgatct ttcttgagag gaaaaagttc   6000
atgatagaaa aatctttttt gagatggtgg cttaatgtga tgatgatctt tcttgagagg   6060
aaaaaaaaga ttcattatag gagattttga tttagctcct ttccaccgat attaaatgag   6120
gagcatgcat gctgattgct gataaggatc tgattttttt atcccctctt ctttgaacag   6180
acaagaaata ggctctgaat ttctgattga ttatttgtac atgcagaagg gcgaattcga   6240
cctaggccaa gtttgtacaa aaaagcaggc ttgataacca accatggtcc gtcctgtaga   6300
aaccccaacc cgtgaaatca aaaaactcga cggcctgtgg gcattcagtc tggatcgcga   6360
aaactgtgga attgatcagc gttggtggga aagcgcgtta caagaaagcc gggcaattgc   6420
tgtgccaggc agttttaacg atcagttcgc cgatgcagat attcgtaatt atgcgggcaa   6480
cgtctggtat cagcgcgaag tctttatacc gaaaggttgg gcaggccagc gtatcgtgct   6540
gcgtttcgat gcggtcactc attacggcaa agtgtgggtc aataatcagg aagtgatgga   6600
gcatcagggc ggctatacgc catttgaagc cgatgtcacg ccgtatgtta ttgccgggaa   6660
aagtgtacgt aagtttctgc ttctaccttt gatatatata taataattat cattaattag   6720
tagtaatata atatttcaaa tatttttttc aaaataaaag aatgtagtat atagcaattg   6780
cttttctgta gtttataagt gtgtatattt taatttataa cttttctaat atatgaccaa   6840
aatttgttga tgtgcaggta tcaccgtttg tgtgaacaac gaactgaact ggcagactat   6900
cccgccggga atggtgatta ccgacgaaaa cggcaagaaa aagcagtctt acttccatga   6960
tttctttaac tatgccggaa tccatcgcag cgtaatgctc tacaccacgc cgaacacctg   7020
ggtggacgat atcaccgtgg tgacgcatgt cgcgcaagac tgtaaccacg cgtctgttga   7080
ctggcaggtg gtggccaatg gtgatgtcag cgttgaactg cgtgatgcgg atcaacaggt   7140
ggttgcaact ggacaaggca ctagcgggac tttgcaagtg gtgaatccgc acctctggca   7200
accgggtgaa ggttatctct atgaactgtg cgtcacagcc aaaagccaga cagagtgtga   7260
tatctacccg cttcgcgtcg gcatccggtc agtggcagtg aagggcgaac agttcctgat   7320
taaccacaaa ccgttctact ttactggctt tggtcgtcat gaagatgcgg acttgcgtgg   7380
caaaggattc gataacgtgc tgatggtgca cgaccacgca ttaatggact ggattggggc   7440
caactcctac cgtacctcgc attaccctta cgctgaagag atgctcgact gggcagatga   7500
acatggcatc gtggtgattg atgaaactgc tgctgtcggc tttaacctct ctttaggcat   7560
tggtttcgaa gcgggcaaca agccgaaaga actgtacagc gaagaggcag tcaacgggga   7620
aactcagcaa gcgcacttac aggcgattaa agagctgata gcgcgtgaca aaaaccaccc   7680
aagcgtggtg atgtggagta ttgccaacga accggatacc cgtccgcaag gtgcacggga   7740
atatttcgcg ccactggcgg aagcaacgcg taaactcgac ccgacgcgtc cgatcacctg   7800
cgtcaatgta atgttctgcg acgctcacac cgataccatc agcgatctct ttgatgtgct   7860
gtgcctgaac cgttattacg gatggtatgt ccaaagcggc gatttggaaa cggcagagaa   7920
ggtactggaa aaagaacttc tggcctggca ggagaaactg catcagccga ttatcatcac   7980
cgaatacggc gtggatacgt tagccgggct gcactcaatg tacaccgaca tgtggagtga   8040
agagtatcag tgtgcatggc tggatatgta tcaccgcgtc tttgatcgcg tcagcgccgt   8100
cgtcggtgaa caggtatgga atttcgccga ttttgcgacc tcgcaaggca tattgcgcgt   8160
tggcggtaac aagaaaggga tcttcactcg cgaccgcaaa ccgaagtcgg cggctttttct  8220
```

-continued

```
gctgcaaaaa cgctggactg gcatgaactt cggtgaaaaa ccgcagcagg gaggcaaaca   8280
atgaatcaaa cccagctttc ttgtacaaag tgggagctcg atcgttcaaa catttggcaa   8340
taaagtttct taagattgaa tcctgttgcc ggtcttgcga tgattatcat ataatttctg   8400
ttgaattacg ttaagcatgt aataattaac atgtaatgca tgacgttatt tatgagatgg   8460
gtttttatga ttagagtccc gcaattatac atttaatacg cgatagaaaa caaaatatag   8520
cgcgcaaact aggataaatt atcgcgcgcg gtgtcatcta tgttactaga tcgaattcaa   8580
ctttattata catagttgat aattcactgg ccggccctg tctatcttgt tgggaaaagc   8640
cgacctaccc ggacgcgatt acttaagcaa aagatactat cgaacgaaga aagctagtag   8700
gtagactata tcaggcctga ttgtcgtttc ccgccttcag tttaaactat cagtgtttga   8760
caggatatat tggcgggtaa acctaagaga aaagagcgtt tattagaata atcggatatt   8820
taaaagggcg tgaaaaggtt tatccgttcg tccatttgta tgtcaatatt gggggggggg   8880
gaaagccacg ttgtgtctca aaatctctga tgttacattg cacaagataa aaatatatca   8940
tcatgaacaa taaaactgtc tgcttacata aacagtaata caaggggtgt tcgccaccat   9000
gagccatatc cagcgtgaaa cctcgtgctc ccgcccgcgc ctcaattcca atatggatgc   9060
cgacctttat ggctacaagt gggcgcgcga caacgtcggc cagtcgggcg cgaccattta   9120
tcggctttat ggcaaacccg atgccccgga actgttcctg aagcacggca aaggcagcgt   9180
cgcaaacgat gtcaccgatg agatggtccg cctgaactgg cttaccgagt tcatgccgct   9240
gccgacgatt aagcatttca tccgtacccc ggacgatgcc tggctcttga ccacggccat   9300
tccgggcaaa acggcctttc aggtccttga agagtacccg gactccggtg agaatatcgt   9360
ggacgccctc gcggtcttcc tccgccgttt gcatagcatc cccgtgtgca actgcccctt   9420
caactcggac cgggttttcc gcctggcaca ggcccagtcg cgcatgaata acggcctcgt   9480
tgacgcgagc gatttcgacg atgaacggaa tggctggccg gtggaacagg tttggaagga   9540
aatgcacaaa ctgcttccgt tctcgccgga ttcggtggtc acgcatggtg atttttccct   9600
ggataatctg atctttgacg agggcaagct gatcggctgc atcgacgtgg gtcgcgtcgg   9660
tatcgccgac cgctatcagg acctggcgat cttgtggaat tgcctcggcg agttctcgcc   9720
ctcgctccag aagcgcctgt tccagaagta cggcatcgac aacccggata tgaacaagct   9780
ccagttccac ctcatgctgg acgaattttt ttgaacagaa ttggttaatt ggttgtaaca   9840
ctggcagagc attacgctga cttgacggga cggcggcttt gttgaataaa tcgaactttt   9900
gctgagttga aggatcgatg agttgaagga ccccgtagaa aagatcaaag gatcttcttg   9960
agatcctttt tttctgcgcg taatctgctg cttgcaaaca aaaaaaccac cgctaccagc  10020
ggtggtttgt ttgccggatc aagagctacc aactcttttt ccgaaggtaa ctggcttcag  10080
cagagcgcag ataccaaata ctgtccttct agtgtagccg tagttaggcc accacttcaa  10140
gaactctgta gcaccgccta catacctcgc tctgctaatc ctgttaccag tggctgctgc  10200
cagtggcgat aagtcgtgtc ttaccgggtt ggactcaaga cgatagttac cggataaggc  10260
gcagcggtcg ggctgaacgg ggggttcgtg cacacagccc agcttggagc gaacgaccta  10320
caccgaactg agatacctac agcgtgagct atgagaaagc gccacgcttc ccgaagggag  10380
aaaggcggac aggtatccgg taagcggcag ggtcggaaca ggagagcgca cgagggagct  10440
tccaggggga aacgcctggt atctttatag tcctgtcggg tttcgccacc tctgacttga  10500
gcgtcgattt ttgtgatgct cgtcaggggg gcggagccta tggaaaaacg ccagcaacgc  10560
```

-continued

```
ggcctttttta cggttcctgg ccttttgctg gccttttgct cacatgttct ttcctgcgtt  10620
atcccctgat tctgtggata accgtattac cgcctttgag tgagctgata ccgctcgccg  10680
cagccgaacg accgagcgca gcgagtcagt gagcgaggaa gcggaagagc gcctgatgcg  10740
gtattttctc cttacgcatc tgtgcggtat ttcacaccgc ataggccgcg ataggccgac  10800
gcgaagcggc ggggcgtagg gagcgcagcg accgaagggt aggcgctttt tgcagctctt  10860
cggctgtgcg ctggccagac agttatgcac aggccaggcg ggttttaaga gttttaataa  10920
gttttaaaga gttttaggcg gaaaaatcgc ctttttctc ttttatatca gtcacttaca  10980
tgtgtgaccg gttcccaatg tacggctttg ggttcccaat gtacgggttc cggttcccaa  11040
tgtacggctt tgggttccca atgtacgtgc tatccacagg aaagagacct tttcgacctt  11100
tttcccctgc tagggcaatt tgccctagca tctgctccgt acattaggaa ccggcggatg  11160
cttcgccctc gatcaggttg cggtagcgca tgactaggat cgggccagcc tgccccgcct  11220
cctccttcaa atcgtactcc ggcaggtcat ttgacccgat cagcttgcgc acggtgaaac  11280
agaacttctt gaactctccg gcgctgccac tgcgttcgta gatcgtcttg aacaaccatc  11340
tggcttctgc cttgcctgcg gcgcggcgtg ccaggcggta gagaaaacgg ccgatgccgg  11400
ggtcgatcaa aaagtaatcg gggtgaaccg tcagcacgtc cgggttcttg ccttctgtga  11460
tctcgcggta catccaatca gcaagctcga tctcgatgta ctccggccgc ccggtttcgc  11520
tctttacgat cttgtagcgg ctaatcaagg cttcaccctc ggataccgtc accaggcggc  11580
cgttcttggc cttcttggta cgctgcatgg caacgtgcgt ggtgtttaac cgaatgcagg  11640
tttctaccag gtcgtctttc tgctttccgc catcggctcg ccggcagaac ttgagtacgt  11700
ccgcaacgtg tggacggaac acgcggccgg gcttgtctcc cttcccttcc cggtatcggt  11760
tcatggattc ggttagatgg gaaaccgcca tcagtaccag gtcgtaatcc cacacactgg  11820
ccatgccggc ggggcctgcg gaaacctcta cgtgcccgtc tggaagctcg tagcggatca  11880
cctcgccagc tcgtcggtca cgcttcgaca gacggaaaac ggccacgtcc atgatgctgc  11940
gactatcgcg ggtgcccacg tcatagagca tcggaacgaa aaaatctggt tgctcgtcgc  12000
ccttgggcgg cttcctaatc gacggcgcac cggctgccgg cggttgccgg gattctttgc  12060
ggattcgatc agcggcccct tgccacgatt caccggggcg tgcttctgcc tcgatgcgtt  12120
gccgctgggc ggcctgcgcg gccttcaact tctccaccag gtcatcaccc agcgccgcgc  12180
cgatttgtac cgggccggat ggtttgcgac cgctcacgcc gattcctcgg gcttgggggt  12240
tccagtgcca ttgcagggcc ggcagacaac ccagccgctt acgcctggcc aaccgcccgt  12300
tcctccacac atggggcatt ccacggcgtc ggtgcctggt tgttcttgat tttccatgcc  12360
gcctccttta gccgctaaaa ttcatctact catttattca tttgctcatt tactctggta  12420
gctgcgcgat gtattcagat agcagctcgg taatggtctt gccttggcgt accgcgtaca  12480
tcttcagctt ggtgtgatcc tccgccggca actgaaagtt gacccgcttc atggctggcg  12540
tgtctgccag gctggccaac gttgcagcct tgctgctgcg tgcgctcgga cggccggcac  12600
ttagcgtgtt tgtgcttttg ctcattttct ctttacctca ttaactcaaa tgagttttga  12660
tttaatttca gcggccagcg cctggacctc gcgggcagcg tcgccctcgg gttctgattc  12720
aagaacggtt gtgccggcgg cggcagtgcc tgggtagctc acgcgctgcg tgatacggga  12780
ctcaagaatg ggcagctcgt acccggccag cgcctcggca acctcaccgc cgatgcgcgt  12840
gcctttgatc gcccgcgaca cgacaaaggc cgcttgtagc cttccatccg tgacctcaat  12900
gcgctgctta accagctcca ccaggtcggc ggtggcccaa atgtcgtaag ggcttggctg  12960
```

caccggaatc agcacgaagt cggctgcctt gatcgcggac acagccaagt ccgccgcctg 13020
gggcgctccg tcgatcacta cgaagtcgcg ccggccgatg gccttcacgt cgcggtcaat 13080
cgtcgggcgg tcgatgccga caacggttag cggttgatct tcccgcacgg ccgcccaatc 13140
gcgggcactg ccctggggat cggaatcgac taacagaaca tcggccccgg cgagttgcag 13200
ggcgcgggct agatgggttg cgatggtcgt cttgcctgac ccgcctttct ggttaagtac 13260
agcgataacc ttcatgcgtt ccccttgcgt atttgtttat ttactcatcg catcatatac 13320
gcagcgaccg catgacgcaa gctgttttac tcaaatacac atcacctttt tagatgatca 13380

<210> SEQ ID NO 57
<211> LENGTH: 641
<212> TYPE: DNA
<213> ORGANISM: zea mays

<400> SEQUENCE: 57
gggttcgcgc tcgcgtccgg ggtcggggac tggcacgccg tgctgctgga ggccgtcatg 60
acgttcggcc tcatgtacgc ctactacgcc acggtgatcg acccgaagcg ggggcacgtg 120
ggcaccatcg cgccgctggc cgtgggcttc ctgctcggcg ccaacgtgct ggcgggaggg 180
ccctttcgac ggcgcaggga tgaacccggc gcgggtcttc ggcccggcgc tcgtcgggtg 240
gcggtggagg caccactggg tgtactggct gggccctttc ctcggcgccg ggcttgcagg 300
gctggtgtac gagtacctgg ttatcccgtc cgccgacgcc gccgtgcccc acgcgcacca 360
gccgctcgcg ccagaggact actagcttga aaattgtatt gtggggtcgt gtaagtggtt 420
aataaggggg gcataggtac gtacttgtct gtcgccccag cgtgtgttgg agacggtgaa 480
tcaggtgatg tgtacatgct gcttcactgt agtgtatgtg tatgtgtatg tagtaaataa 540
ttccaagtat ataaggcacg acttgtgtag tatcatatct ggttctgact tctgattatc 600
taaagggaag gattcgaatg tctagaaaaa aaaaaaaaaa a 641

<210> SEQ ID NO 58
<211> LENGTH: 633
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t

<400> SEQUENCE: 58
ctcaacttcg tgccgctaag attatncggg gcaatatgta atggctatga gccggtacca 60
tcctctggta aaacaagcca actcttccat ttcgccaagg aaaaaatggc ggctcgctgg 120
gctagacttc gtgcagctgt ggcagcctca gacatcttta ctctccctta tgagctatct 180
ggctattgta gcttttccaa tgagactgtc accgccaatc ctccatttgc atggcttcgc 240
tacaacaagg atgatattga agatctggag gccttcctac tcgagaaaaa gattatcact 300
cgaggtggca caaggtttgg agtggatgca agggctgtca gagttagtat ggttgacaca 360
gaccaagcct tcaatgtgtt catcaatcgt ctggccacaa tgaagtgaaa tttcagtgca 420
aattaataaa gcactttgtg gctactacaa ggatgaccgc gttctagatg gaacaatcga 480
tgctttggaa agcttaataa tgttttatgt tgttgaataa ttccgtgtgt tttcgggtat 540
gttgtgtaat actcaatgtc aaatcctatg cttaatcgat gttgtggtcc atcctgttat 600
cagcatggcc aattatnaaa aaaaaaaaaa aaa 633

<210> SEQ ID NO 59
<211> LENGTH: 1179
<212> TYPE: DNA
<213> ORGANISM: Zea mays
<220> FEATURE:
<221> NAME/KEY: misc_feature
<222> LOCATION: (278)..(278)
<223> OTHER INFORMATION: n is a, c, g, or t

<400> SEQUENCE: 59
ggggggggtt ttccccccgg ttgggggga agccctttga agggggaacc cagggttttg 60
gggggcccgg ctcctcttca tcttttccgg gccgggttgt cgcgtgtctt tccctgccaa 120
tggcggcccc ccccctgacg ttgttttccc ggccccggtt tattttttt ccccatttgt 180 gcccactatt taaactttgc gctctaccgt tgggctggtg atgccaatac attagatgcc 240
gacacatgta ttgagctcgt ctgctcccca aacacccntg atggtggcct ccggaagcct 300
gtcatcaaat ccaagtctag caagcctgtt tatgacttcg cctactactg gccgcagtac 360
acacccatca ccgaggcagc tgcccatgat atcatgctgt tcactgtctc caaatgcacc 420
ggccatgccg gcaccaggct ggggtgggca ttggtgaagg atactaaggt ggctcagaag 480
atgatcaagt ttatagagct caacacaatc ggtgtatcca aggactctca acttcgtgcc 540
gctaagatta tcggggcaat atgtaatggc tatgagccgg taccatcctc tggtaaaaca 600
agccaactct tccatttcgc caaggaaaaa atggcggctc gctgggctag acttcgtgca 660
gctgtggcag cctcagacat ctttactctc ccttatgagc tatctggcta ttgtagcttt 720
tccaatgaga ctgtcaccgc caatcctcca tttgcatggc ttcgctacaa caaggatgat 780
attgaagatc tggaggcctt cctactcgag aaaaagatta tcactcgagg tggcacaagg 840
tttggagtgg atgcaagggc tgtcagagtt agtatggttg acacagacca agccttcaat 900
gtgttcatca atcgtctggc cacaatgaag tgaaatttca gtgcaaatta ataaagcact 960
ttgtggctac tacaaggatg accgcgttct agatggaaca atcgatgctt tggaaagctt 1020
aataatgttt tatgttgttg aataattccg tgtgttttcg ggtatgttgt gtaatactca 1080
atgtcaaatc ctatgcttaa tcgatgttgt ggtccatcct gttatcagca tggccaatta 1140
tatatggatg accgtcactg ctgaaaaaaa aaaaaaaaa 1179

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
ctggccgtgg gcttcctgct 20

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
aagggcccag ccagtacacc ca 22

<210> SEQ ID NO 62
<211> LENGTH: 24
<212> TYPE: DNA
<213> ORGANISM: Artificial Sequence
<220> FEATURE:
<223> OTHER INFORMATION: primer

<400> SEQUENCE: 62
tggaggcacc actgggtgta ctgg 24

<210> SEQ ID NO 63
<211> LENGTH: 24
<212> TYPE: DNA
<213> ORGANISM: Artificial Sequence
<220> FEATURE:
<223> OTHER INFORMATION: primer

<400> SEQUENCE: 63
gctagtagtc ctctggcgcg agcg 24

<210> SEQ ID NO 64
<211> LENGTH: 24
<212> TYPE: DNA
<213> ORGANISM: Artificial Sequence
<220> FEATURE:
<223> OTHER INFORMATION: primer

<400> SEQUENCE: 64
gccaactctt ccatttcgcc aagg 24

<210> SEQ ID NO 65
<211> LENGTH: 24
<212> TYPE: DNA
<213> ORGANISM: Artificial Sequence
<220> FEATURE:
<223> OTHER INFORMATION: primer

<400> SEQUENCE: 65
ggaggattgg cggtgacagt ctca 24

<210> SEQ ID NO 66
<211> LENGTH: 23
<212> TYPE: DNA
<213> ORGANISM: Artificial Sequence
<220> FEATURE:
<223> OTHER INFORMATION: primer

<400> SEQUENCE: 66
aggaaaaaat ggcggctcgc tgg 23

<210> SEQ ID NO 67
<211> LENGTH: 23
<212> TYPE: DNA
<213> ORGANISM: Artificial Sequence
<220> FEATURE:
<223> OTHER INFORMATION: primer

<400> SEQUENCE: 67
ccatgcaaat ggaggattgg cgg 23

<210> SEQ ID NO 68
<211> LENGTH: 23
<212> TYPE: DNA
<213> ORGANISM: Artificial Sequence
<220> FEATURE:

<223> OTHER INFORMATION: primer

<400> SEQUENCE: 68
gtaaagttct tcctgatctg aat 23

<210> SEQ ID NO 69
<211> LENGTH: 18
<212> TYPE: DNA
<213> ORGANISM: Artificial Sequence
<220> FEATURE:
<223> OTHER INFORMATION: primer

<400> SEQUENCE: 69
tcggaagcag ccttaata 18

<210> SEQ ID NO 70
<211> LENGTH: 3985
<212> TYPE: DNA
<213> ORGANISM: Zea mays

<400> SEQUENCE: 70
taactcatat ccggttagat accaactaca catattgaat agcataaatc taataaatat 60
atggcgcaat gaaaatagta aataattaaa tatgagtaaa taatatgatg acaataatga 120
ataatattgg aacatgtaca ttgaccctat tttgctaata tatacttatt atatttgctt 180
aatttggtag gatgtatatg tgattgaggc gggtataaat tatccatagg tatgtgggta 240
taaatagtct atacttatac ccatactcat atacccgacg ggtatatgat tgtgtccatt 300
gccatatctg cgggtaaaaa actcattata tacttgtcct tataagtaaa acctgttgga 360
cactagagtt taggtaccat ataattatta attttgaacg aaggaagtaa tttgcagcgt 420
attaaggtgc ttctggtcta gaagaaatgt cacaatgttt ggtgttagtt tttggtgaaa 480
tttaaggtta attacttttt gaaagatgtt tccactaggt ggaaccgaaa gaaacggtgc 540
caaacacacc ttacaacaag aaaatatttg taaaaaaatt attttgaata agatgtctaa 600
aaatagaaag cgtgtatact ttaggacgga ggaatacata tgtatgattg ggaaaaccga 660
aaacgtacac ctcctcgctg caatacgctg gtgacttggc agttcgatcg cacccagcgg 720
ataaagatga gcacggagaa ctcacaaggc acagccgcac aggcaggcac cagcgcgaac 780
gcatggacgg gcggcccctg agacgtgccg cccagctggc ccgctgcgcc cacacgtggc 840
gcggagctgc gcgcggctcg gccacgttat aagccacgcg cgctggccgt cgccgcacct 900
cctgactact gcacactcgt ctccgcagtt tgaaacgaag cccgcggcta ctgcaagcta 960
ctccgtctcc gtagctaaag gagaggtagg tttttatttg gcgacgacat gagcacgggc 1020
gtgcgaccgg ggcggcggtt cacggtgggg cggagcgagg acgccacgca cccggacacc 1080
atccgcgccg ccatctccga gttcatcgcc accgccatct tcgtcttcgc cgccgaggga 1140
tccgtcctct cgctcggtac gcacgcacgc acgcttcgtc ttccgatccg ctcgaaagtg 1200
ttcgacgacg acgacgacga tgcgtgtggg gtttgccgtt tatttaattt attgttgtgt 1260
tgtgtgcgca gggaagatgt accacgacat gagcacggcg ggcggcctgg tggctgtggc 1320
gctggcgcac gcgctggccc tggccgtggc cgtggcagtg gccgtcaaca tctcgggcgg 1380
gcacgtgaac ccggcggtca ccttcggcgc gctcgtcggc ggccgcgtct ccctcgtccg 1440
cgcggtcttg tactgggtcg cgcagctgct gggcgccgtc gccgccacgc tgctcctgcg 1500
gctcgccacg gggggcatgc ggccgccggg gttcgcgctc gcgtccgggg tcggggactg 1560
gcacgccgtg ctgctggagg ccgtcatgac gttcggcctc atgtacgcct actacgccac 1620

-continued

```
ggtgatcgac ccgaagcggg ggcacgtggg caccatcgcg ccgctggccg tgggcttcct   1680
gctcggcgcc aacgtgctgg cgggagggcc cttcgacggc gcagggatga acccggcgcg   1740
ggtcttcggc ccggcgctcg tcgggtggcg gtggaggcac cactgggtgt actggctggg   1800
ccctttcctc ggcgccgggc ttgcagggct ggtgtacgag tacctggtta tcccgtccgc   1860
cgacgccgcc gtgccccacg cgcaccagcc gctcgcgcca gaggactact agcttgaaaa   1920
ttgtattgtg gggtcgtgta agtggttaat aagggggggca taggtacgta cttgtctgtc   1980
gccccagcgt gtgttggaga cggtgaatca ggtgatgtgt acatgctgct tcactgtagt   2040
gtatgtgtat gtgtatgtag taaataattc caggtatata aggcacgact tgtgtagtat   2100
catatctggt tctgacttct gattatctaa agggaaggat tcgaatgtct ggatttggat   2160
gtctgaagat tcgaattaac atcagaatgt ttcctaatga agtgctaata tagatactat   2220
ggatgttaaa tggacgtatc cgacgaattt ggtggtttaa gatttcgaca aaattcataa   2280
aaccatttaa aacttattgt taatactaat tacaaataat tttaaatttt aataatatac   2340
tagaaaactg atgtacacca tttaaaatat tgaaaaatat ttatattata aataaataat   2400
tatgttaatc ttacattagt aggagtatca taggaatttt tagaatctaa aatacaaata   2460
tatttaatat acaaaagaat atatttagag tctaaaatat aaatatacct ggtataaata   2520
atttatggaa aaatatattc ataatttgtt tgtaatatga tttttaccaa ctataaatac   2580
atcgataaaa caaattaata cttattatga tgttatgttt caaatcaaat aagtgtccaa   2640
atatgactcg aattcaaagt attcgttcat atggattcgt tttcatatgt attcgatccg   2700
aattcatccc tatctatttc gtactcgcat tatcgcatta ccagttaagg gatgttccga   2760
tttttggtg gattatgaag tcaaattaga agagtgaccg caggatgagc tccctcccct   2820
gaatcgccta gcccctgacc cctgcaaccc acctcaccgg cgtgtcccca accoctacaa   2880
ccatgtcgaa cgttgcccgg ccgatgcagc ccctcactgc aagtatctag aggatgtcgc   2940
aaccctcagc tggccaccac ctcagtggtc agcgccacgg gctttaggta aggatcatat   3000
cttcccgaga ccacttcttc aagatctctt cctgcacaac ttctccacca tttggtcgtc   3060
tccgatcgtt cataaacatg ttgcgttcat cttgttcgtc ccaaccttct cctcatccca   3120
cttcaccaat gacttcgtta gcaacatgtt gagcttcgct tcgacggtgc caccgtttcg   3180
cctacacgta gcttgcaaac atcggcctcc actgatgatc taccctaaac ccaaaacaca   3240
tctagtgtac gccagtcggc ccccactgct cctagctttg agcgagacag cggcgttgcc   3300
tccaccttcg gctcctcgtc gcttgacgcc atccagtcct agggtggtga gtcctctggc   3360
tccaatgaaa gcattggaca gggtgacgtg ggaggcaacc acaacagtac cttgagacat   3420
ggatgccccc tgcgaccatg ccctcaaaaa tcgcatcctt catgcctata ccatcgaggg   3480
gcagtggttg agctggaatc catgatctgt ctatgcgcct gcctccagtg catcgccccc   3540
gaagtgctag tggatctgct accctcctct aggtgtgtgg caatcctctt gttcaactcc   3600
caagcccatc gcaagctcat ccgcgccctc aaccccctgg cctttgaagg tatgtcccac   3660
tccttcgagc acctggagga aacatccaac cgcttcattc atgtccctgt gtggcttgct   3720
cttcccgtgt cgatcgactt cccaccgaag cgtcgaatcg ctatgtcgtc caccacgcct   3780
ttgcggctgg ctgtgaagtc agggaaatcc atgccaatga cctgaacccc aactacttta   3840
ggcctatctg ggtcgtcatc gaggtcaacc accaccttga catcccgcac gagctctaga   3900
tctccgaaag gcgtggaatt actagagaag ggtgtgtggc ctaggtgctg ctggtccgaa   3960
```

ttggccaaga cgtgagtagc tggat 3985

<210> SEQ ID NO 71
<211> LENGTH: 4565
<212> TYPE: DNA
<213> ORGANISM: Zea mays

<400> SEQUENCE: 71
aacgccccgt taaggtatta ctcgtaattt ttctatagca tttaaatgtg ttggataatc 60
ttttgcatgg atatgtgttg tgaattcgca ccatgtgccc acgaaagcag catggggatc 120
gccccaccaa ttttttttta ccagctctaa ctctcaacca gaaaacatgc aaatttattt 180
gtcattgcac accagcaacc tagggatggt aatcccaaaa tgcaatgatt tttagagcat 240
agatgtgggc gaatttacct aactatggat atgttaattg acaataaaac accataacca 300
ctgggttcat gggtacgagt atggttttgt acatgaaaga ataaacttat gagagtgtgt 360
atatactcaa catacaagta taattcccaa agccatctcc aacctattgt agtccaaaat 420
atgcatggtc caacaagcac acctattgac atgcatataa gccatcacat atatatatac 480
actaattttt actattacat atgttatata tttatagata tatgttattt gtttatattg 540
tcagtgttta ctgcgtgtgt tatatttttt ttcttaggta cggtgtaggt aaccaccgtg 600
tctatctcga cacgcgtacg ggcacaaaat tacatcaaca catggtatga gatttttcat 660
gtgtcaaata aattttgatg gctagtttaa aaacttaaat cactcatgag attaccggag 720
acgattgagg ggaaaatttc ctagtattac ggacggaatt taagtttttc aaactatccc 780
taataaaata aatatgggta tgtaggtatg agcgcgatac catagggtat atacctgttg 840
cggcgggact gcaggtttgg tgacagctaa aaacatgcat ttaggtgttg aatcttgatt 900
atttgcagtt aatcgtgctt gctgtgttgc cgcaaacacg agattcacac cctgatgagc 960
ggagccaggc tgcccttgct tcgattcacg gtggccgtcg tcccggccag gccagcacac 1020
cagtccaatc cacatagcaa caaccgcgcc tcggtcagtt atagatgcgt ggccttctga 1080
aacaaaccct catatggggt cacgccgcac tcacacatgc atccataaac cctcagcaga 1140
gccttgtgtc gcgtcctctc ctcgataacc caggccacat cgtccttccg cgccgcgccg 1200
ccggcgacct aacaacccag aggcctcagc accgcacgct tgcacgtacg tccaggcgcg 1260
ctcgccgtta cgcccacggg gatccaggct ttccttcgct gccgttgctg gtcgagtgcg 1320
ccacgccgaa aggtgatcga gctgacgagc gctagacgcc accggccggc gcggcgtggc 1380
aaggcaagac gccgtgcggg tctcgccctc gtcagctata agaccgcatc ccccccctgcg 1440 gagggaggca cacacacaga cacagcgctc tcactagcct cgcattccgt ccctgcagtg 1500
caggggcagg ccggtgaggt ctgggagagg aggaggagga ggaggaggag gaggaggaga 1560
tggccggtag ggagagcggc gggatggcgg cggcgctgcg ctgcgctgga aggatcggga 1620
tcctggccac cgtcgcagtg aacctcgcgt ggatcgcgac gtacatccgc cggcgctact 1680
tcggcggcgg gaaccgatcc gacaacaacg gtggcggcgg ggaggtggag ccgtcaagag 1740
ggaagccgcc ggtcacttcg gactccatcg tcaacctcga tcagtgagtg atatgctttg 1800
ctgcctgggg atccgatcca tcatcgataa atcactcgtt attattttta ccgtctgtac 1860
tgtatgtatt ggtctctccc actgctcgtc catcgatcta ttctgtcctg ctggagtcac 1920
tagtgaaggt ccgttccatt tggggaacca gatcgagccc tagctatgca tatatgtgag 1980
tgaggcatct ggaacgaaga cgtacactag tgaagtcccg ctcagggtcc tgccctctcc 2040
atctagcaag gacatgtgca tcgatccttg ttgcctgatt agttgttgat tattagcagc 2100

-continued

```
tagtgtttgt atacttttcc tgattaattg cagatatata gtagtatttg tttatttcgt   2160
ttgattatta tatatatcgt gcttttgttc tgtttgtttg tttggttggt taattattta   2220
ggaaatagtg cgaagttaaa atagagatgg gttggaaaag atcgaaatgg catatatagt   2280
ggccctaaac caaaatatac atactgttag tttcagacaa aacagtacag ccttgcaatt   2340
accaacccct tatacacata tagatgcatg gacgagtact cttatttgaa tcttaacttt   2400
gttgactgtt ctctgtatgc tatgaactta atcgtcgtcg tccatgcaaa gcatgcatgc   2460
tactgtatgt ttttgacttt tggttggttg gttgcagtgg cgacccgact atgtacgagg   2520
agttctggcg cggcacagga gatagcgcct cgatcttcat ccctggttgg caaacaatga   2580
gctacttctc cgacctcggc ggcatctgtt ggttcctgga gcctggattc gagcgcgagg   2640
tgcggcgtct ccacaggctc gtggggaatg ccgttgtaga cgggtaccat gtgctcgtcg   2700
ggacaggctc cactcagctc tttcaggccg tgctgtacgc gctctcacct gcaagtgacg   2760
gcacacccat gaacgtcgtc tcaccggcac cgtactactc ggtaagaata cgttcagcca   2820
tcaaccaatc aatcaataaa attgtggttc gattgattaa tcatctgcta gctgatgatc   2880
gattttgaac acatgtgcag tcttacccat ctgtgaccaa ctatctaaac tctgcgctct   2940
accgttgggc tggtgatgcc aatacatttg atggcgacac atgtattgag ctcgtctgct   3000
ccccaaacaa ccctgatggt ggcctccgga agcctgtcat caaatccaag tctagcaagc   3060
ctgtttatga cttcgcctac tactggccgc agtacacacc catcaccgag gcagctgccc   3120
atgacatcat gctgttcacc gtctccaaat gcaccggcca tgccggcacc aggctggggt   3180
aaccatttct tggtcatcag ttgttaattt catatatata cacgtagtaa ttacgagata   3240
tgatatgaag tacggtggtt tgtttacgtg gagatgcttg taggtgggca ttggtgaagg   3300
atactaaggt ggctcagaag atgatcaagt ttatagagct caacacaatc ggtgtatcca   3360
aggactctca acttcgtgcc gctaagatta tcggggcaat atgtaatggc tatgagccgg   3420
taccatcctc tggtaaaaca agccaactct tccatttcgc caaggaaaaa atggcggctc   3480
gctgggctag acttcgtgca gctgtggcag cctcagacat ctttactctc ccttatgagc   3540
tatctggcta ttgtagcttt tccaatgaga ctgtcaccgc caatcctcgt aaggaaccac   3600
acattttaaa tttccattct tacatctacg actagtgcaa ttatattgtt gtttttatgc   3660
ttttatttgt aaataacatc gtcgaggaca aaaaaaaact cattattttc cttggttagc   3720
atttgcatgg cttcgctaca acaaggatga tattgaagat ctggaggcct tcctactcga   3780
gaaaaagatt atcactcgag gtggcacaag gtttggagtg gatgcaaggg ctgtcagagt   3840
tagtatggtt gacacagacc aagccttcaa tgtgttcatc aatcgtctgg ccacaatgaa   3900
gtgaaatttc agtgcaaatt aataaagcac tttgtggcta ctacaaggat gaccgcgttc   3960
tagatggaac aatcgatgct ttggaaagct taataatgtt ttatgttgtt gaataattcc   4020
gtgtgttttc gggtatgttg tgtaatactc aatgtcaaat cctatgctta atcgatgttg   4080
tggtccatcc tgttatcagc atggccaatt atatatggat gaccgtcact gctcagtctt   4140
tactcctaat tacatggcaa gtgtttaatg gtgcttcaat atcagttgat gactataact   4200
tggtactaaa gcaggatggt acactaacgt gtcactaatt ttttacagtg acattttttt   4260
aaaacaaatc actaacgact gtgcacatgt gatatctatt gtaaaaacgt gtcaataata   4320
tcgaaatatg gtaataaccc agtgacatct tttattttac gtgtctctat tgtgatctgt   4380
ttagtgacat gtacatataa atatgtcact ggctttagac gtcaaattta tttagtgaag   4440
```

tgtatataga aacatgtcac tgacttcaga tgtcagatct gtttagtgac atgtatttaa 4500
atgcacgtca caaatactta taccttagtg atgtgtatta agaaacatgt cactggtttt 4560
aaatg 4565

<210> SEQ ID NO 72
<211> LENGTH: 21
<212> TYPE: DNA
<213> ORGANISM: Artificial Sequence
<220> FEATURE:
<223> OTHER INFORMATION: primer

<400> SEQUENCE: 72
taactcatat ccggttagat a 21

<210> SEQ ID NO 73
<211> LENGTH: 24
<212> TYPE: DNA
<213> ORGANISM: Artificial Sequence
<220> FEATURE:
<223> OTHER INFORMATION: primer

<400> SEQUENCE: 73
gtcgtcgcca aataaaaacc tacc 24

<210> SEQ ID NO 74
<211> LENGTH: 22
<212> TYPE: DNA
<213> ORGANISM: Artificial Sequence
<220> FEATURE:
<223> OTHER INFORMATION: primer

<400> SEQUENCE: 74
atttaaatgt gttggataat ct 22

<210> SEQ ID NO 75
<211> LENGTH: 23
<212> TYPE: DNA
<213> ORGANISM: Artificial Sequence
<220> FEATURE:
<223> OTHER INFORMATION: primer

<400> SEQUENCE: 75
ctcctcctcc tcctcctcct cct 23

<210> SEQ ID NO 76
<211> LENGTH: 15
<212> TYPE: DNA
<213> ORGANISM: Artificial Sequence
<220> FEATURE:
<223> OTHER INFORMATION: consensus motif

<400> SEQUENCE: 76
attgacccta ttttg 15

<210> SEQ ID NO 77
<211> LENGTH: 11
<212> TYPE: DNA
<213> ORGANISM: Artificial Sequence
<220> FEATURE:
<223> OTHER INFORMATION: consensus motif

<400> SEQUENCE: 77
tatttgctta a 11

-continued

<210> SEQ ID NO 78
<211> LENGTH: 11
<212> TYPE: DNA
<213> ORGANISM: Artificial Sequence
<220> FEATURE:
<223> OTHER INFORMATION: consensus motif

<400> SEQUENCE: 78
caccaaacat t 11

<210> SEQ ID NO 79
<211> LENGTH: 11
<212> TYPE: DNA
<213> ORGANISM: Artificial Sequence
<220> FEATURE:
<223> OTHER INFORMATION: consensus motif

<400> SEQUENCE: 79
aggttaatta c 11

<210> SEQ ID NO 80
<211> LENGTH: 15
<212> TYPE: DNA
<213> ORGANISM: Artificial Sequence
<220> FEATURE:
<223> OTHER INFORMATION: consensus motif

<400> SEQUENCE: 80
ggtgacttgg cagtt 15

<210> SEQ ID NO 81
<211> LENGTH: 11
<212> TYPE: DNA
<213> ORGANISM: Artificial Sequence
<220> FEATURE:
<223> OTHER INFORMATION: consensus motif

<400> SEQUENCE: 81
ggggccgccc g 11

<210> SEQ ID NO 82
<211> LENGTH: 13
<212> TYPE: DNA
<213> ORGANISM: Artificial Sequence
<220> FEATURE:
<223> OTHER INFORMATION: consensus motif

<400> SEQUENCE: 82
tgagacgtgc cgc 13

<210> SEQ ID NO 83
<211> LENGTH: 11
<212> TYPE: DNA
<213> ORGANISM: Artificial Sequence
<220> FEATURE:
<223> OTHER INFORMATION: consensus motif

<400> SEQUENCE: 83
cgggccagct g 11

<210> SEQ ID NO 84
<211> LENGTH: 13
<212> TYPE: DNA
<213> ORGANISM: Artificial Sequence
<220> FEATURE:
<223> OTHER INFORMATION: consensus motif

<400> SEQUENCE: 84
cgccacgtgt ggg 13

<210> SEQ ID NO 85
<211> LENGTH: 13
<212> TYPE: DNA
<213> ORGANISM: Artificial Sequence
<220> FEATURE:
<223> OTHER INFORMATION: consensus motif

<400> SEQUENCE: 85
ccacacgtgg cgc 13

<210> SEQ ID NO 86
<211> LENGTH: 13
<212> TYPE: DNA
<213> ORGANISM: Artificial Sequence
<220> FEATURE:
<223> OTHER INFORMATION: consensus motif

<400> SEQUENCE: 86
ctccgcgcca cgt 13

<210> SEQ ID NO 87
<211> LENGTH: 13
<212> TYPE: DNA
<213> ORGANISM: Artificial Sequence
<220> FEATURE:
<223> OTHER INFORMATION: consensus motif

<400> SEQUENCE: 87
ggctcggcca cgt 13

<210> SEQ ID NO 88
<211> LENGTH: 13
<212> TYPE: DNA
<213> ORGANISM: Artificial Sequence
<220> FEATURE:
<223> OTHER INFORMATION: consensus motif

<400> SEQUENCE: 88
tataacgtgg ccg 13

<210> SEQ ID NO 89
<211> LENGTH: 13
<212> TYPE: DNA
<213> ORGANISM: Artificial Sequence
<220> FEATURE:
<223> OTHER INFORMATION: consensus motif

<400> SEQUENCE: 89
ttataagcca cgc 13

<210> SEQ ID NO 90
<211> LENGTH: 15
<212> TYPE: DNA
<213> ORGANISM: Artificial Sequence
<220> FEATURE:
<223> OTHER INFORMATION: consensus motif

<400> SEQUENCE: 90
cctgactact gcaca 15

<210> SEQ ID NO 91
<211> LENGTH: 11

<212> TYPE: DNA
<213> ORGANISM: Artificial Sequence
<220> FEATURE:
<223> OTHER INFORMATION: consensus motif

<400> SEQUENCE: 91
aacctacctc t 11

<210> SEQ ID NO 92
<211> LENGTH: 11
<212> TYPE: DNA
<213> ORGANISM: Artificial Sequence
<220> FEATURE:
<223> OTHER INFORMATION: consensus motif

<400> SEQUENCE: 92
tccatgcaaa a 11

<210> SEQ ID NO 93
<211> LENGTH: 11
<212> TYPE: DNA
<213> ORGANISM: Artificial Sequence
<220> FEATURE:
<223> OTHER INFORMATION: consensus motif

<400> SEQUENCE: 93
aacatgcaaa t 11

<210> SEQ ID NO 94
<211> LENGTH: 15
<212> TYPE: DNA
<213> ORGANISM: Artificial Sequence
<220> FEATURE:
<223> OTHER INFORMATION: consensus motif

<400> SEQUENCE: 94
attgacaata aaaca 15

<210> SEQ ID NO 95
<211> LENGTH: 10
<212> TYPE: DNA
<213> ORGANISM: Artificial Sequence
<220> FEATURE:
<223> OTHER INFORMATION: consensus motif

<400> SEQUENCE: 95
caaagccatc 10

<210> SEQ ID NO 96
<211> LENGTH: 11
<212> TYPE: DNA
<213> ORGANISM: Artificial Sequence
<220> FEATURE:
<223> OTHER INFORMATION: consensus motif

<400> SEQUENCE: 96
accatgcata t 11

<210> SEQ ID NO 97
<211> LENGTH: 15
<212> TYPE: DNA
<213> ORGANISM: Artificial Sequence
<220> FEATURE:
<223> OTHER INFORMATION: consensus motif

<400> SEQUENCE: 97

-continued attgacatgc atata                                                    15

<210> SEQ ID NO 98
<211> LENGTH: 11
<212> TYPE: DNA
<213> ORGANISM: Artificial Sequence
<220> FEATURE:
<223> OTHER INFORMATION: consensus motif

<400> SEQUENCE: 98
gacatgcata t                                                        11

<210> SEQ ID NO 99
<211> LENGTH: 15
<212> TYPE: DNA
<213> ORGANISM: Artificial Sequence
<220> FEATURE:
<223> OTHER INFORMATION: consensus motif

<400> SEQUENCE: 99
tttgacacat gaaaa                                                    15

<210> SEQ ID NO 100
<211> LENGTH: 13
<212> TYPE: DNA
<213> ORGANISM: Artificial Sequence
<220> FEATURE:
<223> OTHER INFORMATION: consensus motif

<400> SEQUENCE: 100
taccacctgt tgc                                                      13

<210> SEQ ID NO 101
<211> LENGTH: 11
<212> TYPE: DNA
<213> ORGANISM: Artificial Sequence
<220> FEATURE:
<223> OTHER INFORMATION: consensus motif

<400> SEQUENCE: 101
caccaaacct g                                                        11

<210> SEQ ID NO 102
<211> LENGTH: 11
<212> TYPE: DNA
<213> ORGANISM: Artificial Sequence
<220> FEATURE:
<223> OTHER INFORMATION: consensus motif

<400> SEQUENCE: 102
aacatgcatt t                                                        11

<210> SEQ ID NO 103
<211> LENGTH: 11
<212> TYPE: DNA
<213> ORGANISM: Artificial Sequence
<220> FEATURE:
<223> OTHER INFORMATION: consensus motif

<400> SEQUENCE: 103
cgattaactg c                                                        11

<210> SEQ ID NO 104
<211> LENGTH: 13
<212> TYPE: DNA
<213> ORGANISM: Artificial Sequence
<220> FEATURE:
<223> OTHER INFORMATION: consensus motif

<400> SEQUENCE: 104
acgacggcca ccg 13

<210> SEQ ID NO 105
<211> LENGTH: 15
<212> TYPE: DNA
<213> ORGANISM: Artificial Sequence
<220> FEATURE:
<223> OTHER INFORMATION: consensus motif

<400> SEQUENCE: 105
actgaccgag gcgcg 15

<210> SEQ ID NO 106
<211> LENGTH: 11
<212> TYPE: DNA
<213> ORGANISM: Artificial Sequence
<220> FEATURE:
<223> OTHER INFORMATION: consensus motif

<400> SEQUENCE: 106
tctataactg a 11

<210> SEQ ID NO 107
<211> LENGTH: 13
<212> TYPE: DNA
<213> ORGANISM: Artificial Sequence
<220> FEATURE:
<223> OTHER INFORMATION: consensus motif

<400> SEQUENCE: 107
cagaaggcca cgc 13

<210> SEQ ID NO 108
<211> LENGTH: 11
<212> TYPE: DNA
<213> ORGANISM: Artificial Sequence
<220> FEATURE:
<223> OTHER INFORMATION: consensus motif

<400> SEQUENCE: 108
cacatgcatc c 11

<210> SEQ ID NO 109
<211> LENGTH: 13
<212> TYPE: DNA
<213> ORGANISM: Artificial Sequence
<220> FEATURE:
<223> OTHER INFORMATION: consensus motif

<400> SEQUENCE: 109
acccaggcca cat 13

<210> SEQ ID NO 110
<211> LENGTH: 13
<212> TYPE: DNA
<213> ORGANISM: Artificial Sequence
<220> FEATURE:
<223> OTHER INFORMATION: consensus motif

<400> SEQUENCE: 110
acgtacgtgc aag 13

<210> SEQ ID NO 111
<211> LENGTH: 13
<212> TYPE: DNA
<213> ORGANISM: Artificial Sequence
<220> FEATURE:
<223> OTHER INFORMATION: consensus motif

<400> SEQUENCE: 111
gagtgcgcca cgc 13

<210> SEQ ID NO 112
<211> LENGTH: 13
<212> TYPE: DNA
<213> ORGANISM: Artificial Sequence
<220> FEATURE:
<223> OTHER INFORMATION: consensus motif

<400> SEQUENCE: 112
cgagctgacg agc 13

<210> SEQ ID NO 113
<211> LENGTH: 13
<212> TYPE: DNA
<213> ORGANISM: Artificial Sequence
<220> FEATURE:
<223> OTHER INFORMATION: consensus motif

<400> SEQUENCE: 113
ctagacgcca ccg 13

<210> SEQ ID NO 114
<211> LENGTH: 13
<212> TYPE: DNA
<213> ORGANISM: Artificial Sequence
<220> FEATURE:
<223> OTHER INFORMATION: consensus motif

<400> SEQUENCE: 114
tgccttgcca cgc 13

<210> SEQ ID NO 115
<211> LENGTH: 13
<212> TYPE: DNA
<213> ORGANISM: Artificial Sequence
<220> FEATURE:
<223> OTHER INFORMATION: consensus motif

<400> SEQUENCE: 115
atagctgacg agg 13

<210> SEQ ID NO 116
<211> LENGTH: 14144
<212> TYPE: DNA
<213> ORGANISM: Artificial Sequence
<220> FEATURE:
<223> OTHER INFORMATION: vector

<400> SEQUENCE: 116
gcaagctgtt ttactcaaat acacatcacc tttttagatg atcagtgatt ttgtgccgag 60
ctgccggtcg gggagctgtt ggctggctgg tggcaggata tattgtggtg taaacaaatt 120
gacgcttaga caacttaata acacattgcg gacgtcttta atgtactgaa tttagttact 180
gatcactgat taagtactga tatcggtacc aagcttccgc ggctgcagtg cagcgtgacc 240
cggtcgtgcc cctctctaga gataatgagc attgcatgtc taagttataa aaaattacca 300

-continued

```
catatttttt ttgtcacact tgtttgaagt gcagtttatc tatctttata catatattta    360
aactttactc tacgaataat ataatctata gtactacaat aatatcagtg ttttagagaa    420
tcatataaat gaacagttag acatggtcta aaggacaatt gagtattttg acaacaggac    480
tctacagttt tatcttttta gtgtgcatgt gttctccttt tttttgcaa atagcttcac     540
ctatataata cttcatccat tttattagta catccattta gggtttaggg ttaatggttt    600
ttatagacta atttttttag tacatctatt ttattctatt ttagcctcta aattaagaaa    660
actaaaactc tattttagtt tttttattta atagtttaga tataaaatag aataaaataa    720
agtgactaaa aattaaacaa atacccttta agaaattaaa aaaactaagg aaacattttt    780
cttgtttcga gtagataatg ccagcctgtt aaacgccgtc gacgagtcta acggacacca    840
accagcgaac cagcagcgtc gcgtcgggcc aagcgaagca gacggcacgg catctctgtc    900
gctgcctctg gacccctctc gagagttccg ctccaccgtt ggacttgctc cgctgtcggc    960
atccagaaat tgcgtggcgg agcggcagac gtgagccggc acggcaggcg gcctcctcct   1020
cctctcacgg caccggcagc tacgggggat tcctttccca ccgctccttc gctttccctt   1080
cctcgcccgc cgtaataaat agacaccccc tccacaccct ctttccccaa cctcgtgttg   1140
ttcggagcgc acacacacac aaccagatct cccccaaatc cacccgtcgg cacctccgct   1200
tcaaggtacg ccgctcgtcc tccccccccc ccccctctc taccttctct agatcggcgt    1260
tccggtccat ggttagggcc cggtagttct acttctgttc atgtttgtgt tagatccgtg   1320
tttgtgttag atccgtgctg ctagcgttcg tacacggatg cgacctgtac gtcagacacg   1380
ttctgattgc taacttgcca gtgtttctct ttggggaatc ctgggatggc tctagccgtt   1440
ccgcagacgg gatcgatttc atgatttttt ttgtttcgtt gcatagggtt tggtttgccc   1500
ttttccttta tttcaatata tgccgtgcac ttgtttgtcg ggtcatcttt tcatgctttt   1560
ttttgtcttg gttgtgatga tgtggtctgg ttgggcggtc gttctagatc ggagtagaat   1620
tctgtttcaa actacctggt ggatttatta attttggatc tgtatgtgtg tgccatacat   1680
attcatagtt acgaattgaa gatgatggat ggaaatatcg atctaggata ggtatacatg   1740
ttgatgcggg ttttactgat gcatatacag agatgctttt tgttcgcttg gttgtgatga   1800
tgtggtgtgg ttgggcggtc gttcattcgt tctagatcgg agtagaatac tgtttcaaac   1860
tacctggtgt atttattaat tttggaactg tatgtgtgtg tcatacatct tcatagttac   1920
gagtttaaga tggatggaaa tatcgatcta ggataggtat acatgttgat gtgggtttta   1980
ctgatgcata tacatgatgg catatgcagc atctattcat atgctctaac cttgagtacc   2040
tatctattat aataaacaag tatgttttat aattatttcg atcttgatat acttggatga   2100
tggcatatgc agcagctata tgtggatttt tttagccctg ccttcatacg ctatttattt   2160
gcttggtact gtttcttttg tcgatgctca ccctgttgtt tggtgttact tctgcagccc   2220
gggggatcca ctagttctag aaaccatggc caccgccgcc gccgcgtcta ccgcgctcac   2280
tggcgccact accgctgcgc ccaaggcgag gcgccgggcg cacctcctgg ccacccgccg   2340
cgccctcgcc gcgcccatca ggtgctcagc ggcgtcaccc gccatgccga tggctccccc   2400
ggccaccccg ctccggccgt ggggccccac cgatccccgc aagggcgccg acatcctcgt   2460
cgagtccctc gagcgctgcg gcgtccgcga cgtcttcgcc taccccggcg gcacgtccat   2520
ggagatccac caggcactca cccgctcccc cgtcatcgcc aaccacctct tccgccacga   2580
gcaaggggag gcctttgcgg cctccggcta cgcgcgctcc tcgggccgcg tcggcgtctg   2640
```

```
catcgccacc tccggccccg gcgccaccaa ccttgtctcc gcgctcgccg acgcgctgct   2700
cgattccgtc cccatggtcg ccatcacggg acaggtgccg cgacgcatga ttggcaccga   2760
cgccttccag gagacgccca tcgtcgaggt cacccgctcc atcaccaagc acaactacct   2820
ggtcctcgac gtcgacgaca tcccccgcgt cgtgcaggag gctttcttcc tcgcctcctc   2880
tggtcgaccg gggccggtgc ttgtcgacat ccccaaggac atccagcagc agatggcggt   2940
gcctgtctgg gacaagccca tgagtctgcc tgggtacatt gcgcgccttc ccaagccccc   3000
tgcgactgag ttgcttgagc aggtgctgcg tcttgttggt gaatcccggc gccctgttct   3060
ttatgttggc ggtggctgcg cagcatctgg tgaggagttg cgacgctttg tggagctgac   3120
tggaatcccg gtcacaacta ctcttatggg cctcggcaac ttccccagcg acgacccact   3180
gtctctgcgc atgctaggta tgcatggcac ggtgtatgca aattatgcag tggataaggc   3240
cgatctgttg cttgcacttg gtgtgcggtt tgatgatcgt gtgacaggga agattgaggc   3300
ttttgcaagc agggctaaga ttgtgcacgt tgatattgat ccggctgaga ttggcaagaa   3360
caagcagcca catgtgtcca tctgtgcaga tgttaagctt gctttgcagg gcatgaatgc   3420
tcttcttgaa ggaagcacat caaagaagag ctttgacttt ggctcatgga acgatgagtt   3480
ggatcagcag aagagggaat tccccccttgg gtataaaaca tctaatgagg agatccagcc   3540
acaatatgct attcaggttc ttgatgagct gacgaaaggc gaggccatca tcggcacagg   3600
tgttgggcag caccagatgt gggcggcaca gtactacact tacaagcggc caaggcagtg   3660
gttgtcttca gctggtcttg gggctatggg atttggtttg ccggctgctg ctggtgcttc   3720
tgtggccaac ccaggtgtta ctgttgttga catcgatgga gatggtagct ttctcatgaa   3780
cgttcaggag ctagctatga tccgaattga gaacctcccg gtgaaggtct ttgtgctaaa   3840
caaccagcac ctggggatgg tggtgcagtg ggaggacagg ttctataagg ccaacagagc   3900
gcacacatac ttgggaaacc cagagaatga aagtgagata tatccagatt tcgtgacgat   3960
cgccaaaggg ttcaacattc cagcggtccg tgtgacaaag aagaacgaag tccgcgcagc   4020
gataaagaag atgctcgaga ctccagggcc gtacctcttg gatataatcg tcccacacca   4080
ggagcatgtg ttgcctatga tccctaatgg tggggctttc aaggatatga tcctggatgg   4140
tgatggcagg actgtgtact gatctaaaat ccagcaagca actgatctaa aatccagcaa   4200
gcaccgcctc cctgctagta caagggtgat atgtttttat ctgtgtgatg ttctcctgta   4260
ttctatcttt ttttgtaggc cgtcagctat ctgttatggt aatcctatgt agcttccgac   4320
cttgtaattg tgtagtctgt tgttttcctt ctggcatgtg tcataagaga tcatttaagt   4380
gccttttgct acatataaat aagataataa gcactgctat gcagtggttc tgaattggct   4440
tctgttgcca aatttaagtg tccaactggt ccttgctttt gttttcgcta tttttttcct   4500
tttttagtta ttattatatt ggtaatttca actcaacata tgatgtatgg aataatgcta   4560
gggctgcaat ttcaaactat tttacaaacc agaatggcat tttcgtggtt tgaggggagt   4620
gaaaaaaaat gaggcatttg actgaattag ttacctgatc cattttcgtg gtttggatca   4680
ttggaattaa attccattct aataatagta attttggcat atatcaatta agttaattcg   4740
gttttatgca aaatatattt gtatactatt attatcaaga tgtcggagat atttatatgc   4800
tacattttta ctatacagga gtgagatgaa gagtgtcatg taagttacac agtagaaaca   4860
aattctatta atgcataaaa tcatttccat catccaccct atgaatttga gatagaccta   4920
tatctaaact ttgaaaagtg gttgaatatc aaattccaaa ttaaataagt tattttattg   4980
agtgaattct aatttctcta aaacgaaggg atctaaacgc cctctaaagc taatttggaa   5040
```

-continued actcaaactt tcttagcatt ggaggggatt gagaaaaaat attaattcat tttcatctca 5100
atcattcaat ctccaaagag atttgagttc cttattagtc tgttccatgc atcaaatcgg 5160
ctcaatgtgt cattatttgc catgacgatt gacgagttgt tctggggcct agcgctttcc 5220
acgccgatgt gctggggcct ggtcctggag aagacagctt gatatttaaa gctatcaatt 5280
gtttcaattg attcccactt catttttcta aatgtagaaa acggtgacgt ataagaaaaa 5340
gaatgaatta ggacttttat tccgtacact aatctagagc ggccgcaagc ttgtacaacg 5400
cgtaccggtt aattaaatta cgccaagcta tcaactttgt atagaaaagt tggcgcccta 5460
ggcggccgca ctaagcgcta tttaaattaa ctcatatccg gttagatacc aactacacat 5520
attgaatagc ataaatctaa taaatatatg gcgcaatgaa aatagtaaat aattaaatat 5580
gagtaaataa tatgatgaca ataatgaata atattggaac atgtacattg accctatttt 5640
gctaatatat acttattata tttgcttaat ttggtaggat gtatatgtga ttgaggcggg 5700
tataaattat ccataggtat gtgggtataa atagtctata cttataccca tactcatata 5760
cccgacgggt atatgattgt gtccattgcc atatctgcgg gtaaaaaact cattatatac 5820
ttgtccttat aagtaaaacc tgttggacac tagagtttag gtaccatata attattaatt 5880
ttgaacgaag gaagtaattt gcagcgtatt aaggtgcttc tggtctagaa gaaatgtcac 5940
aatgtttggt gttagttttt ggtgaaattt aaggttaatt actttttgaa agatgtttcc 6000
actaggtgga accgaaagaa acggtgccaa acacacctta caacaagaaa atatttgtaa 6060
aaaaattatt ttgaataaga tgtctaaaaa tagaaagcgt gtatacttta ggacggagga 6120
atacatatgt atgattggga aaaccgaaaa cgtacacctc ctcgctgcaa tacgctggtg 6180
acttggcagt tcgatcgcac ccagcggata aagatgagca cggagaactc acaaggcaca 6240
gccgcacagg caggcaccag cgcgaacgca tggacgggcg gcccctgaga cgtgccgccc 6300
agctggcccg ctgcgcccac acgtggcgcg gagctgcgcg cggctcggcc acgttataag 6360
ccacgcgcgc tggccgtcgc cgcacctcct gactactgca cactcgtctc cgcagtttga 6420
aacgaagccc gcggctactg caagctactc cgtctccgta gctaaaggag aggtaggttt 6480
ttatttggcg acgacacgta cggcctaggc cttcacctgc ggagggtaag atccgatcac 6540
catcttctga atttctgttc ttgatctgtc atgtataata actgtctagt cttggtgttg 6600
gtgagatgga aattcggtgg atctcggaag ggatattgtt cgtttgctgg ggtttttttt 6660
gtgtgttgtg atccgtagag aatttgtgtt tatccatgtt gttgatcttg gtatgtattc 6720
atgacatatt gacatgcatg tgttgtatgt gtcatatgtg tgcctctcct tgggatttgt 6780
tttggataat agaacatgtt atggactcaa tagtctgtga acaaatcttt ttttagatgg 6840
tggccaaatc tgatgatgat ctttcttgag aggaaaaagt tcatgataga aaaatctttt 6900
ttgagatggt ggcttaatgt gatgatgatc tttcttgaga ggaaaaaaaa gattcattat 6960
aggagatttt gatttagctc ctttccaccg atattaaatg aggagcatgc atgctgattg 7020
ctgataagga tctgattttt ttatcccctc ttctttgaac agacaagaaa taggctctga 7080
atttctgatt gattatttgt acatgcagaa gggcgaattc gacctaggcc aagtttgtac 7140
aaaaaagcag gcttgataac caaccatggt ccgtcctgta gaaaccccaa cccgtgaaat 7200
caaaaaactc gacggcctgt gggcattcag tctggatcgc gaaaactgtg gaattgatca 7260
gcgttggtgg gaaagcgcgt tacaagaaag ccgggcaatt gctgtgccag gcagttttaa 7320
cgatcagttc gccgatgcag atattcgtaa ttatgcgggc aacgtctggt atcagcgcga 7380

-continued

```
agtctttata ccgaaaggtt gggcaggcca gcgtatcgtg ctgcgtttcg atgcggtcac   7440
tcattacggc aaagtgtggg tcaataatca ggaagtgatg gagcatcagg gcggctatac   7500
gccatttgaa gccgatgtca cgccgtatgt tattgccggg aaaagtgtac gtaagtttct   7560
gcttctacct ttgatatata tataataatt atcattaatt agtagtaata taatatttca   7620
aatatttttt tcaaaataaa agaatgtagt atatagcaat tgcttttctg tagtttataa   7680
gtgtgtatat tttaatttat aacttttcta atatatgacc aaaatttgtt gatgtgcagg   7740
tatcaccgtt tgtgtgaaca acgaactgaa ctggcagact atcccgccgg gaatggtgat   7800
taccgacgaa aacggcaaga aaaagcagtc ttacttccat gatttcttta actatgccgg   7860
aatccatcgc agcgtaatgc tctacaccac gccgaacacc tgggtggacg atatcaccgt   7920
ggtgacgcat gtcgcgcaag actgtaacca cgcgtctgtt gactggcagg tggtggccaa   7980
tggtgatgtc agcgttgaac tgcgtgatgc ggatcaacag gtggttgcaa ctggacaagg   8040
cactagcggg actttgcaag tggtgaatcc gcacctctgg caaccgggtg aaggttatct   8100
ctatgaactg tgcgtcacag ccaaaagcca gacagagtgt gatatctacc cgcttcgcgt   8160
cggcatccgg tcagtggcag tgaagggcga acagttcctg attaaccaca aaccgttcta   8220
ctttactggc tttggtcgtc atgaagatgc ggacttgcgt ggcaaaggat tcgataacgt   8280
gctgatggtg cacgaccacg cattaatgga ctggattggg gccaactcct accgtacctc   8340
gcattaccct tacgctgaag agatgctcga ctgggcagat gaacatggca tcgtggtgat   8400
tgatgaaact gctgctgtcg gctttaacct ctctttaggc attggtttcg aagcgggcaa   8460
caagccgaaa gaactgtaca gcgaagaggc agtcaacggg gaaactcagc aagcgcactt   8520
acaggcgatt aaagagctga tagcgcgtga caaaaaccac ccaagcgtgg tgatgtggag   8580
tattgccaac gaaccggata cccgtccgca aggtgcacgg gaatatttcg cgccactggc   8640
ggaagcaacg cgtaaactcg acccgacgcg tccgatcacc tgcgtcaatg taatgttctg   8700
cgacgctcac accgatacca tcagcgatct ctttgatgtg ctgtgcctga accgttatta   8760
cggatggtat gtccaaagcg gcgatttgga aacggcagag aaggtactgg aaaaagaact   8820
tctggcctgg caggagaaac tgcatcagcc gattatcatc accgaatacg gcgtggatac   8880
gttagccggg ctgcactcaa tgtacaccga catgtggagt gaagagtatc agtgtgcatg   8940
gctggatatg tatcaccgcg tctttgatcg cgtcagcgcc gtcgtcggtg aacaggtatg   9000
gaatttcgcc gattttgcga cctcgcaagg catattgcgc gttggcggta acaagaaagg   9060
gatcttcact cgcgaccgca aaccgaagtc ggcggctttt ctgctgcaaa aacgctggac   9120
tggcatgaac ttcggtgaaa aaccgcagca gggaggcaaa caatgaatca aacccagctt   9180
tcttgtacaa agtgggacct aggatcgttc aaacatttgg caataaagtt tcttaagatt   9240
gaatcctgtt gccggtcttg cgatgattat catataattt ctgttgaatt acgttaagca   9300
tgtaataatt aacatgtaat gcatgacgtt atttatgaga tgggttttta tgattagagt   9360
cccgcaatta tacatttaat acgcgataga aaacaaaata tagcgcgcaa actaggataa   9420
attatcgcgc gcggtgtcat ctatgttact agatcgaatt caactttatt atacatagtt   9480
gataattcac tgggccggcc aggccttagt tactaatcag tgatcagatt gtcgtttccc   9540
gccttcagtt taaactatca gtgtttgaca ggatatattg gcgggtaaac ctaagagaaa   9600
agagcgttta ttagaataat cggatattta aaagggcgtg aaaaggttta tccgttcgtc   9660
catttgtatg tcaatattgg ggggggggga aagccacgtt gtgtctcaaa atctctgatg   9720
ttacattgca caagataaaa atatatcatc atgaacaata aaactgtctg cttacataaa   9780
```

-continued

```
cagtaataca aggggtgttc gccaccatga gccatatcca gcgtgaaacc tcgtgctccc   9840
gcccgcgcct caattccaat atggatgccg acctttatgg ctacaagtgg gcgcgcgaca   9900
acgtcggcca gtcgggcgcg accatttatc ggctttatgg caaacccgat gccccggaac   9960
tgttcctgaa gcacggcaaa ggcagcgtcg caaacgatgt caccgatgag atggtccgcc  10020
tgaactggct taccgagttc atgccgctgc cgacgattaa gcatttcatc cgtaccccgg  10080
acgatgcctg gctcttgacc acggccattc cgggcaaaac ggcctttcag gtccttgaag  10140
agtacccgga ctccggtgag aatatcgtgg acgccctcgc ggtcttcctc cgccgtttgc  10200
atagcatccc cgtgtgcaac tgccccttca actcggaccg ggttttccgc ctggcacagg  10260
cccagtcgcg catgaataac ggcctcgttg acgcgagcga tttcgacgat gaacggaatg  10320
gctggccggt ggaacaggtt tggaaggaaa tgcacaaact gcttccgttc tcgccggatt  10380
cggtggtcac gcatggtgat tttccctgg ataatctgat ctttgacgag ggcaagctga  10440
tcggctgcat cgacgtgggt cgcgtcggta tcgccgaccg ctatcaggac ctggcgatct  10500
tgtggaattg cctcggcgag ttctcgccct cgctccagaa gcgcctgttc cagaagtacg  10560
gcatcgacaa cccggatatg aacaagctcc agttccacct catgctggac gaattttttt  10620
gaacagaatt ggttaattgg ttgtaacact ggcagagcat tacgctgact tgacgggacg  10680
gcggctttgt tgaataaatc gaacttttgc tgagttgaag gatcgatgag ttgaaggacc  10740
ccgtagaaaa gatcaaagga tcttcttgag atcctttttt tctgcgcgta atctgctgct  10800
tgcaaacaaa aaaaccaccg ctaccagcgg tggtttgttt gccggatcaa gagctaccaa  10860
ctctttttcc gaaggtaact ggcttcagca gagcgcagat accaaatact gtccttctag  10920
tgtagccgta gttaggccac cacttcaaga actctgtagc accgcctaca tacctcgctc  10980
tgctaatcct gttaccagtg gctgctgcca gtggcgataa gtcgtgtctt accgggttgg  11040
actcaagacg atagttaccg gataaggcgc agcggtcggg ctgaacgggg ggttcgtgca  11100
cacagcccag cttggagcga acgacctaca ccgaactgag atacctacag cgtgagctat  11160
gagaaagcgc cacgcttccc gaagggagaa aggcggacag gtatccggta agcggcaggg  11220
tcggaacagg agagcgcacg agggagcttc caggggggaaa cgcctggtat ctttatagtc  11280
ctgtcgggtt tcgccacctc tgacttgagc gtcgattttt gtgatgctcg tcaggggggc  11340
ggagcctatg gaaaaacgcc agcaacgcgg cctttttacg gttcctggcc ttttgctggc  11400
cttttgctca catgttcttt cctgcgttat cccctgattc tgtggataac cgtattaccg  11460
cctttgagtg agctgatacc gctcgccgca gccgaacgac cgagcgcagc gagtcagtga  11520
gcgaggaagc ggaagagcgc ctgatgcggt attttctcct tacgcatctg tgcggtattt  11580
cacaccgcat aggccgcgat aggccgacgc gaagcggcgg ggcgtaggga gcgcagcgac  11640
cgaagggtag gcgctttttg cagctcttcg gctgtgcgct ggccagacag ttatgcacag  11700
gccaggcggg ttttaagagt tttaataagt tttaaagagt tttaggcgga aaaatcgcct  11760
tttttctctt ttatatcagt cacttacatg tgtgaccggt tcccaatgta cggctttggg  11820
ttcccaatgt acgggttccg gttcccaatg tacggctttg ggttcccaat gtacgtgcta  11880
tccacaggaa agagaccttt tcgacctttt tcccctgcta gggcaatttg ccctagcatc  11940
tgctccgtac attaggaacc ggcggatgct tcgccctcga tcaggttgcg gtagcgcatg  12000
actaggatcg ggccagcctg ccccgcctcc tccttcaaat cgtactccgg caggtcattt  12060
gacccgatca gcttgcgcac ggtgaaacag aacttcttga actctccggc gctgccactg  12120
```

cgttcgtaga tcgtcttgaa caaccatctg gcttctgcct tgcctgcggc gcggcgtgcc 12180
aggcggtaga gaaaacggcc gatgccgggg tcgatcaaaa agtaatcggg gtgaaccgtc 12240
agcacgtccg ggttcttgcc ttctgtgatc tcgcggtaca tccaatcagc aagctcgatc 12300
tcgatgtact ccggccgccc ggtttcgctc tttacgatct tgtagcggct aatcaaggct 12360
tcaccctcgg ataccgtcac caggcggccg ttcttggcct tcttggtacg ctgcatggca 12420
acgtgcgtgg tgtttaaccg aatgcaggtt tctaccaggt cgtctttctg ctttccgcca 12480
tcggctcgcc ggcagaactt gagtacgtcc gcaacgtgtg gacggaacac gcggccgggc 12540
ttgtctccct tcccttcccg gtatcggttc atggattcgg ttagatggga aaccgccatc 12600
agtaccaggt cgtaatccca cacactggcc atgccggcgg ggcctgcgga aacctctacg 12660
tgcccgtctg gaagctcgta gcggatcacc tcgccagctc gtcggtcacg cttcgacaga 12720
cggaaaacgg ccacgtccat gatgctgcga ctatcgcggg tgcccacgtc atagagcatc 12780
ggaacgaaaa aatctggttg ctcgtcgccc ttgggcggct tcctaatcga cggcgcaccg 12840
gctgccggcg gttgccggga ttctttgcgg attcgatcag cggccccttg ccacgattca 12900
ccggggcgtg cttctgcctc gatgcgttgc cgctgggcgg cctgcgcggc cttcaacttc 12960
tccaccaggt catcacccag cgccgcgccg atttgtaccg ggccggatgg tttgcgaccg 13020
ctcacgccga ttcctcgggc ttgggggttc cagtgccatt gcagggccgg cagacaaccc 13080
agccgcttac gcctggccaa ccgcccgttc ctccacacat ggggcattcc acggcgtcgg 13140
tgcctggttg ttcttgattt tccatgccgc ctcctttagc cgctaaaatt catctactca 13200
tttattcatt tgctcattta ctctggtagc tgcgcgatgt attcagatag cagctcggta 13260
atggtcttgc cttggcgtac cgcgtacatc ttcagcttgg tgtgatcctc cgccggcaac 13320
tgaaagttga cccgcttcat ggctggcgtg tctgccaggc tggccaacgt tgcagccttg 13380
ctgctgcgtg cgctcggacg gccggcactt agcgtgtttg tgcttttgct cattttctct 13440
ttacctcatt aactcaaatg agttttgatt taatttcagc ggccagcgcc tggacctcgc 13500
gggcagcgtc gccctcgggt tctgattcaa gaacggttgt gccggcggcg gcagtgcctg 13560
ggtagctcac gcgctgcgtg atacgggact caagaatggg cagctcgtac ccggccagcg 13620
cctcggcaac ctcaccgccg atgcgcgtgc ctttgatcgc ccgcgacacg acaaaggccg 13680
cttgtagcct tccatccgtg acctcaatgc gctgcttaac cagctccacc aggtcggcgg 13740
tggcccaaat gtcgtaaggg cttggctgca ccggaatcag cacgaagtcg gctgccttga 13800
tcgcggacac agccaagtcc gccgcctggg gcgctccgtc gatcactacg aagtcgcgcc 13860
ggccgatggc cttcacgtcg cggtcaatcg tcgggcggtc gatgccgaca acggttagcg 13920
gttgatcttc ccgcacggcc gcccaatcgc gggcactgcc ctggggatcg gaatcgacta 13980
acagaacatc ggccccggcg agttgcaggg cgcgggctag atgggttgcg atggtcgtct 14040
tgcctgaccc gcctttctgg ttaagtacag cgataacctt catgcgttcc ccttgcgtat 14100
ttgtttattt actcatcgca tcatatacgc agcgaccgca tgac 14144

<210> SEQ ID NO 117
<211> LENGTH: 14627
<212> TYPE: DNA
<213> ORGANISM: Artificial Sequence
<220> FEATURE:
<223> OTHER INFORMATION: vector

<400> SEQUENCE: 117
gtgattttgt gccgagctgc cggtcgggga gctgttggct ggctggtggc aggatatatt 60

-continued

```
gtggtgtaaa caaattgacg cttagacaac ttaataacac attgcggacg tctttaatgt    120
actgaattta gttactgatc actgattaag tactgatatc ggtaccaagc ttccgcggct    180
gcagtgcagc gtgacccggt cgtgcccctc tctagagata atgagcattg catgtctaag    240
ttataaaaaa ttaccacata tttttttgt cacacttgtt tgaagtgcag tttatctatc    300
tttatacata tatttaaact ttactctacg aataatataa tctatagtac tacaataata    360
tcagtgtttt agagaatcat ataaatgaac agttagacat ggtctaaagg acaattgagt    420
attttgacaa caggactcta cagttttatc tttttagtgt gcatgtgttc tccttttttt    480
ttgcaaatag cttcacctat ataatacttc atccatttta ttagtacatc catttagggt    540
ttagggttaa tggtttttat agactaattt ttttagtaca tctattttat tctattttag    600
cctctaaatt aagaaaacta aaactctatt ttagtttttt tatttaatag tttagatata    660
aaatagaata aaataaagtg actaaaaatt aaacaaatac cctttaagaa attaaaaaaa    720
ctaaggaaac atttttcttg tttcgagtag ataatgccag cctgttaaac gccgtcgacg    780
agtctaacgg acaccaacca gcgaaccagc agcgtcgcgt cgggccaagc gaagcagacg    840
gcacggcatc tctgtcgctg cctctggacc cctctcgaga gttccgctcc accgttggac    900
ttgctccgct gtcggcatcc agaaattgcg tggcggagcg gcagacgtga gccggcacgg    960
caggcggcct cctcctcctc tcacggcacc ggcagctacg gggggattcct ttcccaccgc   1020
tccttcgctt tcccttcctc gcccgccgta ataaatagac accccctcca caccctcttt   1080
ccccaacctc gtgttgttcg gagcgcacac acacacaacc agatctcccc caaatccacc   1140
cgtcggcacc tccgcttcaa ggtacgccgc tcgtcctccc cccccccccc cctctctacc   1200
ttctctagat cggcgttccg gtccatggtt agggcccggt agttctactt ctgttcatgt   1260
ttgtgttaga tccgtgtttg tgttagatcc gtgctgctag cgttcgtaca cggatgcgac   1320
ctgtacgtca gacacgttct gattgctaac ttgccagtgt ttctctttgg ggaatcctgg   1380
gatggctcta gccgttccgc agacgggatc gatttcatga ttttttttgt ttcgttgcat   1440
agggtttggt ttgccctttt cctttatttc aatatatgcc gtgcacttgt ttgtcgggtc   1500
atcttttcat gctttttttt gtcttggttg tgatgatgtg gtctggttgg gcggtcgttc   1560
tagatcggag tagaattctg tttcaaacta cctggtggat ttattaattt tggatctgta   1620
tgtgtgtgcc atacatattc atagttacga attgaagatg atggatggaa atatcgatct   1680
aggataggta tacatgttga tgcgggtttt actgatgcat atacagagat gctttttgtt   1740
cgcttggttg tgatgatgtg gtgtggttgg gcggtcgttc attcgttcta gatcggagta   1800
gaatactgtt tcaaactacc tggtgtattt attaattttg gaactgtatg tgtgtgtcat   1860
acatcttcat agttacgagt ttaagatgga tggaaatatc gatctaggat aggtatacat   1920
gttgatgtgg gttttactga tgcatataca tgatggcata tgcagcatct attcatatgc   1980
tctaaccttg agtacctatc tattataata aacaagtatg ttttataatt atttcgatct   2040
tgatatactt ggatgatggc atatgcagca gctatatgtg gattttttta gccctgcctt   2100
catacgctat ttatttgctt ggtactgttt cttttgtcga tgctcaccct gttgtttggt   2160
gttacttctg cagcccgggg gatccactag ttctagaaac catggccacc gccgccgccg   2220
cgtctaccgc gctcactggc gccactaccg ctgcgcccaa ggcgaggcgc cgggcgcacc   2280
tcctggccac ccgccgcgcc ctcgccgcgc ccatcaggtg ctcagcggcg tcacccgcca   2340
tgccgatggc tccccccggcc accccgctcc ggccgtgggg ccccaccgat ccccgcaagg   2400
```

-continued

```
gcgccgacat cctcgtcgag tccctcgagc gctgcggcgt ccgcgacgtc ttcgcctacc   2460
ccggcggcac gtccatggag atccaccagg cactcacccg ctcccccgtc atcgccaacc   2520
acctcttccg ccacgagcaa ggggaggcct ttgcggcctc cggctacgcg cgctcctcgg   2580
gccgcgtcgg cgtctgcatc gccacctccg gccccggcgc caccaacctt gtctccgcgc   2640
tcgccgacgc gctgctcgat tccgtcccca tggtcgccat cacgggacag gtgccgcgac   2700
gcatgattgg caccgacgcc ttccaggaga cgcccatcgt cgaggtcacc cgctccatca   2760
ccaagcacaa ctacctggtc ctcgacgtcg acgacatccc ccgcgtcgtg caggaggctt   2820
tcttcctcgc ctcctctggt cgaccggggc cggtgcttgt cgacatcccc aaggacatcc   2880
agcagcagat ggcggtgcct gtctgggaca agcccatgag tctgcctggg tacattgcgc   2940
gccttcccaa gccccctgcg actgagttgc ttgagcaggt gctgcgtctt gttggtgaat   3000
cccggcgccc tgttctttat gttggcggtg gctgcgcagc atctggtgag gagttgcgac   3060
gctttgtgga gctgactgga atcccggtca caactactct tatgggcctc ggcaacttcc   3120
ccagcgacga cccactgtct ctgcgcatgc taggtatgca tggcacggtg tatgcaaatt   3180
atgcagtgga taaggccgat ctgttgcttg cacttggtgt gcggtttgat gatcgtgtga   3240
cagggaagat tgaggctttt gcaagcaggg ctaagattgt gcacgttgat attgatccgg   3300
ctgagattgg caagaacaag cagccacatg tgtccatctg tgcagatgtt aagcttgctt   3360
tgcagggcat gaatgctctt cttgaaggaa gcacatcaaa gaagagcttt gactttggct   3420
catggaacga tgagttggat cagcagaaga gggaattccc ccttgggtat aaaacatcta   3480
atgaggagat ccagccacaa tatgctattc aggttcttga tgagctgacg aaaggcgagg   3540
ccatcatcgg cacaggtgtt gggcagcacc agatgtgggc ggcacagtac tacacttaca   3600
agcggccaag gcagtggttg tcttcagctg gtcttggggc tatgggattt ggtttgccgg   3660
ctgctgctgg tgcttctgtg gccaacccag gtgttactgt tgttgacatc gatggagatg   3720
gtagctttct catgaacgtt caggagctag ctatgatccg aattgagaac ctcccggtga   3780
aggtctttgt gctaaacaac cagcacctgg ggatggtggt gcagtgggag gacaggttct   3840
ataaggccaa cagagcgcac acatacttgg gaaacccaga gaatgaaagt gagatatatc   3900
cagatttcgt gacgatcgcc aaagggttca acattccagc ggtccgtgtg acaaagaaga   3960
acgaagtccg cgcagcgata aagaagatgc tcgagactcc agggccgtac ctcttggata   4020
taatcgtccc acaccaggag catgtgttgc ctatgatccc taatggtggg gctttcaagg   4080
atatgatcct ggatggtgat ggcaggactg tgtactgatc taaaatccag caagcaactg   4140
atctaaaatc cagcaagcac cgcctccctg ctagtacaag ggtgatatgt ttttatctgt   4200
gtgatgttct cctgtattct atcttttttt gtaggccgtc agctatctgt tatggtaatc   4260
ctatgtagct tccgaccttg taattgtgta gtctgttgtt ttccttctgg catgtgtcat   4320
aagagatcat ttaagtgcct tttgctacat ataaataaga taataagcac tgctatgcag   4380
tggttctgaa ttggcttctg ttgccaaatt taagtgtcca actggtcctt gcttttgttt   4440
tcgctatttt tttccttttt tagttattat tatattggta atttcaactc aacatatgat   4500
gtatggaata atgctagggc tgcaatttca aactatttta caaaccagaa tggcattttc   4560
gtggtttgag gggagtgaaa aaaaatgagg catttgactg aattagttac ctgatccatt   4620
ttcgtggttt ggatcattgg aattaaattc cattctaata atagtaattt tggcatatat   4680
caattaagtt aattcggttt tatgcaaaat atatttgtat actattatta tcaagatgtc   4740
ggagatattt atatgctaca tttttactat acaggagtga gatgaagagt gtcatgtaag   4800
```

-continued

```
ttacacagta gaaacaaatt ctattaatgc ataaaatcat ttccatcatc caccctatga   4860
atttgagata gacctatatc taaactttga aaagtggttg aatatcaaat tccaaattaa   4920
ataagttatt ttattgagtg aattctaatt tctctaaaac gaagggatct aaacgccctc   4980
taaagctaat ttggaaactc aaactttctt agcattggag gggattgaga aaaaatatta   5040
attcattttc atctcaatca ttcaatctcc aaagagattt gagttcctta ttagtctgtt   5100
ccatgcatca aatcggctca atgtgtcatt atttgccatg acgattgacg agttgttctg   5160
gggcctagcg ctttccacgc cgatgtgctg gggcctggtc ctggagaaga cagcttgata   5220
tttaaagcta tcaattgttt caattgattc ccacttcatt tttctaaatg tagaaaacgg   5280
tgacgtataa gaaaaagaat gaattaggac ttttattccg tacactaatc tagagcggcc   5340
gcaagcttgt acaacgcgta ccggttaatt aaattacgcc aagctatcaa ctttgtatag   5400
aaaagttggc gccctaggcg gccgcactaa gcgctattta aatgtgttgg ataatctttt   5460
gcatggatat gtgttgtgaa ttcgcaccat gtgcccacga aagcagcatg ggatcgcccc   5520
caccaatttt tttttaccag ctctaactct caaccagaaa acatgcaaat ttatttgtca   5580
ttgcacacca gcaacctagg gatggtaatc ccaaaatgca atgattttta gagcatagat   5640
gtgggcgaat ttacctaact atggatatgt taattgacaa taaaacacca taaccactgg   5700
gttcatgggt acgagtatgg ttttgtacat gaaagaataa acttatgaga gtgtgtatat   5760
actcaacata caagtataat tcccaaagcc atctccaacc tattgtagtc caaaatatgc   5820
atggtccaac aagcacacct attgacatgc atataagcca tcacatatat atatacacta   5880
atttttacta ttacatatgt tatatattta tagatatatg ttatttgttt atattgtcag   5940
tgtttactgc gtgtgttata tttttttct taggtacggt gtaggtaacc accgtgtcta   6000
tctcgacacg cgtacgggca caaaattaca tcaacacatg gtatgagatt tttcatgtgt   6060
caaataaatt ttgatggcta gtttaaaaac ttaaatcact catgagatta ccggagacga   6120
ttgaggggaa aatttcctag tattacggac ggaatttaag tttttcaaac tagccctaat   6180
aaaataaata tgggtatgta ggtatgagcg cgataccacc tgttgcggcg ggactgcagg   6240
tttggtgaca gctagaaaca tgcatttagg tgttgaatct tgattatttg cagttaatcg   6300
tgcttgctgt gttgccgcaa acacgagatt cacaccctga tgagcggagc caggctgccc   6360
ttgcttcgat tcacggtggc cgtcgtcccg gccaggccag cacaccagtc caatccacat   6420
agcaacaacc gcgcctcggt cagttataga tgcgtggcct tctgaaacaa accctcatat   6480
ggggtcacgc cgcactcaca catgcatcca taaaccctca gcagagcctt gtgtcgcgtc   6540
ctctcctcga taacccaggc cacatcgtcc ttccgcgccg cgccgccggc gacctaacaa   6600
cccagaggcc tcagcaccgc acgcttgcac gtacgtccag gcgcgctcgc cgttacgccc   6660
acggggatcc aggctttcct tcgctgccgt tgctggtcga gtgcgccacg ccgaaaggtg   6720
atcgagctga cgagcgctag acgccaccgg ccggcgcggc gtggcaaggc aagacgccgt   6780
gcgggtctcg ccctcgtcag ctataagacc gcatcccccc ctgcggaggg aggcacacac   6840
acagacacag cgctctcact agcctcgcat tccgtccctg cagtgcaggg gcaggccggt   6900
gaggtctggg agaggaggag gaggaggagg aggagcgtac ggcctaggcc ttcacctgcg   6960
gagggtaaga tccgatcacc atcttctgaa tttctgttct tgatctgtca tgtataataa   7020
ctgtctagtc ttggtgttgg tgagatggaa attcggtgga tctcggaagg gatattgttc   7080
gtttgctggg gtttttttg tgtgttgtga tccgtagaga atttgtgttt atccatgttg   7140
```

-continued

```
ttgatcttgg tatgtattca tgacatattg acatgcatgt gttgtatgtg tcatatgtgt   7200
gcctctcctt gggatttgtt ttggataata gaacatgtta tggactcaat agtctgtgaa   7260
caaatctttt tttagatggt ggccaaatct gatgatgatc tttcttgaga ggaaaaagtt   7320
catgatagaa aaatcttttt tgagatggtg gcttaatgtg atgatgatct ttcttgagag   7380
gaaaaaaaag attcattata ggagattttg atttagctcc tttccaccga tattaaatga   7440
ggagcatgca tgctgattgc tgataaggat ctgatttttt tatcccctct tctttgaaca   7500
gacaagaaat aggctctgaa tttctgattg attatttgta catgcagaag ggcgaattcg   7560
acctaggcca agtttgtaca aaaaagcagg cttgataacc aaccatggtc cgtcctgtag   7620
aaaccccaac ccgtgaaatc aaaaaactcg acggcctgtg ggcattcagt ctggatcgcg   7680
aaaactgtgg aattgatcag cgttggtggg aaagcgcgtt acaagaaagc cgggcaattg   7740
ctgtgccagg cagttttaac gatcagttcg ccgatgcaga tattcgtaat tatgcgggca   7800
acgtctggta tcagcgcgaa gtctttatac cgaaaggttg ggcaggccag cgtatcgtgc   7860
tgcgtttcga tgcggtcact cattacggca aagtgtgggt caataatcag gaagtgatgg   7920
agcatcaggg cggctatacg ccatttgaag ccgatgtcac gccgtatgtt attgccggga   7980
aaagtgtacg taagtttctg cttctacctt tgatatatat ataataatta tcattaatta   8040
gtagtaatat aatatttcaa atattttttt caaaataaaa gaatgtagta tatagcaatt   8100
gcttttctgt agtttataag tgtgtatatt ttaatttata acttttctaa tatatgacca   8160
aaatttgttg atgtgcaggt atcaccgttt gtgtgaacaa cgaactgaac tggcagacta   8220
tcccgccggg aatggtgatt accgacgaaa acggcaagaa aaagcagtct tacttccatg   8280
atttctttaa ctatgccgga atccatcgca gcgtaatgct ctacaccacg ccgaacacct   8340
gggtggacga tatcaccgtg gtgacgcatg tcgcgcaaga ctgtaaccac gcgtctgttg   8400
actggcaggt ggtggccaat ggtgatgtca gcgttgaact gcgtgatgcg gatcaacagg   8460
tggttgcaac tggacaaggc actagcggga ctttgcaagt ggtgaatccg cacctctggc   8520
aaccgggtga aggttatctc tatgaactgt gcgtcacagc caaaagccag acagagtgtg   8580
atatctaccc gcttcgcgtc ggcatccggt cagtggcagt gaagggcgaa cagttcctga   8640
ttaaccacaa accgttctac tttactggct ttggtcgtca tgaagatgcg gacttgcgtg   8700
gcaaaggatt cgataacgtg ctgatggtgc acgaccacgc attaatggac tggattgggg   8760
ccaactccta ccgtacctcg cattaccctt acgctgaaga gatgctcgac tgggcagatg   8820
aacatggcat cgtggtgatt gatgaaactg ctgctgtcgg ctttaacctc tctttaggca   8880
ttggtttcga agcgggcaac aagccgaaag aactgtacag cgaagaggca gtcaacgggg   8940
aaactcagca agcgcactta caggcgatta aagagctgat agcgcgtgac aaaaaccacc   9000
caagcgtggt gatgtggagt attgccaacg aaccggatac ccgtccgcaa ggtgcacggg   9060
aatatttcgc gccactggcg gaagcaacgc gtaaactcga cccgacgcgt ccgatcacct   9120
gcgtcaatgt aatgttctgc gacgctcaca ccgataccat cagcgatctc tttgatgtgc   9180
tgtgcctgaa ccgttattac ggatggtatg tccaaagcgg cgatttggaa acggcagaga   9240
aggtactgga aaaagaactt ctggcctggc aggagaaact gcatcagccg attatcatca   9300
ccgaatacgg cgtggatacg ttagccgggc tgcactcaat gtacaccgac atgtggagtg   9360
aagagtatca gtgtgcatgg ctggatatgt atcaccgcgt ctttgatcgc gtcagcgccg   9420
tcgtcggtga acaggtatgg aatttcgccg attttgcgac ctcgcaaggc atattgcgcg   9480
ttggcggtaa caagaaaggg atcttcactc gcgaccgcaa accgaagtcg gcggcttttc   9540
```

-continued

```
tgctgcaaaa acgctggact ggcatgaact tcggtgaaaa accgcagcag ggaggcaaac   9600
aatgaatcaa acccagcttt cttgtacaaa gtgggaccta ggatcgttca aacatttggc   9660
aataaagttt cttaagattg aatcctgttg ccggtcttgc gatgattatc atataatttc   9720
tgttgaatta cgttaagcat gtaataatta acatgtaatg catgacgtta tttatgagat   9780
gggtttttat gattagagtc ccgcaattat acatttaata cgcgatagaa aacaaaatat   9840
agcgcgcaaa ctaggataaa ttatcgcgcg cggtgtcatc tatgttacta gatcgaattc   9900
aactttatta tacatagttg ataattcact gggccggcca ggccttagtt actaatcagt   9960
gatcagattg tcgtttcccg ccttcagttt aaactatcag tgtttgacag gatatattgg  10020
cgggtaaacc taagagaaaa gagcgtttat tagaataatc ggatatttaa aagggcgtga  10080
aaaggtttat ccgttcgtcc atttgtatgt caatattggg ggggggggaa agccacgttg  10140
tgtctcaaaa tctctgatgt tacattgcac aagataaaaa tatatcatca tgaacaataa  10200
aactgtctgc ttacataaac agtaatacaa ggggtgttcg ccaccatgag ccatatccag  10260
cgtgaaacct cgtgctcccg cccgcgcctc aattccaata tggatgccga cctttatggc  10320
tacaagtggg cgcgcgacaa cgtcggccag tcgggcgcga ccatttatcg gctttatggc  10380
aaacccgatg ccccggaact gttcctgaag cacggcaaag gcagcgtcgc aaacgatgtc  10440
accgatgaga tggtccgcct gaactggctt accgagttca tgccgctgcc gacgattaag  10500
catttcatcc gtaccccgga cgatgcctgg ctcttgacca cggccattcc gggcaaaacg  10560
gcctttcagg tccttgaaga gtacccggac tccggtgaga atatcgtgga cgccctcgcg  10620
gtcttcctcc gccgtttgca tagcatcccc gtgtgcaact gccccttcaa ctcggaccgg  10680
gttttccgcc tggcacaggc ccagtcgcgc atgaataacg gcctcgttga cgcgagcgat  10740
ttcgacgatg aacggaatgg ctggccggtg gaacaggttt ggaaggaaat gcacaaactg  10800
cttccgttct cgccggattc ggtggtcacg catggtgatt tttccctgga taatctgatc  10860
tttgacgagg gcaagctgat cggctgcatc gacgtgggtc gcgtcggtat cgccgaccgc  10920
tatcaggacc tggcgatctt gtggaattgc ctcggcgagt tctcgccctc gctccagaag  10980
cgcctgttcc agaagtacgg catcgacaac ccggatatga acaagctcca gttccacctc  11040
atgctggacg aatttttttg aacagaattg gttaattggt tgtaacactg gcagagcatt  11100
acgctgactt gacgggacgg cggctttgtt gaataaatcg aacttttgct gagttgaagg  11160
atcgatgagt tgaaggaccc cgtagaaaag atcaaaggat cttcttgaga tccttttttt  11220
ctgcgcgtaa tctgctgctt gcaaacaaaa aaaccaccgc taccagcggt ggtttgtttg  11280
ccggatcaag agctaccaac tctttttccg aaggtaactg gcttcagcag agcgcagata  11340
ccaaatactg tccttctagt gtagccgtag ttaggccacc acttcaagaa ctctgtagca  11400
ccgcctacat acctcgctct gctaatcctg ttaccagtgg ctgctgccag tggcgataag  11460
tcgtgtctta ccgggttgga ctcaagacga tagttaccgg ataaggcgca gcggtcgggc  11520
tgaacggggg gttcgtgcac acagcccagc ttggagcgaa cgacctacac cgaactgaga  11580
tacctacagc gtgagctatg agaaagcgcc acgcttcccg aagggagaaa ggcggacagg  11640
tatccggtaa gcggcagggt cggaacagga gagcgcacga gggagcttcc agggggaaac  11700
gcctggtatc tttatagtcc tgtcgggttt cgccacctct gacttgagcg tcgatttttg  11760
tgatgctcgt caggggggcg gagcctatgg aaaaacgcca gcaacgcggc ctttttacgg  11820
ttcctggcct tttgctggcc ttttgctcac atgttctttc ctgcgttatc ccctgattct  11880
```

-continued gtggataacc gtattaccgc ctttgagtga gctgataccg ctcgccgcag ccgaacgacc 11940
gagcgcagcg agtcagtgag cgaggaagcg gaagagcgcc tgatgcggta ttttctcctt 12000
acgcatctgt gcggtatttc acaccgcata ggccgcgata ggccgacgcg aagcggcggg 12060
gcgtagggag cgcagcgacc gaagggtagg cgctttttgc agctcttcgg ctgtgcgctg 12120
gccagacagt tatgcacagg ccaggcgggt tttaagagtt ttaataagtt ttaaagagtt 12180
ttaggcggaa aaatcgcctt ttttctcttt tatatcagtc acttacatgt gtgaccggtt 12240
cccaatgtac ggctttgggt tcccaatgta cgggttccgg ttcccaatgt acggctttgg 12300
gttcccaatg tacgtgctat ccacaggaaa gagacctttt cgaccttttt cccctgctag 12360
ggcaatttgc cctagcatct gctccgtaca ttaggaaccg gcggatgctt cgccctcgat 12420
caggttgcgg tagcgcatga ctaggatcgg gccagcctgc cccgcctcct ccttcaaatc 12480
gtactccggc aggtcatttg acccgatcag cttgcgcacg gtgaaacaga acttcttgaa 12540
ctctccggcg ctgccactgc gttcgtagat cgtcttgaac aaccatctgg cttctgcctt 12600
gcctgcggcg cggcgtgcca ggcggtagag aaaacggccg atgccggggt cgatcaaaaa 12660
gtaatcgggg tgaaccgtca gcacgtccgg gttcttgcct tctgtgatct cgcggtacat 12720
ccaatcagca agctcgatct cgatgtactc cggccgcccg gtttcgctct ttacgatctt 12780
gtagcggcta atcaaggctt caccctcgga taccgtcacc aggcggccgt tcttggcctt 12840
cttggtacgc tgcatggcaa cgtgcgtggt gtttaaccga atgcaggttt ctaccaggtc 12900
gtctttctgc tttccgccat cggctcgccg gcagaacttg agtacgtccg caacgtgtgg 12960
acggaacacg cggccgggct tgtctccctt cccttcccgg tatcggttca tggattcggt 13020
tagatgggaa accgccatca gtaccaggtc gtaatcccac acactggcca tgccggcggg 13080
gcctgcggaa acctctacgt gcccgtctgg aagctcgtag cggatcacct cgccagctcg 13140
tcggtcacgc ttcgacagac ggaaaacggc cacgtccatg atgctgcgac tatcgcgggt 13200
gcccacgtca tagagcatcg gaacgaaaaa atctggttgc tcgtcgccct tgggcggctt 13260
cctaatcgac ggcgcaccgg ctgccggcgg ttgccgggat tctttgcgga ttcgatcagc 13320
ggccccttgc cacgattcac cggggcgtgc ttctgcctcg atgcgttgcc gctgggcggc 13380
ctgcgcggcc ttcaacttct ccaccaggtc atcacccagc gccgcgccga tttgtaccgg 13440
gccggatggt ttgcgaccgc tcacgccgat tcctcgggct tgggggttcc agtgccattg 13500
cagggccggc agacaaccca gccgcttacg cctggccaac cgcccgttcc tccacacatg 13560
gggcattcca cggcgtcggt gcctggttgt tcttgatttt ccatgccgcc tcctttagcc 13620
gctaaaattc atctactcat ttattcattt gctcatttac tctggtagct gcgcgatgta 13680
ttcagatagc agctcggtaa tggtcttgcc ttggcgtacc gcgtacatct tcagcttggt 13740
gtgatcctcc gccggcaact gaaagttgac ccgcttcatg gctggcgtgt ctgccaggct 13800
ggccaacgtt gcagccttgc tgctgcgtgc gctcggacgg ccggcactta gcgtgtttgt 13860
gcttttgctc attttctctt tacctcatta actcaaatga gttttgattt aatttcagcg 13920
gccagcgcct ggacctcgcg ggcagcgtcg ccctcgggtt ctgattcaag aacggttgtg 13980
ccggcggcgg cagtgcctgg gtagctcacg cgctgcgtga tacgggactc aagaatgggc 14040
agctcgtacc cggccagcgc ctcggcaacc tcaccgccga tgcgcgtgcc tttgatcgcc 14100
cgcgacacga caaaggccgc ttgtagcctt ccatccgtga cctcaatgcg ctgcttaacc 14160
agctccacca ggtcggcggt ggcccaaatg tcgtaagggc ttggctgcac cggaatcagc 14220
acgaagtcgg ctgccttgat cgcggacaca gccaagtccg ccgcctgggg cgctccgtcg 14280
atcactacga agtcgcgccg gccgatggcc ttcacgtcgc ggtcaatcgt cgggcggtcg 14340
atgccgacaa cggttagcgg ttgatcttcc cgcacggccg cccaatcgcg ggcactgccc 14400
tggggatcgg aatcgactaa cagaacatcg gccccggcga gttgcagggc gcgggctaga 14460
tgggttgcga tggtcgtctt gcctgacccg cctttctggt taagtacagc gataaccttc 14520
atgcgttccc cttgcgtatt tgtttattta ctcatcgcat catatacgca gcgaccgcat 14580
gacgcaagct gttttactca aatacacatc accttttag atgatca 14627

<210> SEQ ID NO 118
<211> LENGTH: 82
<212> TYPE: PRT
<213> ORGANISM: Oryza sativa

<400> SEQUENCE: 118

Met Ser Cys Cys Gly Gly Asn Cys Gly Cys Gly Ser Gly Cys Gln Cys
1 5 10 15

Gly Ser Gly Cys Gly Gly Cys Lys Met Tyr Pro Glu Met Ala Glu Glu
20 25 30

Val Thr Thr Thr Gln Thr Val Ile Met Gly Val Ala Pro Ser Lys Gly
35 40 45

His Ala Glu Gly Leu Glu Ala Gly Ala Ala Ala Gly Ala Gly Ala Glu
50 55 60

Asn Gly Cys Lys Cys Gly Asp Asn Cys Thr Cys Asn Pro Cys Asn Cys
65 70 75 80

Gly Lys

<210> SEQ ID NO 119
<211> LENGTH: 583
<212> TYPE: DNA
<213> ORGANISM: Oryza sativa

<400> SEQUENCE: 119
gtaagatccg atcaccatct tctgaatttc tgttcttgat ctgtcatgta taataactgt 60
ctagtcttgg tgttggtgag atggaaattc ggtggatctc ggaagggata ttgttcgttt 120
gctggggttt tttttgtgtg ttgtgatccg tagagaattt gtgtttatcc atgttgttga 180
tcttggtatg tattcatgac atattgacat gcatgtgttg tatgtgtcat atgtgtgcct 240
ctccttggga tttgttttgg ataatagaac atgttatgga ctcaatagtc tgtgaacaaa 300
tcttttttta gatggtggcc aaatctgatg atgatctttc ttgagaggaa aaagttcatg 360
atagaaaaat cttttttgag atggtggctt aatgtgatga tgatctttct tgagaggaaa 420
aaaaagattc attataggag attttgattt agctcctttc caccgatatt aaatgaggag 480
catgcatgct gattgctgat aaggatctga tttttttatc ccctcttctt tgaacagaca 540
agaaataggc tctgaatttc tgattgatta tttgtacatg cag 583

<210> SEQ ID NO 120
<211> LENGTH: 1492
<212> TYPE: DNA
<213> ORGANISM: Artificial Sequence
<220> FEATURE:
<223> OTHER INFORMATION: promoter variant

<400> SEQUENCE: 120
gtgttggata atcttttgca vggatatgtg ttgtgaattc gcaccavgtg cccacgaaag 60
cagcavgggg atcgccccac caattttttt ttaccagctc taactctcaa ccagaaaaca 120
tgcaaattta tttgtcattg cacaccagca acctagggat ggtaatccca aaatgcaatg 180
atttttagag catagatgtg ggcgaattta cctaactatg gatatgttaa ttgacaataa 240
aacaccataa ccactgggtt catgggtacg agtatggttt tgtacatgaa agaataaact 300
tbtgagagtg tgtatatact caacatacaa gtataattcc caaagccatc tccaacctat 360
tgtagtccaa aatavgcatg gtccaacaag cacacctatt gacavgcata taagccatca 420
catatatata tacactaatt tttactatta catatgttat atatttatag atatatgtta 480
tttgtttata ttgtcagtgt ttactgcgtg tgttatattt tttttcttag gtacggtgta 540
ggtaaccacc gtgtctatct cgacacgcgt acgggcacaa aattacatca acacatggta 600
tgagattttt catgtgtcaa ataaattttg atggctagtt taaaaactta aatcactcat 660
gagattaccg gagacgattg aggggaaaat ttcctagtat tacggacgga atttaagttt 720
ttcaaactag ccctaataaa ataaatatgg gtatgtaggt atgagcgcga taccacctgt 780
tgcggcggga ctgcaggttt ggtgacagct agaaacavgc atttaggtgt tgaatcttga 840
ttatttgcag ttaatcgtgc ttgctgtgtt gccgcaaaca cgagattcac accctgatga 900
gcggagccag gctgcccttg cttcgattca cggtggccgt cgtcccggcc aggccagcac 960
accagtccaa tccacavagc aacaaccgcg cctcggtcag ttatagbtgc gtggccttct 1020
gaaacaaacc ctcatatggg gtcacgccgc actcacacat gcatccataa accctcagca 1080
gagccttgtg tcgcgtcctc tcctcgataa cccaggccac atcgtccttc cgcgccgcgc 1140
cgccggcgac ctaacaaccc agaggcctca gcaccgcacg cttgcacgta cgtccaggcg 1200
cgctcgccgt tacgcccacg gggatccagg ctttccttcg ctgccgttgc tggtcgagtg 1260
cgccacgccg aaaggtgatc gagctgacga gcgctagacg ccaccggccg gcgcggcgtg 1320
gcaaggcaag acgccgtgcg ggtctcgccc tcgtcagcta taagaccgca tcccccgctg 1380
cggagggagg cacacacaca gacacagcgc tctcactagc ctcgcattcc gtccctgcag 1440
tgcaggggca ggccggtgag gtctgggaga ggaggaggag gbggaggagg ag 1492

<210> SEQ ID NO 121
<211> LENGTH: 1492
<212> TYPE: DNA
<213> ORGANISM: Artificial Sequence
<220> FEATURE:
<223> OTHER INFORMATION: promoter variant

<400> SEQUENCE: 121
gtgttggata atcttttgcb vhgatbvhtg ttgtgaattc gcaccbvhtg cccacgaaag 60
cagcbvhggg atcgccccac caattttttt ttaccagctc taactctcaa ccagaaaacb 120
vhcaaattta tttgtcattg cacaccagca acctagggbv hgtaatccca aabvhcabvh 180
atttttagag catagbvhtg ggcgaattta cctaactbvh gatbvhttaa ttgacaataa 240
aacaccataa ccactgggtt cbvhggtacg agtbvhgttt tgtacbvhaa agaataaact 300
tbvhagagtg tgtatatact caacatacaa gtataattcc caaagccatc tccaacctat 360
tgtagtccaa aatbvhcbvh gtccaacaag cacacctatt gacbvhcata taagccatca 420
catatatata tacactaatt tttactatta catbvhttat atatttatag atatbvhtta 480
tttgtttata ttgtcagtgt ttactgcgtg tgttatattt tttttcttag gtacggtgta 540
ggtaaccacc gtgtctatct cgacacgcgt acgggcacaa aattacatca acacbvhgtb 600
vhagattttt cbvhtgtcaa ataaattttg bvhgctagtt taaaaactta aatcactcbv 660

-continued

```
hagattaccg gagacgattg aggggaaaat ttcctagtat tacggacgga atttaagttt    720

ttcaaactag ccctaataaa ataaatbvhg gtbvhtaggt bvhagcgcga taccacctgt    780

tgcggcggga ctgcaggttt ggtgacagct agaaacbvhc atttaggtgt tgaatcttga    840

ttatttgcag ttaatcgtgc ttgctgtgtt gccgcaaaca cgagattcac accctgbvha    900

gcggagccag gctgcccttg cttcgattca cggtggccgt cgtcccggcc aggccagcac    960

accagtccaa tccacatagc aacaaccgcg cctcggtcag ttatagbvhc gtggccttct   1020

gaaacaaacc ctcatbvhgg gtcacgccgc actcacacbv hcatccataa accctcagca   1080

gagccttgtg tcgcgtcctc tcctcgataa cccaggccac atcgtccttc cgcgccgcgc   1140

cgccggcgac ctaacaaccc agaggcctca gcaccgcacg cttgcacgta cgtccaggcg   1200

cgctcgccgt tacgcccacg gggatccagg ctttccttcg ctgccgttgc tggtcgagtg   1260

cgccacgccg aaaggtgatc gagctgacga gcgctagacg ccaccggccg gcgcggcgtg   1320

gcaaggcaag acgccgtgcg ggtctcgccc tcgtcagcta taagaccgca tccccccctg   1380

cggagggagg cacacacaca gacacagcgc tctcactagc ctcgcattcc gtccctgcag   1440

tgcaggggca ggccggtgag gtctgggaga ggaggaggag gaggaggagg ag           1492
```

<210> SEQ ID NO 122
<211> LENGTH: 1492
<212> TYPE: DNA
<213> ORGANISM: Artificial Sequence
<220> FEATURE:
<223> OTHER INFORMATION: promoter variant

<400> SEQUENCE: 122

```
gtgttggata atcttttgcb vhgatbvhtg ttgtgaattc gcaccbvhtg cccacgaaag     60

cagcbvhggg atcgccccac caattttttt ttarcagctc taactctcaa ccagaaaacb    120

vhcaaattta tttgtcrttg cacaccagca acctagggbv hgtaatccca aabvhcabvh    180

atttttagag catagbvhtg ggcgaattta rctaactbvh gatbvhttaa ttgacaataa    240

aacaccataa ccactgggtt cbvhggtarg agtbvhgttt tgtarbvhaa agaataaact    300

tbvhagagtg tgtatatart caacatacaa gtataattcc caaagccatc tccaacctat    360

tgtagtccaa aatbvhcbvh gtccaacaag cacacctatt gacbvhcata taagccatcr    420

catatatata tacactaatt tttactatta catbvhttat atatttatag atatbvhtta    480

tttgtttata ttgtcagtgt ttartgcgtg tgttatattt tttttcttag gtacggtgta    540

ggtaaccacc gtgtctatct cgacacgcgt acgggcacaa aattacatca acacbvhgtb    600

vhagattttt cbvhtgtcaa ataaattttg bvhgctagtt taaaaactta aatractcbv    660

hagattaccg gagacgattg aggggaaaat ttcctagtat tacggacgga atttaagttt    720

ttraaactag ccctaataaa ataaatbvhg gtbvhtaggt bvhagcgcga tarcacctgt    780

tgcggcggga ctgcaggttt ggtgacagct agaaacbvhc atttaggtgt tgaatcttga    840

ttatttgcag ttaatcgtgc ttgctgtgtt gccgcaaaca cgagattrac accctgbvha    900

gcggagccag gctgcccttg cttcgattra cggtggccgt cgtcccggcc aggccagcac    960

accagtccaa tccacatagc aacaaccgcg cctcggtcag ttatagbvhc gtggccttct   1020

gaaacaaacc ctratbvhgg gtcacgccgc actracacbv hcatccataa accctragca   1080

gagccttgtg tcgcgtcctc tcctcgataa cccaggccac atcgtccttc cgcgccgcgc   1140

cgccggcgac ctaacaaccc agaggcctca gcaccgcacg cttgcacgta cgtccaggcg   1200

cgctcgccgt targcccacg gggatccagg ctttccttcg ctgccgttgc tggtcgagtg   1260
```

cgccacgccg aaaggtgatc gagctgacga gcgctagacg ccaccggccg gcgcggcgtg 1320
gcaaggcaag acgccgtgcg ggtctcgccc tcgtragcta taagaccgca tccccccctg 1380
cggagggagg cacacacaca gacacagcgc tctractagc ctcgcattcc gtccctgcag 1440
tgcaggggca ggccggtgag gtctgggaga ggaggaggag gaggaggagg ag 1492

<210> SEQ ID NO 123
<211> LENGTH: 1008
<212> TYPE: DNA
<213> ORGANISM: Artificial Sequence
<220> FEATURE:
<223> OTHER INFORMATION: consensus motif

<400> SEQUENCE: 123
taactcatat ccggttagat accaactaca catattgaat agcataaatc taataaatat 60
bvhgcgcabv haaaatagta aataattaaa tbvhagtaaa taatbvhbvh acaatabvha 120
ataatattgg aacbvhtaca ttgaccctat tttgctaata tatacttatt atatttgctt 180
aatttggtag gbvhtatbvh tgattgaggc gggtataaat tatccatagg tbvhtgggta 240
taaatagtct atacttatac ccatactcat atacccgacg ggtatbvhat tgtgtccatt 300
gccatatctg cgggtaaaaa actcattata tacttgtcct tataagtaaa acctgttgga 360
cactagagtt taggtaccat ataattatta attttgaacg aaggaagtaa tttgcagcgt 420
attaaggtgc ttctggtcta gaagaabvht cacabvhttt ggtgttagtt tttggtgaaa 480
tttaaggtta attacttttt gaaagbvhtt tccactaggt ggaaccgaaa gaaacggtgc 540
caaacacacc ttacaacaag aaaatatttg taaaaaaatt attttgaata agbvhtctaa 600
aaatagaaag cgtgtatact ttaggacgga ggaatacatb vhtbvhattg ggaaaaccga 660
aaacgtacac ctcctcgctg caatacgctg gtgacttggc agttcgatcg cacccagcgg 720
ataaagbvha gcacggagaa ctcacaaggc acagccgcac aggcaggcac cagcgcgaac 780
gcbvhgacgg gcggcccctg agacgtgccg cccagctggc ccgctgcgcc cacacgtggc 840
gcggagctgc gcgcggctcg gccacgttat aagccacgcg cgctggccgt cgccgcacct 900
cctgactact gcacactcgt ctccgcagtt tgaaacgaag cccgcggcta ctgcaagcta 960
ctccgtctcc gtagctaaag gagaggtagg tttttatttg gcgacgac 1008

<210> SEQ ID NO 124
<211> LENGTH: 1008
<212> TYPE: DNA
<213> ORGANISM: Artificial Sequence
<220> FEATURE:
<223> OTHER INFORMATION: promoter variant

<400> SEQUENCE: 124
taactcatat ccggttagat accaactaca catattgaat agcataaatc taataaatat 60
bvhgcgcabv haaaatagta aataattaaa tbvhagtaaa taatbvhbvh acaatabvha 120
ataatattgg aacbvhtaca ttgaccctat tttgctaata tatarttatt atatttgctt 180
aatttggtag gbvhtatbvh tgattgaggc gggtataaat tatccatagg tbvhtgggta 240
taaatagtct atacttatar ccatactcat atacccgacg ggtatbvhat tgtgtccatt 300
gccatatctg cgggtaaaaa actrattata tacttgtcct tataagtaaa acctgttgga 360
cactagagtt taggtarcat ataattatta attttgaacg aaggaagtaa tttgcagcgt 420
attaaggtgc ttctggtcta gaagaabvht cacabvhttt ggtgttagtt tttggtgaaa 480

-continued

```
tttaaggtta attarttttt gaaagbvhtt tccactaggt ggaaccgaaa gaaacggtgc    540

caaacacacc ttaraacaag aaaatatttg taaaaaaatt attttgaata agbvhtctaa    600

aaatagaaag cgtgtatact ttaggacgga ggaataratb vhtbvhattg ggaaaaccga    660

aaacgtacac ctcctcgctg caatargctg gtgacttggc agttcgatcg cacccagcgg    720

ataaagbvha gcacggagaa ctracaaggc acagccgcac aggcaggcac cagcgcgaac    780

gcbvhgacgg gcggcccctg agacgtgccg cccagctggc ccgctgcgcc cacacgtggc    840

gcggagctgc gcgcggctcg gccacgttat aagccacgcg cgctggccgt cgccgcacct    900

cctgactact gcacactcgt ctccgcagtt tgaaacgaag cccgcggcta rtgcaagcta    960

rtccgtctcc gtagctaaag gagaggtagg tttttatttg gcgacgac               1008
```

<210> SEQ ID NO 125
<211> LENGTH: 1198
<212> TYPE: DNA
<213> ORGANISM: Artificial Sequence
<220> FEATURE:
<223> OTHER INFORMATION: promoter variant

<400> SEQUENCE: 125

```
tcccgtgtcc gtcaatgtga tactactagc atagtactag taccatgcat acacacagca     60

ggtcggccgc ctggatggat cgatgatgat actacatcat cctgtcatcc atccaggcga    120

tctagaaggg gcgtggctag ctagcaaact gtgaccggtt tttctacgcc gataataata    180

ctttgtcatg gtacagacgt acagtactgg ttatatatat ctgtagattt caactgaaaa    240

gctaggatag ctagattaat tcctgagaaa cacagataaa attcgagctt ggctatagat    300

gacaaaacgg aagacgcatg cattggacga cgtatgcaat gcgagcgcgt ctcgtgtcgt    360

cccgtccaag tctggcgatc tcacgccacg tgctcaacag ctcaaggact gttcgtcacc    420

agcgttaaat tcattgaagg gatgacgcat ttcggcattt gtcattgctt gtagctatat    480

atatatatcc aacagatttc tctcaagctt ttgtatgcgt gaatgtaaag tctagcttat    540

acgacagcac gtgcagatat attaacgtca ttattaggtg gagagcaagb tgcatgatct    600

ggtagaaatt gtcgaaaaca caagagagag tgaagtgcac acttctggta taggagtgta    660

tacgccgctg gttggtgggc aatgcgcgcc gcaatattgg ccabtgaaac ctagcaacgc    720

ccactcgcca cgccccbtga btggcccccg cacghcagcg agccagccag tgcccgcgcg    780

cggcccagcc hgagtcggcg gaacgcgcca cgggggacha ggcgcccgag ggccgaggca    840

gcgcggcavg gcaagcaagc cgaagcgggc aagcgacctg cavgcagccc ctgcdcctcg    900

ccctcgtcag tcgtcccagc ctcccactgg aatccaccca acccgccctt cctctdcaaa    960

gcacgcgccc cgcgactcgc ctccgcctac gtgtcggcag cgtccccgcc ggtcgcccac   1020

gtaccccgcc ccgttctccc acgtgcccct ccctctgcgc gcgtccgatt ggctgacccg   1080

cccttcttaa gccgcgccag cctcctgtcc gggccccaac gccgtgctcc gtcgtcgtct   1140

ccgcccccag agtgatcgag cccactgacc tggcccccga gcctcagctc gtgagtcc     1198
```

<210> SEQ ID NO 126
<211> LENGTH: 1198
<212> TYPE: DNA
<213> ORGANISM: Artificial Sequence
<220> FEATURE:
<223> OTHER INFORMATION: promoter variant

<400> SEQUENCE: 126

```
tcccgtgtcc gtcabvhtga tactactagc atagtactag taccbvhcat acacacagca     60
```

ggtcggccgc ctggbvhgat cgbvhbvhat actacatcat cctgtcatcc atccaggcga 120
tctagaaggg gcgtggctag ctagcaaact gtgaccggtt tttctacgcc gataataata 180
ctttgtcbvh gtacagacgt acagtactgg ttatatatat ctgtagattt caactgaaaa 240
gctaggatag ctagattaat tcctgagaaa cacagataaa attcgagctt ggctatagbv 300
hacaaaacgg aagacgcbvh cattggacga cgtbvhcabv hcgagcgcgt ctcgtgtcgt 360
cccgtccaag tctggcgatc tcacgccacg tgctcaacag ctcaaggact gttcgtcacc 420
agcgttaaat tcattgaagg gbvhacgcat ttcggcattt gtcattgctt gtagctatat 480
atatatatcc aacagatttc tctcaagctt ttgtbvhcgt gabvhtaaag tctagcttat 540
acgacagcac gtgcagatat attaacgtca ttattaggtg gagagcaagb vhcbvhatct 600
ggtagaaatt gtcgaaaaca caagagagag tgaagtgcac acttctggta taggagtgta 660
tacgccgctg gttggtgggc abvhcgcgcc gcaatattgg ccabvhaaac ctagcaacgc 720
ccactcgcca cgccccbvha bvhgcccccg cacghcagcg agccagccag tgcccgcgcg 780
cggcccagcc ggagtcggcg gaacgcgcca cgggggacha ggcgcccgag ggccgaggca 840
gcgcggcbvh gcaagcaagc cgaagcgggc aagcgacctg cbvhcagccc ctgcdcctcg 900
ccctcgtcag tcgtcccagc ctcccactgg aatccaccca acccgccctt cctctdcaaa 960
gcacgcgccc cgcgactcgc ctccgcctac gtgtcggcag cgtccccgcc ggtcgcccac 1020
gtaccccgcc ccgttctccc acgtgcccct ccctctgcgc gcgtccgatt ggctgacccg 1080
cccttcttaa gccgcgccag cctcctgtcc gggccccaac gccgtgctcc gtcgtcgtct 1140
ccgcccccag agtgatcgag cccactgacc tggcccccga gcctcagctc gtgagtcc 1198

<210> SEQ ID NO 127
<211> LENGTH: 1198
<212> TYPE: DNA
<213> ORGANISM: Artificial Sequence
<220> FEATURE:
<223> OTHER INFORMATION: promoter variant

<400> SEQUENCE: 127
tcccgtgtcc gtcabvhtga tactartagc atagtactag taccbvhcat aracacagca 60
ggtcggccgc ctggbvhgat cgbvhbvhat actaratcat cctgtcatcc atccaggcga 120
tctagaaggg gcgtggctag ctagcaaact gtgaccggtt tttctargcc gataataata 180
ctttgtcbvh gtacagacgt aragtactgg ttatatatat ctgtagattt caactgaaaa 240
gctaggatag ctagattaat tcctgagaaa cacagataaa attcgagctt ggctatagbv 300
hacaaaacgg aagacgcbvh cattggacga cgtbvhcabv hcgagcgcgt ctcgtgtcgt 360
cccgtccaag tctggcgatc tracgccacg tgctcaacag ctcaaggact gttcgtcacc 420
agcgttaaat tcattgaagg gbvhacgcat ttcggcattt gtrattgctt gtagctatat 480
atatatatcc aacagatttc tctraagctt ttgtbvhcgt gabvhtaaag tctagcttat 540
acgacagcac gtgcagatat attaacgtra ttattaggtg gagagcaagb vhcbvhatct 600
ggtagaaatt gtcgaaaaca caagagagag tgaagtgcac acttctggta taggagtgta 660
targccgctg gttggtgggc abvhcgcgcc gcaatattgg ccabvhaaac ctagcaacgc 720
ccactcgcca cgccccbvha bvhgcccccg cacghcagcg agccagccag tgcccgcgcg 780
cggcccagcc ggagtcggcg gaacgcgcca cgggggacha ggcgcccgag ggccgaggca 840
gcgcggcbvh gcaagcaagc cgaagcgggc aagcgacctg cbvhcagccc ctgcdcctcg 900
ccctcgtrag tcgtcccagc ctcccactgg aatccaccca acccgccctt cctctdcaaa 960
gcacgcgccc cgcgactcgc ctccgcctac gtgtcggcag cgtccccgcc ggtcgcccac 1020
gtaccccgcc ccgttctccc acgtgcccct ccctctgcgc gcgtccgatt ggctgacccg 1080
cccttcttaa gccgcgccag cctcctgtcc gggccccaac gccgtgctcc gtcgtcgtct 1140
ccgcccccag agtgatcgag cccactgacc tggcccccga gcctragctc gtgagtcc 1198

<210> SEQ ID NO 128
<211> LENGTH: 5084
<212> TYPE: DNA
<213> ORGANISM: Zea mays

<400> SEQUENCE: 128
tgtcattatg tttaaaatat tgtgttagac tattgtataa ccgtaacttg ttatgttgtt 60
atgtctatcg atgttctaca caatagtgaa gataagtaat tcatgcatta tccgatatcc 120
gaccatacaa tattcgtatc cgtatcccac gtttatctgt atctgtctcg tttctaacta 180
tctgtatccg atcttgaata cgatcgaaat ataatagggt aggatataga atgatctacc 240
attcgttcat atccgtccga tttttatctc tatccaaacc tctatcgaca actgcgaata 300
cgttgttgtg gttgcagaac acggatgact ttctcgtccg gcgataacca gtgaaaacca 360
atgatttttc tcgttatcgg tgtagaccga gatacgaaaa ccgatccggt ttttagtgta 420
tttcggtttc aaaattagaa atataaaagt taaattttga tcaacaaaac gggttttgaa 480
aaaaatcgaa acgagaatga aatccctgtt gcggaaccat cgtctacaag tcgccggtgc 540
ccatgaagca tgaacgaact gcaacaggca acagccaagc aaggctcgca ttaactgtag 600
catggctccc tcgccaacag ctgtaggctg tagcgcagcg cgcacaggcg gcagaagcac 660
cggatcatgc tattgctagc tccagcgcag gcgtgtggcc tctggcgtcg tcgcaggcag 720
ccctcgcgac gcgcgccgag tcctctgaga aaccccgctc gggccagccg gccgacccca 780
ctcgccagga cagggagcgc gcgcgcggca tgcgtcgacc acgcgctgcc gcgcgcacct 840
gcgcccgcca atggcagcgc ggccactcgt cgcgcgccct tcctgtccgg tcgccacggc 900
gcgcagcaca tgccgcgcat gcagcagaaa acgattaaag agatcgcgcc agtggcgtcc 960
aaaaggcagg ctagacgcta gagctaagct aggctaccaa ggccccggcc cggttggtct 1020
cgtgcggctg gctaccaagg ctagctaggc ccgtggttgg gttccagtcg gacatggcgc 1080
ttgggctttt gcgttgcatg catgcatgtc ccacgtgtgt tggctcgtgt acgaggagtg 1140
tgtacgtatc cggccttacg tgtcccgtgt ccgtcaatgt gatactacta gcatagtact 1200
agtaccatgc atacacacag caggtcggcc gcctggatgg atcgatgatg atactacatc 1260
atcctgtcat ccatccaggc gatctagaag gggcgtggct agctagcaaa ctgtgaccgg 1320
tttttctacg ccgataataa tactttgtca tggtacagac gtacagtact ggttatatat 1380
atctgtagat ttcaactgaa aagctaggat agctagatta attcctgaga aacacagata 1440
aaattcgagc ttggctatag atgacaaaac ggaagacgca tgcattggac gacgtatgca 1500
atgcgagcgc gtctcgtgtc gtcccgtcca agtctggcga tctcacgcca cgtgctcaac 1560
agctcaagga ctgttcgtca ccagcgttaa attcattgaa gggatgacgc atttcggcat 1620
ttgtcattgc ttcttgtagc tatatatata tccaacagat ttctctcaag cttttgtatg 1680
cgtgaatgta aagtctagct tatacgacag cacgtgcaga tacattaacg tcattaggtg 1740
gagagcaaag atctggtgga aattgtcgaa aacacaagag agagtgaagt gcacacttct 1800
gggtatagga gctaaggagt gtatacgccg ctggttggtg ggcaatgcgc gccgcaatat 1860

-continued

```
tggccaatga aacctagcaa cgcccactcg ccacgcccca tgaatggccc ccgcacggca   1920
gcgagccagc cagtgcccgc gcgcggccca gccggagtcg gcggaacgcg ccacggggga   1980
cgaggcgccc gagggccgag gcatggcaag caagccgaag cgggcaagcg acccgcatgc   2040
agcccctgcc cctcgccctc gtcccagcct cccactggaa tccacccaac ccgcccttcc   2100
tctccaaagc acgcgccccg cgactcgcct ccgcctacgt gtcggcagcg tccccgccgg   2160
tcgcccacgt accccgcccc gttctcccac gtgcccctcc ctctgcgcgc gtccgattgg   2220
ctgacccgcc cttcttaagc cgcgccagcc tcctgtccgg gccccaacgc cgtgctccgt   2280
cgtcgtctcc gcccccagag tgatcgagcc cactgacctg gcccccgagc ctcagctcgt   2340
gagtccggca ccgcgcctcg ccatggccat ggtgcagccg gcggacacgg ccgtcaaggc   2400
caacgagatc ctggcgcggt tccggcccat cgcgcccaag cccacactgg cagcagccgc   2460
cgccgccgcc gcggcgcccg tggcgcaggc cgcggccgag ggcgtcgtgg ccgcgaaccg   2520
cgtgctgtgc catctgcaga gcaggccgtg ccgcgcgcgc aagcgcggcc gccccaccgt   2580
cgtgccggtg tcgcccaagt cgggcgcgca gccgcccgcg aagcggagga gagcctctac   2640
gccgtacccg cctctccggt gcgcggcggc gaccacgggg gcgcatgtgt ccgcggtcgt   2700
cccaggcagt gcgcgtctcc caccggcgag tgcgggtgtc gaagacatcg cgaaggcggc   2760
ggcggcggcg gcgacagagg aggggaggga cgtccccgtg gagcgcgacc tgctgcggaa   2820
gctgctggag cccagggtca tatcgccgcg ggcggtgcgc ccggtgtggt ctgccatcca   2880
cgtcgggtgc atccaccgca ccgacgacgc ggcctgcacc gacgccgccg tctcgaagac   2940
ggcggttcag gtggaggcgg agctggaggt cgacgcgctc ccggcggtgg tctccgactc   3000
aggcaaccgc gtccggctcg tgaacgacgc gtacaaggag atggtggggc agcccgagtg   3060
cccgtggctc gacgccgtgg ctgccacgtc gaggaggatc agcggggagg tggcgctggt   3120
ggtagcggac cggtcctctc tgccggactc gtacggggcg ttcacatgca cggcaaagat   3180
cgagtgggag gacgacggga aggtcacctc catcgctgca ccctgcgacg tcagccggct   3240
gcagtgcgag tccagggatt acctcttcgc ctggaggttc cgcaccgccg ccgccgacgc   3300
cgacgcatcc gttggacaca gctccgagga gattagtgag agttagggaa gcttgagctg   3360
catccaatga aaccaagtgc atagactaag ccgctagctg catgttaaaa ctgagcagct   3420
tcctctttcg cgaagtccaa taggatgtag acccagttct gaaatcctga gtaaatataa   3480
gatgttgact ggagaatgca aaggaagtat aacctgccct ttcaggaaac tgacctaccc   3540
gactctcatt tcataactgc gtgggttgcc catgaacaca cggacatgca agagtggtcg   3600
tgcgtagcga ctggcagctc atttgtgaat gtgtgatagg gccaaaagca agtaggcgtc   3660
atcattcaac tcagaaatgg catgatgtat cttttcagat accagccaag aaagcacaca   3720
aggttgcaaa agcaatgtca tccacgaatt aacgttttgg aagtacaagt acaccatttt   3780
gtttgattgc acatcatgct tattacaagt ttgatagatg cattctctag ttcgtacttt   3840
aacaatgggc acggttgaaa gcaaaataaa atcgagccag gaggaaaacg acatcgtgcc   3900
aatgtcagca tcacagatgt ctcgagctca tgcttgctcc gcttttggag ggcctctcca   3960
cttgaagttc tcagcgtagg ccttaggctg catggttgaa aaacagtccg gttatcacac   4020
ccaagccgat gtattttcag caacaccgat tagcaatcag aaggaaaaaa tattaattca   4080
aacgcaaaca caactattct attagcacaa aacatggcay gtttgagcca tatctcacat   4140
atgacagaca ccaaatgatg caattggctg gacagtaatg caggttatca ccttataatg   4200
```

-continued aagcatagca atggaaaggt gaaaccattc ctccagttca tgatagatac actactttga 4260
aatgtcccaa agcaagctta ttccggcagc tgtattgctt taagctagca attgcttcta 4320
taatattacg gtaaagtaca gctcggtcct ggcagccgta ccaaaagcaa aagtccagtc 4380
aagcaaagac tactggtaat gagccagttc catcgcctga ttggacctgt gcccggacgg 4440
ccagtacaaa ccaataacac gcacgttgca tcaaataatt ggatatcaga cttgtacagt 4500
gtcaggcaag taaagaaata gcgcaggaga atgatttttg gcctcactgt tttagctttc 4560
aggacattcc acaagcatgc aaatatttaa cttcgataac catatcacct gtatgcccgt 4620
atctgttcct tactgcttat caaataattg tgttttgatg tagtaatgca ttttctgctt 4680
gtaattctac atgctggcat aacatagtga acgacacata cctcaaatgc taaagcaaag 4740
tcgctggtct atgggataac aagtctgatt cttagcaggt agggggagta tatgtcttac 4800
gtgtaagaat gcatgcaccg cgagaaaact gccaaaacag cagtcacatt gcatcaacac 4860
acatggtttc aacctactga gtacatggca gctagcccta gcagcttgtc cttatccaca 4920
tcctgctaac gaaagatagg gttcaagggt caaccaggat ggtaaaactt cgccaactgt 4980
tcctagtcca cacattcata ttcatcgtat ctacaacatt aatgccgatt ttggctttct 5040
ctttccaacc tctgacgtat cagattctca gttacaaaaa aaaa 5084

<210> SEQ ID NO 129
<211> LENGTH: 1198
<212> TYPE: DNA
<213> ORGANISM: Artificial Sequence
<220> FEATURE:
<223> OTHER INFORMATION: promoter variant

<400> SEQUENCE: 129
tcccgtgtcc gtcaatgtga tactactagc atagtactag taccatgcat acacacagca 60
ggtcggccgc ctggatggat cgatgatgat actacatcat cctgtcatcc atccaggcga 120
tctagaaggg gcgtggctag ctagcaaact gtgaccggtt tttctacgcc gataataata 180
ctttgtcatg gtacagacgt acagtactgg ttatatatat ctgtagattt caactgaaaa 240
gctaggatag ctagattaat tcctgagaaa cacagataaa attcgagctt ggctatagat 300
gacaaaacgg aagacgcatg cattggacga cgtatgcaat gcgagcgcgt ctcgtgtcgt 360
cccgtccaag tctggcgatc tcacgccacg tgctcaacag ctcaaggact gttcgtcacc 420
agcgttaaat tcattgaagg gatgacgcat ttcggcattt gtcattgctt gtagctatat 480
atatatatcc aacagatttc tctcaagctt ttgtatgcgt gaatgtaaag tctagcttat 540
acgacagcac gtgcagatat attaacgtca ttattaggtg gagagcaaga tgcatgatct 600
ggtagaaatt gtcgaaaaca caagagagag tgaagtgcac acttctggta taggagtgta 660
tacgccgctg gttggtgggc aatgcgcgcc gcaatattgg ccaatgaaac ctagcaacgc 720
ccactcgcca cgccccatga atggcccccg cacgacagcg agccagccag tgcccgcgcg 780
cggcccagcc ggagtcggcg gaacgcgcca cgggggacaa ggcgcccgag ggccgaggca 840
gcgcggcatg gcaagcaagc cgaagcgggc aagcgacctg catgcagccc ctgcacctcg 900
ccctcgtcag tcgtcccagc ctcccactgg aatccaccca acccgccctt cctctacaaa 960
gcacgcgccc cgcgactcgc ctccgcctac gtgtcggcag cgtccccgcc ggtcgcccac 1020
gtaccccgcc ccgttctccc acgtgcccct ccctctgcgc gcgtccgatt ggctgacccg 1080
cccttcttaa gccgcgccag cctcctgtcc gggccccaac gccgtgctcc gtcgtcgtct 1140
ccgcccccag agtgatcgag cccactgacc tggcccccga gcctcagctc gtgagtcc 1198

<210> SEQ ID NO 130
<211> LENGTH: 1198
<212> TYPE: DNA
<213> ORGANISM: Artificial Sequence
<220> FEATURE:
<223> OTHER INFORMATION: promoter variant

<400> SEQUENCE: 130

```
tcccgtgtcc gtcaatgtga tactactagc atagtactag taccatgcat acacacagca      60

ggtcggccgc ctggatggat cgatgatgat actacatcat cctgtcatcc atccaggcga     120

tctagaaggg gcgtggctag ctagcaaact gtgaccggtt tttctacgcc gataataata     180

ctttgtcatg gtacagacgt acagtactgg ttatatatat ctgtagattt caactgaaaa     240

gctaggatag ctagattaat tcctgagaaa cacagataaa attcgagctt ggctatagat     300

gacaaaacgg aagacgcatg cattggacga cgtatgcaat gcgagcgcgt ctcgtgtcgt     360

cccgtccaag tctggcgatc tcacgccacg tgctcaacag ctcaaggact gttcgtcacc     420

agcgttaaat tcattgaagg gatgacgcat ttcggcattt gtcattgctt gtagctatat     480

atatatatcc aacagatttc tctcaagctt ttgtatgcgt gaatgtaaag tctagcttat     540

acgacagcac gtgcagatat attaacgtca ttattaggtg gagagcaaga tgcatgatct     600

ggtagaaatt gtcgaaaaca caagagagag tgaagtgcac acttctggta taggagtgta     660

tacgccgctg gttggtgggc aatgcgcgcc gcaatattgg ccaatgaaac ctagcaacgc     720

ccactcgcca cgccccatga atggccccccg cacggcagcg agccagccag tgcccgcgcg     780

cggcccagcc agagtcggcg gaacgcgcca cgggggacaa ggcgcccgag ggccgaggca     840

gcgcggcatg gcaagcaagc cgaagcgggc aagcgacctg catgcagccc ctgcacctcg     900

ccctcgtcag tcgtcccagc ctcccactgg aatccaccca acccgccctt cctctacaaa     960

gcacgcgccc cgcgactcgc ctccgcctac gtgtcggcag cgtccccgcc ggtcgcccac    1020

gtaccccgcc ccgttctccc acgtgcccct ccctctgcgc gcgtccgatt ggctgacccg    1080

cccttcttaa gccgcgccag cctcctgtcc gggccccaac gccgtgctcc gtcgtcgtct    1140

ccgcccccag agtgatcgag cccactgacc tggcccccga gcctcagctc gtgagtcc      1198
```

<210> SEQ ID NO 131
<211> LENGTH: 1198
<212> TYPE: DNA
<213> ORGANISM: Artificial Sequence
<220> FEATURE:
<223> OTHER INFORMATION: promoter variant

<400> SEQUENCE: 131

```
tcccgtgtcc gtcaatgtga tactactagc atagtactag taccatgcat acacacagca      60

ggtcggccgc ctggatggat cgatgatgat actacatcat cctgtcatcc atccaggcga     120

tctagaaggg gcgtggctag ctagcaaact gtgaccggtt tttctacgcc gataataata     180

ctttgtcatg gtacagacgt acagtactgg ttatatatat ctgtagattt caactgaaaa     240

gctaggatag ctagattaat tcctgagaaa cacagataaa attcgagctt ggctatagat     300

gacaaaacgg aagacgcatg cattggacga cgtatgcaat gcgagcgcgt ctcgtgtcgt     360

cccgtccaag tctggcgatc tcacgccacg tgctcaacag ctcaaggact gttcgtcacc     420

agcgttaaat tcattgaagg gatgacgcat ttcggcattt gtcattgctt gtagctatat     480

atatatatcc aacagatttc tctcaagctt ttgtatgcgt gaatgtaaag tctagcttat     540
```

-continued

```
acgacagcac gtgcagatat attaacgtca ttattaggtg gagagcaaga tgcatgatct    600
ggtagaaatt gtcgaaaaca caagagagag tgaagtgcac acttctggta taggagtgta    660
tacgccgctg gttggtgggc aatgcgcgcc gcaatattgg ccaatgaaac ctagcaacgc    720
ccactcgcca cgccccatga atggcccccg cacgacagcg agccagccag tgcccgcgcg    780
cggcccagcc agagtcggcg gaacgcgcca cgggggacga ggcgcccgag ggccgaggca    840
gcgcggcatg gcaagcaagc cgaagcgggc aagcgacctg catgcagccc ctgcacctcg    900
ccctcgtcag tcgtcccagc ctcccactgg aatccaccca acccgccctt cctctacaaa    960
gcacgcgccc cgcgactcgc ctccgcctac gtgtcggcag cgtccccgcc ggtcgcccac   1020
gtaccccgcc ccgttctccc acgtgcccct ccctctgcgc gcgtccgatt ggctgacccg   1080
cccttcttaa gccgcgccag cctcctgtcc gggccccaac gccgtgctcc gtcgtcgtct   1140
ccgcccccag agtgatcgag cccactgacc tggcccccga gcctcagctc gtgagtcc     1198
```

WHOLE SEED SPECIFIC PROMOTER

RELATED APPLICATIONS

This application is a national stage application (under 35 U.S.C. § 371) of PCT/EP2010/055362, filed Apr. 22, 2010, which claims benefit of European application 09158449.0, filed Apr. 22, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_17418_00076_US. The size of the text file is 130 KB, and the text file was created on Oct. 17, 2011.

The present invention is concerned with the provision of means and methods for gene expression. Specifically, it relates to a polynucleotide comprising an expression control sequence which allows for seed specific expression of a nucleic acid of interest being operatively linked thereto in plants. Furthermore, vectors, host cells, transgenic plants and methods for expressing nucleic acids of interest are provided which are based on the said polynucleotide.

The production of transgenic plants is a fundamental technique of plant biotechnology and, thus, an indispensible prerequisite for fundamental research on plants, and for producing plants having improved, novel properties for agriculture, for increasing the quality of human foods or for producing particular chemicals or pharmaceuticals. A basic prerequisite for transgenic expression of particular genes in plants is the provision of plant-specific promoters. Various plant promoters are known. The constitutive promoters which are currently predominantly used in plants are almost exclusively viral promoters or promoters isolated from *Agrobacterium* such as, the cauliflower mosaic virus promoter CaMV355 (Odell et al. (1985) Nature 313:810-812). As product concepts and transgene modes of action get more complex, constitutive expression is no longer the optimal desired expression pattern. E.g., while manipulation of stress-induced genes may play an important role in improving plant tolerance to stresses, it has been shown that constitutive expression of stress-inducible genes has a severe negative impact on plant growth and development when the stress is not present (Kasuga et al, (1999) Nature Biotechnology 17(3):287-291). Therefore, promoters driving expression which is temporally- and/or spatially-differentiated are desired.

In grain crops of agronomic importance, seed formation is the ultimate goal of plant development. Seeds are harvested for use in food, feed, and industrial products. The utility and value of those seeds are determined by the quantity and quality of protein, oil, and starch contained therein.

Monocot plant seeds can be considered as being comprised of two main compartments: the germ or embryo which comprises the progenitor cells of the plant that will develop from the seed, and the endosperm which serves as a sink of nutritive components (particularly stored starch, proteins and oil) that are consumed during seed germination and early plantlet development. Dicot plant seeds are comprised of mostly the germ portion, as the nutritive function in developing dicot plants is provided from extra-seed nutritive stores.

Many promoters have been identified and characterized that are capable of driving transgene expression in various combinations of spatial and temporal expression patterns.

Also, some promoters which govern expression in plant seeds are known in the art. The known promoters govern expression in parts of plant seeds or in the entire seed. For example, promoters of seed storage proteins were shown to drive expression pivotally in the seed. These include promoters of phaseolins (U.S. Pat. No. 5,504,200, Bustos M. M. et al., Plant Cell. 1989, 2(9): 839-53), 2S albumin (Joseffson L. G. et al., J. Biol. Chem. 1987, 262: 12196-12201), legumin (Shirsat A et al., Mol Gen Genet. 1989, 215(2): 326-331), USP (unknown seed protein; Bäumlein H, et al., Molecular & General Genetics 1991, 225(3): 459-67) napin (Stalberg K., et al., L. Planta 1996, 199: 515-519), saccharose binding protein (WO 00/26388) or LeB4 (Bäumlein H. et al., Mol Gen Genet. 1991, 225: 121-128). A cryptic promoter with specificity for the capsule was identified in tobacco by "T-DNA tagging" (Fobert P. R. et al., Plant Journal 1994, 6(4): 567-77; U.S. Pat. No. 5,824,863; WO 99/53067).

Seed-specific promoters which direct expression in the entire seed, and thus in both the endosperm and the embryo, are only described for dicots, rather than for monocots. The only available promoters for whole seed expression in monocots are constitutive promoters which do express in both major seed compartments, but also drive transgene expression in most or all other tissues.

However, means and methods for reliably governed expression of nucleic acids of interest in the entire seed of monocots are not yet available and are highly desirable.

Thus, the technical problem underlying this invention may be seen as the provision of means and methods which allow for complying with the aforementioned needs. The technical problem is solved by the embodiments characterized in the claims and herein below.

Accordingly, the present invention relates to a polynucleotide comprising an expression control sequence which allows for seed specific expression of a nucleic acid of interest being operatively linked thereto in plants, said expression control sequence being selected from the group consisting of:

(a) an expression control sequence having a nucleic acid sequence as shown in any one of SEQ ID NOs: 1 to 3;
(b) an expression control sequence having a nucleic acid sequence which is at least 80% identical to a nucleic acid sequence shown in any one of SEQ ID NOs: 1 to 3;
(c) an expression control sequence having a nucleic acid sequence which hybridizes under stringent conditions to a nucleic acid sequence as shown in any one of SEQ ID NOs: 1 to 3;
(d) an expression control sequence having a nucleic acid sequence which hybridizes to a nucleic acid sequences located upstream of an open reading frame sequence shown in any one of SEQ ID NOs: 4, 6 or 8;
(e) an expression control sequence having a nucleic acid sequence which hybridizes to a nucleic acid sequences located upstream of an open reading frame sequence encoding an amino acid sequence as shown in any one of SEQ ID NOs: 5, 7 or 9;
(f) an expression control sequence having a nucleic acid sequence which hybridizes to a nucleic acid sequences located upstream of an open reading frame sequence being at least 80% identical to an open reading frame sequence as shown in any one of SEQ ID NOs: 4, 6 or 8, wherein the open reading frame encodes a seed protein;
(g) an expression control sequence having a nucleic acid sequence which hybridizes to a nucleic acid sequences located upstream of an open reading frame encoding an amino acid sequence being at least 80% identical to an amino acid sequence as shown in any one of SEQ ID NOs: 5, 7 or 9, wherein the open reading frame encodes a seed protein;

(h) an expression control sequence obtainable by 5' genome walking or by thermal asymmetric interlaced polymerase chain reaction (TAIL-PCR) on genomic DNA from the first exon of an open reading frame sequence as shown in any one of SEQ ID NOs: 4, 6 or 8; and (i) an expression control sequence obtainable by 5' genome walking or TAIL PCR on genomic DNA from the first exon of an open reading frame sequence being at least 80% identical to an open reading frame as shown in any one of SEQ ID NOs: 4, 6 or 8, wherein the open reading frame encodes a seed protein; and (j) an expression control sequence obtainable by 5' genome walking or TAIL PCR on genomic DNA from the first exon of an open reading frame sequence encoding an amino acid sequence being at least 80% identical to an amino acid sequence encoded by an open reading frame as shown in any one of SEQ ID NOs: 5, 7 or 9, wherein the open reading frame encodes a seed protein.

The term “polynucleotide” as used herein refers to a linear or circular nucleic acid molecule. Preferably, it encompasses DNA molecules. The polynucleotide of the present invention is characterized in that it shall comprise an expression control sequence as defined elsewhere in this specification. In addition to the expression control sequence, the polynucleotide of the present invention, preferably, further comprises at least one nucleic acid of interest being operatively linked to the expression control sequence and/or at least one a termination sequence or transcription. Thus, the polynucleotide of the present invention, preferably, comprises an expression cassette for the expression of at least one nucleic acid of interest.

Instead of a nucleic acid of interest or in addition to the nucleic acid of interest, at least one expression cassette can also comprise a multiple cloning site and/or a termination sequence for transcription. In such a case, the multiple cloning site is, preferably, arranged in a manner as to allow for operative linkage of a nucleic acid to be introduced in the multiple cloning site with the expression control sequence. In addition to the aforementioned components, the polynucleotide of the present invention, preferably, could comprise components required for homologous recombination, i.e. flanking genomic sequences from a target locus. However, also contemplated is a polynucleotide which essentially consists of the said expression control sequence.

The term “expression control sequence” as used herein refers to a nucleic acid which is capable of governing the expression of another nucleic acid operatively linked thereto, e.g. a nucleic acid of interest referred to elsewhere in this specification in detail. An expression control sequence as referred to in accordance with the present invention, preferably, comprises sequence motifs which are recognized and bound by polypeptides, i.e. transcription factors. The said transcription factors shall upon binding recruit RNA polymerases, preferably, RNA polymerase I, II or III, more preferably, RNA polymerase II or III, and most preferably, RNA polymerase II. Thereby the expression of a nucleic acid operatively linked to the expression control sequence will be initiated. It is to be understood that dependent on the type of nucleic acid to be expressed, i.e. the nucleic acid of interest, expression as meant herein may comprise transcription of RNA polynucleotides from the nucleic acid sequence (as suitable for, e.g., anti-sense approaches or RNAi approaches) or may comprises transcription of RNA polynucleotides followed by translation of the said RNA polynucleotides into polypeptides (as suitable for, e.g., gene expression and recombinant polypeptide production approaches). In order to govern expression of a nucleic acid, the expression control sequence may be located immediately adjacent to the nucleic acid to be expressed, i.e. physically linked to the said nucleic acid at its 5" end. Alternatively, it may be located in physical proximity. In the latter case, however, the sequence must be located so as to allow functional interaction with the nucleic acid to be expressed. An expression control sequence referred to herein, preferably, comprises between 200 and 5,000 nucleotides in length. More preferably, it comprises between 500 and 2,500 nucleotides and, more preferably, between 1,000 and 1,500 nucleotides. As mentioned before, an expression control sequence, preferably, comprises a plurality of sequence motifs which are required for transcription factor binding or for conferring a certain structure to the polynucleotide comprising the expression control sequence. Sequence motifs are also sometimes referred to as cis-regulatory elements and, as meant herein, include promoter elements as well as enhancer elements. The expression control sequence of the present invention allows for seed specific expression and, thus, comprises cis-regulatory elements which can recruit RNA polymerases in said tissue as to enable tissue-specific transcription of nucleic acids operatively linked to the said expression control sequence. Preferred expression control sequences to be included into a polynucleotide of the present invention have a nucleic acid sequence as shown in any one of SEQ ID NOs: 1 to 3.

Further preferably, an expression control sequence comprised by a polynucleotide of the present invention has a nucleic acid sequence which hybridizes to a nucleic acid sequences located upstream of an open reading frame sequence shown in any one of SEQ ID NOs: 4, 6 or 8, i.e. is a variant expression control sequence. It will be understood that expression control sequences may slightly differ in its sequences due to allelic variations. Accordingly, the present invention also contemplates an expression control sequence which can be derived from an expression control sequence as shown in any one of SEQ ID NOs: 1 to 3. Said expression control sequences are capable of hybridizing, preferably under stringent conditions, to the upstream sequences of the open reading frames shown in any one of SEQ ID NOs. 5, 6 or 8, i.e. to the expression control sequences shown in any one of SEQ ID NOs.: 1 to 3. Stringent hybridization conditions as meant herein are, preferably, hybridization conditions in 6× sodium chloride/sodium citrate (SSC) at approximately 45° C., followed by one or more wash steps in 0.2×SSC, 0.1% SDS at 53 to 65° C., preferably at 55° C., 56° C., 57° C., 58° C., 59° C., 60° C., 61° C., 62° C., 63° C., 64° C. or 65° C. The skilled worker knows that these hybridization conditions differ depending on the type of nucleic acid and, for example when organic solvents are present, with regard to the temperature and concentration of the buffer. For example, under “standard hybridization conditions” the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (base pairs) in length and a G+C content of 50% in the absence of formamide. Such hybridizing expression control sequences are, more preferably, at least 70%, at least 80%, at least 90%, at least 91%, at least 92%, at least 93%, at least 94% at least 95%, at least 96%, at least 97%, at least 98%, or at least 99% identical to the expression control sequences as shown in any one of SEQ ID NOs.: 1 to 3. The percent identity values are, preferably, calculated over the entire nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins 1989, CABIOS, 5: 151-153) or the programs Gap and BestFit (Needleman 1970 J. Mol. Biol. 48; 443-453 and Smith 1981, Adv. Appl. Math. 2; 482-489), which are part of the GCG software packet (Genetics Computer Group, 575 Science Drive, Madison, Wis., USA 53711 version 1991), are to be used. The sequence identity values recited above in percentage (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

Moreover, expression control sequences which allow for seed specific expression can not only be found upstream of the aforementioned open reading frames having a nucleic acid sequence as shown in any one of SEQ D NOs. 4, 6 or 8. Rather, expression control sequences which allow for seed specific expression can also be found upstream of orthologous, paralogous or homologous genes (i.e. open reading frames). Thus, also preferably, an variant expression control sequence comprised by a polynucleotide of the present invention has a nucleic acid sequence which hybridizes to a nucleic acid sequences located upstream of an open reading frame sequence being at least 70%, more preferably, at least 80%, at least 90%, at least 91%, at least 92%, at least 93%, at least 94% at least 95%, at least 96%, at least 97%, at least 98%, or at least 99% identical to a sequence as shown in any one of SEQ ID NOs: 4, 6 or 8. The said variant open reading shall encode a polypeptide having the biological activity of the corresponding polypeptide being encoded by the open reading frame shown in any one of SEQ ID NOs.: 4, 6 or 8. In this context it should be mentioned that the open reading frame shown in SEQ ID NO: 4 encodes a polypeptide having the amino acid sequence shown in SEQ ID NO: 5 and, preferably, encodes a seed protein. The open reading frame shown in SEQ ID NO: 6 encodes a polypeptide having the amino acid sequence shown in SEQ ID NO: 7 and, preferably, encodes a seed protein, more specifically, a tonoplast intrinsic protein 3-1. The open reading frame shown in SEQ ID NO: 8 encodes a polypeptide having the amino acid sequence shown in SEQ ID NO: 9 and, preferably, encodes a seed protein.

Also preferably, a variant expression control sequence comprised by a polynucleotide of the present invention is (i) obtainable by 5' genome walking or TAIL PCR from an open reading frame sequence as shown in any one of SEQ ID NOs: 4, 6 or 8 or (ii) obtainable by 5" genome walking or TAIL PCR from a open reading frame sequence being at least 80% identical to an open reading frame as shown in any one of SEQ ID NOs: 4, 6 or 8. Variant expression control sequences are obtainable without further ado by the genome walking technology or by thermal asymmetric interlaced polymerase chain reaction (TAIL-PCR) which can be carried out as described in the accompanying Examples by using, e.g., commercially available kits.

Variant expression control sequences referred to in this specification for the expression control sequence shown in SEQ ID NO: 1, preferably, comprise at least 10, at least 20, at least 30, or all of the sequence motifs recited in Table 4. Variant expression control sequences referred to in this specification for the expression control sequence shown in SEQ ID NO: 2, preferably, comprise at least 10, at least 20, at least 30, at least 40, at least 50 or all of the sequence motifs recited in Table 9. Variant expression control sequences referred to in this specification for the expression control sequence shown in SEQ ID NO: 3, preferably, comprise at least 10, at least 20, at least 30, at least 40, at least 50 or all of the sequence motifs recited in Table 10.

Examples for preferred variant expression control sequences are shown in SEQ ID NOs: 120, 121, and 122 (variants of SEQ ID NO:3), in SEQ ID NOs:123 and 124 (variants of SEQ ID NO:2), and in SEQ ID NOs: 125, 126, and 127 (variants of SEQ ID NO:1). Compared to the corresponding expression control sequences, the aforementioned variants (as shown in SEQ ID NOs 120 to 127) do not comprise start codons (ATG). The starts codons are either replaced by BVH or by BVH plus a stop codon between any two start codons (according to the IUPAC nomenclature: B represents C or G or T, V represents A or C or G, and H represents A or C or T). Thus, variant expression control sequence may be obtained by mutating putative start codons as described above. Further examples for variant expression control sequences are shown in SEQ ID NOs: 129, 130, and 131 (variants of SEQ ID NO: 1). The aforementioned expression control sequences do not comprise short open reading frames showing homology to toxic or allergenic peptides or polypeptides (see Example 3).

It will be understood that non-essential sequences of the expression control sequence of the invention can be deleted without significantly impairing the properties mentioned. Delimitation of the expression control sequence to particular essential regulatory regions can also be undertaken with the aid of a computer program such as the PLACE program ("Plant Cis-acting Regulatory DNA Elements") (Higo K et al. (1999) Nucleic Acids Res 27:1, 297-300) or the BIOBASE database "Transfac" (Biologische Datenbanken GmbH, Braunschweig). By such measures, variant expression control sequences as specified above can be artificially generated. Moreover, processes for mutagenizing nucleic acid sequences are known to the skilled worker and include, e.g., the use of oligonucleotides having one or more mutations compared with the region to be mutated (e.g. within the framework of a site-specific mutagenesis). Primers having approximately 15 to approximately 75 nucleotides or more are typically employed, with preferably about 10 to about 25 or more nucleotide residues being located on both sides of a sequence to be modified. Details and procedure for said mutagenesis processes are familiar to the skilled worker (Kunkel et al. (1987) Methods Enzymol 154:367-382; Tomic et al. (1990) Nucl Acids Res 12:1656; Upender et al. (1995) Biotechniques 18(1):29-30; U.S. Pat. No. 4,237,224). A mutagenesis can also be achieved by treatment of, for example, vectors comprising the expression control sequence of the invention with mutagenizing agents such as hydroxylamine. Mutagenesis also yields variant polynucleotides of the invention as specified above.

The expression control sequence comprised by the polynucleotide of the present invention allows for a seed specific expression. Particularly, said expression control sequence allows for specific expression in both the embryo and endosperm of the seed and, thus, in the whole seed. Thus, "seed" as used herein refers, preferably, to endosperm and embryonic tissues. Preferably, the expression control sequence according to the present invention allows for seed-specific expression in all stages of seed development (e.g. in maize seeds up to 35 to 40 days after pollination, see Examples). Moreover, the expression control sequence may also allow for expression in pollen (see Examples). "Specific" in the sense of the invention means that the nucleic acids of interest being operatively linked to the expression control sequence referred to herein will be predominantly (i.e. preferably) expressed in the indicated tissues or cells when present in a plant. It will be understood that an exclusive expression in a tissue is usually not achieved by a tissue specific promoters. Rather, a tissue specific promoter seems to be preferably switch on in some tissues, while nevertheless having still some background activity in other tissues. This phenomenon is known as leaky expression. However, with specific expression in this invention is meant predominant expression in the plant tissue referred to herein. A predominant expression as meant herein is characterized by a statistically significantly higher amount of detectable transcription in the said tissue or cells with respect to other plant tissues. A statistically significant higher level of expression is, preferably, an amount being at least two-fold, three-fold, fourfold, five-fold, ten-fold, hundred-fold, five hundred-fold or thousand-fold of the level found in at least one of the other tissues with detectable transcription. Alternatively, it is an expression in the indicated tissue or cell whereby the level of expression in other tissues or cells is less than 1%, 2%, 3%, 4%, 5%, 10% or, most preferably, 15% of the overall (whole plant) level of expression. The level of expression directly correlates to the amount of transcripts (i.e. RNA) or polypeptides encoded by the transcripts present in a cell or tissue. Suitable techniques for measuring transcription either based on RNA or polypeptides are well known in the art. Tissue or cell specificity alternatively and, preferably in addition to the above, means that the expression is restricted or almost restricted to the indicated tissue or cells, i.e. there is essentially no detectable transcription in other tissues. Almost restricted as meant herein means that unspecific expression is detectable in less than ten, less than five, less than four, less than three, less than two or one other tissue(s).

Seed specific expression can be determined, for example, by comparing the expression of a nucleic acid of interest, e.g., a reporter gene such as [beta]-glucuronidase (GUS), operatively linked to the expression control sequence in the following tissues and developmental stages: 1) roots and leaves at 5-leaf stage, 2) stem at V-7 stage, 3) leaves, husk, and silk at flowering stage, 4) Spikelets/Tassel at pollination, 5) Ear or Kernels at 5, 10, 15, 20, and 25 days after pollination (see also Examples). Preferably, expression of the nucleic acid of interest can be determined in Ear or Kernels at 5, 10, 15, 20, and 25 days after pollination in said assay as shown in the accompanying Figures. The expression of the nucleic acid of interest can be determined by various well known techniques, e.g., by Northern Blot or in situ hybridization techniques as described in WO 02/102970, and, preferably, as described in the accompanying Examples. Transgenic plants for analyzing seed specific expression can be also generated by techniques well known to the person skilled in the art and as discussed elsewhere in this specification.

The term "nucleic acid of interest" refers to a nucleic acid which shall be expressed under the control of the expression control sequence referred to herein. Preferably, a nucleic acid of interest encodes a polypeptide the presence of which is desired in a cell or plant as referred to herein and, in particular, in a plant seed. Such a polypeptide could be any functionally active or inert protein that accumulates in the seed and/or bestows a beneficial effect to the plant or seed upon it's expression. It is to be understood that if the nucleic acid of interest encodes a polypeptide, transcription of the nucleic acid in RNA and translation of the transcribed RNA into the polypeptide may be required. A nucleic acid of interest, also preferably, includes biologically active RNA molecules and, more preferably, antisense RNAs, ribozymes, micro RNAs or siRNAs. Said biologically active RNA molecules can be used to modify the amount of a target polypeptide present in a cell or plant. For example, an undesired enzymatic activity in a seed can be reduced due to the seed specific expression of an antisense RNAs, ribozymes, micro RNAs or siRNAs. The underlying biological principles of action of the aforementioned biologically active RNA molecules are well known in the art. Moreover, the person skilled in the art is well aware of how to obtain nucleic acids which encode such biologically active RNA molecules. It is to be understood that the biologically active RNA molecules may be directly obtained by transcription of the nucleic acid of interest, i.e. without translation into a polypeptide. Preferably, at least one nucleic acid of interest to be expressed under the control of the expression control sequence of the present invention is heterologous in relation to said expression control sequence, i.e. it is not naturally under the control thereof, but said control has been produced in a non-natural manner (for example by genetic engineering processes).

The term "operatively linked" as used herein means that the expression control sequence of the present invention and a nucleic acid of interest, are linked so that the expression can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5' end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 700 bp, 500 bp, 300 bp, 100 bp, 80 bp, 60 bp, 40 bp, 20 bp, 10 bp or 5 bp.

Advantageously, it has been found in the studies underlying the present invention that (whole) seed specific expression of a nucleic acid of interest can be reliably achieved by expressing said nucleic acids of interest under the control of an expression control sequence from maize or a variant expression control sequence as specified above (see, e.g., Tables 4A, 11, and 12). Thanks to the present invention, it is possible to (i) specifically manipulate biochemical processes in seed tissues, e.g., by expressing heterologous enzymes or biologically active RNAs as referred to above or (ii) to produce heterologous proteins in said seed tissues. In principle, the present invention contemplates the use of the polynucleotide, the vector, the host cell or the plant for the expression of a nucleic acid of interest. Seed-specific promoters described in the prior art only confer expression in the embryo or endosperm of the seed of a monocot, rather than in the whole seed.

The present invention also relates to a vector comprising the polynucleotide of the present invention.

The term "vector", preferably, encompasses plasmids, expression vectors, T-DNA vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride coprecipitation, DEAE-dextran-mediated transfection, lipofection, natural competence, carbon-based clusters, chemically mediated transfer, electroporation or particle bombardment (e.g., "gene-gun"). Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J.

Preferably, the vector referred to herein is suitable as a cloning vector, i.e. replicable in microbial systems. Such vectors ensure efficient cloning in bacteria and, preferably, yeasts or fungi and make possible the stable transformation of plants. "Cloning vectors" typically contain restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide, e.g., kanamycin resistance, streptomycin resistance, spectinomycin resistance, tetracycline resistance, hygromycin resistance or ampicillin resistance.

Those vector systems which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are pBin19, pBI101, pBinAR, pGPTV, pSUN, pPZP and pCAMBIA. An overview of binary vectors and their use can be found in Hellens et al, Trends in Plant Science (2000) 5, 446-451. Furthermore, by using appropriate cloning vectors, the polynucleotide of the invention can be introduced into host cells and/or plants and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225.

Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTIACH5, which is known as octopine synthase (Gielen et al., EMBO J. 3 (1984) 835 et seq.) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie et al., 1987, Nucl. Acids Research 15:8693-8711). Other preferred sequences for the use in functional linkage in plant gene expression cassettes are targeting sequences which are required for targeting the gene product of the nucleic acid of interest into its relevant cell compartment (for a review, see Kermode, Crit. Rev. Plant Sci. 15, 4 (1996) 285-423 and references cited therein), for example into the vacuole, the nucleus, all types of plastids, such as amyloplasts, chromoplasts, the extracellular space, the mitochondria, the endoplasmic reticulum, oil bodies, peroxisomes and other compartments of plant cells.

It is to be understood that a binary vector or any other vector can be modified by common DNA recombination techniques, multiplied in *E. coli*, and introduced into *Agro-*

*bacterium* by e.g., electroporation or other transformation techniques (Mozo and Hooykaas, Plant Mol. Biol. 16:917-918 (1991)).

The present invention also contemplates a host cell comprising the polynucleotide or the vector of the present invention.

Host cells are, preferably, transgenic cells or cell lines derived from plants. More preferably, said host cells are derived from monocotyledonous plants. Preferred monocotyledonous plants are described elsewhere herein. The host cells derived from plants encompass cells of certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

It is to be understood that the polynucleotide or vector according to the present invention may also be present in prokaryotic or eukaryotic single cell organism (also referred to as micro-organisms), particularly for cloning purpose (for example, in *E. coli*), and for plant transformation (for example, in *Agrobacterium*). Thus, the term "host cell", preferably, also encompasses prokaryotic or eukaryotic single cell organisms (also referred to as micro-organisms). Particularly contemplated as prokaryotic host cells in the context of the present invention are Rhizobiaceae cells, in particular of the genus *Agrobacterium*. Preferred *Agrobacterium* cells are *Agrobacterium tumefaciens* and *Agrobacterium rhizogenes* cells.

*Agrobacterium* is a soil born phytopathogen that integrates a piece of DNA (T-DNA) into the genome of a plant (Chilton, et al., 1977 Cell 11: 263-271; Hoekema, et al., 1985 Nature 303: 179-180; Bevan, 1984 Nucleic Acids Res. 12: 8711-8721; Sheng and Citovsky, 1996 The Plant Cell, Vol. 8.1699-1710). Preferably, the *Agrobacterium* cells/strains are disarmed, i.e. lack the crown gall disease mediating properties or lack the hairy-root disease mediating properties but otherwise providing the functions for plant infection. *Agrobacterium* cells in the context of the present invention are, preferably, selected from LBA4404, GV2260, GV3600, EHA101, EHA105, AGL-1, LBA9402, GV3101, COR341, COR356, UIA143, pCH32, BIBAC2, C58C1, pMP90 and AGT121. In a preferred embodiment the *Agrobacterium* cell is selected from the group consisting of C58C1, EHA101, pMP90, and LBA4404.

How to culture the aforementioned *Agrobacterium* species is well known to the person skilled in the art.

The present invention also relates to a transgenic plant or seed thereof, comprising the polynucleotide or the vector of the present invention.

The polynucleotide or vector may be present in the cytoplasm of cells of said plant or seed thereof. Preferably, the polynucleotide or vector is stably integrated into the genome of cells comprised by said plant or plant seed. How to stably integrate a polynucleotide or a vector (particularly a T-DNA vector) into the genome of a plant cell is well known in the art and described elsewhere herein. In the context of the present invention it is particularly envisaged that the polynucleotide or vector shall be stably integrated into the genome by *Agrobacterium*-mediated transformation.

Preferred plants to be used for transgenic plants according to the present invention are monocotyledonous plants.

A "monocotyledonous plant" as used herein, preferably, refers to a flowering plant with one cotyledon in the seed. Particularly preferred monocotyledonous plants (herein also referred to as monocots) are maize, wheat, rice, barley, oat, rye, sorghum, millet, tricelate, banana, ryegrass or *coix*. The term "monocotyledonous plant" includes, preferably, plants of the genera of the subfamilies Andropogonoideae (particularly, the genera *Saccharum, Sorghum*, or *Zea*), Arundineae (particularly, the genus *Phragmites*), Oryzoideae (particularly, the genus *Oryza*), Panicoideae, and, more preferably, Pooideae (Festuciadeae) (particularly, the genera *Poa, Festuca, Lolium, Trisetum, Agrostis, Phleum, Dactylis, Alopecurus, Avena, Triticum, Secale*, and *Hordeum*). Preferred monocotyledonous plants are *Avena sativa* (oats), *Saccharum officinarum* (sugarcane), *Triticum dicoccum* (Emmer wheat), *Triticum monococcum* (Einkorn wheat), *Triticum spelta* (spelt wheat), *Triticum durum* (wheat), *Triticum turgidum, Triticum aestivum* (wheat), *Zea mays* (maize/corn), *Panicum miliaceum* (common millet), *Pennisetum thiphoides* (Bulrush millet), *Hordeum vulgare* or *H. sativum* (barley), *Oryza sativa* (rice), *Zizania aquatica* (wild rice), *Secale cereale* (rye), *Sorghum bicolor* (*S. vulgare*) (sorghum). More preferred are wheat (*Triticum* spp.), rice (*Oryza* spp.), barley (*Hordeum* spp.), oats (*Avena* spp.), rye (*Secale* spp.), corn (*Zea mays*), sorghum and millet (*Pennisettum* spp).

Most preferably, the monocotyledonous plant is *Zea mays*.

Furthermore envisaged by the present invention are certain tissues, organs and parts of said monocotyledonous plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

Transgenic plants or transgenic host cells according to the present invention may be obtained by transformation techniques as published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225; Transgenic Plants: Methods and Protocols Editor: Leandro Peña, Instituto Valenciano de Investigaciones Agrarias, Valencia Spain Series: Methods in Molecular Biology, volume 286 (2004) or in WO2006/133983. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

The present invention also relates to a method for expressing a nucleic acid of interest in a host cell comprising (a) introducing the polynucleotide or the vector of the present invention into the host cell; and
(b) expressing at least one nucleic acid of interest in said host cell.

The polynucleotide or vector of the present invention can be introduced into the host cell by suitable transfection or transformation techniques as specified elsewhere in this description. The nucleic acid of interest will be expressed in the host cell under suitable conditions. To this end, the host cell will be cultivated under conditions which, in principle, allow for transcription of nucleic acids. Moreover, the host cell, preferably, comprises the exogenously supplied or endogenously present transcription machinery required for expressing a nucleic acid of interest by the expression control sequence. Preferably, said host cell is a cell of a monocotyledonous plant.

Moreover, the present invention encompasses a method for expressing a nucleic acid of interest in a plant comprising (a) introducing the polynucleotide or the vector of the present invention into the plant; and (b) expressing at least one nucleic acid of interest in said plant.

The polynucleotide or vector of the present invention can be introduced into the plant by suitable techniques as specified elsewhere in this description.

Also, the present invention also relates to a method for seed-specific expression of a nucleic acid of interest in a plant comprising (a) introducing the polynucleotide or the vector of the present invention into the plant; and (b) expressing at least one nucleic acid of interest in said plant.

In the following, some preferred embodiments pertaining to the present invention are described in more detail.

In a preferred embodiment, the polynucleotide of the present invention also comprises further genetic control sequences. A genetic control sequence as referred to in accordance with the present invention is to be understood broadly and means all sequences having an influence on the coming into existence of the function of the transgenic expression cassette of the invention. Genetic control sequences modify for example the transcription and translation in eukaryotic organisms. The expression cassettes of the invention, preferably, comprise as additional genetic control sequence one of the promoters of the invention 5-upstream from the particular nucleic acid sequence to be expressed transgenically, and a terminator sequence 3'-downstream, and if appropriate further usual regulatory elements, in each case functionally linked to the nucleic acid sequence to be expressed transgenically.

Genetic control sequences also comprise further promoters, promoter elements or minimal promoters which are able to modify the expression-controlling properties. It is thus possible for example through genetic control sequences for tissue-specific expression to take place additionally in dependence on particular stress factors. Corresponding elements are described for example for water stress, abscisic acid (Lam E and Chua N H, (1991) J Biol Chem 266(26): 17131-17135) and heat stress (Schoffl F et al. (1989) Mol Gen Genetics 217(2-3):246-53). A further possibility is for further promoters which make expression possible in further plant tissues or in other organisms such as, for example, *E. coli* bacteria to be functionally linked to the nucleic acid sequence to be expressed. Suitable plant promoters are in principle all the promoters described above. It is conceivable for example that a particular nucleic acid sequence is described by a promoter (for example one of the promoters of the invention) in one plant tissue as sense RNA and translated into the corresponding protein, while the same nucleic acid sequence is transcribed by another promoter with a different specificity in a different tissue into antisense RNA, and the corresponding protein is down-regulated. This can be implemented by an expression cassette of the invention by the one promoter being positioned in front of the nucleic acid sequence to be expressed transgenically, and the other promoter behind.

It has been shown that untranslated regions may have significant functions in the regulation of gene expression. Thus, it has been shown that 5'-untranslated sequences may enhance the transient expression of heterologous genes. They may moreover promote tissue specificity (Rouster J et al. (1998) Plant J. 15:435-440.). Conversely, the 5'-untranslated region of the opaque-2 gene suppresses expression. Deletion of the corresponding region of this gene leads to an increase in gene activity (Lohmer S et al. (1993) Plant Cell 5:65-73). Further 5'-untranslated sequences and introns with expression-promoting function are known to the skilled worker. McElroy and coworkers (McElroy et al. (1991) Mol Gen Genet. 231(1):150-160) reported on a construct based on the rice actin 1 (Act1) promoter for transforming monocotyledonous plants. Use of the Act1 intron in combination with the 35S promoter in transgenic rice cells led to an expression rate which was increased ten-fold compared with the isolated 35S promoter. Optimization of the sequence environment of the translation initiation site of the reporter gene [beta]-glucuronidase (GUS) resulted in a four-fold increase in GUS expression in transformed rice cells. Combination of the optimized translation initiation site and of the Act1 intron resulted in a 40-fold increase in GUS expression by the CaMV35S promoter in transformed rice cells; similar results have been obtained with transformed corn cells. Overall, it was concluded from the investigations described above that the expression vectors based on the Act1 promoter are suitable for controlling sufficiently strong and constitutive expression of foreign DNA in transformed cells of monocotyledonous plants.

Moreover, the expression profile of the expression control region of the invention may be enhanced with expression enhancing introns and/or transcriptions termination sequences.

Thus, in a preferred embodiment the polynucleotide of the invention comprises at least one additional element selected from the group consisting of a) 5'-untranslated regions, and b) intron encoding sequences, and c) transcription termination sequences.

The “intron encoding sequence” is, preferably, an intron encoding an expression enhancing intron from a monocotyledonous plant. More preferably the intron encoding sequence is an intron from an ubiquitin, actin or alcohol dehydrogenase gene. Most preferably, the intron encoding sequence is a first intron of a plant gene encoding a Metallothionin 1 polypeptide (MET1), a metallothionein-like polypeptide (MET-like) or a functional equivalent or ortholog thereof.

Preferred first introns from plant gene encoding a metallothionein-like polypeptide (or of functional equivalent or homolog thereof) are disclosed in WO2006/094976 and WO2008/099013 which are hereby incorporated by reference. Preferably, said first intron is derived from a MET-like gene from a monocotyledonous plant. More preferably, said first intron is derived from *Oryza sativa* (see Examples). Even more preferably, the first intron is derived from a MET-like gene encoding of polypeptide as shown in SEQ ID NO: 118. Most preferably, the first intron of a plant gene encoding a Metallothionin 1 has a sequence as shown in SEQ ID NO: 119.

It is also comtemplated that the intron encoding region is a variant of a first intron of a plant gene encoding a Metallothionin-like protein, particularly, a variant of a first intron having a sequence as shown in SEQ ID NO: 120. Such variant, preferably, is at least 70%, at least 80%, at least 90%, at least 91%, at least 92%, at least 93%, at least 94% at least 95%, at least 96%, at least 97%, at least 98%, or at least 99% identical to said first intron. How to determine the degree of identity is described elsewhere herein.

Preferably, the intron encoding sequence is inserted in the expression construct in the 5'-untranslated region of the nucleic acid of interest, which should be expressed (i.e., between the expression control sequence and the protein coding sequence (open reading frame) or the nucleic acid of interest).

Advantageously, it has been shown in the context of the present invention that the Met1-1 intron enhances the expression of the expression control sequences according to the present invention in seed tissue.

The expression cassette may also comprise one or more so-called enhancer sequences functionally linked to the promoter, which make increased transgenic expression of the nucleic acid sequence possible. It is also possible to insert additional advantageous sequences, such as further regulatory elements or terminators, at the 3' end of the nucleic acid sequences which are to be expressed transgenically.

Control sequences additionally mean those which make homologous recombination or insertion into the genome of a host organism possible or which allow deletion from the genome. It is possible in homologous recombination for example for the natural promoter of a particular gene to be replaced by one of the promoters of the invention. Methods such as the cre/lox technology permit tissue-specific deletion, which is inducible in some circumstances, of the expression cassette from the genome of the host organism (Sauer B. (1998) Methods. 14(4):381-92). In this case, particular flanking sequences are attached (lox sequences) to the target gene and subsequently make deletion possible by means of cre recombinase. The promoter to be introduced can be placed by means of homologous recombination in front of the target gene which is to be expressed transgenically by linking the promoter to DNA sequences which are, for example, homologous to endogenous sequences which precede the reading frame of the target gene. Such sequences are to be regarded as genetic control sequences. After a cell has been transformed with the appropriate DNA construct, the two homologous sequences can interact and thus place the promoter sequence at the desired site in front of the target gene, so that the promoter sequence is now functionally linked to the target gene and forms an expression cassette of the invention. The selection of the homologous sequences determines the promoter insertion site. It is possible in this case for the expression cassette to be generated by homologous recombination by means of single or double reciprocal recombination. In single reciprocal recombination there is use of only a single recombination sequence, and the complete introduced DNA is inserted. In double reciprocal recombination the DNA to be introduced is flanked by two homologous sequences, and the flanking region is inserted. The latter process is suitable for replacing, as described above, the natural promoter of a particular gene by one of the promoters of the invention and thus modifying the location and timing of gene expression. This functional linkage represents an expression cassette of the invention. To select successfully homologously recombined or else transformed cells it is usually necessary additionally to introduce a selectable marker. Various suitable markers are mentioned below. The selection marker permits selection of transformed from untransformed cells. Homologous recombination is a relatively rare event in higher eukaryotes, especially in plants. Random integrations into the host genome predominate. One possibility of deleting randomly integrated sequences and thus enriching cell clones having a correct homologous recombination consists of using a sequence-specific recombination system as described in U.S. Pat. No. 6,110,736.

Polyadenylation signals suitable as genetic control sequences are plant polyadenylation signals and, preferably, those from *Agrobacterium tumefaciens.*

In a particularly preferred embodiment, the expression cassette comprises a terminator sequence which is functional in plants. Terminator sequences which are functional in plants means, in general, sequences able to bring about termination of transcription of a DNA sequence in plants. Examples of suitable terminator sequences are the OCS (octopine synthase) terminator and the NOS (nopaline synthase) terminator. However, plant terminator sequences are particularly preferred. Plant terminator sequences means in general sequences which are a constituent of a natural plant gene. Particular preference is given in this connection to the terminator of the potato cathepsin D inhibitor gene (GenBank Acc. No.: X74985) or to the terminator of the field bean storage protein gene VfLEIB3 (GenBank Acc. No.: Z26489). These terminators are at least equivalent to the viral or T-DNA terminators described in the art.

The skilled worker is also aware of a large number of nucleic acids and proteins whose recombinant expression is advantageous under the control of the expression cassettes or processes of the invention. Some examples of nucleic acids of interest whose expression provides the desired advantageous effects are mentioned below.

The skilled worker is further aware of a large number of genes through whose repression or switching off by means of expression of an appropriate antisense RNA it is possible likewise to achieve advantageous effects. Non-restrictive examples of advantageous effects which may be mentioned are: facilitated production of a transgenic organism for example through the expression of selection markers, achievement of resistance to abiotic stress factors (heat, cold, aridity, increased moisture, drought, environmental toxins, UV radiation), achievement of resistance to biotic stress factors (pathogens, viruses, insects and diseases), improvement in human or animal food properties, improvement in the growth rate of the yield. Preferably, the biotic stress factor is a seed-borne disease (mainly fungal diseases e.g. common bunt (*Tilletia tritici*); leaf stripe (*Pyrenophora graminea*), and loose smut (*Ustilago nuda*) mainly in barley.

Moreover, the largest use of grain, particularly of maize grain, is for feed or food. Introduction of genes that alter the composition of the grain may greatly enhance the feed or food value. The primary components of grain are starch, protein, and oil. Each of these primary components of grain may be improved by altering its level or composition. The primary components of grain are starch, protein, and oil. Each of these primary components of grain may be improved by altering its level or composition (meaning the nutritive value of the building blocks for each component, or alternatively the respective structures of oils and starches can be modified so as to improve their nutritive content).

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. The levels of these essential amino acids in seeds and grain may be elevated by mechanisms which include the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway that are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation. Additionally, the introduced DNA may encode enzymes, which degrade zeines. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes are, e.g., those that encode acetyl-CoA carboxylase, ACP-acyltransferase, beta-ketoacyl-ACP synthase, plus other well-known fatty acid biosynthetic activities.

Genes may be introduced that enhance the nutritive value of the starch component of the grain, for example by increasing the degree of branching, resulting in improved utilization of the starch in cows by delaying its metabolism.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like.

The properties of starch may be beneficially altered by changing the ratio of amylose to amylopectin, the size of the starch molecules, or their branching pattern. Through these changes a broad range of properties may be modified which include, e.g., in gelatinization temperature, heat of gelatinization, clarity of films and pastes. To accomplish these changes in properties, genes that encode granule-bound or soluble starch synthase activity or branching enzyme activity may be introduced alone or combination. DNA such as antisense constructs may also be used to decrease levels of endogenous activity of these enzymes.

Additionally, some cereal grains used in feed and food applications possess insufficient quantities of vitamins and must be supplemented to provide adequate nutritive value; introduction of genes that enhance vitamin biosynthesis in seeds may be envisioned including, for example, vitamins A, E, $B_{12}$, choline, and the like.

In addition, it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, e.g., any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Useful nucleic acid sequences of interest that can be combined with the expression control sequence of the present invention include, preferably, those encoding seed storage proteins, fatty acid pathway enzymes, tocopherol biosynthetic enzymes, amino acid biosynthetic enzymes, and starch branching enzymes.

The expression control sequences according to the present invention may be used for expression of metabolic enzymes for use in the food-and-feed sector, for example of phytases and cellulases. Especially preferred are nucleic acids such as the artificial cDNA which encodes a microbial phytase (GenBank Ace. No.: A19451) or functional equivalents thereof. Expression of genes which bring about an accumulation of fine chemicals such as of tocopherols, tocotrienols or carotenoids. An example which may be mentioned is phytoene desaturase. Preferred are nucleic acids which encode the Narcissus pseudonarcissus photoene desaturase (GenBank Ace. No.: X78815) or functional equivalents thereof.

The expression control sequences according to the present invention may be used for expression of nucleic acids of interest which modified oils production (U.S. Pat. No. 6,444,876), high oil production (U.S. Pat. Nos. 5,608,149 and 6,476,295), or modified fatty acid content (U.S. Pat. No. 6,537,750). Preferred fatty acid pathway enzymes include thioesterases (U.S. Pat. Nos. 5,512,482; 5,530,186; 5,945,585; 5,639,790; 5,807,893; 5,955,650; 5,955,329; 5,759,829; 5,147,792; 5,304,481; 5,298,421; 5,344,771; and 5,760,206), diacylglycerol acyltransferases (U.S. Patent Publications 200301 15632A1 and 20030028923A1), and desaturases (U.S. Pat. Nos. 5,689,050; 5,663,068; 5,614,393; 5,856,157; 6,117,677; 6,043,411; 6,194,167; 5,705,391; 5,663,068; 5,552,306; 6,075,183; 6,051,754; 5,689, 050; 5,789,220; 5,057,419; 5,654,402; 5,659,645; 6,100,091; 5,760,206; 6,172,106; 5,952,544; 5,866,789; 5,443,974; and 5,093,249) all of which are incorporated herein by reference.

Production of neutraceuticals such as, for example, polyunsaturated fatty acids such as, for example, arachidonic acid or EP (eicosapentaenoic acid) or DHA (docosahexaenoic acid) by expression of fatty acid elongases and/or desaturases or production of proteins having an improved nutritional value such as, for example, having a high content of essential amino acids (e.g. the methionine-rich 2S albumin gene of the Brazil nut). Preferred nucleic acids are those which code for the methionine-rich 2S albumin from *Bertholletia excelsa* (GenBank Acc. No.: AB044391), the [Delta]6-acyllipid desaturase from *Physcomitrella patens* (GenBank Acc. No.: AJ222980; Girke et al. (1998) Plant J 15:3948), the [Delta]6-desaturase from *Mortierelia alpina* (Sakuradani et al. (1999) Gene 238:445-453), the [Delta]5-desaturase from *Caenorhabditis elegans* (Michaelson et al. 1998, FEBS Letters 439:215-218), the [Delta]5-fatty acid desaturase (des-5) from *Caenorhabditis elegans* (GenBank Acc. No.: AF078796), the [Delta]5-desaturase from *Mortierella* alpina (Michaelson et al. J Biol Chem 273:19055-19059), the [Delta]6-elongase from *Caenorhabditis elegans* (Beaudoin et al. (2000) Proc Natl. Acad Sci USA 97:6421-6426), the [Delta]6-elongase from *Physcomitrella patens* (Zank et al. (2000) Biochemical Society Transactions 28:654-657) or functional equivalents thereof.

Achieving an increased storage ability in cells which normally comprise few storage proteins or lipids with the aim of increasing the yield of these substances, for example by expression of an acetyl-CoA carboxylase. Preferred nucleic acids are those which code for the acetyl-CoA carboxylase (accase) from *Medicago sativa* (GenBank Acc. No.: L25042) or functional equivalents thereof. Further examples of advantageous genes are mentioned for example in Dunwell J M (2000) J Exp Bot. 51 Spec No:487-96. Alternatively, an increased storage protein content might be advantageous for high-protein product production. Preferred seed storage proteins include zeins.

The nucleic acid of interest may also confer resistance to seed-related diseases caused by viruses, bacteria, fungi, insects (e.g. by expressing a suitable Bt gene) and nematodes.

For example, the nucleic acid of interest may confer resistance to fungi known to affect stored seeds such as fungi of the genus *Aspergillus, Penicilium* or *Fusarium* (particularly *Fusarium moniliformere*. Resistance against *Fusarium* can be, preferably, achieved by operably linking the expression control sequences according to the present invention to a nucleic acid sequence encoding Cry-1A(b) or any other Cry variant which confer resistance to *Fusarium.*

Moreover, the nucleic acid of interest may confer resistance to the nematode *Anguina tritici* can cause significant crop loss to Emmer (*Triticum monococcum*), rye (*Secale cereale*), spelt (*T. spelta*), and wheat (*T. aestivum*).

Also, the nucleic acid of interest may confer resistance to *Cnephasia* species, particularly, to cereal tortrix (*Cnephasia pumicana*) and leaf rollers such as *Cnephasia longana.*

It is also contemplated that the nucleic acid of interest may confer resistance to grey field slugs such as *Deroceras reticulatum* or *Deroceras agreste.*

Resistance to viruses may be produced through expression of novel genes. For example, it has been demonstrated that expression of a viral coat protein in a transgenic plant can impart resistance to infection of the plant by that virus and perhaps other closely related viruses. It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses.

Expression of the nucleic acids under the control of the promoters of the invention is possible in any desired cell compartment such as, for example, the endomembrane system, the vacuole and the chloroplasts. Desired glycosylation reactions, especially foldings and the like, are possible by utilizing the secretory pathway. Secretion of the target protein to the cell surface or secretion into the culture medium, for example on use of suspension-cultured cells or protoplasts, is also possible. The target sequences necessary for this purpose can thus be taken into account in individual vector variations and be introduced, together with the target gene to be cloned, into the vector through use of a suitable cloning strategy. It is possible to utilize as target sequences both gene-intrinsic, where present, or heterologous sequences. Additional heterologous sequences which are preferred for the functional linkage, but not restricted thereto, are further targeting sequences to ensure the subcellular localization in apoplasts, in the vacuole, in plastids, in the mitochondrion, in the endoplasmic reticulum (ER), in the cell nucleus, in elaioplasts or other compartments; and translation enhancers' such as the 5' leader sequence from tobacco mosaic virus (Gallie et al. (1987) Nucl Acids Res 15 8693-8711) and the like. The process for transporting proteins which are not localized per se in the plastids in a targeted fashion into the plastids is described (Klosgen R B & Weil J H (1991) Mol Gen Genet. 225(2):297-304; Van Breusegem F at al. (1998) Plant Mol Biol 38(3):491-496).

Preferred sequences are a) small subunit (SSU) of the ribulose-bisphosphate carboxylase (Rubisco ssu) from pea, corn, sunflower b) transit peptides derived from genes of plant fatty acid biosynthesis such as the transit peptide of the plastidic acyl carrier protein (ACP), the stearyl-ACP desaturase, [beta]-ketoacyl-ACP synthase or the acyl-ACP thioesterase c) the transit peptide for GBSSI (starch granule bound starch synthase 1)

d) LHCP II genes.

The target sequences may be linked to other target sequences which differ from the transit peptide-encoding sequences in order to ensure a subcellular localization in the apoplast, in the vacuole, in the plastids, in the mitochondrion, in the endoplasmic reticulum (ER), in the cell nucleus, in the elaioplasts or other compartments. It is also possible to employ translation enhancers such as the 5' leader sequence from tobacco mosaic virus (Gallie et al. (1987) Nucl Acids Res 15:8693-8711) and the like.

The skilled worker is also aware that he needs not express the genes described above directly by use of the nucleic acid sequences coding for these genes, or repress them for example by anti-sense. He can also use for example artificial transcription factors of the type of zinc finger proteins (Beerli R R et al. (2000) Proc Natl Aced Sci USA 97(4):1495-500). These factors bind in the regulatory regions of the endogenous genes which are to be expressed or repressed and result, depending on the design of the factor, in expression or repression of the endogenous gene. Thus, the desired effects can also be achieved by expression of an appropriate zinc finger transcription factor under the control of one of the promoters of the invention.

The expression cassettes of the invention can likewise be employed for seed-specific suppression or reduction of replication or/and translation of target genes by gene silencing.

The expression cassettes of the invention can also be employed for seed-specific expression of nucleic acids which mediate so-called antisense effects and are thus able for example to reduce the expression of a target protein.

Preferred genes and proteins whose suppression is the condition for an advantageous phenotype comprise by way of example, but non-restrictively:

a) reduction in the expression of allergenic proteins as described for example in Tada Y et al. (1996) FEBS Lett 391(3):341-345 or Nakamura R (1996) Biosci Biotechnol Biochem 60(8):1215-1221.

b) shifting the amylose/amylopectin content in starch by suppression of branching enzyme Q, which is responsible for [alpha]-1,6-glycosidic linkage. Corresponding procedures are described (for example in Schwall G P et al. (2000) Nat Biotechnol 18(5):551-554). Preferably used for this purpose are nucleic acid sequences like that of the starch branching enzyme II of potato (GenBank Acc. No.: AR123356; U.S. Pat. No. 6,169,226) or its homologs from other genera and species.

An "antisense" nucleic acid means primarily a nucleic acid sequence which is wholly or partly complementary to at least part of the sense strand of said target protein. The skilled worker is aware that he can use alternatively the cDNA or the corresponding gene as starting template for corresponding antisense constructs. The antisense nucleic acid is preferably complementary to the coding region of the target protein or a part thereof. The antisense nucleic acid may, however, also be complementary to the non-coding region of a part thereof. Starting from the sequence information for a target protein, an antisense nucleic acid can be designed in a manner familiar to the skilled worker by taking account of the base-pair rules of Watson and Crick. An antisense nucleic acid may be complementary to the whole or a part of the nucleic acid sequence of a target protein. In a preferred embodiment, the antisense nucleic acid is an oligonucleotide with a length of for example 15, 20, 25, 30, 35, 40, 45 or 50 nucleotides.

The antisense nucleic acid comprises in a preferred embodiment [alpha]-anomeric nucleic acid molecules. [alpha]-Anomeric nucleic acid molecules form in particular double-stranded hybrids with complementary RNA in which the strands run parallel to one another, in contrast to the normal [beta] units (Gaultier et al. (1987) Nucleic Acids Res 15:6625-6641). The use of the sequences described above in sense orientation is likewise encompassed and may, as is familiar to the skilled worker, lead to cosuppression. The expression of sense RNA to an endogenous gene may reduce or switch off its expression, similar to that described for antisense approaches (Goring et al. (1991) Proc Natl Aced Sci USA 88:1770-1774; Smith et al. (1990) Mol Gen Genet. 224:447-481; Napoli et al. (1990) Plant Cell 2:279-289; Van der Krol et al. (1990) Plant Cell 2:291-299). It is moreover for the introduced construct to represent the gene to be reduced wholly or only in part. The possibility of translation is unnecessary.

It is also very particularly preferred to use processes such as gene regulation by means of double-stranded RNA (double-stranded RNA interference). Corresponding processes are known to the skilled worker and described in detail (e.g. Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). Express reference is made to the processes and methods described in the indicated references. Highly efficient suppression of native genes is brought about here through simultaneous introduction of strand and complementary strand.

It is possible and advantageous to couple the antisense strategy with a ribozyme process. Ribozymes are catalytically active RNA sequences which, coupled to the antisense sequences, catalytically cleave the target sequences (Tanner N K FEMS Microbiol Rev. 1999; 23 (3):257-75). This may increase the efficiency of an antisense strategy. Expression of ribozymes for reducing particular proteins is known to the skilled worker and described for example in EP-A1 0 291 533, EP-A1 0 321 201 and EP-A1 0 360 257. Suitable target sequences and ribozymes can be determined as described by Steinecke (Ribozymes, Methods in Cell Biology 50, Galbraith et al. eds. Academic Press, Inc. (1995), 449-460) by secondary structure calculations of ribozyme RNA and target RNA and by the interaction thereof (Bayley C C et al., Plant Mol. Biol. 1992; 18(2):353-361; Lloyd A M and Davis R W et al., Mol Gen Genet. 1994 March; 242(6):653-657). Examples which should be mentioned are hammerhead ribozymes (Haselhoff and Gerlach (1988) Nature 334:585-591). Preferred ribozymes are based on derivatives of the tetrahymena L-19 IVS RNA (U.S. Pat. Nos. 4,987,071; 5,116,742). Further ribozymes having selectivity for an L119 mRNA can be selected (Bartel D and Szostak J W (1993) Science 261:1411-1418).

In a further embodiment, target protein expression can be reduced by using nucleic acid sequences which are complementary to regulatory elements of the target protein genes, form with the latter a triple helical structure and thus prevent gene transcription (Helene C (1991) Anticancer Drug Des. 6(6):569-84; Helene C et al. (1992) Ann NY Acad Sci 660:27-36; Maher L J (1992) Bioassays 14(12):807-815).

The expression cassettes of the invention and the vectors derived therefrom may comprise further functional elements. The term functional element is to be understood broadly and means all elements which have an influence on production, multiplication or function of the expression cassettes of the invention or vectors or organisms derived therefrom. Non-restrictive examples which may be mentioned are:

a) Reporter genes or proteins code for easily quantifiable proteins and ensure via an intrinsic color or enzymic activity an assessment of transformation efficiency or of the site or time of expression (Schenborn E, Groskreutz D (1999) Mol Biotechnol 13(1):2944). Examples which should be mentioned are:

green fluorescence protein (GFP) (Chui W L et al., Curr Biol 1996, 6:325-330; Leffel S M et al., Biotechniques. 23(5):912-8, 1997; Sheen et al. (1995) Plant Journal 8(5): 777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 15:267-271; WO 97/41228), chloramphenicol transferase (Fromm et al. (1985) Proc Natl Acad Sci USA 82:5824-5828), luciferase (Millar et al. (1992) Plant Mol Biol Rep 10:324-414; Ow et al. (1986) Science, 234:856-859); permits detection of bioluminescence., [beta]-galactosidase, codes for an enzyme for which various chromogenic substrates are available, [beta]-glucuronidase (GUS) (Jefferson et al. (1987) EMBO J. 6:3901-3907) or the uidA gene which encodes an enzyme for various chromogenic substrates, R-locus gene product protein which regulates the production of anthocyanin pigments (red coloration) in plant tissues and thus makes direct analysis possible of the promoter activity without adding additional auxiliaries or chromogenic substrates (Dellaporta et al., In: Chromosome Structure and Function: Impact of New Concepts, 18th Stadler Genetics Symposium 11:263-282, 1988), [beta]-lactamase (Sutcliffe (1978) Proc Natl Acad Sci USA 75:3737-3741), enzyme for various chromogenic substrates (e.g. PADAC, a chromogenic cephalosporin), xyIE gene product (Zukowsky et al. (1983) Proc Natl Aced Sci USA 80:1101-1105), catechol dioxygenase, which can convert chromogenic catechols, alpha-amylase (Ikuta et al. (1990) Biol Technol. 8:241-242, tyrosinase (Katz at al. (1983) J Gen Microbiol 129:2703-2714), enzyme which oxidizes tyrosine to DOPA and dopaquinone which subsequently form the easily detectable melanin, aequorin (Prasher et al. (1985) Biochem Biophys Res. Commun 126(3):1259-1268), can be used in calcium-sensitive bioluminescence detection.

b) Origins of replication which ensure a multiplication of the expression cassettes or vectors of the invention in, for example, *E. coli*. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

c) Elements for example "border sequences" which make *agrobacteria*-mediated transfer into plant cells possible for transfer and integration into the plant genome, such as, for example, the right or left border of the T-DNA or the vir region.

d) Multiple cloning regions (MCS) permit and facilitate the insertion of one or more nucleic acid sequences.

The skilled worker is aware of various ways of obtaining an expression cassette of the invention. The production of an expression cassette of the invention takes place for example by fusing one of the expression control sequence of the invention with a nucleic acid sequence of interest to be expressed, if appropriate with a sequence coding for a transit peptide which is preferably positioned between the promoter and the respective nucleic acid sequence, and with a terminator or polyadenylation signal. Conventional techniques of recombination and cloning are used for this purpose (as described above).

It is also possible analogously for a nucleic acid sequence to be expressed transgenically to be placed, for example by homologous recombination, behind the endogenous, natural promoter, resulting in an expression cassette of the invention which controls the expression of the nucleic acid sequence to be expressed transgenically.

In principle, the invention also contemplates cells, cell cultures, parts—such as, for example, roots, leaves, seeds etc. in the case of transgenic plant organisms—and transgenic propagation material such as seeds or fruits, derived from the transgenic organisms described above.

Genetically modified plants of the invention which can be consumed by humans and animals may also be used as human food or animal food for example directly or after processing in a manner known per se.

A further aspect of the invention, thus, relates to the use of the transgenic organisms of the invention described above and of the cells, cell cultures, parts—such as, for example, roots, leaves, seeds etc. in the case of transgenic plant organisms—and transgenic propagation material such as seeds or fruits derived therefrom for producing human or animal foods, pharmaceuticals or fine chemicals.

Preference is further given to a process for the recombinant production of pharmaceuticals or fine chemicals in host organisms, where a host organism is transformed with one of the expression cassettes or vectors described above, and this expression cassette comprises one or more structural genes which code for the desired fine chemical or catalyze the biosynthesis of the desired fine chemical, the transformed host organism is cultured, and the desired fine chemical is isolated from the culture medium. This process is widely applicable to fine chemicals such as enzymes, vitamins, amino acids, sugars, fatty acids, natural and synthetic flavorings, aromatizing substances and colorants. The production of tocopherols and tocotrienols, and of carotenoids is particularly preferred. The culturing of the transformed host organisms, and the isolation from the host organisms or from the culture medium takes place by means of processes known to the skilled worker. The production of pharmaceuticals such as, for example, antibodies or vaccines is described in Hood E E, Jilka J M (1999). Curr Opin Biotechnol 10(4):382-6; Ma J K, Vine N D (1999). Curr Top Microbial Immunol 236:275-92.

All references cited in this specification are herewith incorporated by reference with respect to their entire disclosure content and the disclosure content specifically mentioned in this specification.

FIGURES

FIG. 1. Sequence of KG_Fragment 86 (SEQ ID NO: 10)

FIG. 2. Sequence of 62260557.f_o13_1 Maize (SEQ ID NO: 11)

FIG. 3. q-RT-PCR results showing whole seed-specific expression of 62260557.f_o13_1 Maize. [Root_dv: a mixture of roots at 5, 15, 30 days after pollination (DAP); Leaf_du: a mixture of leaves at 5, 15, 30 DAP; Ear: a mixture of ear at 5 and 10 DAP; whole seeds: a mixture of whole seeds at 15, 20, 30 DAP; Endosperm: a mixture of endosperm at 15, 20, 30 DAP; Embryo: a mixture of embryo at 15, 20, 30 DAP; Root_V2+V4: a mixture of root at V2 and V4 stages; Shoot/leaf_V2+V4: a mixture of V2 shoot and V4 leaves; Flower_GS: a mixture of flower and geminating seeds.]

FIG. 4. The corresponding CDS sequence of the KG_Fragment 86 (SEQ ID NO:4)

FIG. 5. Amino acid sequence of the deduced protein of the corresponding gene of KG_Fragment 86 (SEQ ID NO: 5)

FIGS. 6A, 6B, and 6C, combined. The sequence of AZM5_7833 (SEQ ID NO: 128) containing the predicted CDS sequence and the upstream promoter region. The 5' UTR (127 bp) was determined by comparing the genomic sequence to the maize EST sequence and is indicated in italic, the predicted open reading frame is underlined, and the primers used to isolated the promoter region is in bold.

FIG. 7. Sequence of Promoter KG86 (p-KG86) (SEQ ID NO: 1)

Figure 8:
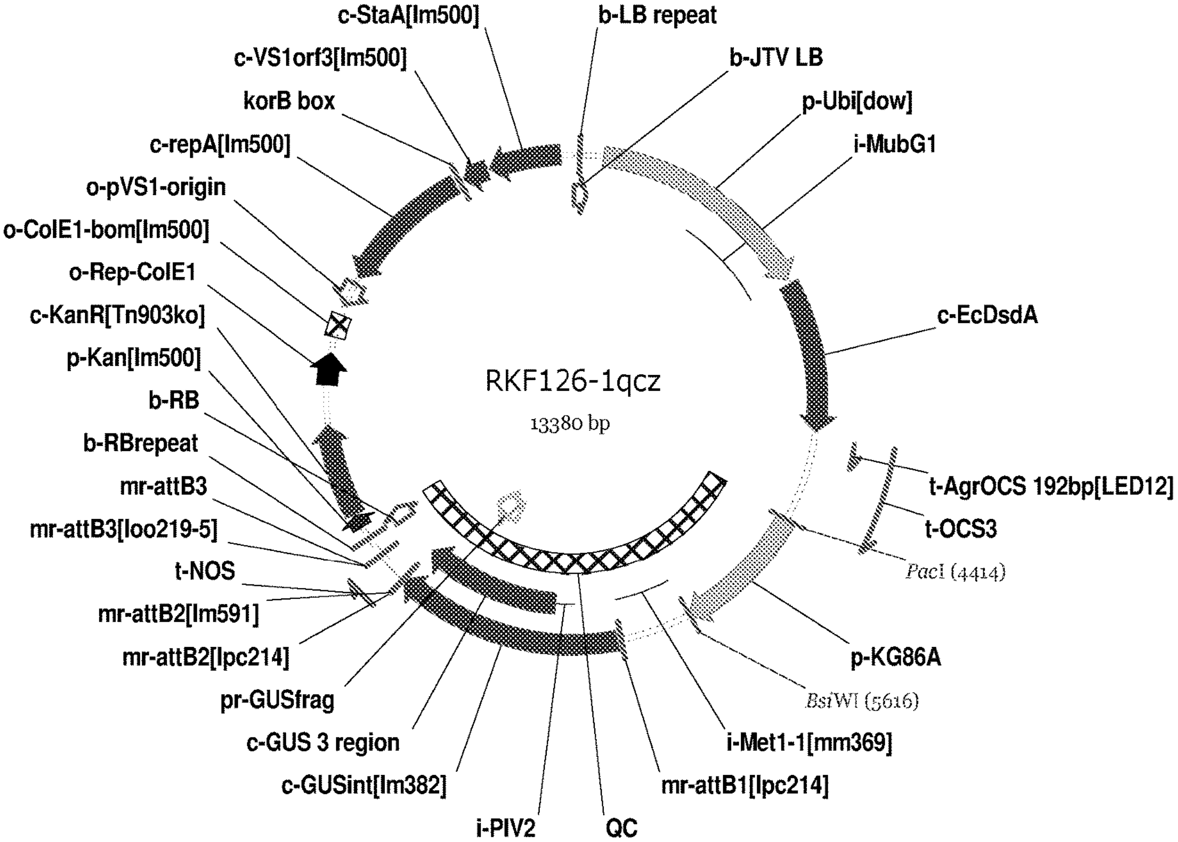

FIG. 8. Diagram of vector RKF126

FIGS. 9A, 9B, 9C, 9D, 9E, and 9F, combined. Sequence of RKF126 (SEQ ID NO: 56)

Figure 10:
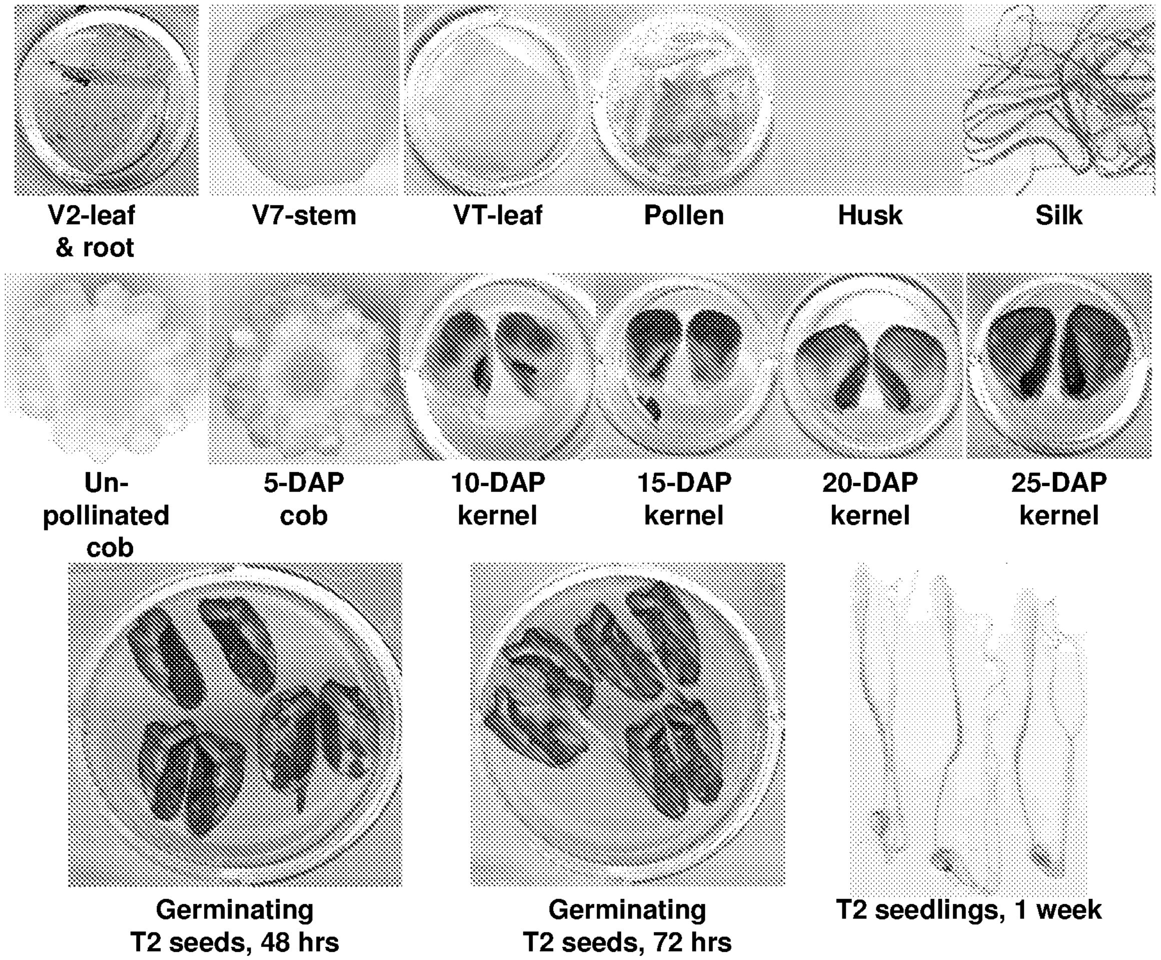

FIG. 10. GUS expression in different tissues at different developmental stages driven by p-KG86 in transgenic maize with RKF126

FIGS. 11A, 11B, and 11C. 11A) Sequences of ZM1s61973481 (SEQ ID NO: 57), 11B) ZM1s01221800 (SEQ ID NO: 58) and 11C) ZM1s62042561 (SEQ ID NO: 59)

Figure 12:
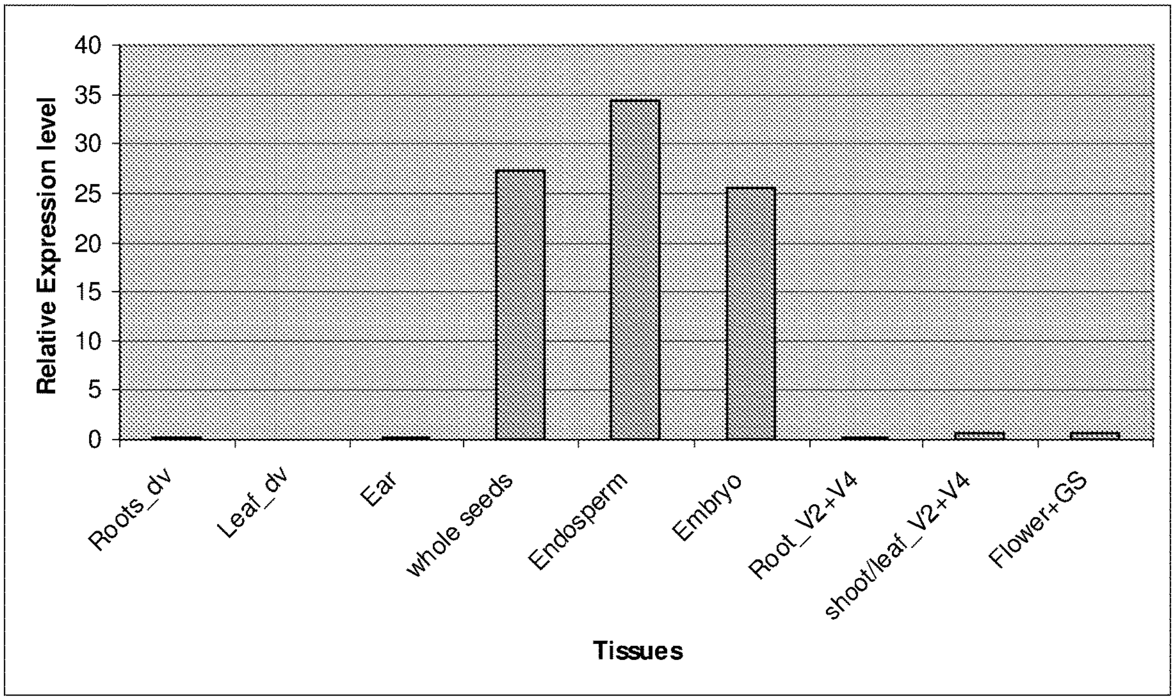

FIG. 12. q-RT-PCR results showing whole seed-specific expression of MAWS42 [Root_dv: a mixture of roots at 5, 15, 30 days after pollination (DAP); Leaf_dv: a mixture of leaves at 5, 15, 30 DAP; Ear: a mixture of ear at 5 and 10 DAP; whole seeds: a mixture of whole seeds at 15, 20, 30 DAP; Endosperm: a mixture of endosperm at 15, 20, 30

DAP; Embryo: a mixture of embryo at 15, 20, 30 DAP; Root_V2+V4: a mixture of root at V2 and V4 stages; Shoot/leaf_V2+V4: a mixture of V2 shoot and V4 leaves; Flower_GS: a mixture of flower and geminating seeds.]

Figure 13:
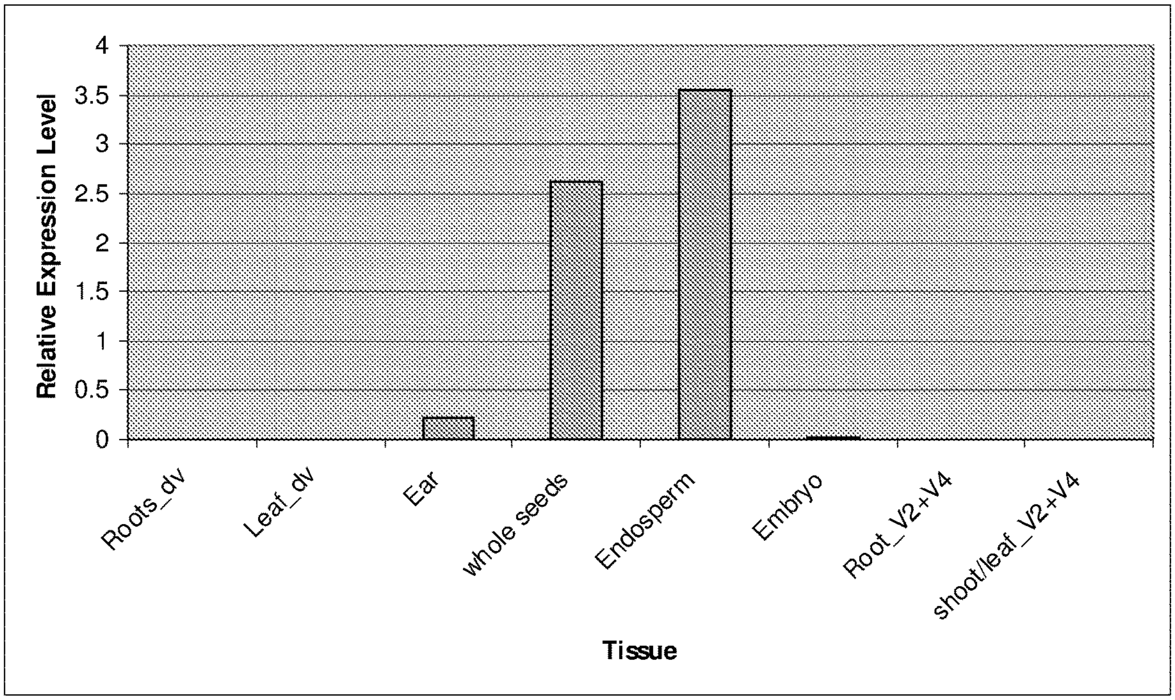

FIG. 13. q-RT-PCR results showing whole seed-specific expression of MAWS45 [Root_dv: a mixture of roots at 5, 15, 30 days after pollination (DAP); Leaf_dv: a mixture of leaves at 5, 15, 30 DAP; Ear: a mixture of ear at 5 and 10 DAP; whole seeds: a mixture of whole seeds at 15, 20, 30 DAP; Endosperm: a mixture of endosperm at 15, 20, 30 DAP; Embryo: a mixture of embryo at 15, 20, 30 DAP; Root_V2+V4: a mixture of root at V2 and V4 stages; Shoot/leaf_V2+V4: a mixture of V2 shoot and V4 leaves; Flower_GS: a mixture of flower and geminating seeds.]

FIG. 14. The corresponding CDS sequence of MAWS42 (SEQ ID NO: 6)

FIG. 15. Amino acid sequence of the ZmTIP3-1 of the corresponding gene to MAWS42 (SEQ ID NO: 7)

FIG. 16. The corresponding CDS sequence of MAWS45 (SEQ ID NO: 8)

FIG. 17. Amino acid sequence of the corresponding gene to MAWS45 (SEQ ID NO: 9)

FIGS. 18A, 18B, 18C, 18D, and 18E. The sequences of AZM5_17960 (SEQ ID NO: 70; FIGS. 18A and 18B, combined) and AZM5_6324 (SEQ ID NO: 71; FIGS. 18C, 18D, and 18E, combined) containing the predicted CDS sequence (ATG bold underlined), the predicted 5'-UTR (italics), and the additional putative promoter sequence The 5' UTR sequences were determined by comparing the genomic sequence to the maize EST.

FIGS. 19A and 19B. Sequences of Promoter MAWS42 (p-MAWS42), SEQ ID NO: 2 (FIG. 19A) and promoter MAWS45 (p-MAWS45), SEQ ID NO: 3 (FIG. 19B), FIG. 20. Diagram of RTP1052

FIGS. 21A, 21B, 21C, 21D, 21E, 21F, and 21G, combined. Sequence of RTP1052 (SEQ ID NO: 116)

Figure 22:
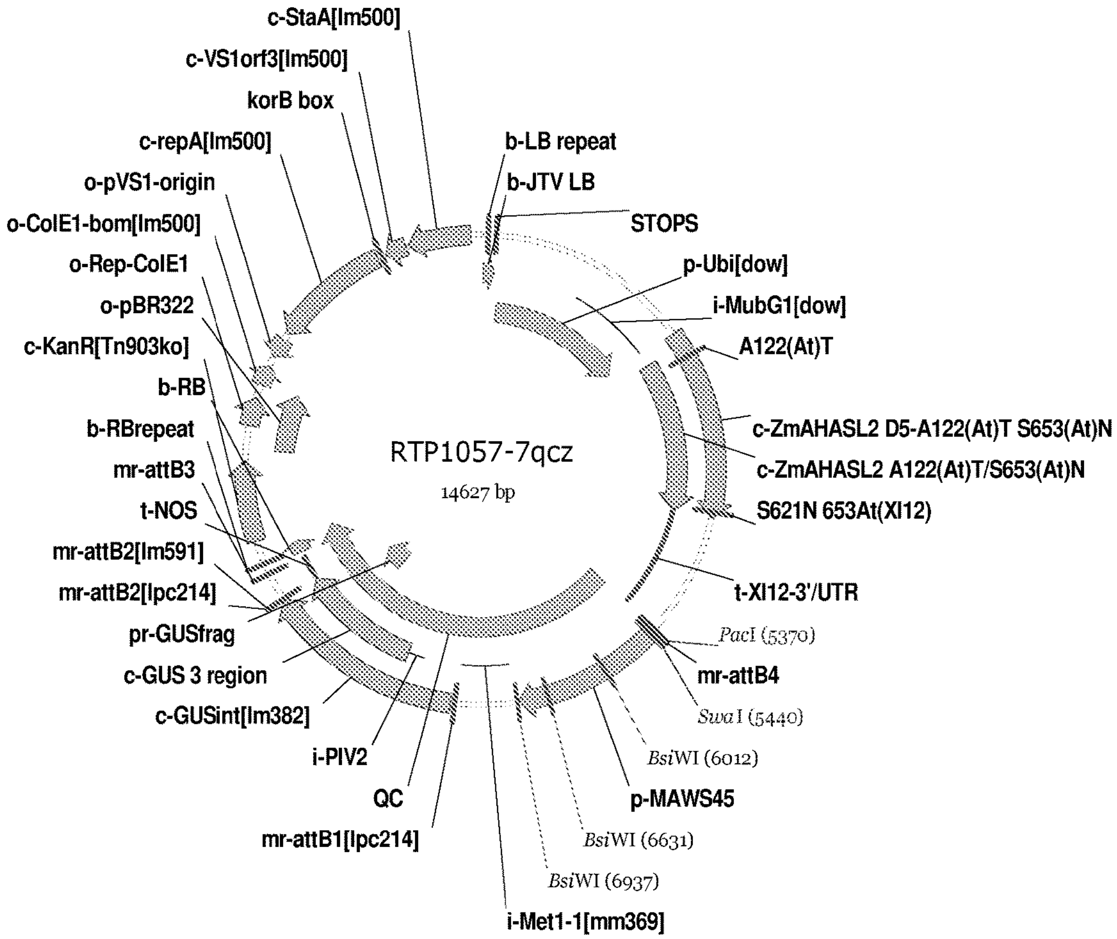

FIG. 22. Diagram of RTP1057

FIGS. 23A, 23B, 23C, 23D, 23E, 23F, and 23G, combined. Sequence of RTP1057 (SEQ ID NO: 117)

Figure 24:
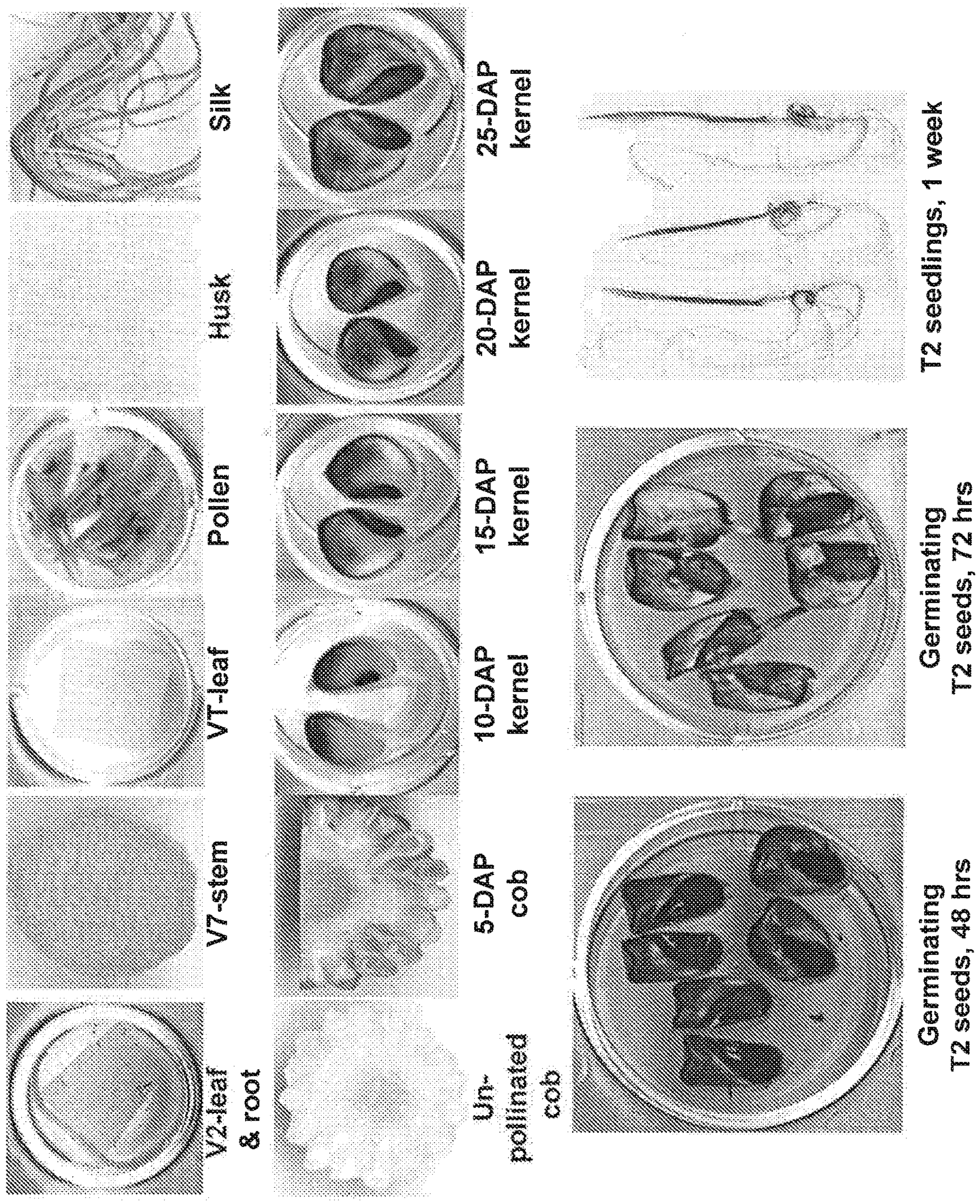

FIG. 24. GUS expression in different tissues at different developmental stages driven by p-MAWS42 in transgenic maize with RTP1052

Figure 25:
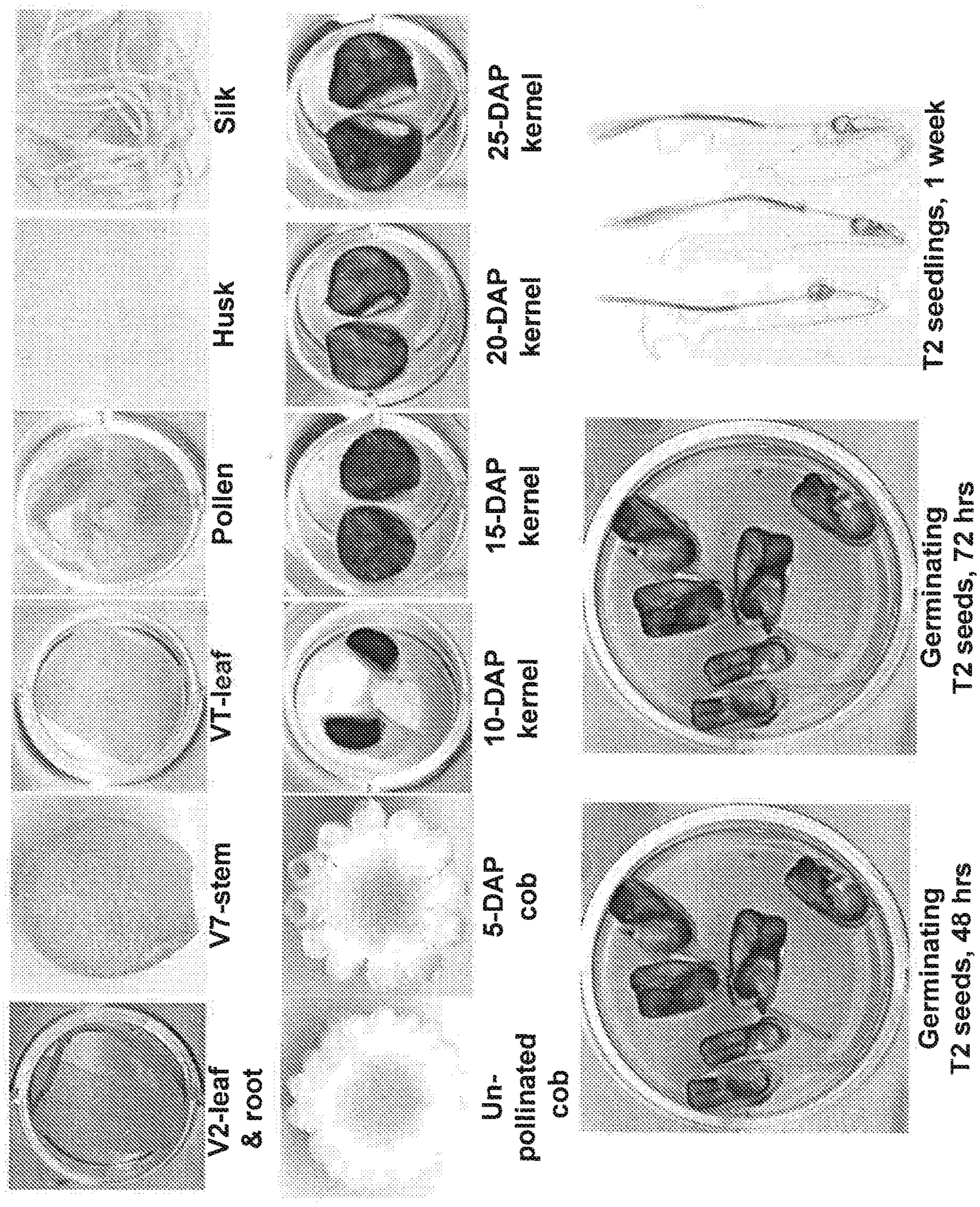

FIG. 25. GUS expression in different tissues at different developmental stages driven by p-MAWS45 in transgenic maize with RTP1057

EXAMPLES

The invention will now be illustrated by the following Examples which are not intended, whatsoever, to limit the scope of this application.

Example 1: Identification and Validation of Maize Whole Seed Promoter KG86

Identification of Transcript of KG86

A maize gene expression profiling analysis was carried out using a commercial supplier of AFLP comparative expression technology (Keygene N.V., P.O. Box 216, 6700 AE Wageningen, The Netherlands) using a battery of RNA samples from 23 maize tissues generated by BASF (Table 1). Among the AFLP bands that were identified as having whole seed specific expression was a 231 bp fragment designated "KG_Fragment 86". The sequence of KG_Fragment 86 is shown in FIG. 1.

TABLE 1

Corn Tissues used for mRNA expression profiling experiment

| Sample No. | Tissue | Timing and number of plants | Days after Pollination |
|---|---|---|---|
| 1 | Root | 9 am (4 plants) | 5 |
| 2 | | 9 am (4 plants) | 15 |
| 3 | | 9 am (4 plants) | 30 |
| 4 | leaf above the ear | 9 am (6 plants) | 5 |
| 5 | | 9 am (6 plants) | 15 |
| 6 | | 9 am (6 plants) | 30 |
| 7 | ear complete | 9 am (6 plants) | 5 |
| 8 | | 9 am (6 plants) | 10 |
| 9 | Whole seed | 9 am (6 plants) | 15 |
| 10 | | 9 am (6 plants) | 20 |
| 11 | | 9 am (6 plants) | 30 |
| 12 | Endosperm | 9 am (6 plants) | 15 |
| 13 | | 9 am (6 plants) | 20 |
| 14 | | 9 am (6 plants) | 30 |
| 15 | Embryo | 9 am (6 plants) | 15 |
| 16 | | 9 am (6 plants) | 20 |
| 17 | | 9 am (6 plants) | 30 |
| 18 | Female pistilate flower | 6 plants | before pollination |
| 19 | germinating seed | 20 seeds | imbibition for 3 days |
| 20 | root, veg. state | | V2 |
| 21 | root, veg. state | | V4 |
| 22 | leaf, veg. State | | V2 |
| 23 | leaf, veg. State | | V4 |

Identification of the Gene Corresponding to KG_Fragment 86

Sequence of KG_Fragment 86 was used as query for BLASTN searching against BASF's in-house database, HySeq All EST. An accession, 62260557.f_o13_1 Maize, showing 97% identities to KG_Fragment 86 was identified as having the highest homology with KG_Fragment 86. The sequence of 62260557.f_o13_1 Maize is shown in FIG. 2.

Confirmation of Expression Pattern of 62260557.f_o13_1 Maize Using Quantitative Reverse Transcriptase-Polymerase Chain Reaction (q RT-PCR)

In order to confirm the native expression pattern of 62260557.f_o13_1 Maize, quantitative reverse transcription PCR (q-RT-PCR) was performed using total RNA isolated from the same materials as were used for the AFLP expression profiling (Table 1).

Primers for qRT-PCR were designed based on the sequences of 62260557.f_o13_1 Maize and of KG_Fragment 86 using the Vector NTI software package (Invitrogen, Carlsbad, Calif., USA). Two sets of primers were used for PCR amplification of 62260557.f_o13_1 Maize (Table 2). The glyceraldehyde-3-phosphate dehydrogenase (GAPDH) gene served as a control for normalization purposes.

TABLE 2

Primer sequences for q-RT-PCR

| Primer | Sequence (SEQ ID NO) |
|---|---|
| 62260557_Forward_1 | CAGCTAGCGGCTTAGTCT (12) |
| 62260557_Reverse_1 | CTCTTCGCCTGGAGGTTC (13) |
| 62260557_Forward_2 | TGGTTTCATTGGATGCAGC (14) |
| 62260557_Reverse_2 | TGCAGTGCGAGTCAGAGA(15) |
| GAPDH_Forward | GTAAAGTTCTTCCTGATCTGAAT (16) |
| GAPDH_Reverse | TCGGAAGCAGCCTTAATA (17) |

q-RT-PCR was performed using SuperScript III Reverse Transcriptase (Invitrogen, Carlsbad, Calif., USA) and SYBR Green QPCR Master Mix (Eurogentec, San Diego, Calif., USA) in an ABI Prism 7000 sequence detection system. cDNA was synthesized using 2-3 ug of total RNA and 1 μL reverse transcriptase in a 20 uL volume. The cDNA was diluted to a range of concentrations (15-20 ng/uL). Thirty to forty ng of cDNA was used for quantitative PCR (qPCR) in a 30 uL volume with SYBR Green QPCR Master Mix following the manufacturer's instruction. The thermocycling conditions were as follows: incubate at 50° C. for 2 minutes, denature at 95° C. for 10 minutes, and run 40 cycles at 95° C. for 15 seconds and 60° C. for 1 minute for amplification. After the final cycle of the amplification, the dissociation curve analysis was carried out to verify that the amplification occurred specifically and no primer dimer product was generated during the amplification process. The housekeeping gene glyceraldehyde-3-phosphate-dehydrogenase (GAPDH, primer sequences in Table 2) was used as an endogenous reference gene to normalize the calculation using the Comparative Ct (Cycle of threshold) value method. The ΔCT value was obtained by subtracting the Ct value of GAPDH gene from the Ct value of the candidate gene (62260557.f_o13_1 Maize), and the relative transcription quantity (expression level) of the candidate gene was expressed as $2^{-\Delta CT}$. The q-RT-PCR results are summarized in FIG. 3. Both primer sets gave the similar expression patterns that are equivalent to the expression patterns obtained from the AFLP data.

Annotation of the KG_Fragment 86

The coding sequence of KG_Fragment 86 was annotated based on the in silico results obtained from both BLASTX search of EST 62260557.f_o13_1 Maize sequence against GenBank protein database (nr) and the result of in silica translation of the sequence using Vector NTI software package. The EST 62260557.f_o13_1 Maize sequence encodes a partial protein with the highest homology to the rice gene annotated as hypothetical protein Osl_025737 (GenBank Accession: EAZ04505.1). The top 15 homologous sequences identified in the BlastX query are presented in Table 3.

TABLE 3

BLASTX search results of the maize EST 62260557.f_o13_1

| Accession | Description | Score | E-value |
|---|---|---|---|
| EAZO4505.1 | hypothetical protein Osl_025737 *Oryza sativa* (*indica* cultivar-group)] | 152 | 8e−36 |
| BAC22280.1 | hypothetical protein [*Oryza sativa* (*japonica*)] | 152 | 8e−36 |
| EAZ40462.1 | hypothetical protein OsJ_023945[*Oryza sativa* (*japonica*)] | 146 | 5e−34 |
| CAO61483.1 | unnamed protein product [*Vitis vinifera*] | 114 | 2e−24 |
| ABK28018.1 | unknown [*Arabidopsis thaliana*] | 100 | 6e−20 |
| NP_001117365.1 | unknown [*Arabidopsis thaliana*] | 100 | 6e−20 |
| AAF99742.1 | F17L21.26 [*Arabidopsis thaliana*] | 100 | 6e−20 |
| XP_001751813.1 | predicted protein [*Physcomitrella patens* subsp. *Patens*] | 75 | 1e−12 |
| XP_001778474.1 | predicted protein [*Physcomitrella patens* subsp. *Patens*] | 74 | 5e−12 |
| CAN72846.1 | hypothetical protein [*Vitis vinifera*] | 69 | 2e−10 |
| XP_001763429.1 | predicted protein [*Physcomitrella patens* subsp. *Patens*] | 67 | 6e−10 |
| CAO14607.1 | unnamed protein product [*Vitis vinifera*] | 55 | 2e−06 |
| NP_001067585.1 | Os11g0241200 [*Oryza sativa* (*japonica*)] | 52 | 1e−05 |
| ABK28287.1 | unknown [*Arabidopsis thaliana*] | 51 | 3e−05 |
| NP_198895.1 | unknown protein [*Arabidopsis thaliana*] | 51 | 3e−05 |

The CDS sequence of KG_Fragment 86 is shown in FIG. 4 and the deduced amino acid sequence is shown in FIG. 5.

Identification of the Promoter Region

For our promoter identification purposes, the sequence upstream of the start codon of the predicted KG_Fragment 86 gene was defined as the promoter p-KG86. To identify this promoter region, the sequence of 62260557.f_o13_1 was mapped to the BASF Plant Science proprietary genomic DNA sequence database, PUB_tigr_maize_genomic_partial_5.0.nt. One maize genomic DNA sequence, AZM5_7833 (5084 bp) was identified. This 5084 bp sequence harboured the CDS of the KG_Fragment 86 and more than 2 kb upstream sequence of the ATG start codon of this gene (FIGS. 6A, 6B and 6C, combined).

Isolation of the Promoter Region by PCR Amplification

The putative promoter region was isolated via genomic PCR using the following sequence specific primers:

```
Forward primer:
tcccgtgtccgtcaatgtgata     (SEQ ID NO: 18)

Reverse primer:
Ggactcacgagctgaggctcgg     (SEQ ID NO: 19)
```

The expected 1198 bp fragment was amplified from maize genomic DNA, and annotated as promoter KG86 (p-KG86). Sequence of p-KG86 was shown in FIG. 7.

PLACE Analysis of the Promoter KG86

Cis-acting motifs in the 1198 bp KG86 promoter region were identified using PLACE (a database of Plant Cis-acting Regulatory DNA elements) using the Genomatix database suite. The results are listed in Table 4. Although no putative consensus TATA box was identified in the forward strand, a CAAT Box motif is found at nucleotide position 701-705 in the forward strand.

TABLE 4

PLACE analysis results of the 1198 bp promoter, p-KG86

| IUPAC | Start pos. | End pos. | Strand | Mismatches | Score | Sequence (SEQ ID NO) |
|---|---|---|---|---|---|---|
| WBOXATNPR1 | 2 | 16 | − | 0 | 1 | ATTGACGGACACGGG (20) |
| DPBFCOREDCDC3 | 2 | 8 | − | 0 | 1 | ACACGGG |
| ASF1MOTIFCAMV | 7 | 19 | − | 0 | 1 | CACATTGACGGAC (21) |
| S1FBOXSORPS1L21 | 41 | 46 | − | 0 | 1 | ATGGTA |
| RYREPEATGMGY2 | 42 | 52 | + | 0 | 1 | ACCATGCATAC (22) |
| DRECRTCOREAT | 61 | 67 | − | 0 | 1 | GCCGACC |
| GCCCORE | 65 | 71 | + | 0 | 1 | GGCCGCC |
| BIHD1OS | 103 | 107 | + | 0 | 1 | TGTCA |
| SORLIP1AT | 131 | 143 | − | 0 | 1 | TAGCTAGCCACGC (23) |
| GT1GMSCAM4 | 159 | 164 | − | 0 | 1 | GAAAAA |
| IBOXCORE | 171 | 177 | + | 0 | 1 | GATAATA |
| TBOXATGAPB | 180 | 185 | + | 0 | 1 | ACTTTG |
| BIHD1OS | 184 | 188 | + | 0 | 1 | TGTCA |
| S1FBOXSORPS1L21 | 188 | 193 | + | 0 | 1 | ATGGTA |
| MYB1AT | 208 | 213 | − | 0 | 1 | TAACCA |
| TATABOX4 | 211 | 217 | − | 0 | 1 | TATATAA |
| MYBST1 | 244 | 250 | + | 0 | 1 | AGGATAG |
| IBOXCORE | 275 | 281 | + | 0 | 1 | GATAAAA |
| BIHD1OS | 300 | 304 | − | 0 | 1 | TGTCA |
| MYBCOREATCYCB1 | 306 | 310 | + | 0 | 1 | AACGG |
| RYREPEATGMGY2 | 315 | 325 | + | 0 | 1 | CGCATGCATTG (24) |
| CCAATBOX1 | 322 | 326 | − | 0 | 1 | CCAAT |
| CGACGOSAMY3 | 328 | 332 | + | 0 | 1 | CGACG |
| CGCGBOXAT | 345 | 350 | + | 0 | 1 | GCGCGT |
| CGCGBOXAT | 345 | 350 | − | 0 | 1 | ACGCGC |
| SURECOREATSULTR11 | 347 | 353 | − | 0 | 1 | GAGACGC |
| DPBFCOREDCDC3 | 351 | 357 | − | 0 | 1 | ACACGAG |
| PALBOXAPC | 362 | 368 | + | 0 | 1 | CCGTCCA |
| CMSRE1IBSPOA | 362 | 368 | − | 0 | 1 | TGGACGG |
| SORL1PIAT | 379 | 391 | + | 0 | 1 | TCTCACGCCACGT (25) |
| ABREATRD2 | 383 | 395 | − | 0 | 1 | GAGCACGTGGCGT (26) |

TABLE 4-continued

PLACE analysis results of the 1198 bp promoter, p-KG86

| IUPAC | Start pos. | End pos. | Strand | Mismatches | Score | Sequence (SEQ ID NO) |
|---|---|---|---|---|---|---|
| CACGTGMOTIF | 384 | 396 | + | 0 | 1 | CGCCACGTGCTCA (27) |
| RAV1AAT | 395 | 399 | + | 0 | 1 | CAACA |
| ASF1MOTIFCAMV | 411 | 423 | − | 0 | 1 | GCTGGTGACGAAC (28) |
| ASF1MOTIFCAMV | 438 | 450 | + | 0 | 1 | AGGGATGACGCAT (29) |
| LTRE1HVBLT49 | 450 | 455 | − | 0 | 1 | CCGAAA |
| BIHD1OS | 460 | 464 | + | 0 | 1 | TGTCA |
| MYBST1 | 485 | 491 | − | 0 | 1 | TGGATAT |
| TATCCAOSAMY | 486 | 492 | + | 0 | 1 | TATCCAA |
| RAV1AAT | 490 | 494 | + | 0 | 1 | CAACA |
| EMHVCHORD | 524 | 532 | + | 0 | 1 | TGTAAAGTC |
| 300ELEMENT | 524 | 532 | + | 0 | 1 | TGTAAAGTC |
| TAAAGSTKST1 | 524 | 530 | + | 0 | 1 | TGTAAAG |
| NTBBF1ARROLB | 525 | 531 | − | 0 | 1 | ACTTTAC |
| CACGTGMOTIF | 544 | 556 | − | 0 | 1 | CTGCACGTGCTGT (30) |
| CACGTGMOTIF | 545 | 557 | + | 0 | 1 | CAGCACGTGCAGA (31) |
| HEXMOTIFTAH3H4 | 561 | 573 | + | 0 | 1 | ATTAACGTCATTA (32) |
| TGACGTVMAMY | 563 | 575 | − | 0 | 1 | AATAATGACGTTA (33) |
| CPBCSPOR | 572 | 577 | + | 0 | 1 | TATTAG |
| RYREPEATGMGY2 | 588 | 598 | − | 0 | 1 | ATCATGCATCT (34) |
| DPBFCOREDCDC3 | 618 | 624 | + | 0 | 1 | ACACAAG |
| OSE2ROOTNODULE | 622 | 626 | − | 0 | 1 | CTCTT |
| MYBPLANT | 667 | 677 | − | 0 | 1 | CACCAACCAGC (35) |
| BOXLCOREDCPAL | 670 | 676 | − | 0 | 1 | ACCAACC |
| CGCGBOXAT | 684 | 689 | + | 0 | 1 | GCGCGC |
| CGCGBOXAT | 684 | 689 | − | 0 | 1 | GCGCGC |
| CCAATBOX1 | 696 | 700 | − | 0 | 1 | CCAAT |
| CCAATBOX1 | 701 | 705 | + | 0 | 1 | CCAAT |
| SORLIP1AT | 721 | 733 | + | 0 | 1 | CCACTCGCCACGC (36) |
| SORLIP2AT | 738 | 748 | − | 0 | 1 | GGGGCCATTCA (37) |
| CGCGBOXAT | 774 | 779 | + | 0 | 1 | CCGCGC |
| CGCGBOXAT | 774 | 779 | − | 0 | 1 | GCGCGG |
| CGCGBOXAT | 776 | 781 | + | 0 | 1 | GCGCGC |
| CGCGBOXAT | 776 | 781 | − | 0 | 1 | GCGCGC |
| SITEIIATCYTC | 777 | 787 | − | 0 | 1 | TGGGCCGCGCG (38) |
| CGCGBOXAT | 778 | 783 | + | 0 | 1 | GCGCGG |
| CGCGBOXAT | 778 | 783 | − | 0 | 1 | CCGCGC |
| DRECRTCOREAT | 793 | 799 | − | 0 | 1 | GCCGACT |
| SORLIP1AT | 801 | 813 | + | 0 | 1 | GAACGCGCCACGG (39) |

TABLE 4-continued

PLACE analysis results of the 1198 bp promoter, p-KG86

| IUPAC | Start pos. | End pos. | Strand | Mismatches | Score | Sequence (SEQ ID NO) |
|---|---|---|---|---|---|---|
| CGCGBOXAT | 803 | 808 | + | 0 | 1 | ACGCGC |
| CGCGBOXAT | 803 | 808 | − | 0 | 1 | GCGCGT |
| SORLIP2AT | 829 | 839 | + | 0 | 1 | AGGGCCGAGGC (40) |
| CGCGBOXAT | 841 | 846 | + | 0 | 1 | GCGCGG |
| CGCGBOXAT | 841 | 846 | − | 0 | 1 | CCGCGC |
| OCTAMOTIF2 | 842 | 849 | + | 0 | 1 | CGCGGCAT |
| BS1EGCCR | 864 | 869 | + | 0 | 1 | AGCGGG |
| RYREPEATBNNAPA | 876 | 886 | − | 0 | 1 | TGCATGCAGGT (41) |
| INTRONLOWER | 877 | 882 | − | 0 | 1 | TGCAGG |
| RYREPEATBNNAPA | 879 | 889 | + | 0 | 1 | TGCATGCAGCC (42) |
| ASF1MOTIFCAMV | 902 | 914 | − | 0 | 1 | ACGACTGACGAGG (43) |
| BOXCPSAS1 | 921 | 927 | + | 0 | 1 | CTCCCAC |
| MYBPZM | 937 | 943 | + | 0 | 1 | CCCAACC |
| CGCGBOXAT | 963 | 968 | + | 0 | 1 | ACGCGC |
| CGCGBOXAT | 963 | 968 | − | 0 | 1 | GCGCGT |
| ABREMOTIFAOSOSEM | 985 | 997 | + | 0 | 1 | GCCTACGTGTCGG (44) |
| DRECRTCOREAT | 992 | 998 | − | 0 | 1 | GCCGACA |
| ABREOSRAB21 | 1014 | 1026 | − | 0 | 1 | GGGTACGTGGGCG (45) |
| UPRMOTIFIIAT | 1025 | 1043 | + | 0 | 1 | CCCGCCCCGTTCTCCCACG (46) |
| MYBCOREATCYCB1 | 1031 | 1035 | − | 0 | 1 | AACGG |
| IRO2OS | 1036 | 1048 | − | 0 | 1 | GGGCACGTGGGAG (47) |
| BOXCPSAS1 | 1036 | 1042 | + | 0 | 1 | CTCCCAC |
| ABREOSRAB21 | 1037 | 1049 | + | 0 | 1 | TCCCACGTGCCCC (48) |
| CGCGBOXAT | 1057 | 1062 | + | 0 | 1 | GCGCGC |
| CGCGBOXAT | 1057 | 1062 | − | 0 | 1 | GCGCGC |
| CGCGBOXAT | 1059 | 1064 | + | 0 | 1 | GCGCGT |
| CGCGBOXAT | 1059 | 1064 | − | 0 | 1 | ACGCGC |
| CCAATBOX1 | 1068 | 1072 | − | 0 | 1 | CCAAT |
| WBOXNTCHN48 | 1072 | 1086 | + | 0 | 1 | GCTGACCCGCCCTTC (49) |
| CGCGBOXAT | 1092 | 1097 | + | 0 | 1 | CCGCGC |
| CGCGBOXAT | 1092 | 1097 | − | 0 | 1 | GCGCGG |
| SORLIP2AT | 1107 | 1117 | − | 0 | 1 | GGGGCCCGGAC (50) |
| SORLIP2AT | 1110 | 1120 | + | 0 | 1 | CGGGCCCCAAC (51) |
| HEXAMERATH4 | 1129 | 1134 | + | 0 | 1 | CCGTCG |
| CGACGOSAMY3 | 1130 | 1134 | − | 0 | 1 | CGACG |
| CGACGOSAMY3 | 1133 | 1137 | − | 0 | 1 | CGACG |
| SURECOREATSULTR11 | 1135 | 1141 | − | 0 | 1 | GAGACGA |
| SITEIIATCYTC | 1154 | 1164 | − | 0 | 1 | TGGGCTCGATC (52) |

TABLE 4-continued

| PLACE analysis results of the 1198 bp promoter, p-KG86 | | | | | | |
|---|---|---|---|---|---|---|
| IUPAC | Start pos. | End pos. | Strand | Mismatches | Score | Sequence (SEQ ID NO) |
| QELEMENTZMZM13 | 1159 | 1173 | – | 0 | 1 | CCAGGTCAGTGGGCT (53) |
| WBOXNTCHN48 | 1164 | 1178 | + | 0 | 1 | ACTGACCTGGCCCCC (54) |
| SORLIP2AT | 1167 | 1177 | – | 0 | 1 | GGGGCCAGGTC (55) |

Binary Vector Construction for Maize Transformation to Evaluate the Function of p-KG86

To facilitate subcloning, the 1198 bp promoter fragment was modified by the addition of a PacI restriction enzyme site at its 5' end and a BsiWI site at its 3' end. The PacI-pKG86-BsiWI promoter fragment was digested and ligated into a PacI and BsiWI digested BPS basic binary vector HF84. HF84 comprises a plant selectable marker expression cassette (p-Ubi::c-EcEsdA::t-NOS) as well as a promoter evaluation cassette that consists of a multiple cloning site for insertion of putative promoters via Pad and BsiWI, rice MET1-1 intron to supply intron-mediated enhancement in monocot cells, GUS reporter gene, and NOS terminator. The resulting binary vector comprising the pKG86::i-MET1::GUS::t-NOS expression cassette was named as RKF126, and was used to evaluate the expression pattern driven by the p-KG86 promoter. FIG. 8 is a diagram of RKF126. Sequence of the binary vector RKF126 is shown in FIGS. 9A, 9B, 9C, 9D, 9E, and 9F, combined.

Promoter Evaluation in Transgenic Maize with RKF126

Expression patterns and levels driven by the p-KG86 promoter were measured using GUS histochemical analysis following the protocol in the art (Jefferson 1987). Maize transformation was conducted using an *Agrobacterium*-mediated transformation system. Ten and five single copy events for T0 and T1 plants were chosen for the promoter analysis. GUS expression was measured at various developmental stages:

1) Roots and leaves at 5-leaf stage

2) Stem at V-7 stage

2) Leaves, husk and silk at flowering stage (first emergence of silk)

3) Spikelets/Tassel (at pollination)

5) Ear or Kernels at 5, 10, 15, 20, and 25 days after pollination (DAP)

The results indicated that promoter p-KG86 of RKF126 expressed specifically in pollen and in whole seeds (FIG. 10).

TABLE 4A

| Summary of tested tissues and relative expression intensities for pKG86 | | | | | | | | | | |
|---|---|---|---|---|---|---|---|---|---|---|
| | Tissues | | | | | | | | | |
| Stages tested | Leaf | Root | Stem | husk | silk | Spikelets/ Tassel/pollen | un-pollinated cob | pollinated cob | embryo | endosperm |
| seedling (5-leaf) | – | – | | | | | | | | |
| V-7 | | | | | | | | | | |
| Flowering (emergence of silk) | – | | | – | – | | – | | | |
| pollination | | | | | | ++ | | | | |
| 5DAP | | | | | | | | + | | |
| 10DAP | | | | | | | | | ++ | ++ |
| 15DAP | | | | | | | | | ++ | ++ |
| 20DAP | | | | | | | | | +++ | +++ |
| 25DAP | | | | | | | | | +++ | +++ |
| 48 hrs after imibibition | | | | | | | | | ++++ | ++++ |
| 72 hrs after imibibition | | | | | | | | | ++++ | ++++ |
| 1 week germination | – | – | | | | | | | | |

– = no expression,
+ = weak expression,
++ = medium expression,
+++ = strong expression,
++++ = very strong expression Example 2: Identification and Validation of Maize Whole Seed Promoter MAWS42 and MAWS45

Identification of Transcript of MAWS42 and MAWS45

A microarray study was conducted to identify transcripts with whole seed-specific expression in maize using the same panel of maize RNA samples shown in Table 1. The twenty-three labeled RNAs of these maize tissues were hybridized separately to 23 of our custom designed BPS maize Affymetrix chips, labeled with fluorescent streptavidin antibody, washed, stained and scanned as instructed in the Affymetrix Expression Analysis Technical Manual.

The chip hybridization data were analyzed using Genedata Specialist software and relative expression level was determined based on the hybridization signal intensity of each tissue.

Three of the BPS maize chip probe sets were selected as candidate transcripts showing 3-8 fold higher expression in whole seeds as compared to other tissues: ZM1s61973481_at, ZM1s61221800_s_at and ZM1s62042561_at. Consensus sequences of ZM1s61973481_at, ZM1s61221800_s_at and ZM1s62042561_at are shown in FIGS. 11A, 11B, and 11C, respectively.

Preliminary sequence analysis indicated that ZM1s61221800 is included in ZM1s62042561, therefore, we considered ZM1s61221800 and ZM1s62042561 to represent the same gene; further studies for this gene were conducted based on ZM1s62042561. For the purpose of presentation convenience we named ZM1s61973481 as candidate MAWS42 and ZM1s62042561 as MAWS45.

Confirmation of Expression Pattern of MAWS42 and MAWS45 Using Quantitative Reverse Transcriptase-Polymerase Chain Reaction (q-RT-PCR)

Confirmation of the native expression patterns of MAWS42 and MAWS45 was carried out via quantitative reverse transcription PCR (q-RT-PCR) using total RNA isolated from the same materials as what used for the chip study (Table 1).

Primers for qRT-PCR were designed based on the sequences of ZM1s61973481 for MAWS42 and ZM1s62042561 for MAWS45 using Vector NTI software package. Two sets of primers were used for PCR amplification of each gene. The sequences of primers are in Table 5. The glyceraldehyde-3-phosphate dehydrogenase (GAPDH) gene served as a control for normalization.

TABLE 5

Primer sequences for q-RT-PCR

| Primer | Sequences (SEQ ID No) |
|---|---|
| MAWS42_Forward_1 | CTGGCCGTGGGCTTCCTGCT (60) |
| MAWS42_Reverse_1 | AAGGGCCCAGCCAGTACACCCA (61) |
| MAWS42_Forward_2 | TGGAGGCACCACTGGGTGTACTGG (62) |
| MAWS42_Reverse_2 | GCTAGTAGTCCTCTGGCGCGAGCG (63) |
| MAWS45_Forward_1 | GCCAACTCTTCCATTTCGCCAAGG (64) |
| MAWS45_Reverse_1 | GGAGGATTGGCGGTGACAGTCTCA (65) |
| MAWS45_Forward_2 | AGGAAAAAATGGCGGCTCGCTGG (66) |
| MAWS45_Reverse_2 | CCATGCAAATGGAGGATTGGCGG (67) |

TABLE 5-continued

Primer sequences for q-RT-PCR

| Primer | Sequences (SEQ ID No) |
|---|---|
| GAPDH_Forward | GTAAAGTTCTTCCTGATCTGAAT (68) |
| GAPDH_Reverse | TCGGAAGCAGCCTTAATA (69) |

q-RT-PCR was performed using SuperScript III Reverse Transcriptase (Invitrogen, Carlsbad, Calif., USA) and SYBR Green QPCR Master Mix (Eurogentec, San Diego, Calif., USA) in an ABI Prism 7000 sequence detection system. cDNA was synthesized using 2-3 □g of total RNA and 1 μL reverse transcriptase in a 20 □L volume. The cDNA was diluted to a range of concentrations (15-20 ng/□L). Thirty to forty ng of cDNA was used for quantitative PCR (qPCR) in a 30 □L volume with SYBR Green QPCR Master Mix following the manufacturer's instruction. The thermocycling conditions were as follows: incubate at 50° C. for 2 minutes, denature at 95° C. for 10 minutes, and run 40 cycles at 95° C. for 15 seconds and 60° C. for 1 minute for amplification. After the final cycle of the amplification, the dissociation curve analysis was carried out to verify that the amplification occurred specifically and no primer dimer product was generated during the amplification process. The housekeeping gene glyceraldehyde-3-phosphate-dehydrogenase (GAPDH, primer sequences in Table 2) was used as an endogenous reference gene to normalize the calculation using the Comparative Ct (Cycle of threshold) value method. The ΔCT value was obtained by subtracting the Ct value of GAPDH gene from the Ct value of the candidate genes. The relative transcription quantity (expression level) of the candidate gene was expressed as 2-ΔCT. The qRT-PCR results were summarized in FIG. 12 and FIG. 13. Both primer sets gave similar expression patterns as were obtained in the microarray study.

Annotation of MAWS42 and MAWS45

The coding sequences corresponding to the MAWS42 and MAWS45 genes were annotated based on the in silico results obtained from both BLASTX of the chip consensus sequences of ZM1s61973481 and of ZM1s62042561 against GenBank protein database (nr) and results from the translation program of Vector NTI software package.

The ZM1s61973481 encodes partially a maize Tonoplast intrinsic protein 3-1(ZmTIP3). The CDS of ZmTIP3-1 (GenBank Accession:NP_0011050321) is shown in FIG. 14, the translated amino acid sequence is shown in FIG. 15, and the top 15 homologous sequences from the BLASTX query are presented in Table 6.

TABLE 6

BLASTX search results of the maize ZM1s61973481 (MAWS42)

| Accession | Description | Score | E-value |
|---|---|---|---|
| NP_001105032.1 | TIP31_MAIZE Aquaporin TIP3-1 (Tonoplast intrinsic protein 3-1) | 150 | 8e−73 |
| NP_001064933.1 | Os10g0492600 [*Oryza sativa* (*japonica*)] | 147 | 4e−64 |
| NP_001105045.1 | TIP32_MAIZE Aquaporin TIP3-2 (Tonoplast intrinsic protein 3-2) (ZmTIP3-2) | 139 | 5e−63 |
| BAA08107.1 | membrane protein MP23 precursor [*Cucurbita* cv. Kurokawa Amakuri] | 98 | 5e−42 |
| CAA44669.1 | tonoplast intrinsic protein [*Phaseolus vulgaris*] | 98 | 4e−40 |
| BAA08108.1 | T10253 membrane protein MP28 [*Cucurbita* cv. Kurokawa Amakuri] | 92 | 6e−39 |
| ABK22410.1 | unknown [*Picea sitchensis*] | 98 | 6e−33 |
| ABK22242.1 | unknown [*Picea sitchensis*] | 94 | 5e−32 |
| NP_001053371.1\| | Os04g0527900 [*Oryza sativa* (*japonica* cultivar-group)] | 85 | 2e−24 |

TABLE 6-continued

| BLASTX search results of the maize ZM1s61973481 (MAWS42) | | | |
|---|---|---|---|
| Accession | Description | Score | E-value |
| CAA64952.1 | tonoplast intrinsic protein [*Tulipa gesneriana*] | 96 | 2e−24 |
| EAY94920.1 | hypothetical protein Osl_016153 [*Oryza sativa* (*indica* cultivar-group)] | 86 | 2e−24 |
| CAB39758.1 | major intrinsic protein [*Picea abies*] | 111 | 4e−24 |
| AAC39480.1 | aquaporin [*Vernicia fordii*] | 87 | 8e−24 |
| CAO62035.1 | unnamed protein product [*Vitis vinifera*] | 110 | 5e−22 |
| BAD04010.1 | tonoplast intrinsic protein [*Prunus persica*] | 109 | 6e−22 |

The ZM1s62042561 (MAWS45) encodes a partial protein that has highest homology to a maize unknown protein (GenBank Accession: ACF84237.1), The CDS of this gene is shown in FIG. 16, the translated amino acid sequence is shown in FIG. 17, and the top 15 homologous sequences from the BLASTX query are presented in Table 7.

TABLE 7

| BLASTX search results of the maize ZM1s62042561 (MAWS45) | | | |
|---|---|---|---|
| Accession | Description | Score | E-value |
| ACF84237.1 | unknown [*Zea mays*] | 536 | e−152 |
| ACG56678.1 | tryptophan aminotransferase [*Zea mays*] | 534 | e−151 |
| NP_001054761.1 | Os05g0169300 [*Oryza sativa* (*japonica* cultivar-group)] | 239 | e−100 |
| EAY96695.1 | hypothetical protein Osl_017928 [*Oryza sativa* (*indica* cultivar-)] | 239 | e−100 |
| EAY96696.1 | hypothetical protein Osl_017929 [*Oryza sativa* (*indica* cultivar-group)] | 233 | 4e−98 |
| EAY72702.1 | hypothetical protein Osl_000549 [*Oryza sativa* (*indica* cultivar-group)] | 167 | 9e−85 |
| BAD68317.1 | putative alliinase precursor [*Oryza sativa Japonica* Group] | 167 | 9e−85 |
| EAZ10701.1 | hypothetical protein OsJ_000526 [*Oryza sativa* (*japonica* cultivar-group)] | 167 | 9e−85 |
| ACF80703.1 | unknown [*Zea mays*] | 204 | 2e−79 |
| EAZ33023.1 | hypothetical protein OsJ_016506 [*Oryza sativa* (*japonica* cultivar-group)] | 158 | 3e−75 |
| AAM69848.1 | putative alliin lyase [*Aegilops tauschii*] | 265 | 1e−73 |
| NP_001042135.1 | Os01g0169800 [*Oryza sativa* (*japonica* cultivar-group)] | 167 | 7e−73 |
| CAO64270.1 | unnamed protein product [*Vitis vinifera*] | 221 | 5e−71 |
| CAN80923.1 | hypothetical protein [*Vitis vinifera*] | 221 | 7e−71 |
| CAO16122.1 | unnamed protein product [*Vitis vinifera*] | 157 | 1e−61 |

Identification of the Promoter Region

The sequences upstream of the start codons of the corresponding genes to MAWS42 and MAWS45 were defined as the putative promoters p-MAWS42 and p-MAWS45. To identify these putative promoter regions, the sequences of ZM1s61973481 and ZM1s62042561 were mapped to the BASF Plant Science proprietary genomic DNA sequence database, PUB_tigr_maize_genomic_partial_5.0.nt. Two maize genomic DNA sequences, AZM5_17960 (3985 bp) and AZM5_6324 (4565 bp) were identified, respectively. The sequence of AZM5_17960 has about 1 kb sequence upstream of the predicted CDS of the corresponding gene to MAWS42 and AZM5_6324 has about 1.5 kb sequence upstream of the predicted CDS of the corresponding gene to MAWS45. These upstream sequences were considered as putative promoter MAWS42 (p-MAWS42) and Promoter MAWS45 (p-MAWS45). FIGS. 18A, and 18B, combined, and FIGS. 18C, 18D, and 18E, combined, show sequences of AZM5_17960 and sequence AZM5_6324, respectively.

Isolation of the Promoter Region by PCR Amplification

The putative promoter sequences were isolated by genomic PCR using the sequence specific primers indicated in Table 8. A fragment of 1008 bp of AZM5_17960 and a fragment of 1492 bp of AZM5_6324 were amplified from maize genomic DNA. These fragments were named as promoter MAWS42 (p-MAWS42) and promoter MAWS45 (p-MAWS45), respectively. Sequences of p-MAWS42 and p-MAWS45 are shown in FIGS. 19A and 19B, respectively.

TABLE 8

| Primers for PCR cloning of pMAWS42 and p-MAWS45 | |
|---|---|
| Primer | Sequence (SEQ ID NO) |
| p-MAWS42_forward | taactcatatccggttagata (72) |
| p-MAWS42_reverse | gtcgtcgccaaataaaaacctacc (73) |
| p-MAWS45_forward | atttaaatgtgttggataatct (74) |
| p-MAWS45_reverse | ctcctcctcctcctcctcctcct (75) |

PLACE Analysis of the Promoters MAWS42 and MAWS45

Cis-acting motifs in the 1008 bp of p-MAWS42 and 1492 bp of p-MAWS45 promoter regions were identified using PLACE (a database of Plant Cis-acting Regulatory DNA elements) using the Genomatix database suite. The results are listed in Table 9 and Table 10.

TABLE 9

PLACE analysis results of the 1008 bp promoter p-MAWS42

| IUPAC | Start pos. | End pos. | Strand | Mismatches | Score | Sequence SEQ ID No) |
|---|---|---|---|---|---|---|
| PREATPRODH | 3 | 8 | + | 0 | 1 | ACTCAT |
| REBETALGLHCB21 | 7 | 13 | – | 0 | 1 | CGGATAT |
| NAPINMOTIFBN | 27 | 33 | + | 0 | 1 | TACACAT |
| CPBCSPOR | 50 | 55 | – | 0 | 1 | TATTAG |
| SEF1MOTIF | 52 | 60 | – | 0 | 1 | ATATTTATT |
| SP8BFIBSP8BIB | 74 | 80 | – | 0 | 1 | TACTATT |
| SEF1MOTIF | 85 | 93 | – | 0 | 1 | ATATTTAAT |
| TATABOXOSPAL | 86 | 92 | – | 0 | 1 | TATTTAA |
| PREATPRODH | 92 | 97 | – | 0 | 1 | ACTCAT |
| BIHD1OS | 109 | 113 | – | 0 | 1 | TGTCA |
| CCAATBOX1 | 126 | 130 | – | 0 | 1 | CCAAT |
| ELRECOREPCRP1 | 140 | 154 | + | 0 | 1 | ATTGACCCTATTTTG (76) |
| CPBCSPOR | 155 | 160 | – | 0 | 1 | TATTAG |
| D3GMAUX28 | 172 | 182 | + | 0 | 1 | TATTTGCTTAA (77) |
| MYBPZM | 186 | 192 | – | 0 | 1 | TCCTACC |
| TATABOX2 | 214 | 220 | + | 0 | 1 | TATAAAT |
| IBOXCORE | 218 | 224 | – | 0 | 1 | GATAATT |
| SREATMSD | 219 | 225 | + | 0 | 1 | ATTATCC |
| MYBST1 | 220 | 226 | – | 0 | 1 | TGGATAA |
| AMYBOX2 | 221 | 227 | + | 0 | 1 | TATCCAT |
| TATCCAOSAMY | 221 | 227 | + | 0 | 1 | TATCCAT |
| TATABOX2 | 239 | 245 | + | 0 | 1 | TATAAAT |
| PREATPRODH | 265 | 270 | + | 0 | 1 | ACTCAT |
| LTRECOREATCOR15 | 274 | 280 | + | 0 | 1 | CCCGACG |
| CGACGOSAMY3 | 276 | 280 | + | 0 | 1 | CGACG |
| HEXAMERATH4 | 276 | 281 | – | 0 | 1 | CCGTCG |
| PREATPRODH | 321 | 326 | + | 0 | 1 | ACTCAT |
| TATABOX4 | 326 | 332 | – | 0 | 1 | TATATAA |
| RAV1AAT | 354 | 358 | – | 0 | 1 | CAACA |
| DPBFCOREDCDC3 | 360 | 366 | + | 0 | 1 | ACACTAG |
| S1FBOXSORPS1L21 | 375 | 380 | – | 0 | 1 | ATGGTA |
| HDZIP2ATATHB2 | 382 | 39D | – | 0 | 1 | TAATAATTA |
| TATABOX3 | 386 | 392 | + | 0 | 1 | TATTAAT |
| TGTCACACMCUCU-MISIN | 448 | 454 | + | 0 | 1 | TGTCACA |
| BIHD1OS | 448 | 452 | + | 0 | 1 | TGTCA |
| MYBPLANT | 454 | 464 | – | 0 | 1 | CACCAAACATT (78) |
| CANBNNAPA | 460 | 468 | – | 0 | 1 | CTAACACCA |
| MYB1LEPR | 464 | 470 | + | 0 | 1 | GTTAGTT |

TABLE 9-continued

PLACE analysis results of the 1008 bp promoter p-MAWS42

| IUPAC | Start pos. | End pos. | Strand | Mismatches | Score | Sequence SEQ ID No) |
|---|---|---|---|---|---|---|
| GT1CORE | 485 | 495 | + | 0 | 1 | AGGTTAATTAC (79) |
| OSE1ROOTNODULE | 502 | 508 | + | 0 | 1 | AAAGATG |
| LTRE1HVBLT49 | 525 | 530 | + | 0 | 1 | CCGAAA |
| MYBCOREATCYCB1 | 533 | 537 | + | 0 | 1 | AACGG |
| 2SSEEDPROTBANAPA | 541 | 549 | + | 0 | 1 | CAAACACAC |
| RAV1AAT | 554 | 558 | + | 0 | 1 | CAACA |
| BOXIINTPATPB | 603 | 608 | + | 0 | 1 | ATAGAA |
| NTBBF1ARROLB | 618 | 624 | + | 0 | 1 | ACTTTAG |
| TAAAGSTKST1 | 619 | 625 | − | 0 | 1 | CCTAAAG |
| PALBOXAPC | 623 | 629 | − | 0 | 1 | CCGTCCT |
| CATATGGMSAUR | 637 | 642 | + | 0 | 1 | CATATG |
| CATATGGMSAUR | 637 | 642 | − | 0 | 1 | CATATG |
| CCAATBOX1 | 647 | 651 | − | 0 | 1 | CCAAT |
| LTRE1HVBLT49 | 657 | 662 | + | 0 | 1 | CCGAAA |
| WBOXHVISO1 | 690 | 704 | + | 0 | 1 | GGTGACTTGGCAGTT (80) |
| REBETALGLHCB21 | 718 | 724 | + | 0 | 1 | CGGATAA |
| SREATMSD | 719 | 725 | − | 0 | 1 | TTTATCC |
| IBOXCORE | 720 | 726 | + | 0 | 1 | GATAAAG |
| TAAAGSTKST1 | 720 | 726 | + | 0 | 1 | GATAAAG |
| OSE1ROOTNODULE | 723 | 729 | + | 0 | 1 | AAAGATG |
| PALBOXAPC | 784 | 790 | − | 0 | 1 | CCGTCCA |
| CMSRE1IBSPOA | 784 | 790 | + | 0 | 1 | TGGACGG |
| SORLIP2AT | 788 | 798 | − | 0 | 1 | GGGGCCGCCCG (81) |
| GCCCORE | 790 | 796 | − | 0 | 1 | GGCCGCC |
| ABRELATERD | 799 | 811 | + | 0 | 1 | TGAGACGTGCCGC (82) |
| SURECOREATSULTR11 | 800 | 806 | + | 0 | 1 | GAGACGT |
| GCCCORE | 806 | 812 | + | 0 | 1 | TGCCGCC |
| SORLIP2AT | 813 | 823 | − | 0 | 1 | CGGGCCAGCTG (83) |
| BS1EGCCR | 820 | 825 | − | 0 | 1 | AGCGGG |
| CACGTGMOTIF | 829 | 841 | − | 0 | 1 | CGCCACGTGTGGG (84) |
| ABREATRD2 | 830 | 842 | + | 0 | 1 | CCACACGTGGCGC (85) |
| DPBFCOREDCDC3 | 832 | 838 | + | 0 | 1 | ACACGTG |
| SORLIP1AT | 834 | 846 | − | 0 | 1 | CTCCGCGCCACGT (86) |
| CGCGBOXAT | 839 | 844 | + | 0 | 1 | GCGCGG |
| CGCGBOXAT | 839 | 844 | − | 0 | 1 | CCGCGC |
| CGCGBOXAT | 849 | 854 | + | 0 | 1 | GCGCGC |
| CGCGBOXAT | 849 | 854 | − | 0 | 1 | GCGCGC |
| CGCGBOXAT | 851 | 856 | + | 0 | 1 | GCGCGG |

TABLE 9-continued

| PLACE analysis results of the 1008 bp promoter p-MAWS42 | | | | | | |
|---|---|---|---|---|---|---|
| IUPAC | Start pos. | End pos. | Strand | Mismatches | Score | Sequence SEQ ID No) |
| CGCGBOXAT | 851 | 856 | – | 0 | 1 | CCGCGC |
| SORLIP1AT | 855 | 867 | + | 0 | 1 | GGCTCGGCCACGT (87) |
| ABREOSRAB21 | 859 | 871 | – | 0 | 1 | TATAACGTGGCCG (88) |
| SORLIP1AT | 867 | 879 | + | 0 | 1 | TTATAAGCCACGC (89) |
| CGCGBOXAT | 876 | 881 | + | 0 | 1 | ACGCGC |
| CGCGBOXAT | 876 | 881 | – | 0 | 1 | GCGCGT |
| CGCGBOXAT | 878 | 883 | + | 0 | 1 | GCGCGC |
| CGCGBOXAT | 878 | 883 | – | 0 | 1 | GCGCGC |
| HEXAMERATH4 | 887 | 892 | + | 0 | 1 | CCGTCG |
| CGACGOSAMY3 | 888 | 892 | – | 0 | 1 | CGACG |
| WBOXNTCHN48 | 901 | 915 | + | 0 | 1 | CCTGACTACTGCACA (90) |
| DPBFCOREDCDC3 | 913 | 919 | + | 0 | 1 | ACACTCG |
| SURECOREATSULTR11 | 917 | 923 | – | 0 | 1 | GAGACGA |
| CGCGBOXAT | 942 | 947 | + | 0 | 1 | CCGCGG |
| CGCGBOXAT | 942 | 947 | – | 0 | 1 | CCGCGG |
| SURECOREATSUTR11 | 963 | 969 | – | 0 | 1 | GAGACGG |
| TAAAGSTKST1 | 974 | 980 | + | 0 | 1 | GCTAAAG |
| MYBPLANT | 982 | 992 | – | 0 | 1 | AACCTACCTCT (91) |
| BOXLCOREDCPAL | 985 | 991 | – | 0 | 1 | ACCTACC |
| CGACGOSAMY3 | 1002 | 1006 | + | 0 | 1 | CGACG |

TABLE 10

| PLACE analysis results of the 1492 bp promoter p-MAWS45 | | | | | | |
|---|---|---|---|---|---|---|
| IUPAC | Start pos. | End pos. | Strand | Mismatches | Score | Sequence |
| RAV1AAT | 2 | 6 | – | 0 | 1 | CAACA |
| TATCCAOSAMY | 4 | 10 | – | 0 | 1 | TATCCAA |
| MYBST1 | 5 | 11 | + | 0 | 1 | TGGATAA |
| SREATMSD | 6 | 12 | – | 0 | 1 | ATTATCC |
| IBOXCORE | 7 | 13 | + | 0 | 1 | GATAATC |
| OSE1ROOTNODULE | 10 | 16 | – | 0 | 1 | AAAGATT |
| -300ELEMENT | 12 | 20 | – | 0 | 1 | TGCAAAAGA |
| RYREPEATBNNAPA | 14 | 24 | – | 0 | 1 | TCCATGCAAAA (92) |
| AMYBOX2 | 20 | 26 | – | 0 | 1 | TATCCAT |
| TATCCAOSAMY | 20 | 26 | – | 0 | 1 | TATCCAT |
| MYBST1 | 21 | 27 | + | 0 | 1 | TGGATAT |
| RAV1AAT | 29 | 33 | – | 0 | 1 | CAACA |
| MYCATRD2 | 44 | 50 | – | 0 | 1 | CACATGG |
| MYCATERD | 45 | 51 | + | 0 | 1 | CATGTGC |

TABLE 10-continued

| PLACE analysis results of the 1492 bp promoter p-MAWS45 | | | | | | |
|---|---|---|---|---|---|---|
| IUPAC | Start pos. | End pos. | Strand | Mismatches | Score | Sequence |
| ANAERO2CONSENSUS | 59 | 64 | + | 0 | 1 | AGCAGC |
| CCAATBOX1 | 80 | 84 | + | 0 | 1 | CCAAT |
| RYREPEATBNNAPA | 117 | 127 | + | 0 | 1 | AACATGCAAAT (93) |
| BIHD1OS | 133 | 137 | + | 0 | 1 | TGTCA |
| DPBFCOREDCDC3 | 142 | 148 | + | 0 | 1 | ACACCAG |
| BOXLCOREDCPAL | 157 | 163 | - | 0 | 1 | ACCATCC |
| S1FBOXSORPS1L21 | 159 | 164 | + | 0 | 1 | ATGGTA |
| AMYBOX2 | 218 | 224 | - | 0 | 1 | TATCCAT |
| TATCCAOSAMY | 218 | 224 | - | 0 | 1 | TATCCAT |
| MYBST1 | 219 | 225 | + | 0 | 1 | TGGATAT |
| WBOXATNPR1 | 230 | 244 | + | 0 | 1 | ATTGACAATAAAACA (94) |
| BIHD1OS | 232 | 236 | - | 0 | 1 | TGTCA |
| MYB1AT | 248 | 253 | + | 0 | 1 | TAACCA |
| SEF3MOTIFGM | 255 | 260 | - | 0 | 1 | AACCCA |
| MYB1AT | 275 | 280 | - | 0 | 1 | AAACCA |
| -10PEFIVPSBD | 291 | 296 | - | 0 | 1 | TATTCT |
| P1BS | 312 | 319 | + | 0 | 1 | GTATATAC |
| P1BS | 312 | 319 | - | 0 | 1 | GTATATAC |
| RAV1AAT | 321 | 325 | + | 0 | 1 | CAACA |
| CIACADIANLELHC | 341 | 350 | + | 0 | 1 | CAAAGCCATC (95) |
| MYBPZM | 351 | 357 | + | 0 | 1 | TCCAACC |
| RYREPEATGMGY2 | 372 | 382 | - | 0 | 1 | ACCATGCATAT (96) |
| RAV1AAT | 384 | 388 | + | 0 | 1 | CAACA |
| WBOXATNPR1 | 398 | 412 | + | 0 | 1 | ATTGACATGCATATA (97) |
| BIHD1OS | 400 | 404 | - | 0 | 1 | TGTCA |
| RYREPEATGMGY2 | 401 | 411 | + | 0 | 1 | GACATGCATAT (98) |
| SORLREP3AT | 426 | 434 | - | 0 | 1 | TGTATATAT |
| SP8BFIBSP8BIB | 443 | 449 | + | 0 | 1 | TACTATT |
| CATATGGMSAUR | 451 | 456 | + | 0 | 1 | CATATG |
| CATATGGMSAUR | 451 | 456 | - | 0 | 1 | CATATG |
| TATABOX4 | 457 | 463 | - | 0 | 1 | TATATAA |
| SEF1MOTIF | 461 | 469 | + | 0 | 1 | ATATTTATA |
| TATABOX2 | 463 | 469 | - | 0 | 1 | TATAAAT |
| ANAERO1CONSENSUS | 481 | 487 | - | 0 | 1 | AAACAAA |
| BIHD1OS | 492 | 496 | + | 0 | 1 | TGTCA |
| DPBFCOREDCDC3 | 507 | 513 | - | 0 | 1 | ACACACG |
| GT1GMSCAM4 | 521 | 526 | - | 0 | 1 | GAAAAA |
| MYB1AT | 543 | 548 | + | 0 | 1 | TAACCA |

TABLE 10-continued

| PLACE analysis results of the 1492 bp promoter p-MAWS45 | | | | | | |
|---|---|---|---|---|---|---|
| IUPAC | Start pos. | End pos. | Strand | Mismatches | Score | Sequence |
| DPBFCOREDCDC3 | 563 | 569 | + | 0 | 1 | ACACGCG |
| CGCGBOXAT | 565 | 570 | + | 0 | 1 | ACGCGT |
| CGCGBOXAT | 565 | 570 | − | 0 | 1 | ACGCGT |
| RAV1AAT | 589 | 593 | + | 0 | 1 | CAACA |
| MYCATERD | 591 | 597 | − | 0 | 1 | CATGTGT |
| DPBFCOREDCDC3 | 591 | 597 | + | 0 | 1 | ACACATG |
| MYCATRD2 | 592 | 598 | + | 0 | 1 | CACATGG |
| S1FBOXSORPS1L21 | 595 | 600 | + | 0 | 1 | ATGGTA |
| CCA1ATLHCB1 | 603 | 610 | − | 0 | 1 | AAAAATCT |
| -300ELEMENT | 604 | 612 | − | 0 | 1 | TGAAAAATC |
| GT1GMSCAM4 | 606 | 611 | − | 0 | 1 | GAAAAA |
| WBOXATNPR1 | 607 | 621 | − | 0 | 1 | TTTGACACATGAAAA (99) |
| MYCATRD2 | 610 | 616 | − | 0 | 1 | CACATGA |
| MYCATERD | 611 | 617 | + | 0 | 1 | CATGTGT |
| DPBFCOREDCDC3 | 611 | 617 | − | 0 | 1 | ACACATG |
| BIHD1OS | 615 | 619 | + | 0 | 1 | TGTCA |
| PREATPRODH | 655 | 660 | + | 0 | 1 | ACTCAT |
| SURECOREATSULTR11 | 671 | 677 | + | 0 | 1 | GAGACGA |
| PALBOXAPC | 703 | 709 | − | 0 | 1 | CCGTCCG |
| GT1GMSCAM4 | 718 | 723 | − | 0 | 1 | GAAAAA |
| CPBCSPOR | 733 | 738 | − | 0 | 1 | TATTAG |
| SEF1MOTIF | 740 | 748 | − | 0 | 1 | ATATTTATT |
| RAV1BAT | 771 | 783 | + | 0 | 1 | TACCACCTGTTGC (100) |
| RAV1AAT | 778 | 782 | − | 0 | 1 | CAACA |
| INTRONLOWER | 792 | 797 | + | 0 | 1 | TGCAGG |
| MYBPLANT | 794 | 804 | − | 0 | 1 | CACCAAACCTG (101) |
| SEBFCONSSTPR10A | 802 | 808 | − | 0 | 1 | CTGTCAC |
| BIHD1OS | 803 | 807 | − | 0 | 1 | TGTCA |
| RYREPEATGMGY2 | 814 | 824 | + | 0 | 1 | AACATGCATTT (102) |
| L1BOXATPDF1 | 818 | 825 | − | 0 | 1 | TAAATGCA |
| RAV1AAT | 828 | 832 | − | 0 | 1 | CAACA |
| MYB2AT | 847 | 857 | − | 0 | 1 | CGATTAACTGC (103) |
| RAV1AAT | 867 | 871 | − | 0 | 1 | CAACA |
| 2SSEEDPROTBANAPA | 875 | 883 | + | 0 | 1 | CAAACACGA |
| DPBFCOREDCDC3 | 878 | 884 | + | 0 | 1 | ACACGAG |
| SORLIP1AT | 931 | 943 | − | 0 | 1 | ACGACGGCCACCG (104) |
| HEXAMERATH4 | 937 | 942 | + | 0 | 1 | CCGTCG |
| CGACGOSAMY3 | 938 | 942 | − | 0 | 1 | CGACG |

TABLE 10-continued

PLACE analysis results of the 1492 bp promoter p-MAWS45

| IUPAC | Start pos. | End pos. | Strand | Mismatches | Score | Sequence |
|---|---|---|---|---|---|---|
| DPBFCOREDCDC3 | 959 | 965 | + | 0 | 1 | ACACCAG |
| CCAATBOX1 | 967 | 971 | + | 0 | 1 | CCAAT |
| SV40COREENHAN | 968 | 975 | – | 0 | 1 | GTGGATTG |
| RAV1AAT | 980 | 984 | + | 0 | 1 | CAACA |
| CGCGBOXAT | 986 | 991 | + | 0 | 1 | CCGCGC |
| CGCGBOXAT | 986 | 991 | – | 0 | 1 | GCGCGG |
| WBOXNTCHN48 | 987 | 1001 | – | 0 | 1 | ACTGACCGAGGCGCG (105) |
| MYB2AT | 997 | 1007 | – | 0 | 1 | TCTATAACTGA (106) |
| SORLIP1AT | 1009 | 1021 | – | 0 | 1 | CAGAAGGCCACGC (107) |
| ANAERO1CONSENSUS | 1022 | 1028 | + | 0 | 1 | AAACAAA |
| AACACOREOSGLUB1 | 1023 | 1029 | + | 0 | 1 | AACAAAC |
| CATATGGMSAUR | 1033 | 1038 | + | 0 | 1 | CATATG |
| CATATGGMSAUR | 1033 | 1038 | – | 0 | 1 | CATATG |
| MYCATERD | 1055 | 1061 | – | 0 | 1 | CATGTGT |
| DPBFCOREDCDC3 | 1055 | 1061 | + | 0 | 1 | ACACATG |
| RYREPEATGMGY2 | 1056 | 1066 | + | 0 | 1 | CACATGCATCC (108) |
| MYCATRD2 | 1056 | 1062 | + | 0 | 1 | CACATGC |
| DPBFCOREDCDC3 | 1085 | 1091 | – | 0 | 1 | ACACAAG |
| IBOXCORE | 1106 | 1112 | + | 0 | 1 | GATAACC |
| SEF3MOTIFGM | 1109 | 1114 | + | 0 | 1 | AACCCA |
| SORLIP1AT | 1110 | 1122 | + | 0 | 1 | ACCCAGGCCACAT (109) |
| CGCGBOXAT | 1130 | 1135 | + | 0 | 1 | CCGCGC |
| CGCGBOXAT | 1130 | 1135 | – | 0 | 1 | GCGCGG |
| CGCGBOXAT | 1135 | 1140 | + | 0 | 1 | CCGCGC |
| CGCGBOXAT | 1135 | 1140 | – | 0 | 1 | GCGCGG |
| GCCCORE | 1138 | 1144 | + | 0 | 1 | CGCCGCC |
| SEF3MOTIFGM | 1156 | 1161 | + | 0 | 1 | AACCCA |
| ACGTOSGLUB1 | 1181 | 1193 | – | 0 | 1 | ACGTACGTGCAAG (110) |
| CGCGBOXAT | 1198 | 1203 | + | 0 | 1 | GCGCGC |
| CGCGBOXAT | 1198 | 1203 | – | 0 | 1 | GCGCGC |
| MYBCOREATCYCB1 | 1207 | 1211 | – | 0 | 1 | AACGG |
| MYBCOREATCYCB1 | 1244 | 1248 | – | 0 | 1 | AACGG |
| SORLIP1AT | 1256 | 1268 | + | 0 | 1 | GAGTGCGCCACGC (111) |
| LTRE1HVBLT49 | 1268 | 1273 | + | 0 | 1 | CCGAAA |
| ASF1MOTIFCAMV | 1280 | 1292 | + | 0 | 1 | CGAGCTGACGAGC (112) |
| SORLIP1AT | 1294 | 1306 | + | 0 | 1 | CTAGACGCCACCG (113) |
| CGCGBOXAT | 1311 | 1316 | + | 0 | 1 | GCGCGG |
| CGCGBOXAT | 1311 | 1316 | – | 0 | 1 | CCGCGC |

TABLE 10-continued

| PLACE analysis results of the 1492 bp promoter p-MAWS45 | | | | | | |
|---|---|---|---|---|---|---|
| IUPAC | Start pos. | End pos. | Strand | Mismatches | Score | Sequence |
| SORLIP1AT | 1316 | 1328 | - | 0 | 1 | TGCCTTGCCACGC (114) |
| SURECOREATSULTR11 | 1340 | 1346 | - | 0 | 1 | GAGACCC |
| ASF1MOTIFCAMV | 1349 | 1361 | - | 0 | 1 | ATAGCTGACGAGG (115) |
| PALBOXAPC | 1429 | 1435 | + | 0 | 1 | CCGTCCC |
| INTRONLOWER | 1434 | 1439 | - | 0 | 1 | TGCAGG |
| INTRONLOWER | 1441 | 1446 | + | 0 | 1 | TGCAGG |

Binary Vector Construction for Maize Transformation to Evaluate the Function of p-MAWS42 and p-MAWS45

Figure 20:
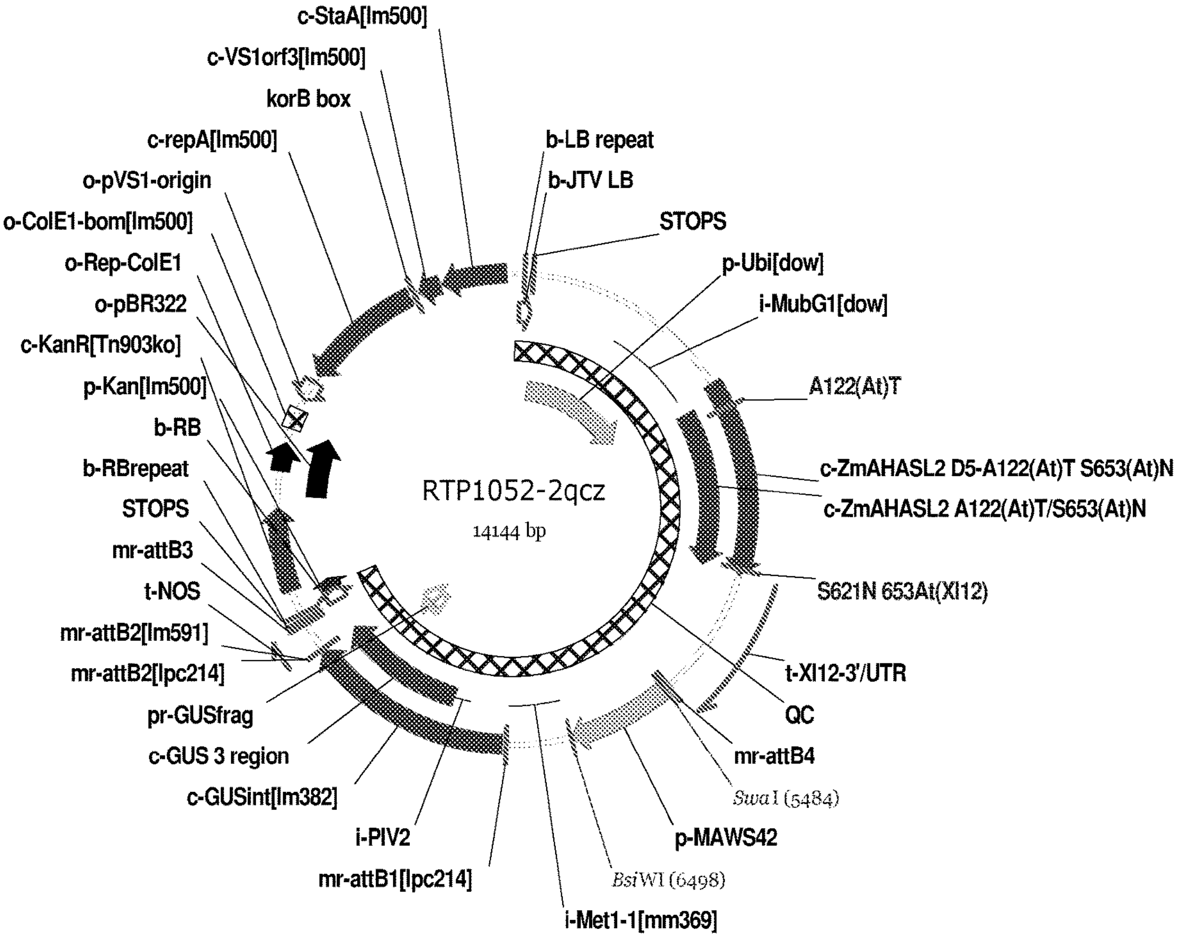

The 1008 bp promoter fragment of p-MAWS42 was amplified by PCR, incorporating a SwaI restriction enzyme site at its 5' end and a BsiWI site at its 3' end. The resulting fragment was digested and ligated into a SwaI and BsiWI digested BPS basic binary vector CB1006. Plasmid CB1006 is a plant transformation vector that comprises a plant selectable marker expression cassette (p-Ubi::c-ZmA-HASL2::t-NOS) as well as a promoter evaluation cassette that consists of a multiple cloning site for insertion of putative promoters via SwaI and BsiWI sites, rice MET1-1 intron to supply intron-mediated enhancement in monocot cells, GUS reporter gene, and NOS terminator. The resulting binary vector comprising the p-MAWS42::i-MET1::GUS::t-NOS expression cassette was named as RTP1052, and was used to evaluate the expression pattern driven by the p-MAWS42 promoter. FIG. 20 is a diagram of RTP1052. Sequence of the binary vector RTP1052 is shown in FIGS. 21A, 21B, 21C, 21D, 21E, 21F, and 21G, combined.

The 1492 bp promoter fragment of p-MAWS45 was amplified by PCR, incorporating a SwaI restriction enzyme site at its 5' end and a BsiWI site at its 3' end. The resulting fragment was digested and ligated into a SwaI and BsiWI digested BPS basic binary vector CB1006. Plasmid CB1006 is a plant transformation vector that comprises a plant selectable marker expression cassette (p-Ubi::c-ZmA-HASL2::t-NOS) as well as a promoter evaluation cassette that consists of a multiple cloning site for insertion of putative promoters via SwaI and BsiWI sites, rice MET1-1 intron to supply intron-mediated enhancement in monocot cells, GUS reporter gene, and NOS terminator. The resulting binary vector comprising the p-MAWS45::i-MET1::GUS::t-NOS expression cassette was named as RTP1057, and was used to evaluate the expression pattern driven by the p-MAWS45 promoter. FIG. 22 is a diagram of RTP1052. Sequence of the binary vector RTP1057 is shown in FIGS. 23A, 23B, 23C, 23D, 23E, 23F, and 23G combined.

Promoter Evaluation in Transgenic Maize with RTP1052 or RTP1057

The expression patterns and levels driven by promoters p-MAWS42 or p-MAWS45 were measured using GUS histochemical analysis following the protocol in the art (Jefferson 1987). Maize transformation was conducted using an *Agrobacterium*-mediated transformation system. Ten and five single copy events for T0 and T1 plants were chosen for the promoter analysis. GUS expression was measured at various developmental stages:

1) Roots and leaves at 5-leaf stage
2) Stem at V-7 stage
2) Leaves, husk and silk at flowering stage (first emergence of silk)
3) Spikelets/Tassel (at pollination)
5) Ear or Kernels at 5, 10, 15, 20, and 25 days after pollination (DAP)

The results indicated that both promoter p-MAWS42 of RTP1052 and promoter p-MAWS45 of RTP1057 expressed specifically in pollen and in whole seeds (FIGS. 24 and 25).

TABLE 11

| Summary of tested tissues and relative expression intensities for pMAWS42 | | | | | | | | | | |
|---|---|---|---|---|---|---|---|---|---|---|
| | Tissues | | | | | | | | | |
| Stages tested | Leaf | Root | Stem | husk | silk | Spikelets/ Tassel/pollen | un-pollinated cob | pollinated cob | embryo | endosperm |
| seedling (5-leaf) | - | - | | | | | | | | |
| V-7 | | | | | | | | | | |
| Flowering (emergence of silk) | - | | | - | - | | - | | | |
| pollination | | | | | | + | | | | |
| 5DAP | | | | | | | | + | | |
| 10DAP | | | | | | | | | ++ | + |
| 15DAP | | | | | | | | | +++ | ++ |
| 20DAP | | | | | | | | | +++ | ++ |
| 25DAP | | | | | | | | | +++ | ++ |

TABLE 11-continued

| Summary of tested tissues and relative expression intensities for pMAWS42 | | | | | | | | | | |
|---|---|---|---|---|---|---|---|---|---|---|
| | Tissues | | | | | | | | | |
| Stages tested | Leaf | Root | Stem | husk | silk | Spikelets/ Tassel/pollen | un-pollinated cob | pollinated cob | embryo | endosperm |
| 48 hrs after imibibition | | | | | | | | | ++++ | ++ |
| 72 hrs after imibibition | | | | | | | | | ++++ | +++ |
| 1 week germination | – | – | | | | | | | | |

– = no expression,
+ = weak expression,
++ = medium expression,
+++ = strong expression,
++++ = very strong expression

TABLE 12

| Summary of tested tissues and relative expression intensities for pMAWS45 | | | | | | | | | | |
|---|---|---|---|---|---|---|---|---|---|---|
| | Tissues | | | | | | | | | |
| Stages tested | Leaf | Root | Stem | husk | silk | Spikelets/ Tassel/pollen | un-pollinated cob | pollinated cob | embryo | endosperm |
| seedling (5-leaf) | – | – | | | | | | | | |
| V-7 | | | | | | | | | | |
| Flowering (emergence of silk) | – | | | – | – | | – | | | |
| pollination | | | | | | + | | | | |
| 5DAP | | | | | | | | + | | |
| 10DAP | | | | | | | | | + | ++++ |
| 15DAP | | | | | | | | | ++ | ++++ |
| 20DAP | | | | | | | | | ++ | ++++ |
| 25DAP | | | | | | | | | ++ | ++++ |
| 48 hrs after imibibition | | | | | | | | | ++ | +++ |
| 72 hrs after imibibition | | | | | | | | | ++ | +++ |
| 1 week germination | – | – | | | | | | | | |

– = no expression,
+ = weak expression,
++ = medium expression,
+++ = strong expression,
++++ = very strong expression

Example 3

The sequence of the pKG86 promoter (SEQ ID NO: 1) was searched for short open reading frames which may confer allergenicity or toxicity using a database comprising allergenic and toxic peptides and polypeptides. Short open reading frames were identified showing homology to peptides or polypeptides comprised by said database. In order to avoid expression of peptides which may be toxic or allergenic, the sequence of pKG86 was modified. The resulting promoters pKG86_12A (SEQ ID NO: 129), pKG86_14A (SEQ ID NO: 130) and pKG86_15A (SEQ ID NO:131) were operably linked to a reporter gene and transformed into *Zea mays* for expression analysis.

The invention claimed is:

1. A polynucleotide comprising:

(i) an expression control sequence which allows for seed specific expression in a plant of a nucleic acid sequence of interest operatively linked thereto, wherein said expression control sequence comprises the nucleic acid sequence of SEQ ID NO: 129, 130 or 131; and (ii) at least one nucleic acid sequence of interest operatively finked and heterologous to the expression control sequence, wherein the expression control sequence allows for specific expression of the at least one nucleic acid sequence of interest in the whole seed of a monocotyledonous plant.

2. The polynucleotide of claim 1, wherein said polynucleotide further comprises a first intron of a plant gene encoding a Metallothionin 1 polypeptide.

3. A vector comprising the polynucleotide of claim 1.

4. The vector of claim 3, wherein said vector is a T-DNA vector.

5. A host cell comprising:

(a) the polynucleotide of claim 1; or (b) a vector comprising the polynucleotide of claim 1.

6. The host cell of claim 5, wherein said host cell is a plant cell.

7. A transgenic plant or plant seed comprising:

(a) the polynucleotide of claim 1; or (b) a vector comprising the polynucleotide of claim 1.

8. The transgenic plant or plant seed of claim 7, wherein said transgenic plant or plant seed is a monocotyledonous plant or a plant seed of a monocotyledonous plant.

9. A method for expressing a nucleic acid sequence of interest in a host cell comprising:

(a) introducing the polynucleotide of claim 1 or a vector comprising said polynucleotide into a host cell; and (b) expressing the at least one nucleic acid sequence of interest in said host cell.

10. The method of claim 9, wherein the host cell is a plant cell.

11. A method for expressing a nucleic acid sequence of interest in a plant or seed thereof comprising:

(a) introducing the polynucleotide of claim 1 or a vector comprising said polynucleotide into a plant or seed thereof; and (b) expressing the at least one nucleic acid sequence of interest in said plant or seed thereof.

12. The method of claim 11, wherein the plant is a monocotyledonous plant.

13. The polynucleotide of claim 2, wherein said first intron comprises the nucleic acid sequence of SEQ ID NO: 119.

14. The polynucleotide of claim 1, wherein the expression control sequence comprises the nucleic acid sequence of SEQ ID NO: 129.

15. The polynucleotide of claim 1, wherein the expression control sequence comprises the nucleic acid sequence of SEQ ID NO: 130.

16. The polynucleotide of claim 1, wherein the expression control sequence comprises the nucleic acid sequence of SEQ ID NO: 131.

17. A polynucleotide comprising:

(i) an expression control sequence which allows for seed specific expression in a plant of a nucleic acid sequence of interest operatively linked thereto, wherein said expression control sequence comprises the nucleic acid sequence of SEQ ID NO: 1; and (ii) at least one nucleic acid sequence of interest operatively linked and heterologous to the expression control sequence, wherein the expression control sequence allows for specific expression of the at least one nucleic acid sequence of interest in the whole seed of a monocotyledonous plant.

18. The polynucleotide of claim 17, wherein said polynucleotide further comprises a first intron of a plant gene encoding a Metallothionin 1 polypeptide.

19. A transgenic plant or plant seed comprising:

(a) the polynucleotide of claim 17; or (b) a vector comprising the polynucleotide of claim 17.

20. A method for expressing a nucleic acid sequence of interest in a host cell comprising:

(a) introducing the polynucleotide of claim 17 or a vector comprising said polynucleotide into a host cell; and (b) expressing the at least one nucleic acid sequence of interest in said host cell.

* * * * *